US00RE44048E

(19) United States
(12) Reissued Patent
Talley et al.

(10) Patent Number: US RE44,048 E
(45) Date of Reissued Patent: Mar. 5, 2013

(54) 4-[5-(4-METHYLPHENYL)-3-(TRIFLUORO METHYL)-1H-PYRAZOL-1-YL]BENZENE SULFONAMIDE FOR THE TREATMENT OF INFLAMMATION OR AN INFLAMMATION-ASSOCIATED DISORDER

(75) Inventors: John J. Talley, St. Louis, MO (US); Stephen R. Bertenshaw, Cheshire, CT (US); Julie M. Miyashiro, Morton Grove, IL (US)

(73) Assignee: G.D. Searle LLC, New York, NY (US)

(21) Appl. No.: 12/205,319

(22) Filed: Sep. 5, 2008

Related U.S. Patent Documents

Reissue of:
(64) Patent No.: 5,760,068
Issued: Jun. 2, 1998
Appl. No.: 08/648,113
PCT Filed: Nov. 14, 1994
PCT No.: PCT/US94/12720
§ 371 (c)(1),
(2), (4) Date: Sep. 6, 1996
PCT Pub. No.: WO95/15316
PCT Pub. Date: Jun. 8, 1995

U.S. Applications:
(62) Division of application No. 08/160,594, filed on Nov. 30, 1993, now Pat. No. 5,466,823.

(51) Int. Cl.
*A61K 31/415* (2006.01)
(52) U.S. Cl. ..... 514/403; 514/406; 514/407
(58) Field of Classification Search ..... 514/403, 514/406, 407
See application file for complete search history.

(56) References Cited

U.S. PATENT DOCUMENTS

| | | | |
|---|---|---|---|
| 3,940,418 | A | 2/1976 | Hamilton |
| 4,146,721 | A | 3/1979 | Rainer |
| 5,134,142 | A | 7/1992 | Matsuo et al. |
| 5,134,155 | A | 7/1992 | Connolly et al. |
| 5,173,470 | A | 12/1992 | Bruening et al. |
| 5,315,012 | A | 5/1994 | Connolly et al. |
| 5,387,693 | A | 2/1995 | Connolly et al. |
| 5,420,141 | A | 5/1995 | Boigegrain et al. |
| 5,434,178 | A | 7/1995 | Talley et al. |
| 5,466,823 | A | 11/1995 | Talley et al. |
| 5,476,944 | A | 12/1995 | Partis et al. |
| 5,504,215 | A | 4/1996 | Talley et al. |
| 5,508,426 | A | 4/1996 | Talley et al. |
| 5,510,496 | A | 4/1996 | Talley et al. |
| 5,516,907 | A | 5/1996 | Talley et al. |
| 5,521,207 | A | 5/1996 | Graneto |
| 5,521,219 | A | 5/1996 | Vazquez et al. |
| 5,563,165 | A | 10/1996 | Talley et al. |
| 5,607,958 | A | 3/1997 | Boigegrain et al. |
| 5,616,592 | A | 4/1997 | Boigegrain et al. |
| 5,635,526 | A | 6/1997 | Boigegrain et al. |
| 5,744,491 | A | 4/1998 | Boigegrain et al. |
| 5,744,493 | A | 4/1998 | Boigegrain et al. |
| 5,753,688 | A | 5/1998 | Talley et al. |
| 5,760,068 | A | 6/1998 | Talley et al. |
| 5,892,053 | A | 4/1999 | Zhi et al. |
| 6,156,781 | A | 12/2000 | Talley et al. |
| 6,413,960 | B1 | 7/2002 | Talley et al. |
| 6,492,411 | B1 | 12/2002 | Talley et al. |
| 6,586,603 | B1 | 7/2003 | Talley et al. |
| 6,716,991 | B1 | 4/2004 | Talley et al. |
| 6,951,949 | B2 | 10/2005 | Talley et al. |

FOREIGN PATENT DOCUMENTS

| | | |
|---|---|---|
| AU | 94/75753 | 10/1993 |
| AU | 9475753 | 5/1995 |
| CA | 959838 | 12/1974 |
| CA | 2088835 | 2/1993 |
| DE | 287719 | 8/1989 |
| EP | 0347773 | 6/1989 |
| EP | 347773 | 12/1989 |
| EP | 0418845 | 3/1991 |
| EP | 477049 | 3/1992 |
| EP | 0554829 | 8/1993 |
| EP | 554829 | 8/1993 |
| EP | 0922697 | 6/1999 |
| EP | 0923933 | 6/1999 |
| EP | 0924201 | 6/1999 |
| WO | 94/4777 | 7/1994 |
| WO | WO95/15316 | 6/1995 |

OTHER PUBLICATIONS

Lima et al. Current Medicinal Chemistry, 2005, 12, 23-49.*
Nov. 15, 2007 Deposition of Michael Orme, Exhibits 2, 5-17, 20.
Jun. 10, 2008 Deposition Ofscott Hauser, Exhibits 21, 22 (22A-Z; 22CC-KK), 23 (23A-23B), 24, 26, 30, 35, 36.
Jun. 10, 2008 Deposition of Kathy Owen, Exhibits 37 (37-1 to 37-27) [37-7A to 37-7KK])-39; 44-46, 49-50.
Jan. 8, 2007 Defendants' First Request for Production of Documents.
Jan. 8, 2007 Defendants' First Set of Interrogatories.
Jan. 12, 2007 Plaintiffs' First Request for Production of Documents.
Jan. 25, 2007 Defendants' Initial Disclosures.
Jan. 26, 2007 Plaintiffs' Initial Rule 26(a)(1) Disclosure Statement to Defendants.
Feb. 12, 2007 Plaintiffs' Response to Defendants' First Request for Production of Documents.
Feb. 12, 2007 Plaintiffs' Response to Defendants' First Set of Interrogatories.

(Continued)

*Primary Examiner* — Kamal Saeed
(74) *Attorney, Agent, or Firm* — A Dean Olson

(57) ABSTRACT

[A class of pyrazolyl benzenesulfonamide compounds is described for use in treating inflammation and inflammation-related disorders. Compounds of particular interest are defined by Formula II:

(II)

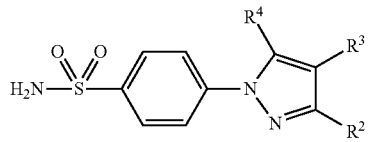

or a pharmaceutically-acceptable salt thereof.] *A method of treating inflammation or an inflammation-associated disorder in a subject by administering a therapeutically-effective dose of 4-[5-(4-methylphenyl)-3-(trifluoromethyl)-1H-pyrazol-1-yl]benzenesulfonamide, or a pharmaceutically-acceptable salt thereof, to the subject.*

7 Claims, No Drawings

OTHER PUBLICATIONS

Feb. 14, 2007 Defendants' Response to Plaintiffs' First Request for Production of Documents.
May 3, 2007 Plaintiffs' Notice of Subpoenas for Production of Documents and Things served upon Cayman Chemical Company, Oxford Biomedical Research, Inc., University of Rochester, Washington University at St. Louis, Dr. Phillip Needleman and Merck & Co., Inc./Merck Sharp & Dohme Limited.
May 4, 2007 Plaintiffs' First Set of Interrogatories to Defendant Pfizer, Inc.
Jun. 5, 2007 Defendant Pfizer Inc.'s Response to Plaintiffs' First Set of Interrogatories.
Jul. 12, 2007 Plaintiffs' Supplemental Response to Defendants' Interrogatory No. 8.
Jul. 25, 2007 Plaintiffs' Request for Admission to Defendant Pfizer, Inc.
Aug. 27, 2007 Defendant Pfizer Inc.'s Response to Plaintiffs' Request for Admission.
Aug. 30, 2007 Merck & Co, Inc.'s and Merck Sharp & Dohme Limited's Responses and Objections to Brigham Young University's and Dr. Daniel L. Simmons' Rule 45 Subpoena Duces Tecum dated May 11, 2007.
16 Sep. 5, 2007 Plaintiffs' Second Request for Production of Documents.
Sep. 21, 2007 Defendants' Notice of Deposition of Michael Orme.
Oct. 1, 2007 Plaintiffs' Amended Subpoena for Documents served on Merck & Co., Inc., Merck Sharp & Dohme Limited.
Oct. 8, 2007 Defendants' Response to Plaintiffs' Second Request for Production of Documents.
Oct. 11, 2007 Plaintiffs' Notice of Subpoena for Production of Documents and Things served upon Teva Pharmaceuticals USA, Inc.
Oct. 12, 2007 Plaintiffs' Notice of Subpoena for Production of Documents and Things served upon University of Connecticut and the University of California, Los Angeles.
Oct. 29, 2007 Plaintiffs' Third Request for Production of Documents.
Oct. 29, 2007 Plaintiffs' Notice of Subpoena for Production of Documents and Things served upon Dr. Harvey Herschman and Dr. Timothy Hla.
Oct. 31, 2007 Plaintiffs' Notice of Subpoena for Production of Documents and Things served upon American Red Cross.
Nov. 5, 2007 Merck & Co., Inc.'s Responses and Objections to Brigham Young University Young University's and Dr. Daniel L. Simmons's Second Amended Rule 45 Subpoena Duces Tecum Dated Oct. 9, 2007.
Nov. 8, 2007 Plaintiffs' Notice of Subpoena for Production of Documents and Things served upon the Monsanto Company.
Nov. 12, 2007 Notice of Taking Video Deposition of Michael Orme.
Nov. 20, 2007 Defendants' Notice of Subpoena for Production of Documents and Things to Plaintiffs to Merck & Co., Inc., Merck Sharp & Dohme Limited.
Dec. 3, 2007 Defendants' Response to Plaintiffs' Third Request for Production of Documents.
Dec. 17, 2007 Merck & Co, Inc.'s Responses and Objections to Pfizer, Inc.'s Rule 45 Subpoena Duces Tecum Served Nov. 28, 2007.
Jan. 11, 2008 Plaintiffs' Second Set of Interrogatories to Defendant Pfizer, Inc.
Jan. 29, 2008 Plaintiffs' Fourth Request for Production of Documents.
Feb. 11, 2008 Defendants' Second Request for Production of Documents to Plaintiffs.
Feb. 12, 2008 Plaintiffs' Notice of Subpoena for Production of Documents and Things to Chandler Chicco Agency, David L. DeWitt and Michigan State University.
Feb. 13, 2008 Plaintiffs' 30(b)(6) Notice of Deposition to Pfizer.
Feb. 13, 2008 Defendant Pfizer Inc.'s Response to Plaintiffs' Second Set of Interrogatories.
Feb. 22, 2008 Defendant Pfizer's Response and Objections to Plaintiffs' 30(b)(6) Notice of Deposition to Pfizer.
Feb. 22, 2008 Defendants' Notice of Subpoenas for Production of Documents and Things to Fish & Richardson P.C. and Harvard University.
Feb. 25, 2008 Plaintiffs' Notice of Subpoenas for Production of Documents and Things to Jaime L. Masferrer, Karen Seibert, Amiram Raz and Peter C. Isakson.
Feb. 27, 2008 Plaintiffs' Third Set of Interrogatories to Defendant Pfizer, Inc.
Mar. 4, 2008 Defendants' Response to Plaintiffs' Fourth Request for Production of Documents.
Mar. 7, 2008 Subpoena for Production of Documents and Things served upon Fish & Richardson, P.C. by Defendants.
Mar. 7, 2008 Subpoena for Production of Documents and Things served upon Harvard University by Defendants.
Mar. 7, 2008 Subpoena served upon Dr. Peter C. Isakson by Plaintiffs.
May 2, 2008 Plaintiffs Fifth Requests for Production of Documents to Defendants.
May 9, 2008 Subpoena Duces Tecum in a Civil Case to Lynn Astle.
May 9, 2008 Notice of Taking Video Deposition of Lynn Astle.
May 9, 2008 Defendants' Third Request for Production of Documents.
May 27, 2008 Defendants' Notice of Subpoenas for Deposition and Production of Documents and Things to Weilin Xie, Jeffrey Chipman and Gary Evett.
May 29, 2008 Plaintiffs' Rule 30(b)(6) Deposition Required by the Court of Pfizer, Inc.
Jun. 4, 2008 Plaintiffs' Amended Rule 30(b)(6) Deposition Required by the Court of Pfizer, Inc.
Jun. 4, 2008 Defendants' Response to Plaintiffs' Fifth Requests for Production of Documents.
Jun. 11, 2008 Plaintiffs' Response to Defendants' First Set of Requests for Admission to Plaintiff Brigham Young University.
Jun. 11, 2008 Plaintiffs' Response to Defendants' First Set of Requests for Admission to Plaintiff Dr. Daniel L. Simmons.
Jun. 12, 2008 Plaintiffs' Response to Defendants' Third Request for Production of Documents.
Jun. 27, 2008 Plaintiffs' Supplemental Response to Defendants' Interrogatory No. 4.
Index of of Documents Cited in BYU's Supplemental Response to Interrogatory No. 4.
Jul. 21, 2008 Discovery Stipulation between Plaintiffs and Teva Pharmaceuticals USA, Inc.
Aug. 12, 2008 Defendants' Supplemental Response to Plaintiffs' First Request for Admission.
1 Oct. 18, 2006 Complaint DI 1.
2 Oct. 18, 2006 Motion and Consent of Sponsoring Local Counsel for Pro Hac Vice Admission of L. Richard Williams for Plaintiffs DI 2.
3 Oct. 18, 2006 Motion and Consent of Sponsoring Local Counsel for Pro Hac Vice Admission of Leo R. Beus for Plaintiffs DI 3.
4 Oct. 18, 2006 Motion and Consent of Sponsoring Local Counsel for Pro Hac Vice Admission of Adam C. Anderson for Plaintiffs DI 4.
5 Oct. 18, 2006 Motion and Consent of Sponsoring Local Counsel for Pro Hac Vice Admission of Timothy J. Paris for Plaintiffs DI 5.
6 Oct. 18, 2006 Motion and Consent of Sponsoring Local Counsel for Pro Hac Vice Admission of Scot C. Stirling for Plaintiffs DI 6.
7 Oct. 24, 2006 Notice of Appearance of Counsel by Lee Andelin for Plaintiffs DI 8.
8 Oct. 24, 2006 Orders Granting Motion for Pro Hac Vice Admissions of Scot Stirling, L. Richard Williams, Leo Beus, Adam Anderson and Timothy Paris on behalf of Plaintiffs DI 10.
9 Oct. 25, 2006 Motion and Consent of Sponsoring Local Counsel for Pro Hac Vice Admission of Stephen M. Craig for Plaintiffs DI 9.
10 Oct. 30, 2006 Order Granting Motion for Pro Hac Vice Admission of Stephen M. Craig for Plaintiffs DI 12.
11 Nov. 13, 2006 Joint Motion and Stipulation for Order Extending Defendants' Time to Respond to the Complaint DI 17.
12 Nov. 14, 2006 Order granting Joint Motion and Stipulation for Order Extending Defendants' Time to Respond to the Complaint DI 18.
13 Nov. 14, 2006 Docket Entry Updating Answer Deadlines.
14 Nov. 16, 2006 Motion and Consent of Local Counsel for Pro Hac Vice Admission of Lisa A. Schneider for Defendants DI 19.
15 Nov. 16, 2006 Motion and Consent of Local Counsel for Pro Hac Vice Admission of Charles W. Douglas for Defendants DI 20.
16 Nov. 16, 2006 Motion and Consent of Local Counsel for Pro Hac Vice Admission of Todd L. Krause for Defendants DI 21.

17 Nov. 16, 2006 Motion and Consent of Local Counsel for Pro Hac Vice Admission of Neil H. Wyland for Defendants DI 22.
18 Nov. 16, 2006 Motion and Consent of Local Counsel for Pro Hac Vice Admission of Richard F. O'Malley, Jr. for Defendants DI 23.
19 Nov. 20, 2006 Notice of Appearance of Counsel by George M. Haley for Defendants DI 24.
20 Nov. 28, 2006 Order Granting Motion for Pro Hac Vice Admission of Charles W. Douglas for Defendants DI 25.
21 Nov. 28, 2006 Order Granting Motion for Pro Hac Vice Admission of Todd L. Krause for Defendants DI 26.
22 Nov. 28, 2006 Order Granting Motion for Pro Hac Vice Admission of Richard F. O'Malley, Jr. For Defendants DI 27.
23 Nov. 28, 2006 Order Granting Motion for Pro Hac Vice Admission of Lisa A. Schneider for Defendants DI 28.
24 Nov. 28, 2006 Order Granting Motion for Pro Hac Vice Admission of Neil H. Wyland for Defendants DI 29.
25 Dec. 13, 2006 Defendants Pfizer Inc., G.D. Searle LLC and Pharmacia Corporation's Answers to Complaint DI 30.
26 Dec. 26, 2006 Notice of Alternative Dispute Resolution Program DI 31.
27 Jan. 26, 2007 Notice of Service of Plaintiffs' Initial Rule 26(a)(1) Disclosure Statement to Defendants DI 32.
28 Jan. 26, 2007 Certificate of Service of Defendants' Initial Disclosures to Plaintiffs DI 33.
29 Feb. 5, 2007 Attorneys' Planning Meeting Report DI 34.
30 Feb. 9, 2007 Motion and Consent of Sponsoring Local Counsel for Pro Hac Vice Admission of Keith C. Ricker for Plaintiffs DI 35.
31 Feb. 13, 2007 Notice of Service of Plaintiffs' Response to Defendants' First Request for Production of Documents and First Set of Interrogatories DI 36.
32 Feb. 20, 2007 Order Granting Motion for Pro Hac Vice Admission of Keith C. Ricker for Plaintiffs DI 37.
33 Mar. 8, 2007 Notice of Appearance by Victoria Romney for Plaintiffs DI 38.
34 May 3, 2007 Notice of Service of Plaintiffs' Notice of Subpoenas for Production of Documents and Things DI 39.
35 May 4, 2007 Notice of Service of Plaintiffs' First Set of Interrogatories to Defendant Pfizer, Inc. DI 40.
36 May 11, 2007 Docket entry regarding Notice of Initial Pretrial Conference regarding Attorneys Planning Meeting Report and Proposed Scheduling Order DI 41.
37 Jun. 5, 2007 Stipulated Motion for Protective Order by Defendant Pfizer; Proposed Protective Order with Exhibit A—Declaration and Agreement to Bound DI 42.
38 Jun. 7, 2007 Protective Order (executed) DI 43.
39 Jun. 29, 2007 Docket Entry regarding Notice Reminder of Attorneys Planning Meeting Report and Initial Pretrial Conference DI 44.
40 Jul. 3, 2007 Docket Entry regarding Notice of Hearing—The Court Vacates Initial Pretrial Conference DI 45.
41 Jul. 9, 2007 Lodged Letter to Judge Kimball from Stephen Craig regarding Attorneys Planning Meeting Report and Proposed Scheduling Order DI 46.
42 Jul. 25, 2007 Notice of Service of Plaintiffs' Request for Admission to Defendant Pfizer, Inc. DI 47.
43 Jul. 30, 2007 Scheduling Order DI 48.
44 Oct. 11, 2007 Notice of Service of Plaintiffs' Subpoena for Production of Documents and Things served upon Teva Pharmaceuticals USA, Inc. DI 49.
45 Oct. 12, 2007 Notice of Service of Plaintiffs' Subpoena for Production of Documents and Things served upon University of Connecticut and the University of California, Los Angeles DI 50.
46 Oct. 29, 2007 Notice of Service of Plaintiffs' Subpoena for Production of Documents and Things served upon Dr. Harvey Herschman and Dr. Timothy Hla DI 51.
47 Oct. 31, 2007 Notice of Service of Plaintiffs' Subpoena for Production of Documents and Things served upon American Red Cross DI 52.
48 Nov. 8, 2007 Stipulation to Amend Protective Order DI 53.
49 Nov. 8, 2007 Notice of Service of Plaintiffs' Subpoena for Production of Documents and Things served upon the Monsanto Company DI 54.
50 Nov. 9, 2007 Order Regarding Stipulation to Amend Protective Order—granting Stipulation to amend paragraph 4(b) (3) of the Protective Order and to substitute S. Craig for E. Davis DI 55.
51 Nov. 12, 2007 Certificate of Service of Defendants' Notice of Taking Video Deposition of Michael Orme DI 56.
52 Nov. 27, 2007 Notice of Service of Defendants' Notice of Subpoena for Production of Documents and Things served upon Merck & Co., Inc./Merck Sharp & Dohme Limited DI 57.
53 Jan. 10, 2008 Plaintiffs' Motion to Compel Immediate Production of Documents DI 58.
54 Jan. 10, 2008 Plaintiffs' Memorandum in Support of Motion to Compel Immediate Production of Documents 59.
55 Jan. 11, 2008 Notice of Service of Plaintiffs' Second Set of Interrogatories to Defendant DI 60.
56 Jan. 14, 2008 Docket Entry regarding Order Referring Case to Magistrate Judge Paul M. Warner DI 61.
57 Jan. 15, 2008 Order of Recusal for Judge Paul W. Warner—Case reassigned to Judge Brooke C. Wells DI 63.
58 Jan. 18, 2008 Plaintiffs' Supplemental Memorandum in Support of Motion to Compel Immediate Production of Documents with Exhibits A & B DI 64.
59 Jan. 22, 2008 Plaintiffs' Motion to Compel Re-Designation of Documents DI 65.
60 Jan. 22, 2008 Plaintiffs' Memorandum in Support Motion to Compel Re-Designation of Documents DI 66.
61 Jan. 22, 2008 Notice of Conventional Filing of Exhibits Supporting Plaintiffs' Motion to Compel Re-Designation of Documents DI 67.
62 Jan. 25, 2008 Defendants' Memorandum in Opposition to Motion to Compel Immediate Production of Documents DI 69.
63 Jan. 25, 2008 Notice of Conventional Filing of Exhibits Supporting Defendants' Memorandum in Opposition to Motion to Compel Immediate Production of Documents DI 70.
64 Jan. 29, 2008 Certificate of Service of Plaintiffs' Fourth Request for Production of Documents DI 72.
65 Feb. 6, 2008 Defendants' Memorandum in Opposition to Motion to Compel Re-Designation of Documents with Exhibits A-E DI 73.
66 Feb. 8, 2008 Plaintiffs' Reply Memorandum/Reply to Response to Motion to Compel Immediate Production of Documents DI 74.
67 Feb. 8, 2008 Notice of Conventional Filing of Exhibits to Plaintiffs' Reply Memorandum/Reply to Response to Motion to Compel Immediate Production of Documents DI 75.
68 Feb. 11, 2008 Docket Entry regarding Notice of Hearing on Motion to Compel Immediate Production of Documents and Motion to Compel Re-Designation of Documents DI 76.
69 Feb. 11, 2008 Notice of Service of Defendants' Second Request for Production of Documents and Things to Plaintiffs DI 77.
70 Feb. 12, 2008 Notice of Service of Plaintiffs' Notice of Subpoenas for Production of Documents and Things to Chandler Chicco Agency, David L. DeWitt and Michigan State University DI 78.
71 Feb. 13, 2008 Notice of Service of Plaintiffs' 30(b)(6) Notice of Deposition to Defendants DI 80.
72 Feb. 15, 2008 Certificate of Service of Defendants' Response to Plaintiffs' Second Set of Interrogatories DI 81.
Mar. 17, 2008 Plaintiffs' Response to Defendants' Second Request for Production of Documents.
Mar. 21, 2008 Dr. Peter Isakson's Objections to Plaintiffs' Mar. 7, 2008 Third-Party Subpoena.
Mar. 31, 2008 Defendant Pfizer Inc.'s Response to Plaintiffs' Third Set of Interrogatories.
Apr. 22, 2008 Defendants' First Set of Requests for Admission to Plaintiff Brigham Young University.
Apr. 22, 2008 Defendants' First Set of Requests for Admission to Plaintiff Dr. Daniel L. Simmons.
Apr. 22, 2008 Exhibits to Defendants' First Set of Requests for Admission to Plaintiffs with Non-Confidential Exhibits 1-29.
73 Feb. 19, 2008 Docket Entry regarding Amended Notice of Hearing on Motion to Compel Immediate Production of Documents and Motion to Compel Re-Designation of Documents DI 82.
74 Feb. 19, 2008 Plaintiffs' Reply to Response to Motion to Compel Re-Designation of Documents DI 83.
75 Feb. 22, 2008 Certificate of Service of Defendants' Responses and Objections to Plaintiffs' 30(b)(6) Notice of Deposition DI 84.

76 Feb. 22, 2008 Defendants' Motion to Strike Reply Memorandum/Reply to Response to Motion to Compel Immediate Production of Documents DI 85.
77 Feb. 22, 2008 Defendants' Memorandum in Support of Motion to Strike Reply Memorandum/Reply to Response to Motion to Compel Immediate Production of Documents with Exhibits A-H DI 86.
78 Feb. 22, 2008 Certificate of Service of Defendants' Notice of Subpoenas for Production of Documents and Things to Fish & Richardson P.C. And Harvard University DI 87.
79 Feb. 25, 2008 Notice of Service of Plaintiffs' Notice of Subpoenas for Production of Documents and Things J. Masferrer, K. Seibert, A. Raz & P. Isakson DI 88.
80 Feb. 27, 2008 Notice of Service of Plaintiffs' Third Set of Interrogatories to Defendants DI 89.
81 Mar. 4, 2008 Certificate of Service of Defendants' Response to Plaintiffs'Fourth Request for Production of Documents DI 90.
82 Mar. 7, 2008 Docket Entry regarding Amended Notice of Hearing on Motion to Compel Immediate Production of Documents, Defendants' Motion to Strike Reply Memorandum/Reply to Response to Motion to Compel Immediate Production of Documents, and Motion to Compel Re-Designation of Documents DI 91.
83 Mar. 12, 2008 Notice of Appearance by Samuel C. Straight for Plaintiffs DI 93.
84 Mar. 12, 2008 Notice of Appearance by Arthur B. Berger for Plaintiffs DI 94.
85 Mar. 12, 2008 Notice of Appearance by M Bettilyon for Plaintiffs DI 95.
86 Mar. 12, 2008 Notice of Appearance by James S. Jardine for Plaintiffs DI 96.
87 Mar. 12, 2008 Notice of Appearance by Rick B. Hoggard for Plaintiffs DI 97.
88 Mar. 13, 2008 Plaintiffs' Memorandum in Response to Defendants' Motion to Strike Reply Memorandum/Reply to Response to Motion to Compel Immediate Production of Documents with Exhibits A-I DI 98.
89 Mar. 13, 2008 Notice of Conventional Filing of Plaintiffs' Memorandum in Response to Defendants' Motion to Strike and Exhibit F Supporting Plaintiffs' Memorandum in Response to Defendants' Motion to Strike DI 99.
90 Mar. 19, 2008 Docket Entry regarding Minute Order granting Motion to Compel and adopting proposed order in part; denying Motion to Strike, granting request for modification of protective order, and finding as moot Motion to Compel DI 101.
91 Mar. 19, 2008 Hearing Transcripts Regarding Motion to Compel and Court's Ruling.
92 Mar. 24, 2008 Defendants' Objections to Plaintiffs' Proposed Orders with Exhibits A-D 102.
93 Mar. 25, 2008 Plaintiffs' Response to Defendants' Objections to Plaintiffs' Proposed Orders with Exhibits A-C DI 103.
94 Mar. 25, 2008 Order Denying Defendants' Motion to Strike Plaintiffs' Reply Memorandum Supporting Its Motion to Compel and Following oral order of Mar. 19, 2008 DI 104.
95 Mar. 26, 2008 Order Deeming Moot Plaintiffs' Motion for Re-Designation with Modifications DI 105.
96 Mar. 26, 2008 Order Granting Plaintiffs' Motion to Compel Immediate Production of Documents DI 106.
97 Apr. 18, 2008 Plaintiffs' Motion to Compel Amended Interrogatory Responses and to Deem Admitted Plaintiffs' Request for Admission DI 107.
98 Apr. 18, 2008 Plaintiffs' Memorandum in Support of Motion to Compel Amended Interrogatory Responses and to Deem Admitted Plaintiffs' Request for Admission DI 108.
99 Apr. 18, 2008 Notice of Conventional Filing of Exhibits Regarding Plaintiffs' Memorandum in Support of Motion to Compel Amended Interrogatory Responses and to Deem Admitted Plaintiffs' Request for Admission DI 109.
100 May 5, 2008 Defendants' Memorandum in Opposition to Plaintiffs' Motion to Compel Amended Interrogatory Responses and to Deem Admitted Plaintiffs' Request for Admission DI 111.
101 May 5, 2008 Index of Exhibits to Defendants' Memorandum in Opposition to Plaintiffs' Motion to Compel Amended Interrogatory Responses and to Deem Admitted Plaintiffs' Request for Admission with Exhibits A-F.
102 May 19, 2008 Plaintiffs' Reply to Response to Motion to Compel Amended Interrogatory Responses and to Deem Admitted Plaintiffs' Request for Admission DI 112.
103 May 27, 2008 Defendants' Motion for Extension of Time to Comply with the Court's Mar. 26, 2008 Order Granting Plaintiffs' Motion to Compel Immediate Production of Documents for Defendant DI 113.
104 May 27, 2008 Defendants' Memorandum in Support of Motion for Extension of Time to Comply with the Court's Mar. 26, 2008 Order Granting Plaintiffs' Motion to Compel Immediate Production of Documents for Defendant DI 114.
105 May 27, 2008 Defendants' Motion for Relief from Order Compelling Discovery with Exhibit A DI 115.
106 May 27, 2008 Defendants' Memorandum in Support of Motion for Relief Discovery from Order Compelling Discovery with Exhibits A-J DI DI 116.
107 May 27, 2008 Defendants' Certification Concerning Discovery Efforts with Exhibits A-KK DI 117.
108 Jun. 5, 2008 Defendants' Motion to Compel Plaintiffs to Supplement Responses to Defendants' Interrogatory No. 8 and for Protective Order DI 118.
109 Jun. 5, 2008 Defendants' Memorandum in Support of Motion to Compel Plaintiffs to Supplement Responses to Defendants' Interrogatory No. 8 and for Protective Order with Exhibits A-J DI 119.
110 Jun. 5, 2008 Defendants' Motion to Compel the Depositions of Weilin Xie, Jeffrey Chipman, and Gary Evett 120.
111 Jun. 5, 2008 Defendants' Memorandum in Support of Motion to Compel the Depositions of Weilin Xie, Jeffrey Chipman, and Gary Evett with Exhibits A-H DI 121.
112 Jun. 5, 2008 Plaintiff' Notice of Removing Counsel from Service List filed by James S. Jardine. Attorney James S Jardine will no longer receive notice from the court in this including final judgment. DI 122.
113 Jun. 13, 2008 Docket Entry regarding Amended Notice of Hearing regarding Defendants' Motion tor extension of Time to Comply with the Court's Mar. 26, 2008 Order, Motion to Compel Amended Interrogatory Responses and to Deem Admitted BYU's Request for Admission, Defendants' Motion for Relief from Order Compelling Discovery, Defendants' Motion to Compel Plaintiffs to Supplement Responses to Defendants' Interrogatory No. 8 and for Protective Order, and Defendants' Motion to Compel the Depositions of Weilin Xie, Jeffrey Chipman and Gary Evett DI.
114 Jun. 16, 2008 Docket Text Order regarding due date for memoranda regarding compliance or noncompliance with the Court's Mar. 26, 2008 Order DI 124.
115 Jun. 17, 2008 Plaintiffs' Memorandum in Opposition to Motion for Extension of Time to Comply with the Court's Mar. 26, 2008 Order Granting BYU's Motion to Compel Immediate Production of Documents with Exhibits A-R DI 125.
116 Jun. 17, 2008 Plaintiffs' Memorandum in Opposition to Motion for Relief From Order Compelling Discovery DI 126.
117 Jun. 24, 2008 Plaintiffs' Memorandum in Opposition to Defendants' Motion to Compel Plaintiffs to Supplement Responses to Defendants' Interrogatory No. 8 and for Protective Order DI 127.
118 Jun. 24, 2008 Plaintiffs' Notice of Conventional Filing of Opposition to Defendants' Motion to Compel the Depositions of Weilin Xie, Jeffrey Chipman, and Gary Evett DI 128.
119 Jun. 30, 2008 Defendants' Reply to Response to Motion for Extension of Time to Comply with the Court's Mar. 26, 2008 Order Granting Plaintiffs' Motion to Compel Immediate Production of Documents DI 130.
120 Jun. 30, 2008 Defendants' Reply to Response to Motion for Relief from Order Compelling Discovery with Exhibits A-J DI 131.
121 Jul. 7, 2008 Defendants' Reply to Response to Motion to Compel the Depositions of Weilin Xie, Jeffrey Chipman, and Gary Evett with Exhibits I-J DI 132.
122 Jul. 7, 2008 Defendants' Reply to Response to Motion to Compel Plaintiffs to Supplement Responses to Defendants' Interrogatory No. 8 and for Protective Order DI 133.
123 Jul. 18, 2008 Notice of Conventional Filing of Defendants' Supplemental Certification Concerning Discovery Efforts and Defendants' Exhibits Supporting Supplemental Certification Concerning Discovery Efforts DI 134.

124 Jul. 18, 2008 Defendants' Supplemental Certification Concerning Discovery Efforts DI 137 (notice of filing).
125 Jul. 18, 2008 Exhibits Supporting Defendants' Supplemental Certification Concerning Discovery Efforts with Non-Confidential Exhibits in the Range 1-84 DI 138.
126 Jul. 18, 2008 Redacted Version of Plaintiffs' Memorandum for Jul. 29, 2008 Hearing with Redacted Exhibits 1-57 D 136.
127 Jul. 18, 2008 Notice of Conventional Filing of Plaintiffs' Memorandum for Jul. 29, 2008 Hearing and Exhibits DI 135.
128 Jul. 18, 2008 Conventionally Filed Non-Confidential Exhibits to Plaintiffs' Memorandum for Jul. 29, 2008 Hearing in the Range 1-57.
129 Jul. 28, 2008 Notice of Conventional Filing of Defendants' Response to Plaintiffs' Memorandum for Jul. 29, 2008 Hearing DI 142.
130 Aug. 5, 2008 Docket Entry regarding Minute Order as to hearing held on Jul. 29, 2008 and granting in part denying in part Motion to Compel Amended Interrogatory Responses and to Deem Admitted BYU's Request for Admission DI 143.
131 Aug. 7, 2008 Transcript of Proceedings held on Jul. 29, 2008—Transcript of Motions Hearing before Judge Brooke C. Wells DI 144.
132 Aug. 12, 2008 Plaintiffs' Proposed Discovery Order Regarding Jul. 29, 2008 Hearing.
133 Aug. 12, 2008 [Proposed] Finding of Facts and Conclusions of Law Regarding Pfizer's Document Production and BYU's Request for Sanctions.
134 Aug. 12, 2008 Notice of Conventional Filing of Defendants' Second Supplemental Certification Concerning Discovery Efforts DI 146.
136 Aug. 15, 2008 Notice of Conventional Filing of Plaintiffs' Response to Defendants' Second Supplemental Certification Concerning Discovery Efforts and Exhibits Thereto DI 148.
137 Aug. 19, 2008 Defendants' Notice of Conventional Filing of Defendants' Reply to Response to Second Supplemental Certification Concerning Discovery Efforts DI 150.
138 Aug. 21, 2008 Order Denying Defendants' Motion to Compel Depositions and Denying in Part and Granting in Part Defendants' Motion for Relief from Order Compelling Discovery. Follows oral order of Aug. 5, 2008 DI 152.
139 Aug. 21, 2008 Order Granting in Part and Denying in Part Defendants' Motion to Compel Plaintiffs to Supplement Responses to Defendants' Interrogatory No. 8 and for Protective Order. Follows oral order of Aug. 5, 2008 DI153.
140 Aug. 21, 2008 Order Granting in Part and Denying in Part Plaintiffs' Motion to Compel Amended Interrogatory Responses and to Deem Admitted BYU's Request for Admission. Follows oral order of Aug. 5, 2008 DI 154.
141 Sep. 8, 2008 Lodged Letter by W. Alper to Judge Wells DI 155.
142 Oct. 9, 2008 Plaintiffs' Stipulated Motion to Amend/Correct Scheduling Order DI 156.
143 Oct. 15, 2008 Defendants' Third Supplemental Certification Concerning Discovery Efforts DI 157.
144 Oct. 22, 2008 Plaintiffs' Preliminary Response to Defendants' Third Supplemental Certification Concerning Discovery Efforts DI 158.
145 Oct. 23, 2008 Amended Scheduling Order regarding Amended Pleadings, Joinder of Parties, Fact Discovery, Expert Discovery, Motions, Final Pretrial Conference, and Jury Trial DI 159.
146 Nov. 12, 2008 Plaintiffs' Supplemental Preliminary Response to Defendants' Third Supplemental Certification Concerning Discovery Efforts DI 160.
147 Nov. 13, 2008 Defendants' Motion to Compel Production of Documents DI 161.
148 Nov. 13, 2008 Defendants' Memorandum in Support of Motion to Compel Production of Documents DI 162.
149 Nov. 13, 2008 Notice of Conventional Filing of Defendants' Exhibits 3 and 16-17 to Defendants' Motion to Compel Production of Documents DI 163.
150 Nov. 13, 2008 Exhibits 1-2, 4-15 and 18 to Defendants' Motion to Compel Production of Documents DI 164.
151 Dec. 4, 2008 Plaintiffs' Second Supplemental Preliminary Response to Defendants' Third Supplemental Certification Concerning Discovery Efforts D 166.
152 Dec. 10, 2008 Plaintiffs' Response to Defendants' Motion to Compel Production of Documents with Non-Confidential Exhibits A-B (Redacted Version) DI 167.
153 Dec. 10, 2008 Notice of Conventional Filing of Exhibit Supporting Plaintiffs' Response to'Defendants' Motion to Compel Production of Documents DI 168.
154 Dec. 15, 2008 Plaintiffs' Third Supplemental Preliminary Response to Defendants' Third Supplemental Certification Concerning Discovery Efforts DI 170.
155 Dec. 22, 2008 Defendants' Reply Brief in Support of Motion to Compel Production of Documents Exhibits 1-4 DI 171.
156 Jan. 7, 2008 Defendants' Motion for Leave From and Modification to the Protective Order DI 172.
157 Jan. 7, 2008 Defendants' Memorandum in Support of Motion for Leave From and Modification to the Protective Order DI 173.
158 Jan. 7, 2008 Notice of Conventional Filing Exhibits A-S and Appendices 1-6 to Defendants' Memorandum in Support of Motion for Leave From and Modification to the Protective Order DI 174.
159 Jan. 8, 2009 Notice of Conventional Filing Exhibits A-S and Appendices 1-6 to Defendants' Memorandum in Support of Motion for Leave From and Modification to the Protective Order DI 175.
160 Jan. 8, 2008 Docket Entry regarding Notice of Status Conference Hearing regarding Defendants' Motion for Extension of Time to Comply with the Court's Mar. 26, 2008 Order Granting BYU's Motion to Compel Immediate Production of Documents DI 176.
161 Jan. 8, 2008 Docket Entry regarding Notice of Hearing on Defendants' Motion to Compel Production of Documents DI 177.
Jan. 7, 2009 Defendant Pfizer's Motion for Leave from Protective Order DI 172.
Defendant Pfizer's Memorandum in support of Motion for Leave from Protective Order DI 173.
Jan. 16, 2009 Notice of Taking Video Deposition of Lynn Astle, Ph.D.
Feb. 2009 Plaintiffs' Proposed, Continued 30(b)(6) Notice of Deposition to Pfizer.
Feb. 4, 2009 Defendants' Amended Notice of Taking Video Deposition of Jeffrey G. Chipman, M.D.
Feb. 4, 2009 Defendants' Amended Notice of Taking Video Deposition of Gary Evett, Ph.D.
Feb. 12, 2009 Plaintiffs' Sixth Request for Production of Documents.
Mar. 11, 2009 Defendants' Amended Notice of Taking Video Deposition of Weilin Xie, Ph.D.
Mar. 16, 2009 Defendant Pfizer Inc.'s Response to Plaintiffs' Sixth Request for Production of Documents.
Mar. 17, 2009 Defendants' Notice of Taking Video Deposition of Dr. Daniel L. Simmons.
May 20, 2009 Plaintiffs' Notice of Taking Video Deposition of Curtis Mathis.
May 20, 2009 Plaintiffs' Notice of Taking Video Deposition of Thomas Warren.
May 28, 2009 Plaintiffs' Notice of Tour of Facility and of Taking Video Deposition of Judy Lewis.
Jan. 14, 2009 Plaintiffs' BYU and Dr. Simmons' Response re Pfizer's Third Supplemental Certification Regarding Discovery Efforts and Memorandum in Support of Motion for Discovery Sanctions Redacted Version (DI 178).
Jan. 14, 2009 BYU and Dr. Simmon's Motion for Discovery Sanctions (DI179).
Jan. 14, 2009 Notice of Conventional Filing of Under Seal Exhibits 2, 6-8, 17-19, 35, 48-51, 59-62, 69-72, 74-75, 77-81, 83-87, 89, 91-94, 100, 101, 107-108, 110, 111, 117-119 and 121 BYU and Dr. Simmons's Response to Pfizer's Third Supplemental Certification Regarding Discovery Efforts and Memorandum in Support of Motion for Discovery Sanctions for Plaintiffs re 178) (DI 180).
Jan. 14, 2009 Exhibits 1, 3-5, 9-16, 20-34, 37-47, 52-58, 63-64, 66-68, 73, 76, 82, 88, 90, 95-99, 102-106, 109, 112-116, 120, 122-131 re 178 Response to Pfizer's Third Supplemental Certification Regarding Discovery Efforts and Memorandum in Support of Motion for Discovery Sanctions filed by Plaintiffs (DI 181).
Jan. 22, 2009 Order Continuing Hearing Set for Jan. 29, 2009 and Amended Notice of Hearing. Status Conference set for Feb. 27, 2009 01:30 PM in Room 436 before Magistrate Judge Brooke C. Wells. Signed by Magistrate Judge Brooke C. Wells on Jan. 22, 2009 (DI 182).

Jan. 22, 2009 Amended Notice of Hearing on Motion re: 113 Defendant's Motion for Extension of Time to comply with the Court's Mar. 26, 2008 Order Granting BYU's Motion to Compel Immediate Production of Documents, 179 Motion for Sanctions (Discovery): (Notice generated by chambers) Motion Hearing set for Feb. 27, 2009 01:30 PM in Room 436 before Magistrate Judge Brooke C. Wells (DI 183).
Jan. 26, 2009 Stipulated Motion for Extension of Times to File Response/Reply as to 172 Motion to Amend/Correct for Leave From and Modification to the Protective Order for Plaintiff (Attachments: Text of Proposed Order) (DI 184).
Jan. 26, 2009 Order granting 184 Motion for Extension of Time to File Response/Reply re 172 Motion to Amend/Correct for Leave From and Modification to the Protective Order: Response due by Feb. 9, 2009. Signed by Magistrate Judge Brooke C. Wells on Jan. 26, 2009 (DI 185).
Jan. 28, 2009 Motion for Extension of Time to File Response/Reply as to 179 Motion for Discovery Sanctions (Exhibits A-B) (DI 186).
Jan. 30, 2009 Minute Order. Proceedings held before Magistrate Judge Brooke C. Wells: Motion Hearing held on Jan. 30, 2009 as to 161 Motion to Compel Production of Documents filed by Defendants and 186 Motion for Extension of Time to File Response/Reply as to 179 Motion for Sanctions (Discovery) for Pfizer. The Court hears oral argument taking under advisement 161 Motion to Compel—journals will be received by the Court for in camera review; granting 186 Motion for Extension of Time to File Response/Reply re 179 Motion for Sanctions (Discovery). Defendant will have until Feb. 16, 2009 to Reply to sanctions motion. (DI 187).
Feb. 3, 2009 Notice of Filing of Official Transcript of Proceedings held on Jan. 30, 2009 before Judge Brooke C. Wells. Court Reporter/Transcriber Karen Murakami, CSR, RPR, Telephone No. 801-328-4800. (DI 188).
Feb. 9, 2009 Notice of Errata by Brigham Young University, Daniel L. Simmons re 178 (Amended Exhibit List, Exhibits 10,13, 32, 33, 96, 104, 112, 127A, 129) (DI 191).
Feb. 9, 2009 Notice of Conventional Filing of Under Seal Exhibit 89 filed by Plaintiffs Brigham Young University, Daniel L. Simmons re 191 (DI 192).
Feb. 9, 2009 Notice of Report to Court by Brigham Young University, Daniel L. Simmons (Exhibits 1-5) (DI 193).
Feb. 9, 2009 Motion for Suspension of Reissue Proceedings filed by Plaintiffs Brigham Young University, Daniel L. Simmons. Motions referred to Brooke C. Wells. (DI 194).
Feb. 9, 2009 Memorandum in Support re 194 Motion for Suspension of Reissue Proceedings filed by Plaintiffs Brigham Young University, Daniel L. Simmons. (Exhibits 1-2) (DI195).
Feb. 9, 2009 Memorandum in Opposition re 172 Motion to Amend/Correct for Leave From and Modification to the Protective Order filed by Plaintiffs Brigham Young University, Daniel L. Simmons. (Exhibits 1-2) (DI 196).
Feb. 13, 2009 Motion Ex Parte Motion to File Overlength Memorandum in Opposition to Plaintiff's Motion for Discovery Sanctions filed by Defendant Pfizer. (Attachments: # 1 Text of Proposed Order [Proposed] Order Regarding Pfizer's Ex Parte Motion to File Overlength Memorandum in Opposition to Plaintiffs' Motion for Discovery Sanctions) Motions referred to Brooke C. Wells. (DI 198).
Feb. 16, 2009 Notice of Conventional Filing Under Seal of Pfizer's Memorandum in Opposition to Plaintiffs' Motion for Discovery Sanctions and Exhibits 1-105 filed by Defendant Pfizer (DI 199).
Feb. 17, 2009 Order granting 198 Ex Parte Motion to File Overlength Memorandum in Opposition to Plaintiff's Motion for Discovery Sanctions. Signed by Magistrate Judge Brooke C. Wells on Feb. 17, 2009. (DI 202).
Feb. 24, 2009 Reply to Response to Motion re 172 Motion to Amend/Correct for Leave From and Modification to the Protective Order filed by Defendant Pfizer (DI 203).
Feb. 24, 2009 Memorandum in Opposition re 194 Motion for Suspension of Reissue Proceedings filed by Defendant Pfizer (DI 204).
Feb. 24, 2009 Notice of Conventional Filing Under Seal of Reply Memorandum and Exhibits in Support of BYU and Dr. Simmons's Motion for Discovery Sanctions filed by Plaintiffs Brigham Young University, Daniel L. Simmons re 179 (DI 205).
Feb. 26, 2009 Amended Notice of Hearing on Motion re: 179 Motion for Sanctions (Discovery) (Notice generated by chambers) Motion Hearing set for Mar. 20, 2009 09:30 AM in Room 230 before Magistrate Judge Brooke C. Wells. (DI 208).
Mar. 9, 2009 Notice of Compliance with Court Order by Brigham Young University, Daniel L. Simmons (DI 209).
Mar. 9, 2009 Reply to Response to Motion re 194 Motion for Suspension of Reissue Proceedings filed by Plaintiffs Brigham Young University, Daniel L. Simmons. (DI 210).
Mar. 9, 2009 Second Amended Notice of Hearing on Motion re: 179 Motion for Sanctions (Discovery) (Notice generated by BCW Chambers) Motion Hearing previously set for Mar. 20, 2009 @ 9:30 a.m. has been Reset for Apr. 7, 2009 at 01:30 PM in Room 220 before Magistrate Judge Brooke C. Wells. (jwd) (Entered: Mar. 9, 2009) (DI 211).
Mar. 12, 2009 Motions No Longer Referred: 194 Motion for Suspension of Reissue Proceedings, 172 Motion to Amend/Correct for Leave From and Modification to the Protective Order because these matters will be heard by Judge Kimball.
Mar. 16, 2009 Motion for Protective Order Regarding Plaintiffs' Sixth Request for Production and Proposed Rule 30(b)(6) Deposition Topics filed by Defendant Pfizer. (Attachments: Text of Proposed Order) Motions referred to Brooke C. Wells ( DI 212).
Mar. 16, 2009 Memorandum in Support re 212 Motion for Protective Order Regarding Plaintiffs' Sixth Request for Production and Proposed Rule 30(b)(6) Deposition Topics Motion for Protective Order Regarding Plaintiffs' Sixth Request for Production and Proposed Rule 30(b)(6) Deposition Topics filed by Defendant Pfizer (Exhibits A-L) (DI 213).
Mar. 20, 2009 Motion for Partial Summary Judgment Regarding Integration of the Research Agreement, Dated Aug. 1, 1991 filed by Defendant Pfizer. (DI 214).
Mar. 20, 2009 Memorandum in Support re 214 Motion for Partial Summary Judgment Regarding Integration of the Research Agreement, Dated Aug. 1, 1991 filed by Defendant Pfizer. (Exhibits 1, 3-11) (DI 215).
Mar. 20, 2009 Notice of Conventional Filing Under Seal of Exhibit No. 2 to Defendants' Memorandum in Support of Motion for Partial Summary Judgment Regarding Integration of the Research Agreement, Dated Aug. 1, 1991 filed by Defendant Pfizer (DI 216).
Mar. 26, 2009 Plaintiffs Motion to Amend/Correct 159 Scheduling Order, filed by Plaintiffs Brigham Young University, Daniel L. Simmons. (Exhibits A-B) Motions referred to Brooke C. Wells. (DI 218).
Apr. 3, 2009 Reply to Response to Motion re 179 Motion for Sanctions (Discovery) (Supplemental) filed by Plaintiffs Brigham Young University, Daniel L. Simmons. (Exhibits 1-3) (DI 219).
Apr. 3, 2009 Response to Motion re 212 Motion for Protective Order Regarding Plaintiffs' Sixth Request for Production and Proposed Rule 30(b)(6) Deposition Topics Motion for Protective Order Regarding Plaintiffs' Sixth Request for Production and Proposed Rule 30(b)(6) Deposition Topics (Redacted) filed by Plaintiffs Brigham Young University, Daniel L. Simmons. (Exhibits 1-12) Redacted Version (DI 220).
Apr. 7, 2009 Minute Entry for proceedings held before Magistrate Judge Brooke C. Wells: Motion Hearing held on Apr. 7, 2009 re 179 Motion for Sanctions (Discovery) filed by Daniel L. Simmons, Brigham Young University. Counsel for both parties present. Court hears arguments. Matter is continued to Apr. 8, 2009 at 9:30 a.m. Court is adjourned. (DI 221).
Apr. 8, 2009 Minute Entry for proceedings held before Magistrate Judge Brooke C. Wells: Motion Hearing held on Apr. 8, 2009 re 179 Motion for Sanctions (Discovery) filed by Daniel L. Simmons, Brigham Young University. Discussion heard. Court takes motion under advisement. Court ordered that by May 11, 2009, the parties shall file the following in electronic format: Plaintiff shall file affidavits regarding attorney's fees ; Defendant shall complete all remaining discovery ; Defendant shall file affidavits by those attorney's that have participated in the discovery process ; Both parties shall file proposed findings of fact. Court Reporter: Kelly Hicken. (Time Start: 9:30, Time End: 11:15, Room 220.) (DI 222).
Apr. 7, 2009 and Apr. 8, 2009 Hearing Transcripts re: Motion for Discovery Sanctions.

Apr. 13, 2009 Memorandum in Opposition re 218 Plaintiff's Motion to Amend/Correct 159 Scheduling Order, filed by Defendant Pfizer (DI 223).
Apr. 17, 2009 Reply to Response to Motion re 212 Motion for Protective Order Regarding Plaintiffs' Sixth Request for Production and Proposed Rule 30(b)(6) Deposition Topics Motion for Protective Order Regarding Plaintiffs' Sixth Request for Production and Proposed Rule 30(b)(6) Deposition Topics filed by Defendant Pfizer. (Exhibit 1) (DI 224).
Apr. 20, 2009 Notice of Hearing on Motion re: 194 Motion for Suspension of Reissue Proceedings, 214 Motion for Partial Summary Judgment Regarding Integration of the Research Agreement, Dated Aug. 1, 1991 : (Notice generated by Kim Jones) Motion Hearing set for Jun. 5, 2009 09:30 AM in Room 220 before Judge Dale A. Kimball. Two hours have been set aside for the hearing. (kmj) (Entered: Apr. 20, 2009) (DI 225).
Apr. 23, 2009 Stipulated Motion for Extension of Time to File Response/Reply as to 214 Motion for Partial Summary Judgment Regarding Integration of the Research Agreement, Dated Aug. 1, 1991 filed by Plaintiff Brigham Young University. (Attachments: Text of Proposed Order) Motions referred to Brooke C. Wells. (DI 226).
Apr. 27, 2009 Order granting 226 Motion for Extension of Time to File Response/Reply re 214 Motion for Partial Summary Judgment Regarding Integration of the Research Agreement, Dated Aug. 1, 1991. Responses due by May 22, 2009. Signed by Judge Dale A. Kimball on Apr. 27, 2009. (DI 227).
Apr. 27, 2009 Reply to Response to Motion re 218 Plaintiff's Motion to Amend/Correct 159 Scheduling Order, filed by Plaintiffs Brigham Young University, Daniel L. Simmons. (Exhibit 1) (DI 228).
Apr. 27, 2009 Reset Deadline as to 194 Motion for Suspension of Reissue Proceedings, 172 Motion to Amend/Correct for Leave From and Modification to the Protective Order, and 214 Motion for Partial Summary Judgment Regarding Integration of the Research Agreement, Dated Aug. 1, 1991. Motion Hearing reset for Jun. 23, 2009 03:00 PM in Room 220 before Judge Dale A. Kimball. Docket Text Only.
May 8, 2009 Motion for Leave to File Motion to Allow in Camera Submission of Affidavits Regarding Discovery Efforts filed by Defendant Pfizer. Motions referred to Brooke C. Wells. (DI 229).
May 8, 2009 Memorandum in Support re 229 Motion for Leave to File Motion to Allow in Camera Submission of Affidavits Regarding Discovery Efforts filed by Defendant Pfizer. (Exhibit 1 and Text of Proposed Order) (DI 230).
May 11, 2009 Notice of Conventional Filing Under Seal of Summary of Affidavits Submitted for in Camera Review Regarding Discovery Efforts and [Proposed] Findings of Fact and Conclusions of Law Regarding BYU's Motion for Discovery Sanctions filed by Defendant Pfizer (DI 231).
May 11, 2009 Affidavit of Mark M. Bettilyon in Support of BYU's Application for Award of Attorneys' Fees and Costs filed by Plaintiffs Brigham Young University, Daniel L. Simmons. (Exhibits 1-8) (DI 232).
May 11, 2009 Affidavit of Leo R. Beus in Support BYU's Application for Award of Attorneys' Fees and Costs filed by Plaintiffs Brigham Young University, Daniel L. Simmons. (Exhibits 1-9) DI 233).
May 11, 2009 Proposed Findings of Fact and Conclusions of Law Brief filed by Plaintiffs Brigham Young University, Daniel L. Simmons. (Exhibit 1) Redacted Version ( DI 234).
May 15, 2009 BYU's Opposition to Pfizer's Motion to Allow in Camera Submission (Exhibit 1) Redacted Version (DI 238).
May 18, 2009 Notice of Hearing on Motion re: 218 Plaintiff's Motion to Amend/Correct 159 Scheduling Order, 212 Motion for Protective Order Re Plaintiffs' Sixth Request for Production and Proposed Rule 30(b)(6) Deposition Topics Motion for Protective Order Re Plaintiffs' Sixth Request for Production and Proposed Rule 30(b)(6) Deposition Topics : (Notice generated by chambers) Motion Hearing set for Jul. 22, 2009 09:30 AM before Magistrate Judge Brooke C. Wells. (DI 239).
May 20, 2009 Plaintiff's Expedited Motion to Preserve and Produce Evidence of COX-2 Related Documents as Described in J. Michael Warner's Affidavit (Redacted) ( DI 240).
May 20, 2009 Plaintiff's Memorandum in Support of Expedited Motion to Preserve and Produce Evidence of COX-2 Related Documents as Described in J. Michael Warner's Affidavit (Redacted) (Exhibits 1-7) (DI 241).
May 21, 2009 Notice of Hearing on Motion re: 218 Plaintiff's Motion to Amend/Correct 159 Scheduling Order ,, 240 Plaintiff's Motion to Compel Preserve and Produce Evidence, 212 Motion for Protective Order Regarding Plaintiffs' Sixth Request for Production and Proposed Rule 30(b)(6) Deposition Topics : (Notice generated by chambers)Motion Hearing set for Jul. 22, 2009 09:30 AM in Room 436 before Magistrate Judge Brooke C. Wells (DI 242).
May 26, 2009 Amended Notice of Hearing on Motion re: 218 Plaintiff's Motion to Amend/Correct 159 Scheduling Order, 212 Motion for Protective Order Regarding Plaintiffs' Sixth Request for Production and Proposed Rule 30(b)(6) Deposition Topics : (Notice generated by chambers) Motion Hearing set for Jul. 22, 2009 09:30 AM in Room 436 before Magistrate Judge Brooke C. Wells. Plaintiff's Motion to Preserve and Produce Evidence vacated and set for earlier date (Jun. 19, 2009) per Court's Order. (DI 244).
May 26, 2009 Notice of Conventional Filing Under Seal of Reply Memorandum in Support of Motion to Allow in Camera Submission of Affidavits Regarding Discovery Efforts filed by Defendant Pfizer (DI 245).
May 26, 2009 Notice of Hearing on Motion re: 240 Plaintiff's Motion to Compel Preserve and Produce Evidence : (Notice generated by chambers) Motion Hearing set for Jun. 18, 2009 01:30 PM in Room 436 before Magistrate Judge Brooke C. Wells (DI 246).
May 26, 2009 Plaintiff's Motion to Strike DI 235, 236 and 243, filed by Plaintiff's Brigham Young University, Daniel L. Simmons. Motions referred to Brooke C. Wells. (DI 247).
May 26, 2009 Plaintiff's Memorandum in Support re 247 Plaintiff's Motion to Strike DI 235, 236 and 243, filed by Plaintiffs Brigham Young University, Daniel L. Simmons. (DI 248).
May 27, 2009 Amended Notice of Hearing on Motion re: 240 Plaintiff's Motion to Compel Preserve and Produce Evidence : (Notice generated by chambers) Motion Hearing set for Jul. 2, 2009 10:00 AM in Room 436 before Magistrate Judge Brooke C. Wells. Hearing scheduled on Jun. 18, 2009 is vacated. (DI 249).
May 27, 2009 Order: Defendant Pfizer shall preserve the evidence at issue; specifically a collection of COX-2 related documents. Motion hearing re 240 Plaintiff's Motion to Compel Preserve and Produce Evidence set for Jun. 18, 2009 01:30 PM in Room 436 before Magistrate Judge Brooke C. Wells. Signed by Magistrate Judge Brooke C. Wells on May 26, 2009. (DI 250).
Jun. 1, 2009 BYU's Opposition to Pfizer's Motion for Partial Summary Judgment Regarding Integration of the Research Agreement, Dated Aug. 1, 1991 (Redacted) (DI 252).
Jun. 1, 2009 Notice of Conventional Filing Under Seal of Exhibits 1-77 to BYU Opposition to Pfizer Motion for Partial Summary Judgment Regarding Integration of the Research Agreement, Dated Aug. 1, 1991 filed by Plaintiffs Brigham Young University, Daniel L. Simmons re 252 Memorandum in Opposition to Motion (DI 253).
Jun. 1, 2009 Declaration of Dr. Daniel L. Simmons re 252 Memorandum in Opposition to Motion, filed by Brigham Young University, Daniel L. Simmons. (DI 254).
Jun. 1, 2009 Plaintiff's (Alternative) Rule 56(f) Motion Opposing Defendants' Motion for Partial Summary Judgment Regarding Integration of the Research Agreement, Dated Aug. 1, 1991 (DI 255).
Jun. 1, 2009 Plaintiff's Memorandum in Support of their (Alternative) Rule 56(f) Motion Opposing Defendants' Motion for Partial Summary Judgment Regarding Integration of the Research Agreement, Dated Aug. 1, 1991 Redacted Version (DI 256).
Jun. 1, 2009 Rule 56(f) Affidavit of L. Richard Williams in Support of (Alternative) Rule 56(f) Motion Opposing Defendants' Motion for Partial Summary Judgment Regarding Integration of the Research Agreement, Dated Aug. 1, 1991 (DI 257).
Jun. 2, 2009 Notice of Conventional Filing Under Seal of (1) BYU's Opposition to Pfizer's Motion for Summary Judgment for Partial Summary Judgment Regarding Integration of the Research Agreement, Dated Aug. 1, 1991, and (2) Plaintiffs' Memorandum in Support of Their Alternative Rule 56(f) Motion Opposing Defendants' Motion for Partial Summary Judgment Regarding Integration of the Research Agreement, dated Aug. 1, 1991 filed by Plaintiffs Brigham Young University, Daniel L. Simmons re 252 Memorandum in Opposition to Motion, 256 Memorandum in Support of Motion (DI 258).
Cocco, M., et al.;1985;Phytotoxic Activity in Pyrazole Derivatives; II Farmaco-Ed. Sci; 40; 272-284.
Feid-Allah; 1981;Trisubstituted Pyrazoles of Possible Antidiabetic and Antibacterial Activity; Pharmazie; 36; 754-756.
Feid-Allah; 1981;Synthesis and spectra of New 3-Carbethoxypyrazole Sulfonylurea Derivatives; Journal of Heterocyclic Chemistry; 18; 1561-1564.
Hamilton, R.; 1976;The Antiarrhythmic and Antiinflammatory Activity of a Series of Tricyclic Pyrazoles; Journal of Heterocyclic Chemistry; 13; 545-553.
Hashem,M.,et al.1976;Novel Pyrazolo, isoxazolo, and Thiazolo Steroidal Systems and Model Analogs Containing Dimethoxylaryl(or Dihydroxylaryl) Groups.;J.of Med.Chem.;19;229-239.
Mokhtar, H.; 1978;Synthesis of Some Substituted Pyrazole-3-carboxylic Acids with Possible Hypoglycemic and Antimicrobial Activity; Pharmazie; 33; 649-651.
Mokhtar, H.; 1988;Synthesis of Trisubstgituted Pyrazoles With Possible Antimicrobial Activity; Pakistan Journal of Science and Industrial Research; 31; 762-767.
Mokhtar, H. et al.; 1990;Synthesis of Nitrogenous Compounds Part II Pakistan Journal of Science and Industrial Research; 33;30-36.
Mokhtar, H.; 1991;Synthesis of Nirogenous Compounds, Part III; Pakistan Journal of Science and Industrial Research; 34; 9-15.
Nicolaus, B.J.R.; 1983; Symbiotic Approach to Drug Design; Decision Making in Drug Research; ed. Franz Gross; Raven Press; NY; 173-188.
Soliman, R. et al.;1983; Synthesis and Antidiabetic Activity of Some Sulfonylurea Derivatives of 3,5-Disubstituted Pyrazoles;Journal of Pharmaceutical Sciences; 72;9; 999-1004.
Soliman, R. et al.; 1984; Synthesis and antidiabetic activity of some sulfonylurea derivatives of 3,5-disubstituted pyrazoles;Chemical Abstracts; p. 444; col. 2.
Soliman, R.,et al.;1987;Prep.and Antidiabetic Activity of New Substituted3,5-Diarylpyrazolesulfonylurea DerivativesII:Structure-Activity RelationshipJ.of Pharm. Sci.;76;626-32.
Soliman, R.,et al.;1981;Prep.and Antidiabetic Activity of New 3-Methyl-5-phenylpyrazolesulfonylurea Derivatives; J.of Pharm. Sci.;70;602-605.
Bandaru Reddy, et al.; 1996; Evaluation of Cyclooxygenase-2 Inhibitor for Potential Chemopreventive Properties in Colon Carcinogenesis; 56; 4566-4569.
Makki;1994; Pyrazole derivatives.PartI.Synthesis and spectra of trisubstituted pyrazoline & pyrazole derivatives w/ possible hypoglycemic acti.;Chem.Abs.;121:11;p. 1023.
Maybridge Chem Co./Ryan Scientific Catalog 9; 1996 USPatent No. 5,508,426; Substituted Pyrazolyl Benzenesulfonamide Compounds For The Treatment of Inflam.Compound No.BTB 06812.
Schorderet, M.; 1992; Pharmacologie; 74; 56.
Mokhtar, H.M; 1985; Synthesis of Trisubstituted Pyrazoles with Possible Antimicrobial Activity; Pakistan Journal of Science and Industrial Research; V.28; No. 1;85-91.
Mokhtar,H.;1988;Synthesis of Nitrogeneous Compounds from δ-Unsaturated1,3-Dicarbonyl Esters. Part I. Subst Pyrazoles, Isoxazoles; J.Chemical Society of Pakistan;10;4;414-24.
Soliman, R., et al; 1978;The Scope of the Reactions of Hydrazines and Hydrazones; Pharmazie; 33; 4; 184-185.
Grimmett, M. R., Advances in Imidazole Chemistry; Advances in Heterocyclic Chemistry, 1970, pp. 106-183, Academic Press, New York and London, vol. 12.
Bartlett et al., "Subst. 3-phenyl-7H-thiazolo(3,2-b)1,2,4)triazin-7-ones as Antiinflam. Agents w/ Immun. Properties." Drugs Under Experim. & Clinic Res. 1989, 521-26; vol. XV.
Bertenshaw et al., "3,4-Diarylthiophenes are Selective COX-2 Inhibitors." Bioorganic & Medicinal Chemistry Lett., 1995, pp. 2919-2922, vol. 5, No. 23.
Bosch et al, "Efficacy & Tolera. of Intramuscular & Oral Meloxicam in Patients w/ Acute Lumbago: A Comp. w/ Intramuscular . . ." Curr. Med. Res. Opin. 1997; p. 29-38; vol. 14; 1.
Dikshit et al., Synthesis and Biological Activity of 2,3- and 3,4-diarylfurans and 2,3,4-triaryl-2,5-dihydrofurans. Indian J. Chem., Sect. B, 1990, pp. 954-960, vol. 29B, No. 3.
Engelhardt, G., Pharmacology of Meloxicam, and New Non-Steroidal Anti-Inflammatory Drug with Improved Safety Profile Through Preferential Inhibition of Cox-2; 1996; 35; 4-12.
Faid-Allah et al., "Pyrazole Derivatives with Possible Hypoglycemic Activity." Indian Journal of Chemistry, 1988, pp. 245-249, vol. 27B, No. 3.
Gans et al., "Anti-Inflam. & Safety Profile of DuP 697, a Novel Orally Effect. Prostaglandin Synth. Inhibitor." Journal of Pharm. and Experim. Therap.; 1990; p. 180-7; v 254; #1.
Gierse et al., "Expression and Selective Inhibition of the Constitutive and Inducible Forms of Human Cyclo-oxygenase." J. Biochem., 1995, pp. 479-484, vol. 305, Part 2.
Gupton et al, The Appl. of Disub. Vinylog. Iminium Salts & Related Synthon. to the Regiocontr. Prep. of Unsymmet. 2,3,4-Trisub. Pyrroles Tetrahedron, 1998, pp. 5075-5088; 54; 18-21.
Hargreaves et al., "A New and Sensitive Method for Measuring Thermal Nociception in Cutaneous Hyperplasia." Pain, 1988, pp. 77-88, vol. 32, No. 1.
Huang et al., "A Novel One-Pot Conversion of Methyl Sulfones to Sulfonamides." Tetrahedron Letters, 1994, pp. 7201-7204, vol. 35, No. 39.
Isakson et al., "Discovery of a Better Aspirin." Advances in Prostaglandin, Thromboxane, and Leukotriene Research, 1995, pp. 49-5 4, vol. 23.
Gauthier et al. Synth. & Biol. Eval. of 2,3-Diarylthiophenes as Select. Cox-2 Inhibitors. Part II: Replacing the Heterocycle. Bioorg. & Med. Chem. Lett. 1996 p. 86-92 V6 #1.
Klose et al. Nichtsteroidale Entzündungshemmer. 13(1). Bis-(4-methoxy phenyl)-2-arylthiopyrimidine. Journal of Heterocyclic Chem. 1982, 1165-1167, V19, No. 4.
Leblanc et al, Synthesis & Biological Eval. of 2,3-diarylthiophenes as Select. COX-2 & COX-1 Inhibitors. Bioorganic & Medicinal Chemistry Letters, 1995, pp. 2123-2128; vol. 5; no.
Masferrer et al., "Cyclooxygenase-2 Inhibitors: A New Approach to the Therapy of Ocular Inflammation." Survey of Ophthalmology, 1995, pp. S35-S40, vol. 41, Suppl. 2.
Patent Evaluations: Pulmonary-Allergy, Derm, Gastrointestinal & Arthritis Novel COX-2 inhibitors, Expert Opinion on Therap. Patents, 1995, vol. 5, No. 4, pp. 357-359.
Penning et al., "3,4-Diarylpyraloles: Potent and Selective Inhibitors of Cyclooxygenase-2." Bioorganic & Medicinal Chemistry Letters, 1997, pp. 2121-2124, vol. 7, No. 16.
Reid et al., "Some New β-Diketones Containing the Trifluoromethy Group." J. Amer. Chem. Soc., 1950, pp. 2948-2952, vol. 72, No. 7.
Seideman et al., "Naproxen and Paracetamol Compared with Naproxen only in Coxarthrosis." Acta Orthopaedica Scandinavica, 1993, pp. 285-288, vol. 64, No. 3.
Seibert et al., "Pharm. & Biochem. Demonst. of the Role of Cyclooxygenase-2 in Inflammation and Pain." Proc. Natl. Acad, Sci. USA, 1994, pp. 12013-12017, vol. 1.
Seifert et al. Naproxen Suppositories in Comb. w/ Oral Naproxen, Indomethacin & Ibuprofen in the Treatment of Rheumatoid Arthritis. Med. Res. & Opin. 1980 p. 38-42. vol. 7, #91.
Tanaka et al. Studies on Anti-platelet Agents IV. A Series of 2-Subst. 4,5-Bis(4-methoxyphenyl) pyrimid. as Novel . . . ; Chem. & Pharm. Bulletin 1994 p. 1828-1834, vol. 42, #9.
Vleeschauwer et al., "Remarkably Mild and Simple Preparations of Sulfinates, Sulfonyl Chlorides and Sulfonamides from Thioanisoles." Syntett 1997, pp. 375-377, vol. 4.
Winter et al. Carrageenin-Induced Edema in Hind Paw of the Rat as an Assay for Antiinflam. Drugs; Proceedings of the Soc. for Experim. Bio. and Medicine, 1962 p. 544-547 V111 #3.
Feb. 1, 2007 Post-Trial Brief of Teva Pharmaceuticals USA, Inc.
Feb. 16, 2007 Post-Trial Reply Brief of Teva Pharmaceuticals USA, Inc.
May 5, 2006 Expert Report of Raymond Baker, Ph.D.
May 5, 2006 Expert Report of Gibert S. Banker, Ph.D, D.Sc.
May 5, 2006 Expert Report of Barry S. Cooperman, Ph.D.
May 5, 2006 Expert Report of George C. Fuller, Ph.D.
May 5, 2006 Expert Report of Dr. Simon Helfgott.
May 5, 2006 Expert Report of Keith B. Leffler.
May 5, 2006 Expert Report of William B. Schultz.
May 5, 2006 Expert Report of Ronald H. Smith.

May 5, 2006 Expert Report of Guenter Trummlitz, Ph.D.
May 5, 2006 Expert Report of Dr. Michael Wolfe.
May 9, 2006 First Supplement to Expert Report of William B. Schultz.
Jun. 23, 2006 Rebuttal Expert Report of Raymond Baker, Ph.D.
Jun. 23, 2006 Rebuttal Expert Report of George C. Fuller, Ph.D.
Jun. 23, 2006 Rebuttal Report of Dr. Simon Helfgott.
Jun. 23, 2006 Rebuttal Report of Keith B. Leffler.
Jun. 23, 2006 Rebuttal Report of Ronald H. Smith.
Jun. 23, 2006 Rebuttal Expert Report of Guenter Trummlitz, Ph.D.
Jun. 23, 2006 Rebuttal Expert Report of Dr. Michael Wolfe.
Jun. 23, 2006 Second Supplement to Expert Report of William B. Schultz and Rebuttal.
Jul. 26, 2006 Surrebuttal Expert Report of Guenter Trummlitz, Ph.D.
Jul. 27, 2006 Surrebuttal Expert Report of Raymond Baker, Ph.D.
Aug. 8, 2006 Surrebuttal Expert Report of Ronald H. Smith (with correction to opening report).
Oct. 19, 2006 Supplemental Expert Report of Guenter Trummlitz, Ph.D.
May 5, 2005 Expert Report of Dr. Henry G. Grabowski.
May 5, 2005 Expert Report of Dr. William Galbraith.
Jun. 23, 2006 Rebuttal Expert Report of Dr. William Galbraith.
Jun. 23, 2006 rebuttal Expert Report of Dr. Henry G. Grabowski.
Jun. 23, 2006 Expert Report of Mark J. Iannini, M.D., M.P.H.
Jun. 23, 2006 Expert Report of Dr. William L. Jorgensen.
Jun. 23, 2006 Expert Report of James W. McGinity, Ph.D.
Jun. 23, 2006 Expert Report of Dr. Peter H. Rheinstein.
Jun. 23, 2006 Expert Report of Timothy Cragin Wang, M.D.
Jun. 23, 2006 Expert Report of Thomas G. wiseman, Esq.
Jun. 23, 2006 Expert Report of Dr. Randall M. Zusman.
Jun. 23, 2006 Expert Report of Dr. Karen Seibert.
Jul. 14, 2009 letter from Joseph M. Reisman to Bryan C. Zielinski.
Series of emails between Joseph Reisman and Bryan Zielinski including Jul. 4, 2009 email from Joseph Reisman to Bryan Zielinski; Jul. 27, 2009 email from Joseph Reisman to Bryan Zielinski; and Jul. 27, 2009 email from Bryan Zielinski to Joseph Riesman.
Jul. 28, 2009 letter from Scott A. Williams to Joseph M. Reisman.
Aug. 11, 2009 letter from Scott A. Williams to Joseph M. Reisman.
Oct. 21, 2009 letter from Sue Eggleston to Bryan Zielinski.
Prosecution history for U.S. Appl. No. 90/009,615 (including Ex Parte Reexamination Request filed on Oct. 23, 2009).
Nov. 4, 2009 Order re: Status of Pfizer's Motion for protective order regarding Plaintiffs sixth request for production and proposed rule 30(b)(6)Deposition Topics.
Nov. 17, 2009 Stipulated Motion for Extension of Time to File Joint Status Update Regarding Plaintiffs' Sixth Request for Production and Proposed Rule 30(b)(6) Deposition Topics; Attached proposed order.
Nov. 18, 2009 Order granting Motion for Extension of Time to file joint status update regarding Plaintiffs sixth request for Production and Proposed Rule 30(b)(6) Deposition Topics.
Nov. 23, 2009 Stipulated Motion for Extension of Time to File Joint Status Update Regarding Plaintiffs' Sixth Request for Production and Proposed Rule (30)(b)(6) Deposition Topics; Attached proposed order.
Nov. 24, 2009 Order granting Motion for Extension of Time to File Joint Status Update Regarding Plaintiffs Sixth Request for Production and Proposed Rule 30(b)(6) Deposition Topics.
Nov. 25, 2009 Order of recusal by Judge Dale A. Kimbal.
Nov. 30, 2009 Order of recusal by Judge Bruce S. Jenkins.
Dec. 15, 2009 Notice of conventional filing of Joint Status Memorandum.
Jan. 21, 2010: Exhibits 4-22 of Defendants Memorandum in Support of Motion for a Hearing to Amend the Discovery Plan.
Exhibit 2 (dated Jul. 22, 2009), Exhibit 3 (dated Feb. 11, 2010) and Exhibit 4 (dated Feb. 25, 2010) to Defendants' memorandum in opposition to Plaintiff's Motion for Dispositive Sanctions.
Exhibit 10 (dated May 23, 2008-Mar. 24, 2010) and Exhibit 11 (dated May 3, 2010) to Defendants' memorandum in opposition to Plaintiff's Motion for Dispositive Sanctions.
Exhibit 13 (dated Jan. 29, 2010) to Defendants' memorandum in opposition to Plaintiff's Motion for Dispositive Sanctions.
Exhibit 15 (dated Apr. 7, 2009) and Exhibit 16 (dated Dec. 2, 2009) to Defendants' memorandum in opposition to Plaintiff's Motion for Dispositive Sanctions.
Exhibit 23 (dated Mar. 19, 2010) to Defendants' memorandum in opposition to Plaintiff's Motion for Dispositive Sanctions.
Exhibit 25 (dated Jun. 2, 2009) and Exhibit 26 (dated May 23, 2008) to Defendants' memorandum in opposition to Plaintiff's Motion for Dispositive Sanctions.
Exhibit 29 (dated Mar. 4, 2010) to Defendants' memorandum in opposition to Plaintiff's Motion for Dispositive Sanctions.
Exhibit 34 (dated Nov. 16, 2007), Exhibit 35 (dated Jul. 16, 2008) and Exhibit 36 (dated Feb. 14, 2008)to Defendants' memorandum in opposition to Plaintiff's Motion for Dispositive Sanctions.
Exhibit 39 (dated Nov. 19, 2009) to Defendants' memorandum in opposition to Plaintiff's Motion for Dispositive Sanctions.
Exhibit 41 (dated Sep. 2, 2008) and Exhibit 42(dated Feb. 10, 2009) to Defendants' memorandum in opposition to Plaintiff's Motion for Dispositive Sanctions.
Exhibit 48(dated Feb. 15, 2010) and Exhibit 49 (dated Apr. 22, 2008) to Defendants' memorandum in opposition to Plaintiff's Motion for Dispositive Sanctions.
Exhibit 51(dated Feb. 3, 2010) and Exhibit 52(dated Jul. 17, 2007) to Defendants' memorandum in opposition to Plaintiff's Motion for Dispositive Sanctions.
Exhibit 61(dated Feb. 7, 2008, Feb. 11, 2008 and Feb. 19, 2008) and Exhibit 62 (dated Jan. 22, 2010) to Defendant's memorandum in opposition to Plaintiff's Motion for Depositive Sanctions.
May 4, 2010 Order denying Plaintiffs' Motion for Dispositive Sanctions.
May 5, 2010 Orders granting pro hac vice admissions.
May 6, 2010 Order regarding hearing set for May 7, 2010.
May 10, 2010 Reply in support of Plaintiffs' motion to set Date to Amend Complaint.
Exhibits 1-4 to May 10, 2010 Reply in support of Plaintiffs' motion to set Date to Amend Complaint.
May 11, 2010 Motion to seal Exhibit 5 to Reply in support of Plaintiffs' motion for Extension of Time Amend Complaint with proposed order.
May 14, 2010 Order sealing Exhibit 5 to Reply in support of Plaintiffs' motion for Extension of Time Amend Complaint.
May 18, 2010 Redacted Plaintiffs' motion to extend trial date.
Exhibits 1-7 to Plaintiffs' May 18, 2010 motion to extend trial date.
May 18, 2010 Plaintiff's Motion to Expedite Briefing Schedule.
May 18, 2010 Notice of Conventional Filing of Plaintiffs' Motion to Extend Trial Date and Exhibits 5 and 6 Thereto.
May 21, 2010 Memorandum in Opposition to Plaintiff's Motion to Expedite Briefing Schedule and Hearing Concerning Plaintiffs' Motion to Extend Trial Date.
Plaintiffs' May 24, 2010 reply in support of motion for expedited briefing schedule and hearing concerning plaintiffs' motion to extend trial date and plaintiffs' emergency motion to adjust date of expert disclosures.
Exhibits 1-7 to Plaintiffs' May 24, 2010 reply in support of motion for expedited briefing schedule and hearing concerning plaintiffs' motion to extend trial date and plaintiffs' emergency motion to adjust date of expert disclosures.
May 26, 2010 Order granting in part and denying in part 419 Motion to Expedite; granting 425 Motion for Extension of Time.
Defendants' May 28, 2010 opposition to Plaintiffs' motion to extend trial date.
Exhibits 1-5 to Defendants' May 28, 2010 opposition to Plaintiffs' motion to extend trial date.
Jun. 2, 2010 Reply in support of Plaintiffs' motion to extend trial date.
Jun. 11, 2010 Order granting in part plaintiffs' motion for extension of time.
Jun. 14, 2010 Order granting in part plaintiffs' motion for extension of time to Amend complaint.
Jun. 24, 2010 Order granting defendants' motions in part.
Plaintiffs' Nov. 18, 2009 Amended 30 (b)(6) Notice of Deposition to Pfizer—James Gierse.
Plaintiffs' Dec. 9, 2009 Amended Rule 30(b)(6) Deposition Notice to Defendants—Designee(s) Pfizer, Inc.(to be determined).

Defendants' Dec. 14, 2009 Fourth Reques or Production of Documents.
Plaintiffs' Dec. 14, 2009 Notice of Taking Video Deposition of Patricia O'Brien.
Plaintiffs' Dec. 15, 2009 Amended Notice of Taking Video Deposition of Patricia O'Brien.
Defendants' Dec. 16, 2009 Fifth Request for Production of Documents.
Plaintiffs' Jan. 19, 2010 Response o Defendants' Fifth Request for Production of Documents.
Plaintiffs' Jan. 20, 2010 Eighth Request for Production of Documents.
Plaintiffs' Feb. 5, 2010 Response to Defendants' Fourth Request for Production of Documents.
Plaintiffs' Feb. 5, 2010 Amended Response to Defendants' Fifth Request for Production of Documents.
Defendants' (Pfizer Inc., G.D. Searle, LLC and Pharmacia Corporation) Feb. 22, 2010 Response to Plaintiffs' Eighth Request for Production of Documents.
Defendants' Feb. 25, 2010 Sixth Request or Production of Documents.
Defendants' Mar. 1, 2010 Response and Objections to Plaintiffs' Amended Rule 30(b)(6) Deposition Notice to Defendants.
Plaintiffs' Apr. 6, 2010 Response to Defendants' Sixth Request for Production of Documents.
Plaintiffs' May 18, 2010 Notice of Taking Video Deposition of Jamie Masferrer.
Defendants' May 28, 2010 Objections to Notice of Deposition of Karen Seibert.
Jun. 21, 2010 Subpoena Served Upon Shaukat Rangwala.
Exhibits 257-259 (Exhibit 257: Dec. 2, 1993 Letter to Editor at Science from Seibert enclosing manuscript; Exhibit 258: Dec. 19, 1995 US Patent 5,476,944; Exhibit 259: May 21, 2008 Letter to Ricker from Spanbauer).
(Exhibit 311) undated Sketch by Karen Seibert.
Exhibits 240-242 (Exhibit 240: May 8, 2009 Coates Letter to A. Anderson; Exhibit 241: Code of Federal Regulations Title 21; Exhibit 242: May 11, 2009 Privilege Log of Pfizer Custodians Outlook Calendar Entries).
Aug. 6, 2010 Stipulated Motion for Extension of Time for Defendants to respond to Plaintiffs' Motion to compel and for Sanctions Attachments: # 1 [Proposed] Order Granting Stipulated Motion for Extension of Time.
Defendant's Aug. 6, 2010 Memorandum in Opposition to Plaintiffs' Motion for Leave to File Overlength Memorandum.
Plaintiffs' Aug. 9, 2010 Reply in Support of Motion for Leave to File Overlength Memorandum Exhibit 1: Letter from K. Owen to L.R. Williams, Aug. 3, 2010 Exhibit 2: Letter from K. Owen to L.R. Williams, Aug. 6, 2010.
Aug. 10, 2010 Order Granting Stipulated Motion for Extension of Time.
Aug. 16, 2010 Stipulated Motion for Extension of Time to File Opposition to Plaintiffs' Motion for Dispositive Sanctions. Exhibit A—[Proposed] Order Granting Stipulated Motion for Extension of Time to File Opposition to Plaintiffs' Motion for Dispositive Sanctions.
Aug. 16, 2010 Defendants' Opposition to Plaintiffs' Motion to Compel Production and for Sanctions.
Aug. 17, 2010 Order granting Stipulated Motion for Extension of Time to File Opposition to Plaintiffs' Motion for Dispositive Sanctions.
Aug. 18, 2010 Order granting Motion for Leave to File Overlength Memorandum.
Aug. 25, 2010 Stipulated Motion for Extension of Time to File Opposition to Plaintiffs' Motion for Dispositive Sanctions Exhibit A: [Proposed] Order Granting Stipulated Motion for Extension of Time to File Opposition to Plaintiffs' Motion for Dispositive Sanctions.
Aug. 26, 2010 Order granting Stipulated Motion fo Extension of Time to File Opposition to Plaintiffs' Motion or Dispositive Sanctions.
Aug. 27, 2010 Memorandum Decision and Order Denying Without Prejudice Plaintiffs' Motion for Sanctions.
Aug. 31, 2010 Motion to Dismiss Counts IX (18 U.S.C. § 1962(c)) and X (18 U.S.C. § 1962 (D)) of Plaintiffs' First Amended Complaint.
Aug. 31, 2010 Memorandum in Support of Motion to Dismiss Counts IX (18 U.S.C. § 1962(c)) and X (18 U.S.C. § 1962 (D)) of Plaintiffs' First Amended Complaint.
Aug. 31, 2010 Defendants' Answers to First Amended Complaint.
Sep. 2, 2010 Plaintiffs' Reply in Support of Motion to Compel Production Exhibit 1: Karen Seibert Deposition Excerpt, Jun. 1, 2010 Exhibit 2: Guidelines for Research Records, Apr. 2, 1985.
Sep. 13, 2010 Notice of Conventional Filing of Defendants' Motion for Partial Summary Judgment on Counts I-III and V-X of the First Amended Complaint on Statute of Limitations Grounds.
Sep. 13, 2010 Notice of Conventional Filing of Defendants' Memorandum in Support of Motion for Partial Summary Judgment on Counts I-III and V-X of the First Amended Complaint on Statute of Limitations Grounds.
Sep. 13, 2010 Notice of Conventional Filing of Pfizer's Exhibits in Support of Defendants' Motion for Partial Summary Judgment on Counts I-III and V-X of the First Amended Complaint on Statute of Limitations Grounds, with Exhibits 1-33.
Sep. 28, 2010 Stipulated Motion for Extension of Time to respond to Defendants' Motion for Partial Summary Judgment Exhibit A: [Proposed] Order Granting Stipulated Motion for Extension of Time.
Sep. 29, 2010 Order Granting Stipulated Motion for Extension of Time to File Responses to Defendants' Motion for Partial Summary Judgment.
Oct. 1, 2010 Plaintiff's Response in Opposition to Motion to Dismiss Counts IX (18 U.S.C. § 1962(c)) and X (18 U.S.C. § 1962 (D)) of Plaintiffs First Amended Complaint.
Oct. 18, 2010 Defendants' Reply Memorandum in Support of Motion to Dismiss Counts IX (18 U.S.C. § 1962(c)) and X (18 U.S.C. § 1962 (D)) of Plaintiffs' First Amended Complaint.
Oct. 21, 2010 Notice of Substitution of Attorneys of Record—Brent O. Hatch replacing Todd L. Krause; David R. Parkinson; Lisa A. Schneider; Neil H. Wyland; Charles W. Douglas and George M. Haley as counsel on behalf of G.D. Searle, G.D. Searle & Company, Monsanto Company, Pfizer Inc. and Pharmacia.
Oct. 27, 2010 Request to Submit for Decision Re: Defendants' Motion to Dismiss Counts IX (18 U.S.C. § 1962(c)) and X (18 U.S.C. § 1962 (D)) of Plaintiffs First Amended Complaint (Oral Argument Requested).
Nov. 1, 2010 Order and Memorandum Granting Plaintiffs' Motion to Compel in Part.
Aug. 17, 2010 Notice of Taking Video Deposition of Mark Currie.
Aug. 23, 2010 Amended Notice of Taking Video Deposition of Dr. Daniela Salvemini.
Aug. 23, 2010 Defendants' Response to Plaintiffs Ninth Request for Production of Documents.
Sep. 10, 2010 Subpoena for the Deposition of Len Lee.
Sep. 14, 2010 Notice of Taking Video Deposition of Ben Zweifel.
Sep 15, 2010 Defendants' Objections to Notice of Deposition of Len Lee.
Sep. 16, 2010 Defendants' Objections to Amended Notice of Deposition of Kathleen Leahy.
Sep. 23, 2010 Defendants' Objections to Notice of Deposition Barry Haymore.
Sep. 23, 2010 Defendants' Objections to Notice of Deposition of Ben Zweifel.
Sep. 23, 2010 Notice of Taking Video Deposition of Scott Hauser.
Sep. 29, 2010 Notice of Taking Video Deposition of John Talley.
Sep. 29, 2010 Notice of Taking Video Deposition of Peter Isakson.
Sep. 29, 2010 Amended Notice of Taking Video Deposition of Joe Bulock.
Sep. 29, 2010 Notice of Taking Video Deposition of Jan Williams.
Sep. 29, 2010 Notice of Taking Video Deposition of Philip Needleman.
Oct. 1, 2010 Amended Notice of Taking Video Deposition of Harvey Herschman, Ph.D.
Oct. 1, 2010 Amended Subpoena for the Deposition of Harvey Herschman, Ph.D.
Oct. 5, 2010 Defendants' Objections to Notice of Deposition of Beverly Reitz.

Oct. 5, 2010 Defendants' Objections to Notice of Deposition of Mark Currie.
Oct. 5, 2010 Subpoena for the Deposition of Mark Currie.
Oct. 12, 2010 Amended Notice of Taking Video Deposition of Dr. Denis Callewaert.
Oct. 12, 2010 Amended Subpoena for Deposition of Dr., Denis Callewaert.
Oct. 13, 2010 Notice of Taking Video Deposition of Earl Wolley.
Oct. 13, 2010 Notice of Taking Video Deposition of Merrill Bateman.
Oct. 13, 2010 Notice of Taking Video Deposition of William Bradshaw.
Oct. 21, 2010 Notice of Taking Video Deposition of Richard U. DeSchutter.
Oct. 27, 2010 Amended Notice of Taking Video Deposition of William Bradshaw.
Nov. 3, 2010 Plaintiffs' Tenth Request for Production of Documents.
Nov. 4, 2010 Defendants' Objections to Notice of Deposition of Peter Isakson.
Nov. 5, 2010 Amended Notice of Taking Video Deposition of Brigham Young University Pursuant to Fed.R.Civ.P.30(b)(6).
Nov. 8, 2010 Amended Notice of Taking Video Deposition of Peter Isakson.
Nov. 9, 2010 Amended Notice of Taking Video Deposition of Peter Isakson.
Plaintiffs' Nov. 12, 2010 Emergency Motion to Extend Time for Response to Defendants' Motion for Partial Summary Judgment.
Nov. 12, 2010 Memorandum in Support of Plaintiffs' Emergency Motion to Extend Time for Response to Defendants' Motion for Partial Summary Judgment with the following exhibits: Exhibit A: Declaration of Adam C. Anderson Exhibit B: Scott Hauser Deposition Excerpts, Oct. 27, 2010 Exhibit C: Dec. 2, 1993 Letter to Editor of Science Magazine from Dr. Seibert Exhibit D: Karen Seibert Deposition Excerpts, Jun. 2, 2010 Exhibit E: Peter Isakson Deposition Excerpts, Dec. 18, 2001 Exhibit F: Scott Hauser Deposition Excerpts, Nov. 11, 2010.
Nov. 12, 2010 Motion to Expedite Response to BYU's Motion for an Extension of Time.
Nov. 15, 2010 Order Granting Plaintiffs' Emergency Motion to Extend Time for Response to Defendants' Motion for Partial Summary Judgment and Denying As Moot Plaintiffs' Motion to Expedite Response.
Nov. 30, 2010 Notice of Service of Subpoena for Production of Documents and Things upon Defendants.
Dec. 17, 2010 Notice of Conventional Filing of Plaintiffs' Response in Opposition to Motion for Partial Summary Judgment on Counts I-III and V-X of the First Amended Complaint on Statute of Limitations Grounds and All Exhibits Thereto.
Plaintiffs' Dec. 18, 2010 Response in Opposition to Motion for Partial Summary Judgment on Counts I-III and V-X of the First Amended Complaint on Statute of Limitations Grounds (Redacted Version).
Dec. 23, 2010 Order Regarding Scheduling Deadlines.
Jan. 14, 2011 Notice of Conventional Filing of Reply Memorandum in Support of Defendants' Motion for Partial Summary Judgment on Counts I-III and V-X of the First Amended Complaint on Statute of Limitations Grounds.
Defendants' Jan. 14, 2011 Motion to Strike Portions of Plaintiffs' Response in Opposition to Motion for Partial Summary Judgment.
Jan. 14, 2011 Notice of Conventional Filing of Memorandum in Support of Defendants' Motion to Strike Portions of Plaintiff's Response in Opposition to Motion for Partial Summary Judgement.
Defendants' Jan. 19, 2011 Motion to Compel Production of Documents and Award of Attorney Fees.
Jan. 19, 2011 Notice of Conventional Filing of Defendants' Memorandum of Point and Authorities in Support of Motion to Compel Production of Documents and Award of Attorneys' Fees.
Jan. 19, 2011 Motion For Admission Pro Hac Vice and Consent of Local Counsel (G. Robert Blakey) with the following Exhibits: Ex. A: Application for Admission Pro Hac Vice Ex. B: [Proposed] Order for Pro Hac Vice Admission.
Defendants' Jan. 26, 2011 Opposition to Plaintiffs' Motion for Admission Pro Hac Vice of G. Robert Blakey.
Jan. 27, 2011 Response to Defendants' Opposition to Plaintiffs' Motion for Admission Pro Hac Vice of G. Robert Blakey.
Jan. 31, 2011 Order for Pro Hac Vice Admission of G. Robert Blakey.
Plaintiffs' Feb. 1, 2011 Response in Opposition to Defendants' Motion to Strike Portions of Plaintiffs' Response to Motion for Partial Summary Judgment, with the following exhibits: Ex. 4: Sep. 2, 1992 Letter to P. Needleman from C. Hardman, BYU-01-1418 Ex. 11: M.K. O'Banion et al., A Serum—and Glucocorticoid-regulated 4-Kilobase mRNA Encodes a Cyclooxygenase-related Protein, J.Biochem, Mar. 1993, p. 6610, PFC01194743-748 Ex. 12: E. Meade, et al, Differential Inhibition of Prostaglandin Endoperoxide Synthase (Cyclooxygenase) Isozymes by Aspirin and Other Non-steroidal Anti-inflamatory Drugs, J. Biochem., Mar. 1993, p. 6610 Ex. 13: U.S. Patent No. 5,344,991 (filed Oct. 29, 1993). Ex. 14: U.S. Patent No. 5,563,165 (filed Jun. 1, 1995). Ex. 15: U.S. Patent No. 5,633,272 (filed Jun. 7, 1995) Ex. 16: U.S. Patent No. 5,760,068 (filed Nov. 14, 1994). Ex. 20: Draft Article submitted to Science Magazine by K. Seibert titled Mediation of Acute Inflammation by Cyclooxygenase-2, Dec. 2, 2003. Ex. 23A: R. Gilbert, et al, Regulation of TIS10/Prostaglandin Synthase-2 Protein and Message in Murine Macrophage Cell Lines Ex. 23B D. Kubuju et al., TIS10, A Phorbol Ester Tumor Promoter-inducible mRNA from Swiss 3T3 Cells, Encodes a Novel Prostaglandin Synthase/Cyclooxygenase Homologue, J. Biochem, 1991, vol. 266, No. 20 Ex. 23C: J. Masferrer et al., In Vivo Glucocorticoids Regulate Cyclooxygenase-2 but not Cyclooxygenase-1 in Peritoneal Macrophages, J. Pharmacol. and Exper. Therap., 1994, vol. 270, No. 3 Ex. 24: D. Simmons *Curriculum Vitae* Ex. 26: Mar. 17, 2000 Letter to E. Bramhall from D. Hoscheit Ex. 27: May 18, 2000 Letter to D. Hoscheit from D. Thomas Ex. 29: Pfizer Fact Sheet—www.stopmedicarefraud.gov/pfizerfactsheet.html Ex. 30: *Pfizer Hit With $141 Million RICO Penalty Over Neurontin Promotion,* Mar. 29, 2010, Law.com Ex. 31: Pfizer to Pay $142.1 Million Over Neurontin Marketing, Jan. 28, 2011, Bloomberg.com Ex. 32: Dec. 13, 2010 Email to A. Anderson from E. Coates at The Monsanto Company, with attached schedules and memos Ex. 34: Amended Declaration of Daniel L. Simmons, Jan. 31, 2011 Ex. 35: Amended Declaration of Randy Bell.
Feb. 1, 2011 Notice of Conventional Filing of Exhibits 1, 2, 3, 5, 6A-C, 7, 8, 9, 10A-B, 17, 18, 19, 21, 22, 25, 28, 33 to Plaintiffs' Response in Opposition to Defendants' Motion to Strike Portions of Plaintiffs' Response to Motion for Partial Summary Judgment.
Feb. 8, 2011 Reply Memorandum in Support of Defendants' Motion to Strike Portions of Plaintiffs' Response in Opposition to Motion for Partial Summary Judgment, with the following exhibit: Ex. A: Jan. 28, 2011 Letter to Mr. Anderson from Ms. Owen.
Feb. 18, 2011 Memorandum in Support of Defendants' Motion to Compel Testimony Pursuant to Notice of 30(b)(6) Deposition, with the following exhibits: Ex. 1: Notice of Taking Video Deposition of Brigham Young University Pursuant to Fed. R. Civ. P. 30(b)(6), Feb. 18, 2011 Ex. 2: http://en.wikipedia.org/wiki/Daniel_L._Simmons ("the Daniel L. Simmons Wiki Page") Ex. 3: http://en.Wikipedia.org/wiki/PTGS2("the COX-2 Wiki Page")Ex. 4: http://en.Wikipedia.org/wiki/COX-2_inhibitor("the COX-2 Inhibitor Wiki Page") Ex. 5: http://en.Wikipedia.org/wiki/COX-3 ("the COX-3 Wiki Page") Ex. 6: Daniel L. Simmons, Creation of Daniel L. Simmons Wiki Page Ex. 7: Daniel L. Simmons, Revisions to the Daniel L. Simmons Wiki Page Ex. 8: PTGS2, Revisions to the COX-2 Wiki Page Ex. 9: Mar. 2010 Revisions to the COX-2 Wiki Page Ex. 10: COX-2 inhibitor, Revisions to the COX-2 Inhibitor Wiki Page Ex. 11: Feb. 16, 2011 Letter from A. Anderson to R. Mulloy Ex. 12: Feb. 17, 2011 Letter from R. Mulloy to A. Anderson.
Defendants' Feb. 14, 2011 Motion to compel Testimony Persuant to Notice of 30(b)(6) Deposition, with the following exhibit: Ex. 1: Statement in Compliance with DUCivR 37-1(a).
Feb. 14, 2011 Memorandum in Support of Defendants' Motion to Compel Testimony Pursuant to Notice of 30(b)(6) Deposition, with the following exhibits: Ex. 1: Amended Notice of Taking Video Deposition of Brigham Young University Pursuant to Fed. R. Civ. P. 30(b)(6), Nov. 5, 2010 Ex. 2: Nov. 18, 2010 Letter to R. Mulloy from A. Anderson Ex. 3: Dec. 10, 2010 Letter to A. Anderson from R. Mulloy Ex. 4: Dec. 20, 2010 Letter to A. Anderson from R. Mulloy Ex. 5: *Foreclosure Mgmt. Co.* v. *Asset Mgmt. Holdings, LLC,* No. 07-2388-DJW, 2008 WL 3895474 (D.Kan. Aug. 21, 2008). Ex. 6:

*Fed. Deposit Ins. Corp.* v. *Hays,* No. CIVASA92CA653EP, 1998 WL 1782547 (W.D. Tex. Jan. 9, 1998). Ex. 7: *E.E.O.C.* v. *Lowe's HIW, Inc.,* Nos. C08-0331-JCC, C08-5053, 2009 WL 811495 (W.D. Wash. Mar. 27, 2009).
Feb. 14, 2011 Motion to Compel Immediate Production of Documents and 30(b)(6) Deposition.
Feb. 14, 2011 Notice of Conventional Filing of Memorandum in Support of Motion to Compel Immediate Production of Documents and 30(b)(6) Deposition.
Feb. 18, 2011 Motion to Compel Immediate Production of Documents and 30(b)(6) Deposition.
Defendants' Feb. 18, 2011 Motion to Compel Testimony Pursuant to Notice of 30(b)(6) Deposition, with the following exhibit: Ex. 1: Statement in Compliance with DUCivR 37-1(a).
Feb. 18, 2011 Notice of Conventional Filing of Memorandum in Support of Motion to Compel Production of Invention Disclosure Statements, Draft Patent Applications, Communications with New Monsanto, and Other Documents.
Feb. 18, 2011 Ex Parte Motion for Leave to File Overlength Memorandum in Support of Plaintiffs' Motion to Compel Production of Invention Disclosure Statements, Draft Patent Applications, Communications with New Monsanto, and Other Documents with accompanying Proposed Order Granting Ex Parte Motion for Leave to File Overlength Memorandum in Support of Plaintiffs' Motion to Compel Production of Invention Disclosure Statements, Draft Patent Applications, Communications with New Monsanto, and Other Documents.
Feb. 22, 2011 Notice of Conventional Filing of Unredacted Version of Plaintiffs' Response to Pfizer's Motion to Compel Production of Documents and Award of Attorney Fees.
Feb. 22, 2011 Response to Pfizer's Motion to Compel Production of Documents and Award of Attorney Fees (Redacted Version), with the following exhibits: Ex. 1: Feb. 26, 2010 Letter to R. Leighton, Pfizer's former counsel, from K. Ricker Ex. 2: Jan. 7, 2011 Letter to B. Hatch from A. Anderson Ex. 3: William Bradshaw Deposition, Oct. 29, 2010 Ex. 4: Mar. 21, 1996 Letter to X. Lu and B. Bradshaw from D. Simmons, Dep. Ex. 608 Ex. 5: Daniel Simmons, Ph.D. Deposition, Apr. 20, 2009 Ex. 6: Merrill Bateman Deposition, Oct. 22, 2010 Ex. 7 Daniel Simmons, Ph.D. Deposition, Apr. 21, 2009, Ex. 8: Oct. 19, 1989 Letter to E. Woolley from D. Simmons, Dep. Ex. 18 Ex. 9: Dec. 11, 1998 Letter to M. Bateman from D. Simmons, Dep. Ex. 19 Ex. 10: Amended and Restated Bylaws of Brigham Young University, Dec. 20, 2002, § 3.03 (Filed Under Seal) Ex. 11: Feb. 28, 2007 Letter to R. O'Malley from L. Beus Ex. 12: Nov. 28, 2007 Letter to L. Schneider from L. R. Williams Ex. 13: Jan. 10, 2008 Letter to L. Schneider from L. R. Williams.
Feb. 23, 2011 Order Denying Ex Parte Motion for Leave to File Overlength Memorandum in Support of Plaintiffs' Motion to Compel Production of Invention Disclosure Statements, Draft Patent Applications, Communications with New Monsanto, and Other Documents.
Feb. 23, 1011 Revised Order Denying Ex Parte Motion for Leave to File Overlength Memorandum in Support of Plaintiffs' Motion to Compel Production of Invention Disclosure Statements, Draft Patent Applications, Communications with New Monsanto, and Other Documents.
Feb. 23, 2011 Request for Status and Scheduling Conference.
Feb. 24, 2011 Motion for Leave to File Overlength Memorandum Responding to Pfizer's Motion to Compel Production of Documents and Award Attorney's Fees with [Proposed] Order Granting Motion for Leave to File Overlength Memorandum Responding to Pfizer's Motion to Compel Production of Documents and Award Attorney's Fees.
Feb. 25, 2011 Notice of Conventional Filing of Memorandum in Support of Motion to Compel Production of Invention Disclosure Statements, Draft Patent Applications, Communications with New Monsanto, and Other Documents.
Feb. 28, 2011 Order Granting Motion for Leave to File Overlength Memorandum Responding to Pfizer's Motion to Compel Production of Documents and Award Attorneys' Fees.
Nov. 11, 2010 Amended Notice of Taking Video Deposition of Jan Williams.
Nov. 16, 2010 Amended Notice of Taking Video Deposition of Joe Bulock.
Nov. 16, 2010 Amended Notice of Taking Video Deposition of Philip Needleman.
Nov. 16, 2010 Amended Subpoena for the Deposition of Joseph Bulock.
Nov. 19, 2010 Notice of Taking Video Deposition of Xiaojun Lu.
Nov. 19, 2010 Notice of Taking Video Deposition of Gary Hooper.
Nov. 19, 2010 Amended Notice of Taking Video Deposition of J. Bevan Ott.
Plaintiffs' Nov. 30, 2010 Notice of Subpoena for the Production of Documents and Things, with the following exhibits: Exhibit A: Nov. 30, 2010 Subpoena for the Deposition of the University of Chicago Exhibit B: Nov. 30, 2010 Subpoena for the Deposition of R. Michael Garavito.
Dec. 1, 2010 Subpoena to Washington University at St. Louis.
Dec. 1, 2010 Amended Notice of Taking Video Deposition of Thomas G. Warren.
Dec. 1, 2010 Notice of Taking Video Deposition of Diana McWilliams.
Defendants' Dec. 6, 2010 Response to Plaintiffs' Tenth Request for Production of Documents.
Defendants' Dec. 7, 2010 Objections to Amended Notice of Video Deposition of Diana McWilliams.
Defendants' Dec. 7, 2010 Objections to Amended Notice of Video Deposition of Thomas G. Warren.
Dec. 9, 2010 Supplemental Rule 26 Disclosures.
Plaintiffs' Dec. 10, 2010 30(b)(6) Notice of Deposition to Pfizer.
Dec. 14, 2010 Notice of Taking Video Deposition of Donald Robertson.
Dec. 14, 2010 Notice of Taking Video Deposition of Morris Robins.
Dec. 27, 2010 Plaintiffs' Eleventh Request for Production of Documents.
Jan. 5, 2011 Amended Notice of Taking Video Deposition of Morris Robins.
Plaintiffs' Jan. 5, 2011: (1) Disclosure of Expert Testimony Subject Areas and (2) Supplemental Disclosure of Percipient Witness Testimony Subject Areas.
Jan. 5, 2011 Amended Notice of Taking Video Deposition of J. Bevan Ott.
Jan. 5, 2011 Amended Notice of Taking Video Deposition of Gary Hooper.
Defendants' Jan. 5, 2011 Responses and Objections to Plaintiff's 30(b)(6) Notice of Deposition.
Defendants' Jan. 6, 2011 Notice of Service of Subpoena for Production of Documents and Things to Bristol—Myers Squib with the following exhibit: Ex. A: Subpoena for Production of Documents and Things to Bristol—Myers Squib.
Jan. 7, 2011 Notice of Taking Video Deposition of Gwen G. Krivi.
Jan. 7, 2011 Subpoena for the Deposition of Gwen G. Krivi.
Defendants' Jan. 7, 2011 Amended Responses and Objections to Plaintiff's 30(b)(6) Notice of Deposition.
Plaintiffs' Jan. 11, 2011 Fourth Set of Interrogatories to Defendants.
Plaintiffs' Jan. 11, 2011 Second Set of Requests for Admission to Defendants.
Plaintiffs' Jan. 11, 2011 Twelfth Request for Production of Documents.
Defendants' Jan. 12, 2011 Identification of Experts.
Defendants' Jan. 19, 2011 Second Set of Interrogatories (Nos. 15-27).
Defendants' Jan. 19, 2011 Second Set of Requests for Admission.
Defendants' Jan. 19, 2011 Seventh Set of Requests for Production (Nos. 1-10).
Plaintiffs' Jan. 19, 2011 Notice of Subpoenas for Production of Documents and Things.
Jan. 19, 2011 Subpoena for the Deposition of Frank A. Fitzpatrick, Ph.D.
Jan. 19, 2011 Subpoena for the Deposition of Lawrence J. Marnett.
Jan. 21, 2011 Notice of Taking Video Deposition of Dave Thomas.
Jan. 21, 2011 Notice of Taking Video Deposition of Steve Castle.
Jan. 21, 2011 Notice of Taking Video Deposition of Dr. Daniel L. Simmons.
Plaintiffs' Jan. 25, 2011 30(b)(6) Notice of Deposition to Pfizer.

Jan. 26, 2011 Subpoena for the Deposition of Elizabeth Harding.
Jan. 26, 2011 Subpoena for the Deposition of Morris Robins.
Defendants' Jan. 31, 2011 Response to Plaintiffs' Eleventh Request for Production of Documents.
Feb. 3, 2011 Amended Subpoena for the Rule 30(b)(6) Deposition of the Monsanto Company.
Feb. 4, 2011 Amended Notice of Taking Video Deposition of Brigham Young University Pursuant to Fed. R. Civ. P. 30(b)(6).
Defendants' Feb. 5, 2011 Responses and Objections to Plaintiff's 30(b)(6) Notice of Deposition to Pfizer.
Jan. 12, 2011 Notice of Taking Video Deposition of Brigham Young University Pursuant to Fed. R. Civ. P. 30(b)(6).
Defendants' Feb. 14, 2011 Responses to Plaintiffs' Fourth Set of Interrogatories.
Defendants' Feb. 14, 2011 Responses to Plaintiffs' Second Set of Requests for Admission.
Defendants' Feb. 14, 2011 Responses to Plaintiffs' Twelfth Request for Production of Documents.
Feb. 18, 2011 Supplemental Rule 26 Disclosures.
Plaintiffs' Feb. 18, 2011 Responses to Defendants' Second Set of Interrogatories.
Plaintiffs' Feb. 18, 2011 Responses to Defendants' Second Set of Requests for Admissions.
Plaintiffs' Feb. 18, 2011 Response to Defendants' Seventh Request for Production of Documents.
Mar. 2, 2011 Order Re: Briefing Schedule and Striking Current Scheduling Order.
Mar. 4, 2011 Order Re: Conduct Before the Court.
Mar. 8, 2011 Second Order Re: Briefing Schedule.
Plaintiff's Mar. 9, 2011 Motion to Compel Production of Sufficient Information to Allow Plaintiffs to Evaluate the Taint from Expert Rzucidlo Or, in the Alternative, to Disqualify Defendants' Counsel.
Mar. 9, 2011 Memorandum in Support of Plaintiffs' Motion to Compel Production of Sufficient Information to Allow Plaintiffs to Evaluate the Taint from Expert Rzucidlo Or, in the Alternative, to Disqualify Defendants' Counsel and the following exhibits: Ex. 4: Defendants' Identification of Experts Ex. 5: Mar. 2, 2011 *BYU* V. *Pfizer* Hearing Transcript Ex. 6: Declaration of Daniel L. Simmons Ex. 7: Declaration of David Thomas Ex. 8: Declaration of Leo R. Beus Ex. 9: Jul. 10, 1999 Consultancy Agreement between Dr. Simmons and Merck Ex. 10: Amended Declaration of Daniel L. Simmons Ex. 12: Declaration of John K. Morris.
Defendants' Mar. 16, 2011 Memorandum in Opposition to Plaintiffs' Motion to Compel and Motion to Disqualify and the following exhibits: Ex. 1: Mar. 2, 2011 *BYU* V. *Pfizer* Hearing Transcript Ex. 2: Defendants' Identification of Experts Ex. 3: Declaration of Brent O. Hatch in Support of Defendants' Memorandum in Opposition to Plaintiffs' Motion to Compel and Motion to Disqualify Ex. 4: Mar. 4, 2011 Letter to B. Hatch from M. Bettilyon Ex. 5: Plaintiffs': (1) Disclosure of Expert Testimony Subject Areas and (2) Supplemental Disclosure of Percipient Witness Testimony Subject Areas Ex. 6: Declaration of Richard T. Mulloy in Support of Defendants' Memorandum in Opposition to Plaintiffs' Motion to Compel and Motion to Disqualify Ex. 7: Declaration of Richard F. O'Malley in Support of Defendants' Memorandum in Opposition to Plaintiffs' Motion to Compel and Motion to Disqualify Ex. 8: Declaration of Eugene C. Rzucidlo Ex. 9: Declaration of Max D. Wheeler Ex. 10: Filed Under Seal.
Mar. 18, 2011 Notice of Status Regarding Plaintiffs' Motion to Compel Production of Sufficient Information to Allow Plaintiffs to Evaluate the Taint from Expert Rzucidlo or, in the Alternative, to Disqualify Defendants' Counsel and the following exhibit: Ex. A: Mar. 8, 2011 Email to B. Hatch from L. Beus regarding resolving the motion to disqualify.
Mar. 25, 2011 Memorandum in Support of Defendants' Request for Attorneys' Fees and Costs.
Mar. 25, 2011 Notice of Conventional Filing of Declaration of John C. Dougherty in Support of Defendants' Request for Attorneys' Fees and Costs and Declaration of Brent O. Hatch in Support of Defendants' Request for Attorneys' Fees and Costs.
Plaintiffs' Apr. 1, 2011 Response to Defendants' Request for Attorneys' Fees and Costs and the following exhibits: Ex. A: Amy Miller, *No More Baby Steps: Pfizer's Top Lawyer Is Out to Change All the Rules,* Corp. Counsel Online, Dec. 21, 2009. Katy Hopkins, *Legal Industry Faces Major Changes,* U.S. News & World Rep., Sep. 9, 2010. Ex. B: Mar. 3, 2011 Letter to Judge Wells from M. Bettilyon Ex. C: Declaration of John K. Morris Ex. D: 05-04 Utah Bar Ethics Advisory Opinions, Sep. 8, 2005.
Apr. 4, 2011 Joint Statement of the Parties Re: Apr. 7, 2011 Status Conference Ex. 01: Missing Documents or Tangible Things as of Apr. 4, 2011.
Apr. 6, 2011 Reply Memorandum in Support of Defendants' Request for Attorneys' Fees and Costs.
Defendants' Apr. 7, 2011 Statement in Support of Their *in Camera* Submission of Privileged Communications Between Pfizer and New Monsanto Inspection.
Apr. 8, 2011 Memorandum Submitting BYU's Privilege Documents for in Camera Review Ex. 01: Mar. 2, 2011 Hearing Transcript Ex. 02: Merrill Bateman Deposition, Oct. 22, 2010 Ex. 03: Daniel Simmons Deposition, Apr. 21, 2009 Ex. 04: Gary Hooper Deposition, Jan. 20, 2011.
Additional Exhibits in Support of Apr. 8, 2011 Memorandum Submitting BYU's Privilege Documents for In Camera Review Ex. 01: Excerpt from Plaintiffs' Opposition, Feb 22, 2011 and Letter to Dr. Hooper Ex. 02: Jun. 24, 1999 Email to Dr. Simmons from Tammy Gustin Ex. 03: Jun. 4, 2007 Memo to Dr. Simmons from Dr. Woolley Ex 06: Nov. 5, 1992 Email from Lynn Astle Ex. 08: Dec. 14, 1992 letter to Dr. Simmons from Ms. Hardman.
Apr. 8, 2011 Declaration of Daniel L. Simmons.
Apr. 8, 2011 Notice of Conventional Filing of Declaration of Michael Orme.
Apr. 12, 2011 Notice of Conventional Filing of Response to Plaintiffs' Memorandum Submitting BYU's Privileged Documents for *in Camera* Review.
BYU's Apr. 15, 2011 Response to Defendants' Statement in Support of Their *in Camera* Submission of Privileged Communications Between Pfizer and New Monsanto (Redacted Version) Ex. 01: Oct. 8, 2008 Letter to L. Williams from N. Wyland Ex. 02: Jul. 29, 2008 Letter to L. Williams from L. Schneider Ex. 03: Apr. 8, 2009 Hearing Transcript Ex. 04: Oct. 4, 2010 Letter to A. Anderson from K. Owen.
Apr. 15, 2011 Notice of Conventional Filing of BYU's Response to Defendants' Statement in Support of Their *In Camera* Submission of Privileged Communications Between Pfizer and New Monsanto (Unredacted Version).
BYU's Apr. 15, 2011 Reply Re Privileged Documents Submitted for in Camera Review.
Amended Apr. 8, 2011 Subpoena to The Monsanto Company.
Mar. 3, 2011 Letter to Magistrate Judge Wells from M. Bettilyon.
Mar. 4, 2011 Letter to Magistrate Wells from B. Hatch in Response to Letter of M. Bettilyon.
Defendants' Apr. 22, 2011Reply to BYU's Responses to Defendants' Statement in Support of Their *In Camera* Submission of Privileged Communications Between Pfizer and New Monsanto.
Apr. 26, 2011 Ex Parte Motion for Leave to File Supplemental Response to Memorandum Submitting BYU's Documents for *In Camera Review*.
May 5, 2011 Amended Scheduling Order.
May 5, 2011 Order Granting Ex Parte Motion for Leave to File Supplemental Response to Memorandum.
May 5, 2011 Motion for Partial Summary Judgment Dismissing Plaintiffs' Claims for Breach of Contract of Paragraphs 3.3 and 3.4 of the Research Agreement.
May 5, 2011 Memorandum in Support of Motion for Partial Summary Judgment Dismissing Plaintiffs' Claims for Breach of Contract of Paragraphs 3.3 and 3.4 of the Research Agreement, including the following Exhibits: Ex. 01. Research AgreementEx, 02: Research Proposal to the Monsanto Company by Daniel L. Simmons, Apr. 5, 1991.
May 5, 2011 Motion for Partial Summary Judgment Re: Paragraph 3.3 of the Research Agreement.
May 5, 2011 Notice of Conventional Filing of Memorandum in Support of Motion for Partial Summary Judgment re: Paragraph 3.3 of the Research Agreement.
May 9, 2011 Joint Statement of the Parties re: May 12, 2011 Status Conference.

May 10, 2011 Order Granting Pro Hac Vice Admission to William F. Lee.
May 10, 2011 Order Granting Pro Hac Vice Admission to Amy K Wigmore.
May 10, 2011 Notice of Appearance by Phillip J. Russell.
May 12, 2011 Order from Apr. 7, 2011 Status Conference.
Apr. 18, 2011 Declaration of Michael S. Wigotsky Regarding Plaintiffs' Access to Biological Materials Stored at Lancaster Laboratories, Feb. 8-9, 2011.
Apr. 18, 2011 Declaration of Stephen M. Craig.
Plaintiffs' May 16, 2011 Supplemental Memorandum Regarding Biological Materials and the following exhibits: Ex. 1: Sep. 24, 2010 Letter to Ms. Owen from Mr. Anderson Ex. 2: May 11, 2009 Letter to Mr. Ricker from Mr. Spanbauer Ex. 3: Oct. 2, 2010 Letter to Mr. Anderson from Ms. Hamilton Ex. 5: Jan. 18, 2011 Letter to Mr. Mulloy from Mr. Ricker.
May 16, 2011 Notice of Conventional Filing of Exhibit 6 to Plaintiffs' Supplemental Memorandum Regarding Biological Materials.
May 18, 2011 Response to and Motion to Strike Plaintiffs' May 16, 2011 Supplemental Memorandum Regarding Biological Materials and the following exhibits: Ex. 1: Declaration of Michael S. Wigotsky Regarding Plaintiffs' Access to Biological Materials Stored at Lancaster Laboratories, Feb. 8-9, 2011 Ex. 2: May 21, 2008 Letter to Mr. Ricker from Mr. Spanbauer Ex. 3: May 11, 2009 Letter to Mr. Ricker from Mr. Spanbauer Ex. 5: Jun. 1, 2010 Letter to Mr. Williams from Mr. Hankinson Ex. 6: Jun. 11, 2010 Letter to Mr. Williams from Mr. Hankinson Ex. 7: Sep. 28, 2010 Letter to Mr. Anderson from Ms. Owen Ex. 8: Oct. 26, 2010 Letter to Mr. Anderson from Ms. Hamilton Ex. 9: May 11, 2011 Letter to Mr. Ricker from Ms. Owen.
May 18, 2011 Notice of Conventional Filing of Exhibit 4 to Response to and Motion to Strike Plaintiffs' May 16, 2011 Supplemental Memorandum Regarding Biological Materials.
Plaintiffs' May 25, 2011 Plaintiffs' Memorandum in Opposition to Defendants' Motion to Strike.
Plaintiffs' May 19, 2011 Amended 30(b)(6) Notice of Deposition to Pfizer.
BYU's May 20, 2011 Responses and Objections to Defendants' 30(b)(6) Notice of Deposition.
May 23, 2011 Amended Subpoena in a Civil Case to The Monsanto Company.
Defendants' May 24, 2011 Responses and Objections to Plaintiffs' Amended 30(b)(6) Notice of Deposition to Pfizer.
Jun. 7, 2011 Stipulated Motion for Extension of Time for Plaintiffs to respond to Defendants' Motions for Partial Summary Judgment Attachment: Proposed Order.
Jun. 8, 2011 Order granting Stipulated Motion for Extension of Time for Plaintiffs to respond to Defendants' Motions for Partial Summary Judgment.
Jun. 8, 2011 Reply Memorandum in Support of Motion to Strike Plaintiffs' May 16, 2011 Supplemental Memorandum Regarding Biological Materials.
Plaintiffs' Jun. 17, 2011 Opposition to Defendants' Motion for Partial Summary Judgment on Plaintiffs' Claims for Breach of Paragraphs 3.3 and 3.4 of the Research Agreement along with the following Exhibits: Ex. 1: Apr. 9, 1991 Letter to D. Simmons from P. Needleman re housekeeping details Ex. 2: Research Agreement, Aug. 1, 1991 Ex. 3: Mar. 23, 1992 Letter to Simmons from Needleman re chicken bleed and grant/award Ex. 4: Apr. 5, 1991 Research Proposal to Monsanto by Simmons Ex. 5: Ex. 7: Witness Statement of Peter Clyde Isakson, *Monsanto* v *Merck,* Aug. 23, 1999 Ex. 9: Feb. 15, 1991 Email from R. Wiegand to P. Needleman re: Karen Seibert Ex. 10: Declaration of Dr. Daniel Simmons, Jun. 1, 2009 Ex. 11: Oct. 19, 1989 Letter to E. Woolley from D. Simmons enclosing enzyme sequences Ex. 12: FDA transcript of open public hearing on Dec. 1, 1998 Ex. 14: Daniel Simmons Deposition, Univ. of Rochester, vol. 1, Jul. 16, 2002 Ex. 15: Daniel Simmons' Deposition, vol. 2, Apr. 21, 2009 Ex. 16: Apr. 1, 1991 Letter to A. Raz from P. Needleman Ex. 21: Larry Swaney Deposition, Jun. 25, 2009 Ex. 22: Apr. 11, 1991 letter to Simmons from Swaney Ex. 23: Weilen Xie Deposition, Mar. 27, 2009 Ex. 24: Apr. 29, 1991 Letter to K. Seibert and J. Masferrer from D. Simmons Ex. 25: Fax to K. Seibert from D. Simmons, handwritten notes dated Apr. 29, 1991 Ex. 26: Philip Needleman Deposition, vol. 1, Nov. 17, 2010 Ex. 29: May 16, 1991 Letter to Simmons from Needleman re: grant Ex. 30: May 21, 1991 letter to Simmons from Swaney re: revised draft agreement Ex. 31: May 23, 1991 Letter to P. Needleman from Simmons re: NIH grant proposal Ex. 33: Fax from K. Siebert to D. Simmons, Jun. 10, 1991 Ex. 34: Lynn Astle Deposition, Feb. 17, 2009 Ex. 35: Jun. 14, 1991 Letter to L Swaney from L. Astle re suggestions for proposed research contract Ex. 36: Jun. 20, 1991 Fax to D. Simmons/L. Astle from L. Swaney re: changes Ex. 37: Jun. 24, 1991 Letter to L. Swaney from L. Astle re: Appendix A of research agreement Ex. 38: Jun. 25, 1991 Memo to P. Needleman from L. Swaney re: Simmons App. A Ex. 39: Jul. 3, 1991 Letter to L. Astle from L. Swaney re: research agreement Ex. 40: Jul. 9, 1991 letter to Swaney from Carol Hardman, BYU encl. executed agreement Ex. 41: Daniel Simmons Deposition, vol. 1, Apr. 20, 2009 Ex. 42: Michael Orme Deposition, Nov. 15, 2007 Ex. 43: Stephen Craig Deposition, May 24, 2011 Ex. 44: Mar. 9, 1992 Email to S. Adams re: Peptide Synthesis Ex. 45: Jul. 17, 1991 handwritten notes to D. Simmons from K. Seibert re: RNA samples Ex. 51: Mar. 17, 1992 Letter to Simmons from Needleman re: No Feedback From You Ex. 52: Mar. 20, 1991 Letter to P. Needleman from D. Simmons with Mar. 20, 1992 Progress Report Ex. 53: May 20, 1992 Letter to P. Needleman from D. Simmons with Post-Termination Report, May 20, 1992 Ex. 54: Sep. 2, 1992 Letter to P. Needleman from C. Hardman, BYU re research agreement completion Ex. 55: U.S Appl. No. 08/004,822 (filed Jan. 15, 1993) Ex. 56: U S. Patent No. 5,466,823 (filed Nov. 30, 1993).
Plaintiffs' Jun. 17, 2011 Response in Opposition to Defendants' Motion for Partial Summary Judgment Re Paragraph 3.3 of the Research Agreement and the following Exhibits: Ex. 2: Michael Orme Deposition, Nov. 15, 2007 Ex. 3: Lynn Astle Deposition, Feb. 17, 2009 Ex. 4: Stephen Craig Deposition, May 24, 2011 Ex. 7: Larry Swaney, Jun. 25, 2009 Ex. 8: Research Agreement, dated Aug. 1, 1991, executed by P. Needleman Ex. 10: Declaration of Daniel Simmons with exhibits, Jun. 17, 2011 Ex. 13: U.S. Patent No. 4,820,827 (filed Feb. 10, 1984) Ex. 17: U.S. Patent No. 5,466,823 (filed Nov. 30, 1993) Ex. 18: Declaration of Vern Norviel in *BYU* v. *Pfizer,* Jun. 17, 2011.
Jun. 17, 2011 Notice of Conventional Filing of Exhibits Filed Under Seal to Plaintiffs' Opposition to Defendants' Motion for Partial Summary Judgment on Plaintiffs' Claims for Breach of Paragraphs 3,3 and 3.4 of the Research Agreement as to the following exhibits: Ex. 6: Jan. 11, 1991 letter to Seibert and Masferrer from Needleman re working group Ex. 8: Jaime Masferrer Deposition, Merck Frosst litigation, Dec. 12, 2000 Ex. 17: JaimeMasferrer Deposition Teva litigation, Dec. 13, 2005 Ex. 18: Karen Seibert Deposition, Merck Frosst litigation, Oct. 17, 2000 Ex. 19: Karen Seibert Deposition, vol. 2, Jun. 2, 2010 Ex. 20: Karen Seibert Deposition, vol. 1, Jun. 1, 2010 Ex. 27: Prescott Expert Report, Feb. 18, 2011 Ex. 46: Karen Seibert Deposition, Teva litigation, Jan. 11, 2006 Ex. 47: Feb. 6, 1992 Email to D. Corley, et al. from K. Leahy Ex. 48: Len Lee notebook #21, Feb. 14, 1992 Ex. 49: Jaime Masferrer notebook 5,043,201, Feb. 5, 1992 Ex. 50: Disclosure of Invention—Lee, Jun. 24, 1992 Ex. 57: Sep. 10, 1991 Fax to S. Hauser from K. Seibert.
Jun. 17, 2011 Notice of Conventional Filing of Exhibits Filed Under Seal to Plaintiffs' Opposition to Defendants' Motion for Partial Summary Judgment re Paragraph 3.3 of the Research Agreement as to the following exhibits: Ex. 1: John Morris Expert Report, Feb. 18, 2011 Ex. 5: Needleman Univ. of Rochester deposition transcript excerpt, Aug. 9, 2002 Ex. 6: Needleman *BYU* v. *Pfizer* deposition transcript excerpt, Nov. 17, 2010 Ex. 9: Simmons' Amended and Supplemental Expert Report—Jun. 10, 2011 Ex. 11: Vern Norviel Expert Report, Feb. 18, 2011 Ex. 12: Prescott Expert Report, Feb. 18, 2011 Ex. 14: Declaration of John Talley, Apr. 9, 2002 Ex. 15: First Witness Statement of William Galbraith, Aug. 23, 1999 Ex. 16: Edward Lentz Expert Report, Feb. 18, 2011.
BYU's Jun. 1, 2011 Responses and Objections to Defendants' 30(b)(6) Notice of Deposition.
Jun. 23, 2011 Memorandum Decision and Order Granting in Part Plaintiffs' Motion to Compel Documents Submitted for in Camera Review.
Jun. 30, 2011 Memorandum Decision and Order Denying Plaintiffs' Request Regarding Materials and Deeming Moot Defendants' Motion to Strike.

Jul. 5, 2011 Stipulated Motion for Extension of Time to File Reply Memoranda in Support of Defendants' Motion for Summary Judgment and the following Exhibit: Exhibit A: Proposed Order.
Jul. 5, 2011 Order Granting Stipulated Motion for Extension of Time to File Reply Memoranda in Support of Defendants' Motions for Summary Judgment.
Jul. 8, 2011 Motion to Strike Portions of Plaintiffs' Opposition to Defendants' Motion for Partial Summary Judgment Regarding Breach of Contract of Paragraphs 3.3 and 3.4 of the Research Agreement.
Jul. 8, 2011 Memorandum in Support of Motion to Strike Portions of Plaintiffs' Opposition to Defendants' Motion for Partial Summary Judgment Regarding Breach of Contract of Paragraphs 3.3 and 3.4 of the Research Agreement.
Jul. 8, 2011 Motion to Strike Portions of Plaintiffs' Opposition to Defendants' Motion for Partial Summary Judgment Re: Paragraph 3.3 of the Research Agreement.
Jul. 8, 2011 Memorandum in Support of Motion to Strike Portions of Plaintiffs' Opposition to Defendants' Motion for Partial Summary Judgment Re: Paragraph 3.3 of the Research Agreement.
Jul. 8, 2011 Reply Memorandum in Support of Motion for Partial Summary Judgment Dismissing Plaintiffs' Claims for Breach of Contract of Paragraphs 3.3 and 3.4 of the Research Agreement; Attachment 1 to Reply Memorandum in Support of Motion for Partial Summary Judgment Dismissing Plaintiffs' Claims for Breach of Contract of Paragraphs 3.3 and 3.4 of the Research Agreement Ex. A: Stephen Craig Dep. Tr., May 24, 2011 Ex. B: May 6, 1991 Letter. to Dr. Needleman from Dr. Simmons.
Jul. 8, 2011 Reply Memorandum in Support of Defendants' Motion for Summary Judgment Regarding Paragraph 3.3 of the Research Agreement; Attachment 1 to Reply Memorandum in Support of Defendants' Motion for Summary Judgment Regarding Paragraph 3.3 of the Research Agreement Ex. A: Stephen Craig Dep. Tr., May 24, 2011 Ex. C: May 21, 1991 Letter to Dr. Simmons from Ms. Swaney Ex. D: Lynn Astle Dep. Tr., Feb. 17, 2009 Ex. E: Daniel Simmons Dep Tr., Jun. 20, 2009.
Excerpted page from Judy Lewis Jun. 2, 2009 deposition transcript.
Dec. 2009 Joint Status Memo, Exhibits P4-P8.
Dec. 2009 Joint Status Memo, Exhibit P13.
Dec. 2009 Joint Status Memo, Exhibits P18-P20.
Oct. 1, 2009 letter from Wyland to Anderson.
Dec. 2009 Joint Status Memo, Exhibits D4-D10.
Dec. 2009 Joint Status Memo, Exhibits D16-D18.
Defendants' Motion for Hearing re To Amend The Discovery Plan (dated Jan. 21, 2010).
Notice of conventional filing of Defendants' Memorandum in Support of Their Motion for a Hearing to Amend the Discovery Plan dated Jan. 22, 2010.
Notice of Withdrawal of Pfizer's Motion for Partial Summary Judgment That Dr. Simmons Is Not an Inventor of the Patents Listed in Count IV of Plaintiffs' Complaint dated Feb. 5, 2010.
Stipulated Motion for Extension of Time in which to respond to the Motion for Hearing to Amend Discovery Plan dated Feb. 5, 2010.
Feb. 5, 2010 Order granting Motion for Extension of Time.
Motion for Admission Pro Hac Vice of John Caleb Dougherty dated Feb. 10, 2010.
Exhibits A, B and C to Motion for Admission Pro Hac Vice of John Caleb Dougherty dated Feb. 10, 2010.
Motion for Admission Pro Hac Vice of Dan K. Webb dated Feb. 10, 2010.
Exhibits A, B and C to Motion for Admission Pro Hac Vice of Dan K. Webb dated Feb. 10, 2010.
Order granting pro hac vice admission of John C. Dougherty dated Feb. 10, 2010.
Notice of Errata to Motion for Pro Hac Vice Admission and Consent of Local Counsel of Dan K. Webb by Pfizer dated Feb. 11, 2010.
D. Utah electronic case filing registration form for D. Webb dated Feb. 9, 2010.
Order granting 336 Motion for Admission Pro Hac Vice of Dan K. Webb dated Feb. 11, 2010.
Motion and Consent of Sponsoring Local Counsel for Admission Pro Hac Vice of Mark C. Dangerfield dated Feb. 18, 2010.
Exhibits A, B, C and D to Motion and Consent of Sponsoring Local Counsel for Admission Pro Hac Vice of Mark C. Dangerfield dated Feb. 18, 2010.
Order granting Motion for Admission Pro Hac Vice of Mark C. Dangerfield dated Feb. 18, 2010.
Defendants' Motion for Protective Order Regarding Marketing Practices Litigation dated Mar. 5, 2010.
Defendants' Memorandum in Support of Motion for Protective Order Regarding Marketing Practices Litigation dated Mar. 5, 2010.
Defendants' Motion for Protective Order Regarding Post-2001 Documents dated Mar. 8, 2010.
Defendants' Memorandum in Support of Motion for Protective Order Regarding Post-2001 Documents dated Mar. 8, 2010.
Exhibits 1-4 to Defendants' Memorandum in Support of Motion for Protective Order Regarding Post-2001 Documents dated Mar. 8, 2010.
Redacted Plaintiffs' Memorandum in Opposition to Defendants' Motion for a Hearing to Amend the Discovery Plan dated Mar. 8, 2010.
Exhibits 1-12 to Redacted Plaintiffs' Memorandum in Opposition to Defendants' Motion for a Hearing to Amend the Discovery Plan dated Mar. 8, 2010.
Notice of conventional filing of Plaintiffs' Memorandum in Opposition to Defendants' Motion for a Hearing to Amend the Discovery Plan dated Mar. 8, 2010.
Redacted Plaintiffs' Memorandum in Support of Motion for Dispositive Sanctions dated Mar. 10, 2010.
Public Exhibits to Redacted Plaintiffs' Memorandum in Support of Motion for Dispositive Sanctions dated Mar. 10, 2010.
Plaintiffs' Motion for Dispositive Sanctions dated Mar. 10, 2010.
Notice of conventional filing of Unredacted Version of Memorandum in Support of Motion for Dispositive Sanctions dated Mar. 10, 2010.
Order Denying Without Prejudice Defendants Motion for a Protective Order dated Mar. 12, 2010.
Motion for Admission Pro Hac Vice of Richard T. Mulloy dated Mar. 12, 2010.
Exhibits A, B and C to Motion for Admission Pro Hac Vice of Richard T. Mulloy dated Mar. 12, 2010.
Motion for Admission Pro Hac Vice of Kahty Owen dated Mar. 12, 2010.
Exhibits A, B and C to Motion for Admission Pro Hac Vice of Kahty Owen dated Mar. 12, 2010.
Plaintiffs' Notice of Third Party Subpoena for Production of Documents dated Mar. 15, 2010.
Order for Pro Hac Vice Admission of Richard T. Mulloy dated Mar. 15, 2010.
Order for Pro Hac Vice Admission of Kathy J. Owen dated Mar. 16, 2010
Stipulated motion to amend protective order dated Mar. 19, 2010.
Proposed amended protective order dated Mar. 19, 2010.
Amended Protective Order dated Mar. 16, 2010.
Motion for Admission Pro Hac Vice of Raymond C. Perkins dated Mar. 12, 2010.
Exhibits A, B and C to Motion for Admission Pro Hac Vice of Raymond C. Perkins dated Mar. 12, 2010.
Order granding pro hac vice admission of Raymond C. Perkins dated Mar. 22, 2010.
Stipulated motion for extension of time dated Mar. 23, 2010.
Proposed order granting stipulated motion for extension of time dated Mar. 23, 2010.
Order granting stipulated motion for extension of time dated Mar. 24, 2010.
Defendants' reply memorandum in support of motion or a hearing to amend the discovery plan dated Mar. 25, 2010.
Order Denying Without Prejudice Defendants Motion for a Protective Order dated Mar. 25, 2010.
Notice of conventional filing of Exhibits 2 and 3 to Defendants' reply memorandum in support of motion for a hearing to amend the discovery plan dated Mar. 25, 2010.
Exhibits 2 and 3 to Defendants' reply memorandum in support of motion for a hearing to amend the discovery plan dated Mar. 25, 2010.
Notice of withdrawal of exhibit dated Mar. 31, 2010.

Notice of conventional filing of BYU's motion to disqualify Winston & Strawn LLP and related documents dated Mar. 31, 2010.
Redacted Plaintiffs' opposition to Defendants' motion for a protective order regarding post-2001 documents dated Apr. 9, 2010.
Public Exhibits 1-25 to Plaintiffs' opposition to Defendants' motion for a protective order regarding post-2001 documents dated Apr. 9, 2010.
Notice of conventional filing of unredacted version of Plaintiffs' opposition to Defendants' motion for a protective order regarding post-2001 documents dated Apr. 9, 2010.
Redacted Plaintiff's memorandum in Opposition to motion for Protective Order Regarding Marketing Practices Litigation dated Apr. 9, 2010.
Public Exhibits 1-31 of Redacted Plaintiff's memorandum in Opposition to motion for Protective Order Regarding Marketing Practices Litigation dated Apr. 9, 2010.
Notice of conventional filing of Plaintiff's memorandum in Opposition to motion for Protective Order Regarding Marketing Practices Litigation dated Apr. 12, 2010.
Plaintiff's motion for Extension of Time Amend Complaint dated Apr. 12, 2010.
Exhibits 1 and 2 to Plaintiff's motion for Extension of Time Amend Complaint dated Apr. 12, 2010.
Order granting Motion for Extension of Time dated Apr. 19, 2010.
Second Amended Protective Order dated Apr. 19, 2010.
Stipulated motion for Extension of Time for Defendants to file their Opposition to Plaintiffs' Motion for Dispositive Sanctions and proposed order dated Apr. 22, 2010.
Order granting Motion for Extension of Time dated Apr. 23, 2010.
Reply to Response to Motion re motion for Protective Order Regarding Marketing Practices Litigation dated Apr. 26, 2010.
Notice of Conventional Filing of Defendants Reply Memorandum in Support of Their Motion for a Protective Order Regarding Post 2001 Documents dated Apr. 26, 2010.
Redacted Reply to Response to Motion re Protective Order Regarding Post-2001 Documents dated Apr. 26, 2010.
Exhibits 1, 2, 3, 8, 9, 10 and 11 to Reply to Response to Motion re motion for Protective Order Regarding Marketing Practices Litigation dated Apr. 26, 2010.
Memorandum in Opposition to Plaintiffs' motion for Extension of Time Amend Complaint dated Apr. 29, 2010.
Stipulated Motion to Intervene for a Limited Purpose filed by Movant Winston & Strawn with proposed order dated Apr. 30, 2010.
Defendants' motion for leave to file an overlength opposition to Plaintiffs' motion for dispositive sanctions with proposed order dated Apr. 30, 2010.
Order granting Motion to Intervene dated May 3, 2010.
Motion for Admission Pro Hac Vice of Kristin S. Escalante dated May 3, 2010.
Exhibits A, B and C to Motion for Admission Pro Hac Vice of Kristin S. Escalante dated May 3, 2010.
Motion for Admission Pro Hac Vice of Brad D. Brian dated May 3, 2010.
Exhibits A, B and C to Motion for Admission Pro Hac Vice of Brad D. Brian dated May 3, 2010.
Motion for Admission Pro Hac Vice of Stuart N. Senator dated May 3, 2010.
Exhibits A, B and C to Motion for Admission Pro Hac Vice of Stuart N. Senator dated May 3, 2010.
Amended Scheduling Order dated May 3, 2010.
Order regarding hearing set for May 7, 2010.
May 20, 2010 letter from A. Anderson L. Schneider.
Notice of Deposition of Brigham Young University Pursuant to Fed. R. Civ. P. 30(b)(6) dated Dec. 14, 2009.
Notice of Deposition of Brigham Young University Pursuant to Fed. R. Civ. P. 30 (b)(6) dated Jan. 13, 2010.
Plaintiffs' Notice of Taking Video Deposition of Karen Seibert (Jun. 1 through Jun. 3, 2010).
Plaintiffs' Notice of Taking Video Deposition of Shaukat Rangwala (Jun. 23, 2010).
Plaintiffs' Notice of Taking Video Deposition of Tom Warren (Jul 1, 2010).
Plaintiffs' Notice of Taking Video Deposition of Beverly Reitz (Jul. 2, 2010).
Plaintiffs' Notice of Taking Video Deposition of Kathleen Leahy and Subpoena (Jul. 16, 2010).
Defendants' Notice of Taking Video Deposition of Steven A. Fleming (Jun. 15, 2010).
Defendants' Notice of Taking Video Deposition of Brigham Young University Pursuant to Fed. R. Civ. P. 30 (b)(6) (Jul. 14, 2010).
Defendants' Notice of Taking Video Deposition of Denis Callewaert and Subpoena (Jul 28, 2010).
Plaintiffs' Amended Notice of Taking Video Deposition of Jaime Masferrer (Jul. 22 and Jul. 23, 2010).
Plaintiffs' Amended Notice of Taking Video Deposition of Shaukat Rangwala (Jun. 23, 2010).
Plaintiffs' Amended Notice of Taking Video Deposition of Beverly Reitz (Jul. 1, 2010).
Oct. 31, 2002 Letter to Olson from Schneider.
Mar. 23, 1992 Letter to Simmons from Needleman.
(Exhibit 278) Article: Jaime L. Masferrer, et al., "Selective Regulation of Cellular Cyclooxygenase by Dexamethasone and Endotoxin in Mice," The American Society for Clinical Investigation, Inc., vol. 86, Oct. 1990, pp. 1375-1379.
(Exhibit 293) Sep. 17, 1999 Hansen Letter to the Nomination Committee for the Edgar M. Queeny Award w/Attachment.
(Exhibit 305) Article: Toshifumi Tetsuka et al., "Antioxidants Inhibit Interleukin-1-induced Cyclooxygenase and Nitric-oxide Synthase Expression in Rat Mesangial Cells", The Journal of Biological Chemistry, vol. 271, No. 20, May 17, 1996, pp. 11689-11693.
(Exhibit 309) May 27, 1997 U.S. Patent 5,633,272—Substituted Isoxazoles for the Treatment of Inflammation, Inventors: J.J. Talley, et al.
(Exhibit 312) Document titled, "7th International Conference on Prostaglandins and Related Compounds, Florence (Italy), May 28-Jun. 1, 1990 Abstract Book" (cover page), attaching several abstracts.
(Exhibit 315) Article: Dean A. Kujubu et al., "TIS10, a Phorbol Ester Tumor Promoter-inducible mRNA from Swiss 3T3 Cells, Encodes a Novel Prostaglandin Synthase/Cyclooxygenase Homologue", The Journal of Biological Chemistry, vol. 266, No. 20, Jul. 15, 1991, pp. 12866-12872.
James Gierse Dec. 2, 2009 30(b)(6) deposition transcript.
Exhibits 223-224 to James Gierse Dec. 2, 2009 30(b)(6) deposition transcript.
Jun. 15, 2010 deposition transcript of Steven Fleming.
Exhibits 120A and 317-318.
(Exhibit 320) Internet Article: "Mogene expects to double revenue," St. Louis Business Journal, Aug. 25, 2009.
(Exhibit 325) Feb. 2, 2010 U.S. Patent No. 7,655,777 B2 Re: Nucleic Acid Molecules Associated With The Tocopherol Pathway; Inventors: S. Rangwala, et al.; Assignee: Monsanto Technology LLC.
Jul. 12, 2011 Notice of Appearance of James S. Jardine.
Jul. 13, 2011 Order Reagrding Additional Documents Submitted by Defendants for In-Camera review.
Jul. 14, 2011 Memorandum Decision and order Granting in Part Defendants' Motion to Compel Documents Submitted for In-Camera Review.
Jul. 22, 2011 Motion and Consent of Sponsoring Local counsel for *Pro Hac Vice* Admission of Britton M. Worthen; Proposed Order and the following exhibits: Exhibit A: Certificate of Good Standing Exhibit B: Application for Admission *Pro Hac Vice* Exhibit C: Electronic Case Filing Registration Form:
Jul. 26, 2011 Order for *Pro Hac Vice* Admission of Britton M. Worthen.
Jul. 26, 2011 Response in Opposition to Defendants' Motion to Strike Portions of Plantiffs' Statement of Material Facts in Opposition to Defendants' Motion for Partial Summary Judgement on Paragraphs 3.3 and 3.4 of the Research Agreement.
Jul. 26, 2011 Response in Opposition to Defendants' Motion to Strike Portions of Plaintiffs' Statement of Material Facts in Opposition to Defendants' Motion for Partial Summary Judgement on Paragraph 3.3 of the Research Aggreement.
Aug. 4, 2011 Order Requesting Additional Briefing.

Aug. 4, 2011 Motion to Correct/Add Citations in Plaintiffs' Opposition to Defendants' Motion for Partial Summary Judgment on Plaintiffs' Claims for Breach of Paragraphs 3.3 and 3.4 of the Research Agreement.
Aug. 4, 2011 Memorandum in Support of Motion to Correct/Add Citations in Plaintiffs' Opposition to Defendants' Motion for Partial Summary Judgment on Plaintiffs' Claims for Breach of Paragraphs and 3.4 of the Research Agreement.
Aug. 4, 2011 Notice of Errata relating to paragraph numbering in Plaintiffs' Response in Opposition to Defendants' Motion for Partial Summary Judgment on Plaintiffs' Claims for Breach of Paragraphs of the research Agreement.
Aug. 4, 2011 Errata to Plaintiffs' Response in Opposition to Defendants' Motion for Partial Summary Judgment on Plaintiffs' Claims for Breach of Paragraph 3.3 of the Research Agreement.
Aug. 12, 2011 Reply Memorandum in Support of Motion to Strike Portions of Plaintiffs' Opposition to Defendants' Motion for Partial Summary Judgment Re: Paragraph 3.3 and 3.4 of the Research Agreement.
Aug. 12, 2011 Reply Memorandum in Support of Motion to Strike Portion of Plaintiffs' Opposition to Defendants' Motion for Partial Summary Judgment Re: Paragraph 3.3 of the Research Agreement.
Aug. 15, 2011 Plaintiffs' Supplemental Brief Regarding Application of the Latent Ambiguity Doctrine, including the following exhibit: Exhibit 4: Oct. 29, 1991 Letter to Dr. Raz from Dr. Needleman.
Aug. 15, 2011 Notice of Conventional Filing of Exhibits 1 through 3 to Plaintiffs' Supplemental Brief Regarding Application of the Latent Ambiguity Doctrine.
Aug. 15, 2011 Defendants' Supplemental Memorandum Re: Issue of Latent Ambiguity As Applied to Defendants' Motion for Partial Summary Judgment.
Aug. 26, 2011 Motion for Partial Summary Judgment Regarding Count III (Breach of Fiduciary Duty) of Plaintiff's First Amended Complaint.
Aug. 26, 2011 Notice of Conventional Filing of Memorandum in Support of Defendants' Motion for Partial Summary Judgment Regarding Count III (Breach of Fiduciary Duty) of Plaintiff's First Amended Complaint and Exhibits.
Sep. 2, 2011 Supplemental Memorandum in Opposition to Defendants' Motion for Partial Summary Judgment Re: Paragraph 3.3 of the Research Agreement and the following Exhibits: Exhibit A: Excerpts of deposition of Stephen Craig, May 24, 2011 Exhibit B: Excerpts of Deposition of Karen Seibert, Jun. 3, 2010.
Sep. 6. 2011 Motion for Pro Hac Vice Admission and Consent of Local counsel of Andrea Weiss Jeffries.
Sep. 6, 2011 Motion for Pro Hac Vice Admission and Consent of Local Counsel Amanda L. Major.
Sep. 6, 2011 Motion for Pro Hac Vice Admission and Consent of Local Counsel James L. Quarles III.
Sep. 6, 2011 Motion for Pro Hac Vice Admission and Consent of Local Counsel Donald W. Ward.
Sep. 6, 2011 Order for Pro Hac Vice Admission of Andrea Weiss Jeffries.
Sep. 6, 2011 Order for Pro Hac Vice Admission of Amanda L. Major.
Sep. 6, 2011 Order for Pro Hac Vice Admission of James L. Quarles III.
Sep. 6, 2011 Order for Pro Hac Vice Admission of Donald W. Ward.
Sep. 9, 2011 Notice of Appearance of Counsel Kevin W. Bates.
Sep. 12, 2011 Motion for Pro Hac Vice Admission and Consent of Local Counsel of Emil R. Whelan.
Sep. 12, 2011 Order for Pro Hac Vice Admission of Emily R. Whelan.
Sep. 19, 2011 Defendants' Supplemental Memorandum in Support of Motion for Summary Judgment Regarding Paragraph 3.3 of the Research Agreement.
Sep. 29, 2011 Consolidated Memorandum in Opposition to Defendants' Motion for Partial Summary Judgment Regarding Count III (Breach of Fiduciary Duty) Plaintiffs' First Amended Complaint, And in Support of Plaintiffs' Cross Motion for Partial Summary Judgment Appendix A. Ex 1: Declaration of Daniel L. Simmons, Jun. 17, 2011 Ex. 2. Research Agreement between BYU and Monsanto Company, effective Aug. 1, 1991 Ex. 3 Dr. Philip Needleman Dep. 1; 516-523, *University of Rochester* v. *G. D. Searle & Co., et al.*, Aug. 9, 2002 Ex. 4: Philip Needleman, Ph D. Dep. 1-4, 145-148. 165-172, 201-204, Nov. 17, 2010 Ex. 5: Expert Report of John Morris, Feb. 18, 2011 Ex. 6. Expert Report of James A. Severson, Ph.D., Jul. 25, 2011 Ex. 7: Lynn Astle Dep. 1; 6-17; 22-25; 54-57; 106-109; 138-141; 146-149, Feb. 17, 2009 Ex. 8: Michael Orme Dep. 1; 18-25; 42-45; 62-65; 74-77; 130-133, Nov. 15, 2007 Ex. 9: Expert Report by Edward T. Lentz, Aug. 25, 2011 Ex. 10: Oct. 19, 1989 Letter to E. Woolley from D. Simmons Ex. 11: Dec. 10, 1998 Letter to G. Hooper from D. Simmons Ex. 12: Amended and Supplemental Expert Report by Daniel L. Simmons, Ph.D. Excerpts, Jun. 10, 2011 Ex. 13: Daniel L. Simmons, Ph.D. Dep. 1-4; 37-44; 149-152; 177-180, *University of Rochester* v. *G. D. Searle & Co., et al*, Jul. 16, 2002 Ex. 14: Monsanto 1991 Annual Report Ex. 15: Larry R. Swaney Dep. 1-4; 21-24; 29-32; 45-64; 77-80, 125-128; 153-160; 165-172, Jun. 25, 2009 Ex. 16: Patent Department Contact List, Sep. 25, 1992 Ex. 17: Monsanto Memo, Subject: Guideline for Research Records, Apr. 2, 1985 Ex. 18: Philip Needleman, Ph.D. Dep. 318-321; 390-393; 418-425, Nov. 18, 2010 Ex. 19: J. Michael Warner, Ph.D. Dep. 1-4; 9-12, May 25, 2011 Ex. 20: Philip Needleman, Ph.D. Biography Ex. 21: Research Proposal to the Monsanto Company by Daniel L. Simmons, Ph.D., Apr. 5, 1991 Ex. 22: Daniel L. Simmons, Ph.D. Dep 1; 34-37, 114-121, Apr. 20, 2009 Ex. 23: Apr. 9, 1991 Letter to Dr. Simmons from Dr. Needleman Ex. 24: Daniel L. Simmons, Ph.D. Dep. 1; 249-252; 257-260; 281-284; 309-312; 365-372, Apr. 21, 2009 Ex. 25: Karen Seibert, Ph.D. Dep. 289-292; 341-352; 501-504, Jun. 2, 2010 Ex. 26: Karen Seibert, Ph.D. Dep. 1-4; 25-28; 149-152, Jun. 1, 2010 Ex 27: Apr. 11, 1991 Letter to Dr. Simmons from Mr. Swaney enclosing Research Agreement Ex. 28: Mark G. Currie, Ph.D. 1; 242-245, Oct. 8, 2010 Ex. 29. Hearing Transcript 1; 20, Aug. 19, 2011 Ex. 30: Stephen Craig Dep. 1-4; 121-124: 137-140; 197-2011, May 24, 2011. Ex. 31 Expert Report of Dr. G. Steven Geis Excerpt Ex. 32: Weilin Xie, Ph.D. Dep. 1, 126-129; 138-141, Mar. 27, 2009 Ex. 33: Philip Needleman, *From a Twinkle in the Eye to a Blockbuster Drug,* Nov.-Dec. 2001 Ex. 34: Apr. 29, 1991 Letter to K. Seibert and J. Masferrer from D. Simmons Ex. 35: Apr. 29, 1991 Fax to D. Simmons from K Seibert Ex. 36: Mar. 20, 1992 Letter to P. Needleman from D. Simmons enclosing Progress Report Ex. 37: May 20, 1992 Letter to P. Needleman from D. Simmons Ex. 38: B. Zweifel Western Blot analysis Ex. 39: May 23, 1992 Letter to P. Needleman from D. Simmons Ex. 40: Jun. 10, 1991 Fax to D. Simmons from K. Seibert Ex. 41: Jun. 14, 1991 Letter to L. Swaney from L. Astle Ex. 42: Jun. 20, 1991 Fax to D. Simmons/L. Astle from L. Swaney Ex. 43: Jul. 9, 1991 Letter to L. Swaney from C. Hardman Ex. 44: Chart Ex. 45: Oct. 29, 1991 Letter to A. Raz from P. Needleman Ex. 46: Laboratory Notebook No. 4,956,601, Issued Dec. 4, 1991 Ex. 47 Scott Hauser Dep. 1-4; 173-176, Oct. 27, 2010 Ex. 48: Telephone bill Ex. 49: Karen Seibert Dep. 1; 186-189, *Pfizer Inc., et al* v. *Teva Pharmaceuticals USA, Inc.,* Jul. 11, 2006 Ex. 50: Feb. 6, 1992 Letter to D. Corley and A. Croissan from K. Leahy Ex. 51: Len F. Lee Notebook No. 21 Excerpt, Issued Feb. 14, 1992 Ex. 52: Jaime L. Masferrer Notebook No. 5,043,201, Issued Feb. 5, 1992 Ex. 53: Disclosure of Invention, Disclosure No. D-07-21-(909) Ex. 54: Mar. 17, 1992 Letter to D. Simmons from P. Needleman Ex. 55: Mar. 23, 1992 Letter to Dr. Simmons from P. Needleman Ex. 56: Sep. 2, 1992 Letter to P. Needleman from C. Hardman Ex. 57: Jan. 5, 1994 Letter for J Maddox from K. Seibert Ex. 58. U.S. Patent No. 5,760,068 (filed Nov. 14, 1994) Ex. 59: Various U.S. Patent face pages and excerpts Ex. 60: Jeffrey Chipman Dep. 1; 122-125, Feb. 20, 2009 Ex. 61 Simmons Grant Application, Title. Prostagllandin Synthase's Role in Transformation by v-src.
Sep. 29, 2011 Plaintiffs' Cross Motion for Partial Summary Judgment on Count III (Breach of Fiduciary Duty) of Their First Amended Complaint.
Oct. 3, 2011 Memorandum Regarding Status Conference, including the following Exhibits: Ex. A: Scheduling Order, Jul. 30, 2007 Ex. B: Jan. 28, 2011 Letter to A. Anderson from K. Owen Ex. C: Feb. 17, 2011 Letter to A. Anderson from R. Mulloy Ex. D: Expert Deposition Calendar Ex. E: Sep. 27, 2011 letter to B. Hatch from M. Dangerfield Ex. F: Subpoena to production Documents, Information, or Objects or To Permit Inspection of Premises in a Civil Action for DNA Solutions Ex. G: Subpeona to Testify at a Deposition in a Civil Action for DNA Solutions Ex. H: Jan. 21, 2011 Letter to B. Hatch from A. Anderson.

Oct. 4, 2011 Plaintiffs' Motion to File Sur-Reply in Support of Supplemental Briefing Regarding Defendants' Motion for Partial Summary Judgment Re Paragraph 3.3 of the Research Agreement.
Oct. 7, 2011 Motion and Consent of Sponsoring Local Counsel for *Pro Hac Vice* Admission of Abigail M. Terhune, including the following exhibits. Ex. A: Application for Admission Pro Hac Vice Ex. B: Electronic Case Filing Registration Form Proposed Order.
Oct. 11, 2011 Order granting Motion for Admission *pro hac vice* of Abigail M. Terhune.
Oct. 11, 2011 Ex Parte Motion for Leave to File Combined Reply Memorandum in Support of Defendants' Motion for Partial Summary Judgment Regarding Count III (Breach of Fiduciary Duty) and in Opposition to Plaintiffs' Cross-Motion for Partial Summary Judgment [Proposed] Order Granting Ex Parte Motion for Leave to File Combined Reply Memorandum in Support of Defendants' Motion for Partial Summary Judgment Regarding Count III (Breach of Fiduciary Duty) and in Opposition to Plaintiffs' Cross-Motion for Partial Summary Judgment.
Oct. 12, 2011 Order granting Ex Parte Motion for Leave to File Combined Reply Memorandum in Support of Defendants' Motion for Partial Summary Judgment Regarding Count III (Breach of Fiduciary Duty) and in Opposition to Plaintiff's Cross-Motion for Partial Summary Judgment.
Oct. 14, 2011 Order Re: Motion for Miscellaneous Relief.
Oct. 14, 2011 Order Denying Plaintiffs' Motions to Limit the Scope and Time of Deposition.
Sep. 15, 2011 Notice of Taking Video Deposition of Randy Bell.
Sep. 15, 2011 Notice of Takin•Video Deposition of Darrell Davis.
Sep. 15, 2011 Notice of Taking Video Deposition of Joseph Dellaria.
Sep. 15, 2011 Notice of Taking Video Deposition of William Galbraith.
Sep. 15, 2011 Notice of Taking Video Deposition of Timothy Hia.
Sep. 15, 2011 Notice of Taking Video Deposition of Edward T. Lentz.
Sep. 15, 2011 Notice of Taking Video Deposition of Arthur Lipman.
Sep. 22, 2011 Notice of Taking Video Deposition of Christine Botosan.
Sep. 22, 2011 Notice of Taking Video Deposition of Richard Hoffman.
Sep. 28, 2011 Notice of Taking Video Deposition of Judy VanDusen.
Sep. 29, 2011 Subpoena to Testify at a Deposition in a Civil Action served upon DNA Solutions.
Sep. 29, 2011 Subpoena to Produce Documents. Information or Objects or to Permit Inspection of Premises in a Civil Action served upon DNA Solutions.
Sep. 29, 2011 Notice of Issuance of Subpoenas upon DNA Solutions.
Sep. 30, 2011 Notice of Taking Video Deposition of Richard Gering.
Sep. 30, 2011 Notice of Taking Video Deposition of Dr. Daniel L. Simmons.
Oct. 4, 2011 Notice of Taking Video Deposition of Dr. Joseph M. Fortunak.
Oct. 4, 2011 Notice of Takin Video Deposition of Dr. G. Steven Geis.
Oct. 4, 2011 Notice of Taking Video Deposition of Dr. Ronald Woodard.
Oct. 7, 2011 Notice of Taking Continued Video Deposition of Dr. Daniel L Simmons.
Oct. 10, 2011 Notice of Taking Video Deposition of Rebecca Eisenberg.
Oct. 10, 2011 Notice of Taking Video Deposition of Vern Norviel.
Oct. 10, 2011 Notice of Taking Video Deposition of James Severson.
Oct. 13, 2011 Notice of Taking Video Deposition of John Ashton.
Oct. 13, 2011 Notice of Taking Video Deposition of George Cunningham.
Oct. 14, 2011 Notice of Taking Video Deposition of Weilin Xie.
Oct. 18, 2011 Notice of Taking Video Deposition of Jeffrey Chipman.
Oct. 18, 2011 Notice of Taking Video Deposition of Malcolm Fraser.
Oct. 18, 2011 Notice of Taking Video Deposition of Stephen Prescott.
Oct. 21, 2011 Amended Notice of Taking Video Deposition of Malcolm Fraser.
Oct. 21, 2011 Notice of Taking Video Deposition of Ashley Stevens.
Oct. 21, 2011 Notice of Taking Video Deposition of Francis M. Wikstrom.
Oct. 21, 2011 Notice of Taking Video Deposition of Michael D. Zimmerman.
Oct. 28, 2011 Combined Reply Memorandum in Support of Defendants' Motion for Partial Summary Judgment Regarding Count III (Breach of Fiduciary Duty) and in Opposition to Plaintiffs' Cross-Motion for Partial Summary Judgment.
Oct. 24, 2011 Amended Notice of Taking Video Deposition of Vern Norviel.
Oct. 25, 2011 Amended Notice of Taking Video Deposition of George Cunningham.
Dec. 9, 2011 Amended Memorandum in Support of Plaintiffs' Renewed Motion for Further Sanctions.
Dec. 9, 2011 Notice of Manual Filing of Exhibits to Amended Memorandum in Support of Plaintiffs' Renewed Motion for Further Sanctions.
Dec. 13, 2011 Stipulated Motion for Extension of Time: Proposed Order.
Dec. 14, 2011 Stipulated Order.
Dec. 19, 2011 Defendants' Expedited Motion to Strike Plaintiffs' Amended Memorandum in Support of Renewed Motion for Further Discovery Sanctions.
Dec. 19, 2011 Memorandum in Support of Defendants' Expedited Motion to Strike Plaintiffs' Amended Memorandum in Support of Renewed Motion for Further Discovery Sanctions and the following Exhibits: Exhibit A: Motion Hearing Transcript, Apr. 8, 2009 Exhibit B: Motion Hearing Transcript, Apr. 7, 2009.
Dec. 22, 2011 Order Regarding Briefing on Defendants' Motion to Strike.
Dec. 22, 2011 Defendants' Response to Plaintiffs' Motion for Partial Summary Judgment Concerning Defendants' Twenty-Eighth and Twenty-Ninth Defenses and the following exhibit: Exhibit 1: Excerpts from L. Astle Dep., Feb. 17, 2009.
Dec. 22, 2011 Memorandum in Opposition to Piaintiffs' Motion for Partial Summary Judgment to Dismiss Defendants Thirty-Second Defense With Prejudice.
Dec. 22, 2011 Response in Opposition to Defendants' Motion for Partial Summary Judgment on Plaintiffs' Claim That Defendants Have Misappropriated "Project" and "Compilation" Trade Secrets (Response to Defendants' Motion No. 6).
Dec. 22, 2011 Response in Opposition to Defendants' Motion for Partial Summary Judgment Regarding Plaintiffs' COX-1 Trade Secret Claims (Response to Defendants' Motion No. 7).
Dec. 22, 2011 Plaintiffs' Response in Opposition to Defendants Motion for Partial Summary Judgment dismissing Plaintiffs' Claim for Breach of Paragraph 3.1 of the Research Agreement (BYU Opposition to Pfizer Motion No. 12).
Dec. 22, 2011 Notice of Conventional Filing of Memorandum in Opposition to Plaintiffs' Motion for Partial Summary Judgment Re: mitigation of Damages and Failure to Patent as Described in Special Defenses Nos. 24 and 25 in the Amended Answer.
Dec. 22, 2011 Plaintiffs' Memorandum in Opposition to Defendants' Motion for Summary Judgment on Plaintiffs' Claim for Correction of Inventorship (BYU Opposition to Pfizer Motion No. 5)
Dec. 22, 2011 Notice of Conventional Filing of Consolidated Exhibits to Plaintiffs' Oppositions to Pfizer's Motions for Summary Judgment 1-13.
Dec. 22, 2011 Plaintiffs' Memorandum in Opposition to Defendants' Motion for Partial Summary Judgment Re: Ownership of the COX-2, Materials (BYU's Opposition to Defendants' Motion No. 10).
Dec. 22, 2011 BYU Memorandum in Opposition to Defendants' Motion for Partial Summary Judgment Regarding Paragraph 3.3 of the Research Agreement (BYU's Opposition to Defendants' Motion No. 10).
Dec. 22, 2011 BYU's Memorandum in Opposition to Pfizer's Motion for Partial Summary Judgment That Plaintiffs' Hypothetical Patent Claims 12-26 May Not be Relied Upon in Support of Any Claim For Relief (BYU's Opposition to Defendants' Motion No. 4).
Dec. 22, 2011 Plaintiffs' Memorandum in Opposition to Defendants' Motion for Partial Summary Judgment That Plaintiffs' Alleged "Two-Cell Assay" Trade Secret Has Been Licensed to Defendants (Plaintiffs' Opposition to Defendants' Motion No. 8).
Dec. 22, 2011 Brigham Young University and Daniel L. Simmons' Response to Defendants' Motion for Partial Summary Judgment Dismissing Plaintiffs' Claim for Breach of Paragraph 1.6 of the Research Agreement (Pfizer Motion No. 11).

Dec. 22, 2011 Plaintiffs' Opposition to Defendants' Motion for Partial Summary Judgment on Exclusions From "Project" (BYU Opposition to Pfizer Motion No. 2).
Dec. 22, 2011 Plaintiffs' Response to Defendants' Motion for Partial Summary Judgment Re Breach of Paragraphs 1.3, 3.4, 3.5 and 3.7 of the Research Agreement (Response to Pfizer MSJ No. 1).
Dec. 22, 2011 Notice of Conventional Filing of Memorandum in Opposition to BYU's Motion for Partial Summary Judgment Regarding Defendants' (Alleged) Breach of Paragraph 4.1 of the Research Agreement and Exhibits 1, 2, 3, 5, 6, 7, 10, 13, 14, 15, 16, 17, 18, 19, 21, 22, 38, 39 and 40.
Dec. 22, 2011 Plaintiffs' Memorandum in Opposition to Defendants' Motion to Dismiss for Lack of Stand (BYU's Oposition to Defendants Motion No. 9).
Dec. 22, 2011 Plaintiffs' Response to Motion for Partial Summary Judgment Re Count II—Implied Covenant of Good Faith and Fair Dealing, Count III—Fiduciary Duty, Count V—Unjust Enrichment, Count VI—Fraud and Count VII—Negligent Misrepresentation of Plaintiffs' First Amended Complaint (BYU Opposition to Defendants' Motion No. 13).
Dec. 22, 2011 Errata to BYU Memorandum in Opposition to Defendants' Motion for Partial Summary Judgment Regarding Paragraph 3.3 of the Research Agreement (BYU's Opposition to Defendants' Motion No. 3) Corrected BYU Memorandum in Opposition to Defendants' Motion for Partial Summary Judgment Regarding Paragraph 3.3 of the Research Agreement (BYU's Opposition to Defendants' Motion No. 3).
Dec. 22, 2011 Index to Memorandum in Opposition to BYU's Motion for Partial Summary Judgment Regarding Defendants' (Alleged) Breach of Paragraph 4.1 of the Research Agreement and the following Exhibits: Exhibit 4: Declaration of Timothy Hla in Support of Defendants' Opposition to BYU's Motion to Partial Summary Judgment Regarding Defendants' (Alleged) Breach Paragraph 4.1 of the Research Agreement Exhibit 8: Dean A. Kujubu et al., TIS10, a Phorboi Ester Tumor Promoter-inducible mRNA from Swiss 3T3 cells, Encodes a Novel Prostaglandin Synthase/Cycooxygenase Homologue, 266(20) J. Biol. Chem., 12866-72 (Jul. 1991) Exhibit 9: May 20, 2012 Letter to P. Needleman from D. Simmons Exhibit 11: Sambrook, *Extraction, Purification and Analysis of Messenger RNA from Eukaryotic Cells,* (1989) Exhibit 12: Dewitt et al., The Aspirin and Heme Binding Sites of Ovine and Murine Prostaglandin Endoperoxide Syntheses, The Journal of Biological Chemistry, 265(9): 5192-5198 (1990)(DeWitt 1990) Exhibit 16: Mar. 20, 1992 Letter to P. Needleman from D. Simmons Exhibit 20: Daniel L. Simmons et al., *Multiple Cyclooxygenases: Cloning of a Mitogen-Inducible Form in Prostaglandins,* Leukotrienes, Lipoxins and PAF, ed. J. Matyn Bailey (1991) Exhibit 23: Glenn D. Rosen et al., *Identification of a Cyclooxygenase-related Gene and its Potential Role in Prostaglandin Formation,* 164(3) Biochemical and Biophysical Research Communications, 1358-65 (1989) Exhibit 24: Jaime L. Masferrer et al., Selective Regulation of Cellular Cyclooxygenase by Dexamethasone and Endotoxin in Mice, 86 J. C1inical Investigation 1375-79 (1990) Exhibit 25: Weilin Xie, *Expression of a mitogen-responsive gene encoding prostaglandin synthase is regulated by mRNA splicing,* Proc. Natl. Acad. Sci, 88:2692-2696 (Apr. 1991) Exhibit 26: Curriculum Vitae of Daniel L. Simmons, Ph.D. Exhibit 28: Bradley S. Retcher, Structure of the Mitogen-Inducibie TIS10 Gene and Demonstration That the TIS10-encoded protein is a Functional Prostaglandin G/H Synthase, 267 J. Biol. Chem, 4338-4344 (Mar. 1992) Exhibit 29: Agreement between Brigham Young University and Oxford Biomedical Research, effective Aug. 1, 1991 Exhibit 30: Agreement between Brigham Young University and Oxford Biomedical Research, effective Sep. 1, 1991 Exhibit 31: Oxford Biomedical Research, Inc. Products & Applications Supply Catalog, vol. No. 2, 1991 Exhibit 32: Oxford Biomedical Research Inc. Products & Applications Supply Catalog, ed 5, 1992 Exhibit 33: Jaime L. Masferrer, et al, *Selective inhibition of inducible cyclooxygenase 2 in vivo is anti-inflammatory and nunulerogenic,* 91 Proc, Natl. Acad, Sci 3228-32 (1994) Exhibit 34: Grant Application, Title: Prostaglandin Synthase's Role in Transformation by v-src Exhibit 35: Grant Application, Title: Molecular Analysis of NSAID-Induced Apostosis Exhibit 36: Karen Seibert et al., *Pharmacological and biochemical damonstration of the role of cyclooxygenase 2 in inflammation and pain,* 91 roc. Natl. Acad. Sci. 12013-17 (1994) Exhibit 37: Karen Seibert et al, *Pharmacological manipulation of cyclo-oxygenase-2 in the inflamed hydronephrotic kidney,* 117 Br. J. Pharmacol. 1016-20 (1996) Exhibit 41: Jaime L. Masferrer, et al., In vivo *Glucocortolds Regulate cyclooxygenese-2 but not Cyclooxygenase-1 in Peritoneal Macrophages,* 270 J. Pharmacol. And Experimental Therapeutics 1340-1344 (1994) Exhibit 42: May 21, 1991 Letter from Monsanto to BYU Exhibit 43: Jun. 20, 1991 fax to D. Simmons from L.R. Swaney Exhibit 44: Jun. 24, 1991 Letter to L.R. Swaney from L. Astle.
Dec. 23, 2011 Notice of Conventional Filing—Amendment to Exhibit 2 to Memorandum in Opposition to BYU's Motion for Partial Summary Judgment Regarding Defendants' (Alleged) Breach of Paragraph 4.1 of the Research Agreement.
Dec. 27, 2011 Plaintiffs'Response to Defendants' Motion for Partial Summary Judgment Re Breach of Paragraph 1.3, 3.4, 3.5 and 3.7 of the Research Agreement (Response to Pfizer MSJ No. 1).
Jan. 3, 2012 BYU's Respnse in Opposition to Pfizer's Motion to Strike Plaintiffs' Amended Memorandum Support of Renewed Motion for Further Discovery Sanctions.
Jan. 6, 2012 Reply Memorandum in Support of Defendants' Expedited Morion to Strike Plaintiffs' Amended Memorandom in Support of Renewed Morion for Further Discovery Sanctions.
Jan. 11, 2012 Order and Memorandum Decision Denying Defendants' Expedited Motion to Strike Plaintiffs' Amended Memorandum in Support of Renewed Motion for Further Discovery Sanctions.
Jan. 24, 2012 Plaintiffs' Reply Memorandum in Support of Motion for Partial Summary Judgment Concerning Defendants' Twenty-Eighth and Twenty-Ninth Defenses.
Jan. 24, 2012 Reply Memorandum in Support of Plaintiffs' Motion Partial Summary Judgment to Discuss Defendants' Thirty-Second defense with Prejudice.
Jan. 24, 2012 Bringham Young University and Daniel L. Simmons's Reply in Support of Motion for Patial Summary Judgment Regarding Defendants' Breach of Paragraph 4.1 of the Research Agreement and the following exibits: Exhibit A: Declaration of Randy Bell, Jan. 23, 2012 Exhibit B: P. O'Brien Dep., Dec. 18, 2009 Exhibit C: J. Mancini Dep., Nov. 7, 2011 Exhibit D: L. Astle Dep., Feb. 17, 2009 Exhibit E: M. Orme Dep., Nov. 15, 2007 Exhibit F: D. Simmons Dep., Apr. 20, 2009 Exhibit G: T. Hla Dep., Sep. 12, 2011 Exhibit H: D. Callewaert, Oct. 19, 2011 Exhibit I: K. Ricker, Jun. 2, 2011.
Jan. 24, 2012 Response to Pfizer's Objections to the Use of BYU's Expert Reports and the following exhibits: Exhibit 1: R. Bell Dep., Sep. 29, 2011 Exhibit 2: S. Prescott Dep., Oct. 25, 2011 Exhibit 3: R. Gering Dep., Oct. 6, 2011 Exhibit 4: E. Lentz Dep., Sep. 22, 2011.
Jan. 24, 2012 Notice of Conventional Filling: Reply Memorandum in Support of Motion for Partial Summary Judgment on Plaintiffs' Claim for Correction of Inventorship (Count IV of the First Amended Complaint) (Defendants' Motion No. 5).
Jan. 24, 2012 Notice of Conventional Filing: Reply Memorandu in Support of Motion for Partial Summary Judgment on Plaintiffs' Claim That Defendants Have Misappropriated "Project" and "Compilation" Trade Secrets (Count VIII of the First Amended Complaint)(Defendant's Motion No. 6).
Jan. 24, 2012 Reply in Support of Motion for Partial Summary Judgment Re: Mitigation of Damages and Failure to Patent.
Jan. 24, 2012 Reply Memorandum in Further Support of Defendants' Motion for Partial Summary Judgment Dismissing Plaintiffs' Claims, for Breach of Paragraphs 1.3, 3.4, 3.5 and 3.7 of the research Agreement (Defendants' Motion No. 1) Attachment 1 to Reply Memorandum in Further Support of Defendants' Motion for Partial Summary Judgment Dismissing Plaintiffs' Claims for Breach of Paragraphs 1.3, 3.4, 3.5 and 3.7 of the Research Agreement (Defendants' Motion No. 1).
Jan. 24, 2012 Reply Memorandum in Further Support of Motion for Partial Summary Judgment on Exclusions from "Project" (Defendants' Motion No. 2) Attachment 1 to Reply Memorandum in Further Support of Motion for Partial Summary Judgment on Exclusions From "Project" (Defendants' Motion No. 2).
Jan. 24, 2012 Reply Memorandum in Support of Defendants' Motion for Partial Summary Judgment Regarding Paragraph 3.3 of the Research Agreement (Defendants' Motion No. 3) Attachment 1 to Reply Memorandum in Support of Defendants' Motion for Partial Summary Judgment Regarding Paragraph 3.3 of the Research Agreement (Defendants' Motion No. 3).
Jan. 24, 2012 Reply Memorandum in Support of Defendants' Motion for Partial Summary Judgment Regarding Plaintiffs' COX-1 Trade Secret Claims (Defendants' Motion No. 7) Attachment to Reply Memorandum in Support of Defendants' Motion for Partial Summary Judgment Regarding Plaintiffs' COX-1 Trade Secret Claims (Defendants' Motion No. 7).
Jan. 24, 2012 Reply Memorandum in Support of Defendants' Motion for Partial Summary Judgment That BYU's Alleged "Two-Cell Assay" Trade Secret Has Been Licensed to Defendants (Defendants' motion No. 8) Attachment to Reply Memorandum in Support of Defendants' Motion for Partial Summary Judgment that BYU's Alleged "Two-Cell Assay" Trade Secret Has Been Licensed to Defendants (Defendants' Motion No. 8).
Jan. 24, 2012 Reply Memorandum in Support of Defendants' Motion to Dismiss for Lack of Standing (Defendants' Motion No. 9).
Jan. 24, 2012 Reply Memorandum in Support of Defendants' Motion for Partial Summary Judgment Re: Ownership of the Cox-2 Materials (Defendants' Motion No. 10) Attachment 1 to Reply Memorandum in Support of Defendants' Motion for Partial Summary Judgment Re: Ownership of the Cox-2 Materials (Defendants' Motion No. 10).
Jan. 24, 2012 Reply Memorandum in Further Support of Defendants' Motion for Partial Summary judgment Dismissing Plaintiffs' Claims for Breach of Paragraph 1.6 of the Research Agreement (Defendants' Motion No. 11) Attachment 1 to Reply Memorandum in Further Support of Defendants' Motion for Partial Summary Judgment Dismissing Plaintiffs' Claims for Breach of Paragraph 1.6 of the Research Agreement (Defendants' Motion No. 11).
Jan. 24, 2012 Reply Memorandum in Further Support of Defendants' Motion for Partial Summary Judgment Dismissing Plaintiffs' Claims for Breach of Paragraph 3.1 of the Research Agreement (Defendants' Motion No. 12) Attachment 1 to Reply Memorandum in Further Support of Defendants' Motion for Partial Summary Judgment Dismissing Plaintiffs' Claims for Breach of Paragraph 3.1 of the Research Agreement (Defendants' Motion No. 12).
Jan. 24, 2012 Reply Memorandum in Support of Defendants' Motion for Partial Summary Judgment on: Count II—Implied Covenant of Good Faith and Fair Dealing, Count III—Fiduciary Duty, Count V—Unjust Enrichment, Count VI—Fraud, and Count VII—Negligent Misrepresentation, of Plaintiffs' First Amended Complaint (Defendants' Motion No. 13).
Jan. 24, 2012 Notice of Conventional Filing: Defendants' Memorandum in Opposition to BYU's Renewed Motion for Further Discovery Sanctions.
Jan. 24, 2012 Notice of Conventional Filing: Exhibits to Defendants' Memorandum in Opposition to BYU's Renewed Motion for Further Discovery Sanctions.
Jan. 31, 2012 Motion for Permission to Provide Certain Documents to Teva Pharmaceuticals That Pfizer Has Labeled as Confidential Under the Protective Order.
Jan. 31, 2012 Memorandum in Support of Motion for Permission to Provide Designated Documents to Teva Pharmaceuticals That Pfizer has Labeled as Confidential Under the Protective Order, and the following Exhibits: Exhibit 1: Agreement between Teva Pharmaceuticals USA, Inc. and Brigham Young University, Jan. 23, 2012 Exhibit 2: Affidavit of *Patricia Marsh O'Brien, C.D. Searle & Co.* v. *NovoPharm Limited,* Oct. 3, 2005 Exhibit 3: Oct. 22, 2007 Letter to L.R. Williams from L. Schneider.
Jan. 31, 2012 Motion to Expedite Consideration of BYU's Motion for Permission to Provide Certain Documents to Teva Pharmaceuticals; Proposed Order Granting Motion to Expedite Consideration of BYU's Motion for Permission to Provide Certain Documents to Teva Pharmaceuticals.
Jan. 31, 2012 Memorandum in Support of Motion to Expedite Consideration of BYU's Motion for Permission to Provide Certain Documents to Teva Pharmaceuticals.
Feb. 1, 2012 Motion to Strike.
Feb. 1, 2012 Memorandum Support of Motion to Strike.
Feb. 2, 2012 Memorandum Decision and Order Denying Motion to Expedite.
Feb. 2, 2012 Stipulation to Extend Time to File Reply Memorandum; Proposed Order Granting Stipulation to Extend Time to File Reply Memorandum.
Feb. 2, 2012 Order Granting Stipulation to Extend Time to File Reply Memorandum.
Feb. 2, 2012 Memorandum Decision and Order Granting Motion to Expedite.
Jan. 31, 2012 Letter to Honorable Stewart from J. Jardine explaining urgency of expediting BYU's motion for permission to provide designated documents to Teva Pharmaceuticals (filed Feb. 2, 2012).
Feb. 14, 2012 Pfizer's Memorandum in Opposition to BYU's Motion for Permission to Provide Designated Documents to Teva Pharmaceuticals That Pfizer Has Labeled as Confidential Under the Protective Order and the following Exhibits: Exhibit 1: Pfizer Inc. 10-K Annual Report, filed on Feb. 29, 2008 Exhibit 2: Pfizer Inc. 10-K Annual Report, filed on Feb. 28, 2011 Exhibit 3: News Release, *Teva Announces Launch of Generic Protonix Tablets, 20 mg and 40 mg Company Increases 2007 EPS Guidance to Between $2.34 and $2.36 Compant to Hold Conference Call at 8:45 a.m. Eastern Time* Exhibit 4: Stipulated Protective Order, *Pfizer Inc.* v. *Teva Phamaceuticals USA Inc.,* Aug. 31, 2004.
Feb. 17, 2012 Reply in Support of Motion for Permission to Provide Designated Documents to Teva Pharmaceuticals That Pfizer Has Labeled as Confidential Under the Protective Order and the following Exhibits: Exhibit 1: News Release, *Pfizer Reports Fourth-Quarter and Full-Year 2011 Results; Updates 2012 Financial Guidance,* Jan. 21, 2012; News Release, *Teva Reports Fourth Quarter and Full-Year 2011 Results,* Feb. 15, 2012 Exhibit 6: Expert Reports Filed in Connection with Summary Judgment Motions List.
Feb. 17, 2012 Memorandum in Opposition to BYU's Motion to Strike.
Feb. 20, 2012 Exhibits to Memorandum in Opposition to BYU's Motion to Strike, as follows: Exhibit 1: Memorandum Decision and Order Denying Plaintiff's Motion to Strike and Granting Defendants' Motion for Summary Judgment, *Gray* v. *Gen. Elec. Co.,* Jun. 3, 2011 Exhibit 2: Reply Memorandum in Support of Defendant's Motion for Summary Judgment, *Gray* v. *Gen. Elec. Co.,* Jan. 31, 2011 Exhibit 3: Appendices A and B, *Gray* v. *Gen. Elec. Co.*.
Feb. 24, 2012 Pfizer's Motion to Correct Memorandum in Opposition of BYU's Motion for Partial Summary Judgment Regarding Defendants' (Alleged) Breach of Paragraph 4.1 of the Research Agreement: [Proposed] Order Granting Pfizer's Motion to Correct Memorandum in Opposition to BYU's Motion for Partial Summary Judgment Regarding Defendants' (Alleged) Breach of Paragraph 4.1 of the Reasearch Agreement.
Feb. 24, 2012 Memorandum in Support of Pfizer's Motion to Correct Memorandum in Opposition to BYU's Motion for Partial Summary Judgment Regarding Defendants' (Alleged) Breach of Paragraph 4.1 of the Research Agreement and the following Exhibit: Exhibit C: Index to the Memorandum in Opposition to BYU's Motion to Partial Summary Judgment Regarding Defendant's (Alleged) Breach of Paragraph 4.1 of the Reasearch Agreement.
Feb. 24, 2012 Notice of Conventional Filing : Exhibits A and B to Memorandum in Support of Pfizer's Motion to Correct Memorandum in Opposition to BYU's Motion for Partial Summary Judgment Re: Defendants' (Alleged) Breach of Paragraph 4,1 of the Research Agreement.
Feb. 24, 2012 Notice of Supplemental Authority and the following Exhibits: Exhibit 1: *Falana* v. *Kent State Univ.,* 2012 U.S App, Lexis 1245 (Jan. 23. 2012) Exhibit 2: *Bard Peripheral Vascular Inc.* v. *C.R. Bard, Inc.,,* 2012 U.S. App. Lexis 2612 (Feb. 10, 2012).
Feb. 24, 2012 Motion for Leave to File Overlength Brief.
Feb. 24, 2012 Reply in Support of Motion for Further Sanctions; Fact Appendix.
Feb. 24, 2012 Notice of Conventional Filing of Exhibits to BYU's Reply in Support of Motion for Further Sanctions.
Feb. 29, 2012 Letter to Hon. Stewart from J. Jardine that BYU will narrow its claim to three patents for correction of inventorship.
Mar. 2, 2012 Response to Pfizer's Objections to the Use of BYU Expert Reports and the following Exhibits: Exhibit 1: Excerpt from R. Bell Deposition dated Sep. 29, 2011 Exhibit 2: Excerpt from Declaration of Randy Bell Exhibit 3: Excerpt from S. Prescott Deposition dated Oct. 25, 2011 Exhibit 4: Excerpt from R. Gering Deposotion dated Oct. 6, 2011.
Mar. 2, 2012 Further Response to Pfizer's Objections to Use of BYU's Expert Repots and the following Exhibits: Exhibit 1: Except from R. Bell Deposition dated Sep. 29, 2011 Exhibit 2: Excerpt from D. Davis Deposition dated Sep. 20, 2011 Exhibit 3: Excerpt from J. Dellaria Deposition dated Sep. 28, 2011 Exhibit 4: Excerpt from R. Eisenberg Deposition dated Oct. 18, 2011 Exhibit 5: Excerpt from A. Fellmeth Deposition dated Sep. 13, 2011 Exhibit 6: Excerpt from M. Fraser Deposition dated Oct. 27, 2011 Exhibit 7: Excerpt from R. Gering Deposition dated Oct. 6, 2011 Exhibit 8: Excerpt from E. Lentz Deposition dated Sep. 22, 2011 Exhibit 9: Excerpt from A. Lipman Deposition dated Sep. 19, 2011 Exhibit 10: Excerpt from V. Norviel Deposition dated Oct. 26, 2011 Exhibit 11: Excerpt from S. Prescott Deposition dated Oct. 25, 2011 Exhibit 12: Excerpt from M. Robins Deposition dated Nov. 17, 2011 Exhibit 13: Excerpt from J. Severson Deposition dated Sep. 20, 2011 Exhibit 14: Excerpt from D. Simmons Deposition dated Oct. 7, 2011.
Mar. 5, 2012 Reply in Support of Motion to Strike.
Mar. 6, 2012 Notice of Supplemental Authority and the following Exhibit: Exhibit 1: *CDC Restoration & Construction LLC* v. *Trademen Contractors, LLC,* 702 Utah Adv. Rep. 56 (Ut. Ct. App. 2012).
Mar. 7, 2012 Order on Hearing Structure and Pretrial Deadlines.
Mar. 9, 2012 Memorandum Decision and Order Denying Motion for Permission to Provide Certain Documents Labeled as Confidential Under the Protective Order.
Mar. 13, 2012 Memorandum Decision and Order on Pfizer's Motions for Partial Summary Judgment Nos. 3 and 11.
Mar. 14, 2012 Supplemental Brief re: Inventorship and the following: Appendix A Exhibit A: Declaration of Randy Bell, Mar. 14, 2012 Exhibit B: Declaration of Edward T. Lentz, Mar. 14, 2012 Exhibit C: Declaration of Rebecca Eisenberg, Mar. 14, 2012 Exhibit D: Plaintiffs' Supplemental Responses to Defendants' First Set of Interrogatories Nos. 1, 2, 9, 11, 13, 20 and 26 and to Defendants' Second Set of Interogatories No. 30. *Pfizer Inc.* v. *Teva Pharms. USA, Inc.,* No. 04-754 (D.N.J.) Dec. 19, 2005 Exhibit E: Hearing Proceedings, Mar. 9, 2012.
Mar. 14, 2012 Pfizer's Supplemental Brief in Support of its Motion for Summary Judgment on Plaintiffs' Claim for Correction of Inventorship (Motion No. 5) and the following: Exhibit 1: Findings of Fact, Conclusions of Law and Order. *Falana* v. *Kent State Univ.,* 5.08 CV 720 (N.D. Ohio), Dec. 14, 2010 Exhibit 2: U.S. Patent No. 6:803,789B2 (filed Jun. 8, 2001).
Nov. 14, 2011 Motion for Partial Summary Judgment Dismissing Plaintiffs' Claims for Breach of Paragraphs 1.3, 3.4,3.5 and 3.7 of the Research Agreement (Defendants' Motion No. 1).
Nov. 14, 2011 Memorandum in Support of Motion for Partial Summary Judgment Dismissing Plaintiffs' Claims for Breach of Paragraphs 1.3, 3.4, 3.5 and 3.7 of the Research Agreement (Defendants' Motion No. 1).
Nov. 14, 2011 Defendants' Motion for Partial Summary Judgment on Exclusions from "Project" (Defendants' Motion No. 2).
Nov. 14, 2011 Memorandum in Support of Defendants' Motion for Partial Summary Judgment on Exclusions from "Project" (Defendants' Motion No. 2).
Nov. 14, 2011 Defendants' Motion for Partial Summary Judgment Regarding Paragraph 3.3 of the Research Agreement (Defendants' Motion No. 3).
Nov. 14, 2011 Memorandum in Support of Defendants' Motion for Partial Summary Judgment Regarding Paragraph 3.3 of the Research Agreement (Defendants' Motion No. 3).
Nov. 14, 2011 Motion for Partial Summary Judgment That Plaintiffs' Hypothetical Patent claims 12-26 May Not Be Relied Upon in Support of Any Claim for Relief (Defendants' Motion No. 4).
Nov. 14, 2011 Plaintiffs' Motion for Partial Summary Judgment concerning Defendants' Twenty-Eighth and Twenty-Ninth Defenses.
Nov. 14, 2011 Plaintiffs' Memorandum in Support of Motion for Partial Summary Judgment Concerning Defendants' Twenty-Eighth and Twenty-Ninth Defenses and the following Exhibit: Exhibit A: "Special Defenses" portion of the Answer to the First Amended Complaint.
Nov. 14, 2011 Plaintiffs' Motion for Partial Summary Judgment to Dismiss Defendants' Thirty-Second Defense with Prejudice.
Nov. 14, 2011 Notice of Conventional Filing of Memorandum in Support of Motion for Partial Summary Judgment That Plaintiffs' Hypothetical Patent Claims 12-26 May Not Be Relied Upon in Support of Any Claim for Relief (Defendants' Motion No. 4).
Nov. 14, 2011 Memorandum in Support of Plaintiffs' Motion for Partial Summary Judgment to Dismiss Defendants' Thirty-Second Defense with Prejudice and the following Exhibit: Exhibit A: "Special Defenses" portion of the Answer to the First Amended Complaint.
Nov. 14, 2011 Motion for Summary Judgment on Plaintiffs' Claim for Correction of Inventorship (Count IV) of the First Amended Complaint) (Defendants' Motion No. 5).
Nov. 14, 2011 Notice of Conventional Filing of Memorandum in Support of Motion for Summary Judgment on Plaintiffs' Claim for Correction of Inventorship (Count IV) of the First Amended Complaint (Defendants' Motion No. 5).
Nov. 14, 2011 Motion for Partial Summary Judgment on Plaintiffs' Claim that Defendants Have Misappropriated "Project" and "Compilation" Trade Secrets (Count VIII of the First Amended Complaint) (Defendants' Motion No. 6).
Nov. 14, 2011 Notice of Conventional filing of Memorandum in Support of Motion for Partial Summary Judgment on Plaintiffs' Claim that Defendants have Misappropriated "Project" and "Compilation" Trade Secrets (Count VIII of the First Amended Complaint)(Defendants' Motion No. 6).
Nov. 14, 2011 Defendants' Motion for Partial Summary Judgment Regarding Plaintiffs' COX-1 Trade Secret Claims (Defendants' Motion No. 7).
Nov. 14, 2011 Notice of Conventional filing of Memorandum in Support of Defendants' Motion for Partial Summary Judgment Regarding Plaintiffs' COX-1 Trade Secret Claims (Defendants' Motion No. 7).
Nov. 14, 2011 Defendants' Motion to Dismiss for Lack of Standing (Defendants' Motion No. 9).
Nov. 14, 2011 Memorandum in Support of Defendants' Motion to Dismiss for Lack of Standing (Defendants' Motion No. 9).
Nov. 14, 2011 Defendants' Motion for Partial Summary Judgment That Plaintiffs' Alleged "Two-Cell Assay" Trade Secret Has been Licensed to Defendants (Defendants' Motion No. 8).
Nov. 14, 2011 Notice of Conventional Filing of Memorandum in Support of Defendants' Motion for Partial Summary Judgment that Plaintiffs' Alleged "Two-Cell Assay" Trade Secret Has been Licensed to Defendants (Defendants' Motion No. 8).
Nov. 14, 2011 Defendants' Motion for Partial Summary Judgment Re: Ownership of the COX-2 Materials (Defendants' Motion No. 10).
Nov. 14, 2011 Plaintiffs' Reply in Support of Cross Motion for Partial Summary Judgment Regarding Fiduciary Duties, including the following Exhibits: Exhibit 1: Declaration of Michael J. Warner, *Univ. of Rochester* v. *G.D. Searle,* No. 00-CV-6161L (W.D.N.Y. Jan 13, 2003) Exhibit 2: Hoffman Dep. 1, 317-324, Oct. 5, 2011 Exhibit 3: Mancini Dep. Draft 1-2, 137, Nov. 7, 2011 Exhibit 4: Declaration of Daniel L. Simmons, Jun. 17, 2011 Exhibit 5: Mar. 20, 1992 Letter to P. Needleman from D. Simmons Exhibit 6: Zmmerman Dep. 1-4, 25-32, Oct. 27, 2011.
Nov. 14, 2011 Defendants' Motion for Partial Summary Judgment Dismissing Plaintiffs' Claim for Breach of Paragraph 1.6 of the Research Agreement (Defendants' Motion No. 11).
Nov. 14, 2011 Memorandum in Support of Defendants' Motion for Partial Summary Judgment Dismissing Plaintiffs' Claim for Breach of Paragraph 1.6 of the Research Agreement (Defendants' Motion No. 11).
Nov. 14, 2011 Defendants' Motion for Partial Summary Judgment Dismissing Plaintiffs' Claim for Breach of Paragraph 3.1 of the Research Agreement (Defendants' Motion No. 12).
Nov. 14, 2011 Memorandum in Support of Defendants' Motion for Partial Summary Judgment Dismissing Plaintiffs' Claim for Breach of Paragraph 3.1 of the Research Agreement (Defendants' Motion No. 12).
Nov. 14, 2011 Declaration of Kevin W. Bates in Support of Defendants' Motions for Summary Judgment on Plaintiffs' Claim for Correction of Inventorship (Count IV of the First Amended Complaint) and the following Exhibits: Exhibit 1: U.S. Patent No. 5,344,991 (filed Oct. 29, 1993) Exhibit 2: U.S. Patent No. 5,380,738 (filed May 21, 1993) Exhibit 3: U.S. Patent No. 5,393,790 (filed Feb. 10, 1994) Exhibit 4: U.S. Patent No. 5,401,765 (filed Nov. 30, 1993) Exhibit 5: U.S. Patent No. 5,418,254 (filed May 4, 1994) Exhibit 6: U.S. Patent No. 5,420,287 (filed Jun. 3, 1994) Exhibit 7: U.S. Patent No. 5,420,343 (filed Aug. 31, 1994) Exhibit 8: U.S. Patent No. 5,434,178 (filed Nov. 30, 1993) Exhibit 9: U.S. Patent No. 5,466,823 (filed Nov. 30, 1993) Exhibit 10: U.S. Patent No. 5,475,018 (filed Nov. 30, 1993) Exhibit 11: U.S. Patent No. 5,476,944 (filed May 19, 1994) Exhibit 12: U.S. Patent No. 5,486,534 (filed Jul. 21, 1994) Exhibit 13: U.S. Patent No. 5,504,215 (filed Jun. 1, 1995) Exhibit 14: U.S. Patent No. 5,508,426 (filed Jun. 1, 1995) Exhibit 15: U.S. Patent No. 5,510,496 (filed Jun. 1, 1995) Exhibit 16: U.S. Patent No. 5,516,907 (filed Jun. 1, 1995) Exhibit 17: U.S. Patent No. 5,521,207 (filed Apr. 6, 1994) Exhibit 18: U.S. Patent No. 5,547,975 (filed Sep. 20, 1994) Exhibit 19: U.S. Patent No. 5,563,165 (filed Jun. 1, 1995) Exhibit 20: U.S. Patent No. 5,565,482 (filed Sep. 29, 1995) Exhibit 21: U.S. Patent No. 5,576,339 (filed Apr. 5, 1995) Exhibit 22: U.S. Patent No. 5,580,985 (filed Sep. 28, 1995) Exhibit 23: U.S. Patent No. 5,596,008 (filed Feb. 10, 1995) Exhibit 24: U.S. Patent No. 5,616,601 (filed Jun. 5, 1995) Exhibit 25: U.S. Patent No. 5,620,999 (filed Jul. 28, 1994) Exhibit 26: U.S. Patent No. 5,633,272 (filed Jun. 7, 1995) Exhibit 27: U.S. Patent No. 5,639,777 (filed Nov. 14, 1994) Exhibit 28: U.S. Patent No. 5,643,933 (filed Jun. 2, 1995) Exhibit 29: U.S. Patent No. 5,663,180 (filed Jul. 15, 1994) Exhibit 30: U.S. Patent No. 5,668,161 (filed Jul. 9, 1996) Exhibit 31: U.S. Patent No. 5,668,161 (filed Jul. 9, 1996) Exhibit 32: U.S. Patent No. 5,670,532 (filed Sep. 25, 1996) Exhibit 33: U.S. Patent No. 5,672,626 (filed Jul. 9, 1996) Exhibit 34: U.S. Patent No. 5,672,627 (filed Jul. 9, 1996) Exhibit 35: U.S. Patent No. 5,686,470 (filed Feb. 10, 1995) Exhibit 36: U.S. Patent No. 5,696,143 (filed Sep. 20, 1994) Exhibit 37: U.S. Patent No. 5,719,163 (filed May 19, 1994) Exhibit 38: U.S. Patent No. 5,736,579 (filed Nov. 18, 1994) Exhibit 39: U.S. Patent No. 5,739,166 (filed Nov. 29, 1994) Exhibit 40: U.S. Patent No. 5,753,688 (filed Sep. 27, 1995) Exhibit 41: U.S. Patent No. 5,756,529 (filed Sep. 29, 1995) Exhibit 42: U.S. Patent No. 5,756,530 (filed Sep. 25, 1996) Exhibit 43: U.S. Patent No. 5,760,068 (filed Nov. 14, 1994) Exhibit 44: U.S. Patent No. 5,859,257 (filed Aug. 14, 1996) Exhibit 45: U.S. Patent No. 5,886,016 (filed Sep. 15, 1995) Exhibit 46: U.S. Patent No. 5,908,852 (filed Nov. 14, 1994) Exhibit 47: U.S. Patent No. 5,916,905 (filed Feb. 8, 1996) Exhibit 48: U.S. Patent No. 5,932,598 (filed Jan. 12, 1998) Exhibit 49: U.S. Patent No. 5,935,990 (filed Dec. 9, 1997) Exhibit 50: U.S. Patent No. 5,972,986 (filed Oct. 14, 1997) Exhibit 51: U.S. Patent No. 5,985,902 (filed Feb. 18, 1997) Exhibit 52: U.S. Patent No. 6,028,072 (filed Jul. 20, 1995) Exhibit 53: U.S. Patent No. 6,045,773 (filed Feb. 24, 1999) Exhibit 54: U.S. Patent No. 6,090,834 (filed Dec. 1, 1998) Exhibit 55: U.S. Patent No. 6,156,781 (filed Nov. 24, 1999) Exhibit 56: U.S. Patent No. 6,274,590 (filed Sep. 14, 2000) Exhibit 57: U.S. Patent No. 6,342,510 (filed Jun. 11, 1996) Exhibit 58: U.S. Patent No. 6,376,528 (filed Oct. 18, 1999).

Exhibit 59: U.S. Patent No. 6,407,140 (filed Jan. 21, 2000) Exhibit 60: U.S. Patent No. 6,413,960 (filed May 30, 2000) Exhibit 61: U.S. Patent No. 6,426,360 (filed May 15, 2000) Exhibit 62: U.S. Patent No. 6,432,999 (filed Jun. 11, 2001) Exhibit 63: U.S. Patent No. 6,436,967 (filed Sep. 14, 2000) Exhibit 64: U.S. Patent No. 6,492,411 (filed Apr. 17, 2002) Exhibit 65: U.S. Patent No. 6,492,413 (filed Mar. 20, 2000) Exhibit 66: U.S. Patent No. 6,512,121 (filed Jun. 11, 2001) Exhibit 67: U.S. Patent No. 6,515,014 (filed Jun. 11, 2001) Exhibit 68: U.S. Patent No. 6,586,603 (filed Oct. 21, 2002) Exhibit 69: U.S. Patent No. 6,599,934 (filed Nov. 13, 2000) Exhibit 70: U.S. Patent No. 6,613,789 (filed Dec. 5, 2001) Exhibit 71: U.S. Patent No. 6,677,364 (filed Dec. 4, 2001) Exhibit 72: U.S. Patent No. 6,677,488 (filed Jan. 30, 2001) Exhibit 73: U.S. Patent No. 6,696,477 (filed Nov. 29, 2001) Exhibit 74: U.S. Patent No. 6,716,991 (filed Mar. 4, 2003) Exhibit 75: U.S. Patent No. 6,753.344 (filed Dec. 12, 2002) Exhibit 76: U.S. Patent No. 6,815,460 (filed Jun. 24, 2002) Exhibit 77: U.S. Patent No. 6,875,785 (filed Sep. 25, 2002) Exhibit 78: U.S. Patent No. 6,951,949 (filed Nov. 3, 2003) Exhibit 79: U.S. Patent No. 6,998,415 (filed Jan. 12, 2004) Exhibit 80: U.S. Patent No. 7,012,094 (filed Apr. 19, 1995) Exhibit 81: U.S. Patent No. 7,030,153 (filed Dec. 27, 2002) Exhibit 82: U.S. Patent No. 7,220,770 (filed Jul. 15, 2005) Exhibit 83: U.S. Patent No. 7,420,061 (filed Sep. 13, 2004).

Nov. 14, 2011 Certificate of Service for Defendants' Memoranda in Support of Motions for Partial Summary Judgment filed under Seal on Nov. 14, 2011.

Nov. 14, 2011 Motion for Partial Summary Judgment Re: Mitigation of Damages and Failure to Patent as Described in Special Defenses Nos. 24 and 25 in the Amended Answer.

Nov. 14, 2011 Memorandum in Support of Motion for Partial Summary Judgment Re: Mitigation of Damages and Failure to Patent as Described in Special Defenses Nos. 24 and 25 in the Amended Answer, including the following Exhibits: Exhibit 1: Declaration of Michael J. Warner, *Univ. of Rochester* v. *G.D. Searle & Co., Inc.,* No. 00-CV-616IL (W.D.N.Y. Jan. 13, 2003) Exhibit 2: Mar. 23, 1992 Letter to D. Simmons from P. Needleman Exhibit 3: Expert Report by Richard Gering, Ph.D., Feb. 18, 2011 Exhibit 4: Counter Report by Richard J. Gering, Ph.D., Aug. 26, 2011 Exhibit 5: Feb. 25, 2011 E-mail from B. Hatch to L. Beus Exhibit 6: Expert Report of Ashley J. Stevens Exhibit 7: Stevens Dep. 1-4, 269-280, Oct. 26, 2011 Exhibit 8: Expert Report by Edward T. Lentz, Feb. 18, 2011.

Nov. 14, 2011 Defendants' Motion for Partial Summary Judgment on Count II—Implied Covenant of Good Faith and Fair Dealing; Count III—Fiduciary Duty; Count V—Unjust Enrichment; Count VI—Fraud; Count VII—Negligent Misrepresentation of Plaintiffs' First Amended Complaint (Defendants' Motion No. 13).

Nov. 14, 2011 Declaration of Phillip J. Russell Filed in Support of Defendants' Motions for Partial Summary Judgment, including the following Exhibits: Exhibit 1: Research Agreement between Brigham Young University and Monsanto Company effective Aug. 1, 1991 Exhibit 3: Defendants' First Set of Interrogatories, Jan. 8, 2007 Exhibit 4: Plaintiffs' Response to Defendants' First Set of Interrogatories, Feb. 12, 2007 Exhibit 6: Plaintiffs' Supplemental Response to Defendants' Interrogatory No. 4, Jun. 27, 2008 Exhibit 7: Response to Defendants' First Set of Requests for Admissions to Brigham Young University, Jun. 11, 2008 Exhibit 9: Apr. 29, 1991 Letter to K. Seibert and Jaime Masferrer from D. Simmons Exhibit 10: Agreement between BYU and Oxford Biomedical Research, Inc. dated Aug. 1, 1991 Exhibit 13: Mar. 27, 1992 letter to P. Needleman from C. Hardman Exhibit 14: May 20, 1992 Letter to P. Needleman from D. Simmons Exhibit 15: May 21, 1992 Letter to P. Needleman from C. Hardman Exhibit 18: Jun. 1, 2011 Letter to B. Hatch from R. Williams Exhibit 19: J. Sambrook et al., Molecular Cloning: a Laboratory Manual, 2d ed. (1989) Exhibit 20: Excerpts from Gans et al., *Anti-Inflammatory and Safety Profile of DuP 697, A Novel Orally Effective Prostaglandin Synthesis Inhibitor,* 254(1) J. Pharm. & Exp. Therapeutics 160 (1990) Exhibit 21: David L. DeWitt et al., *The Aspirin and Heme-binding Sites of Ovine and Murine Prostaglandin Endoperoxide Synthases,* 265 J. Biol. Chem., 5192 (1990) Exhibit 22: Daniel L. Simmons et al., *Multiple Cyclooxygenases: Cloning of a Mitogen-Inducible Form,* Prostaglandins, Leukotrienes, Lipoxins, and PAF: mechanism of Action, Molecular Biology, and Clinical Applications (ed. J. Martyn Bailey) 1991 Exhibit 23: Daniel L. Simmons et al., *Cyclooxygenase isozymes: The Biology ofProstaglandin Synthesis and Inhibition,* 56(3) Pharmacol Rev. 387-437 (2004) Exhibit 24: John Devereux et al., *A Comprehensive Set of Sequence Analysis Programs for the BAX,* 12(1) Nucleic Acids Research 387 (1984) Exhibit 27: U.S. Patent No. 4,820,827 (filed Feb. 10, 1984) Exhibit 30: Excerpts from U.S. Dept. Of Commerce, Manual of Patent Examining Procedure, Rev. 8, Jul. 2010 Exhibit 31: Declaration of Timothy Hla in Support of Defendants' Motion for Partial Summary Judgment Regarding Plaintiffs' COX-1 Trade Secret Claims Exhibit 32: Expert Report of Vern Norveil, Feb. 18, 2011 Exhibit 36: Understanding Biotechnology Law: Protection, Licensing and Intellectual Property Policies, Ch. 5—*Inventorship in the Research Laboratory* (ed. Gail R. Peterson) Exhibit 44: Amended Notice of taking Video Deposition of Brigham Young University Pursuant to Fed. R. Civ. P. 30(b)96), Nov. 5, 2010 Exhibit 47: Excerpts from Craig 30(b)(6) Dep. May 24, 2011 Exhibit 51: Excerpts from Astle Dep., Feb. 17, 2009 Exhibit 59: Excerpts from Swaney Dep., Jun. 25, 2009.

Nov. 14, 2011 Memorandum in Support of Defendants' Motion for Partial Summary Judgment on: Count II—Implied Covenant of Good Faith and Fair Dealing; Count III—Fiduciary Duty; Count V—Unjust Enrichment; Count VI—Fraud; Count VII—Negligent Misrepresentation of Plaintiffs' First Amended Complaint (Defendants' Motion No. 13).
Nov. 14, 2011 Plaintiffs' Motion for Partial Summary Judgment regarding Count I (Breach of Written Contract) of Plaintiffs' First Amended Complaint.
Nov. 14, 2011 Notice of Conventional Filing of Memorandum in Support of Motion for Partial Summary Judgment Regarding Defendants' Breach of Paragraph 4.1 of the Research Agreement.
Nov. 14, 2011 Notice of Conventional Filing of Exhibits 1-59 to BYU's Memorandum in Support of Motion for Partial Summary Judgment Regarding Defendants' Breach of Paragraph 4.1 of the Research Agreement.
Nov. 14, 2011 Plaintiffs' Motion for Leave to File Overlength Memorandum in Support of its Renewed Motion for Further Sanctions.
Nov. 14, 2011 Plaintiffs' Renewed Motion for Further Discovery Sanctions.
Nov. 14, 2011 Notice of Conventional Filing of Exhibits 1-199 to Plaintiffs' Memorandum in Support of Renewed Motion for Further Discovery Sanctions.
Nov. 14, 2011 Memorandum in Support of Plaintiffs' Renewed Motion for Further Discovery Sanctions.
Nov. 14, 2011 Memorandum in Support of Defendants' Motion for Partial Summary Judgment Re: Ownership of the COX-2 materials (Defendants' Motion No. 10).
Nov. 15, 2011 Notice of Conventional Filing of Exhibits 2, 5, 8, 11, 12, 16, 17, 29, 33-35, 37-43, 45, 46, 48-50 and 52-58 to Declaration of Phillip J. Russell filed in support of Defendants' Motions for Partial Summary Judgment.
Nov. 15, 2011 Notice of Conventional Filing of Exhibits 19 and 23 to Declaration of Phillip J. Russell filed in support of Defendatns' Motion for Partial Summary Judgment.
Nov. 15, 2011 Notice of Conventional Filing of Exhibits to Declaration of Kevin W. Bates filed in support of Defendants' Motions for Summary Judgment on Plaintiffs' Claim for Correction of Inventorship (Count IV of the First Amended Complaint).
Nov. 16, 2011 Request to Submit for Decision Re: Motions for Partial Summary Judgment Re: Count III (Breach of Fidiciary Duty) of Plaintiffs' First Amended Complaint.
Nov. 17, 2011 Defendants' Memorandum in Opposition to Plaintiffs' Motion for Leave to File Overlength Memorandum in Support of its Renewed Motion for Further Sanctions, and the following Exhibits: Exhibit A: Motion Hearing Transcript, Mar. 31, 2011 Exhibit B: Status Conference Transcript, Apr. 7, 2011.
Nov. 18, 2011 Plaintiff' Reply in Support of Motion for Leave to File Overlength Memorandum in Support of its Renewed Motion for Further Sanctions.
Nov. 21, 2011 Motion and Consent of Sponsoring Local Counsel for Pro Hac Vice Admission of Hank E. Pearson and the following: Exhibit A: Application for Admission Pro Hac Vice Exhibit B: Electronic Case Filing Registration Form [Proposed] Order for Pro Hac Vice Admission.
Nov. 23, 2011 Order Granting Motion for Admission Pro Hac Vice of Hank E. Pearson.
Nov. 28, 2011 Order Denying Plaintiffs' Motion for Leave to File Excess Pages.
Nov. 10, 2011 Amended Notice of Taking Video Deposition of Morris Robins.
Article: Weilin Xie, et al., "Expression of mitogen-responsive gene encoding prostaglandin synthase is regulated by mRNA splicing," Proceedings of the National Academy of Sciences of the USA, Apr. 1, 1991, vol. 88, No. 7 BYU-18-4303-4304, 4306, 4391-4395.
Article: Daniel Simmons, et al., "Multiple Cyclooxygenases: Cloning of a Mitogen-Inducible Form," Proceedings of the 11$^{th}$ International Washington Spring Symposium at The George Washington University, held May 13-17, 1991, Washington, D.C. BYU-18-1680-1688, 1758-1769.
May 16, 1991 P. Needleman to D. Simmons re grant mechanism BYU-01-1386.
May 1, 1991 Draft Research Agreement between BYU and Monsanto, w/handwritten notes BYU-12-0279-0291.
Jul. 3, 1991 Letter from L.R. Swaney to L. Astle BYU-12-0210.
Executed, Aug. 1, 1991 Research Agreement between BYU and Monsanto BYU-11-0111-0127.
Apr. 14, 2008 Letter from Beus Gilbert to L. Schneider enclosing BYU's updated privilege log as of Apr. 10, 2008.
Subpoena for Deposition, dated May 27, 2008.
1991 Thesis of Jeffrey Chipman, Cloning and Sequencing of a Novel Mouse Prostaglandin G/H Synthase Gene BYU-06-1355-1391.
Aug. 7, 1990 Honors Thesis Submission Form of Jeffrey Chipman BYU-20-0164.
Abstract: Weilin Xie, et al., Cloning and Characterizations of a pp60v-arc-inducible prostaglandin Synthase, 75$^{th}$ Annual Meeting Atlanta, Georgia, Apr. 21-25, 1991, The FASEB Journal, Abstracts Part I ChipmanBYU-08-1021-1022.
Article: G. Evett, et al., Prostaglandin G/H Synthase Isoenzyme 2 Expression in Fibroblasts: Regulation by Dexamethasone, Mitogens, and Oncogenes, Archives of Biochemistry and Biophysics, Oct. 1991 BYU-11-1956-1964.
May 27, 2008 Deposition Subpoena to Gary Evett.
May 27, 2008 Defendants' Notice of Subpoenas' for Deposition and Production of Documents and Things BYU-21-0167-0171.
Article: J. Fu, et al., "The Induction and Suppression of Prostaglandin H2 Synthase (Cyclooxygenase) in Human Monocytes," Journal of Biological Chemistry, vol. 265, No. 26, Oct. 8, pp. 16737-16740, 1990 BYU-UR 000016311-16314; S00356252-S00356255.
1992 Winter Prostaglandin Conference, Jan. 8-11, 1992, Keystone, CO USA—List of Participants BYU-11-1834-1841.
Deposition transcript dated Apr. 20, 2009 and errata for Daniel Simmons.
Deposition transcript dated Apr. 21, 2009 and errata for Daniel Simmons.
Apr. 29, 1991 Seibert Fax to Simmons. BYU-08-0823-0824.
Apr. 5, 1991 Research Proposal to the Monsanto Company by Simmons BYU-11-2376-2378.
Apr. 9, 1991 Needleman Letter to Simmons BYU-20-1566.
May 21, 1991 Swaney Letter to Simmons BYU-11-2375.
Jan. 27, 1991 Department of Health and Human Services Public Health Service, Grant Application Re: Prostaglandin Synthase's Role in Transformation by v-src, submitted by Simmons BYU-12-1087-1119.
Jun. 10, 1991 Seibert Fax to Simmons BYU-08-0818-822.
Jul. 16, 1991 Simmons Fax transmission sheets to Seibert BYU-14-1832-1834.
Nov. 11, 1991 Needleman Letter to Simmons BYU-08-0799.
Mar. 17, 1992 Needleman Letter and Fax to Simmons BYU-03-0201-202.
May 21, 1992 Hardman Letter to Needleman BYU-12-0189.
Sep. 2, 1992 Hardman Letter to Needleman BYU-12-0187.
Article: G. Rosen, T. Birkenmeier, A. Raz, M. Holtzman, "Identification of a Cyclooxygenase-related Gene and Its Potential Role in Prostaglandin Formation," Biochemical and Biophysical research Communications, Nov. 15, 1989, vol. 164, No. 3, 1358-1365 BYU-12-0563-0570.
May 27, 2009 Letter from L. Schneider to M. Bettilyon.
P. Needleman, *From a Twinkle in the Eye to a Blockbuster Drug,* Research Technology Management, Nov.-Dec. 2001m p. 38-41 BYU-PFE831913-BYU-PFE831916.
Feb. 4, 2008 Letter from L. Schneider to L.R. Williams.
Jul. 7, 2088 Letter from L. Schneider to M. Bettilyon.
Sep. 29, 2008 letter from T. Hankinson to L.R. Williams.
Feb. 22, 2002 Monsanto Press Release. BYU-PFE 001414-1415.
Exhibits Supporting Plaintifs' BYU Motion to Compel Immediate Production of Documents [*Motion to Compel Immediate Production fo Documents Already Submitted to PTO on Jun. 19, 2009 (Jun. 19, 2009 IDS NPL Cite Nos. 121-122*).].
Letter from L.R. Williams to L. Schneider dated Sep. 6, 2007 enclosing Monsanto/Searle/Pfizer Notebook Index prepared by BYU.
Letter from L.R. Williams to L. Schneider dated Oct. 25, 2007.
Letter from L.R. Williams to L. Schneider dated Oct. 29, 2007.
Letter from L.R. Williams to L. Schneider dated Dec. 21, 2007.
Letter from L. Schneider to L.R. Williams dated Nov. 20, 2007.
Letter from L.R. Williams to L. Schneider dated Sep. 6, 2007.
Letter from L. Schneider to L.R. Williams dated Oct. 9, 2007.
Plaintiffs' First Request for Production of Documents.

Letter from L.R. Williams to L. Schneider dated Oct. 9, 2007.
Letter from L. Beus to R. O'Malley. dated Feb. 28, 2007 enclosing draft of Stipulated Protective Order.
Email from I. Schneider to A. Anderson, L.R. Williams, and L. Beus dated Mar. 1, 2007.
Letter from I. Schneider to A. Anderson dated Mar. 7, 2007.
Letter from L.R. Williams to L. Schneider dated Mar. 9, 2007.
Email from L. Schneider to L.R. Williams dated 3/30/07 attaching red-lined [Proposed] Protective Order.
Protective Order dated Jun. 7, 2007.
Letter from I. Schneider to L.R. Williams dated Jun. 13, 2007.
Letter from A. Anderson to I. Schneider dated Jun. 11, 2007.
Letter from L. Dobson to L. Schneider dated Jun. 14, 2007.
Letter from L.R. Williams to L. Schneider dated Jun. 13, 2007.
Letter from A. Anderson to L. Schneider dated Jul. 16, 2007 attaching spreadsheets.
Letter from L. Beus to R. O'Malley dated Jul. 31, 2007.
Letter from L.R. Williams to L. Schneider dated Aug. 16, 2007.
Letter from I. Schneider to L.R. Williams dated Aug. 20, 2007.
Letter from N. Kopinski to L.R. Williams dated Aug. 22, 2007.
Letter from L.R. Williams to L. Schneider dated Aug. 24, 2007.
Letter from L.R. Williams to L. Schneider dated Aug. 27, 2007.
Letter from I. Schneider to L.R. Williams dated Aug. 29, 2007.
Letter from N. Kopinski to L.R. Williams dated Aug. 30, 2007 attaching Defendants' Privilege Log.
Letter from L. Beus to L. Schneider dated Aug. 30, 2007 attaching spreadsheet.
Letter from L. Beus to L. Schneider dated Aug. 30, 2007.
Letter from I. Schneider to L.R. Williams dated Sep. 21, 2007.
Letter from L.R. Williams to L. Schneider dated Sep. 27, 2007.
Letter from I. Schneider to L.R. Williams dated Oct. 3, 2007.
Letter from I. Schneider to L.R. Williams dated Oct. 22, 2007.
Letter from I. Schneider to L.R. Williams dated Oct. 29, 2007.
Letter from I. Schneider to L.R. Williams dated Oct. 30, 2007.
Letter from I. Schneider to L.R. Williams dated Nov. 8, 2007.
Letter from L.R. Williams to L. Schneider dated Nov. 9, 2007.
Letter from I. Schneider to L.R. Williams dated Nov. 15, 2007.
Letter from I. Schneider to L.R. Williams dated Jan. 7, 2008 attaching invoices.
Letter from N. Kopinski to L.R. Williams dated Nov. 5, 2007.
Letter from N. Kopinski to L.R. Williams dated Feb. 7, 2008.
Letter from L.R. Williams to I. Schneider dated Jan. 30, 2008.
Letter from N. Kopinski to L.R. Williams dated Nov. 29, 2007.
Letter from L.R. Williams to L. Schneider dated Nov. 30, 2007.
Letter from N. Kopinski to L.R. Williams dated Jan. 23, 2008 enclosing invoices.
Letter from L.R. Williams to L. Schneider dated Jan. 24, 2008 enclosing check.
Exhibits to Plaintiffs' Memorandum in Support of Motion to Compel Amended Interrogatory Responses and to Deem Admitted BYU's Request for Admission.
Defendants' Response to Plaintiffs' First Request for Production of Documents dated Feb. 14, 2007.
Letter from D. Hoscheit to E. Bramhall dated Mar. 17, 2000 (BYU-01-1426).
Plaintiffs' Request for Admission to Plaintiffs dated Jul. 25, 2007.
Defendants' First Request for Admission to Plaintiffs dated Aug. 28, 2007.
Letter from L.R. Williams to L. Schneider dated Sep. 7, 2007.
Letter from L. Schneider to L.R. Williams dated Sep. 21, 2007.
Plaintiffs' Second Set of Interrogatories to Defendants dated Jan. 11, 2008.
Defendants' Response to Plaintiffs' Second Set of Interrogatories dated Feb. 13, 2008.
Letter from L.R. Williams to L. Schneider dated Feb. 20, 2008.
Letter from L. Schneider to L.R. Williams dated Feb. 27, 2008.
Letter from L. Schneider to L.R. Williams dated Oct. 22, 2007.
Letter from L. Schneider to L.R. Williams dated Jan. 16, 2008.
Letter from E. Coates to K. Ricker dated Mar. 18, 2008.
Letter from D.B. Dewey to L. Schneider dated Mar. 26, 2008.
Letter from L.R. Williams to L. Schneider dated Mar. 3, 2008.
Decision and Order (from *University of Rochester* v. *G.D. Searle et al.*) dated Mar. 28, 2002 (UOR 13-01072-UOR 13-01129).
Letter from L.R. Williams to L. Schneider dated Sep. 6, 2007 attaching Monsanto/Searle/Pfizer Notebook Index.
Letter from L. Schneider to L.R: Williams dated Oct. 30, 2007.
Portion of Deposition Transcript for K. Owen dated Jun. 10, 2008.
Letter from N, Kopinski to L.R. Williams dated Aug. 12, 2008.
Letter from N. Kopinski to L.R. Williams dated Aug. 12, 2008.
Letter from L. Schneider to Mark Bettilyon dated Aug. 12, 2008.
Letter from L.R. Williams to L. Schneider dated Jan. 18, 2008.
Letter from D.B. Dewey to L. Schneider dated Jan. 3, 2008 (BYU-PFE 141486).
Letter from N. Kopinski to D.B. Dewey dated Jan. 7, 2008.
Letter from L. Schneider to M. Bettilyon dated Aug. 12, 2008 attaching List of Specific Notebooks Searched for or.
Letter from N. Kopinski to L.R. Williams dated Jul. 23, 2008.
Letter from N. Kopinski to L.R. Williams dated Jul. 24, 2008.
Letter from L. Schneider to L.R. Williams dated Sep. 21, 2008.
Portions of Jul. 29, 2008 hearing transcript.
Letter from K. Ricker to L. Schneider dated Aug. 15, 2008.
T.E. Eling et al., *Prostaglandin H-Synthase Xenobiotic Oxidation,* Animal Reviews of Pharmacology and Toxicology (1990), at 5.
Letter to Judge Wells dated Aug. 1, 2008.
Letter from N. Kopinski to R. Williams dated Aug. 12, 2008.
Letter from N. Kopinski to R. Williams dated Aug. 19, 2008.
Letter from L. Schneider to M. Bettilyon dated Aug. 19, 2008.
Source List for Documents Found in Pfizer's Production in re *University of Rochester* v. *G.D. Searle*.
Letter from L. Schneider to M. Bettilyon dated Oct. 22, 2008.
Letter from L. Schneider to M. Bettilyon dated Oct. 29, 2008.
Letter from T. Hankinson to L.R. Williams dated Aug. 15, 2008.
Letter from L. Schneider to M. Bettilyon dated Aug. 12, 2008 and list of specific notebooks searched for or produced in response to Mar. 26, 2008 Order.
S. Hauser deposition transcript excerpts dated Jun. 10, 2008.
Letter from J. Spanbauer to K. Ricker dated Jul. 17, 2008.
Plaintiffs' First Request for Production of Documents dated Jan. 12, 2007.
Letter from L.R. Williams to N. Wyland dated Apr. 9, 2008.
Letter from N. Wyland to L.R. Williams dated Apr. 23, 2008.
Letter from L.R.Williams to N. Wyland dated May 2, 2008.
Plaintiffs' Fifth Requests for Production of Documents dated May 2, 2008.
Letter from N. Wyland to L.R. Williams dated May 7, 2008.
Letter from L.R. Williams to N. Wyland dated Jun. 26, 2008.
Letter from L.R. Williams to N. Wyland dated Jul. 16, 2008.
Letter from N. Wyland to L.R. Williams dated Jul. 3, 2008.
Notes to consolidated financial statements for Pfizer (BYU-PFE 000829-BYU-PFE 000831.
Defendants' Response to Plaintiffs' Fifth Requests for Production of Documents dated Jun. 4, 2008.
Letter from N. Kopinski to L.R. Williams dated May 23, 2008.
Letter from N. Kopinski to L.R. Williams dated Oct. 10, 2008.
Letter from N. Kopinski to L.R..Williams dated Oct. 23, 2007.
Index of marketing and financial documents from the Searle production.
Feb. 4, 1999 Industry Report from Salomon Smith Barney (BYU-PFE241790-BYU-PFE241820).
Mar. 22, 2000 Industry Update from JPMorgan (PFC00559933-PFC00559948).
Letter from N. Wyland to L.R. Williams dated Aug. 26, 2008.
Letter from L. Schneider to M. Bettilyon dated Sep. 4, 2008.
Letter from L. Schneider to Adam Anderson dated Oct. 10, 2008.
Letter from N. Kopinski to L.R. Williams dated Jul. 24, 2008, including privilege log.
Letter from N. Kopinski to L.R. Williams dated Jul. 28, 2008, including privilege log.
Letter from N. Kopinski to L.R. Williams dated Feb. 12, 2009 including privilege log.
Letter from L. Schneider to L.R. Williams dated May 16, 2007.
Letter from L. Schneider to L.R. Williams dated Aug. 20, 2007.
Excerpt of Transcript Mar. 9, 2008 Motion to Compel Hearing.
Excerpt of Transcript of Jul. 29, 2008 Motion Hearing.
Letter from N. Wyland to L. Beus dated Jan. 14, 2008.
Letter from T. Hankinson to L.R. Williams dated Jan. 28, 2009.

Letter from G. Haley to M. Bettilyon dated Jan. 29, 2009.
Letter from E. Coates to K. Ricker dated Feb. 19, 2009.
Letter L. Schneider to L.R. Williams dated Oct. 22, 2007.
Letter from D. Hoscheit to E. Bramhall dated Mar. 17, 2000 (BYU-PFE 002960- BYU-PFE 002964).
Letter from L.R Williams to L. Schneider dated Oct. 9, 2007.
Letter from L. Schneider to L.R. Williams dated Jul. 29, 2008.
Letter from E. Coates to K. Ricker dated Jul. 17, 2008.
BYU Subpoena to Monsanto Co. dated Nov. 16, 2007.
BYU Amended Subpoena to Monsanto Co. dated Jul. 16, 2008.
Email from A. Anderson to M. Zucker dated Jan. 15, 2009.
Email from E. Coates to A. Anderson dated Jan. 16, 2009.
Letter M. Bettilyon to G. Haley dated Feb. 4, 2009.
Letter from G. Haley to M. Bettilyon dated Feb. 9, 2009.
Journal of Neurochemistry, "Evidence for Two Distinct Forms of Fatty Acid Cyclooxygenase in Brain" T. Lysz & P. Needleman vol. 38, p. 1112 dated Nov. 4, 1982.
Letter G. Haley to M. Bettilyon dated Feb. 6, 2009.
Excerpt of Deposition Transcript of P. Needleman, *IREF* v. *Pfizer,* dated Apr. 24, 2007.
Excerpt of Trial Transcript, *IREF* v. *Prizer,* dated Dec. 18, 2008.
Research-Technology Management, "From a twinkle in the eye to a blockbuster drug: The story of Celebrex holds lessons for R&D leaders everywhere," P. Needleman dated Nov. 2001.
Letter from L. Schneider to M. Bettilyon dated Apr. 22, 2008 with indexes of production enclosed.
Off the Charts: Pay, Profits and Spending by Drug Companies, Families USA, Jul. 2001 (BYU-PFE831921-BYU-PFE831956).
Pharmacia Annual Report 10K Compensation Table (BYU-PFE831917- BYU-PFE831920).
Letter from N. Kopinski to L.R. Williams dated Feb. 12, 2009 with attached privilege log.
Needle-P 10000013599.
Exhibit 2 to Defendants' Memorandum in Support of Motion for Partial Summary Judgment Regarding Integration of the Research Agreement, Dated Aug. 1, 1991 Excerpt of Deposition Transcript of L. Astle.
Letter from *J. Spanbauer* v. *K. Ricker* dated May 11, 2009.
Letter from M. Bettilyon to G. Haley dated May 15, 2009.
Email from J. Spanbauer to M. Bettilyon dated May 19, 2009.
Email from M. Bettilyon to J. Spanbauer dated May 19, 2009.
Email J. Spanbauer to M. Bettilyon dated May 20, 2009.
Letter from J. Spanbauer to M. Bettilyon dated May 20, 2009.
Email from M. Bettilyon to J. Spanbauer dated May 20, 2009.
Email from J. Spanbauer to M. Bettilyon dated May 20, 2009.
Excerpt of transcript from Mar. 19, 2008 Motion to Compel Hearing.
Excerpt of deposition of S. Hauser dated Jun. 10, 2009.
Defendant Pfizer's Responses and Objections to Plaintiffs' 30(b)(6) Notice of Deposition to Pfizer dated Feb. 22, 2008.
Letter from J. Spanbauer to K. Ricker dated May 21, 2008.
Excerpt of transcript from Apr. 7, 2009 motion hearing.
Letter from N. Kopinski to L.R. Williams dated Jul. 17, 2007.
Defendants Pfizer Inc., G.D. Searle LLLC, and Pharmacia Corp.'s Response to Plaintiffs' First Request for Production of Documents dated Feb. 14, 2007.
Letter from L. Schneider to L.R. Williams dated Nov. 8, 2007.
Letter from L. Schneider to L.R. Williams dated Nov. 15, 2007.
Letter from E. Coates to A. Anderson dated May 14, 2009.
Letter from M. Bettilyon to G. Haley dated Mar. 4, 2009.
Letter from G. Haley to M. Bettilyon dated Mar. 10, 2009.
Letter from L. Schneider to M. Bettilyon dated Apr. 22, 2008.
Letter from L. Schneider to M. Bettilyon dated May 5, 2008.
Letter from L. Schneider to M. Bettilyon dated May 27, 2008.
Letter from A. Anderson to L. Schneider dated Jul. 16, 2007.
Letter from A. Anderson to L.R. Williams dated Oct. 3, 2007.
Excerpt of transcript from Apr. 8, 2009 motion hearing.
Letter from L. Schneider to M. Bettilyon dated Apr. 18, 2008.
Excerpt of deposition transcript of D. Simmons.
Letter from N. Kopinski to M. Bettilyon dated Feb. 4, 2009.
Letter from L. Schneider to L.R. Williams dated May 12, 2009.
Letter from N. Kopinski to L.R. Williams dated Jul. 18, 2008.
Exhibit 61—Monsanto 1996 Annual Report.
Set/Reset Deadlines as to Plaintiff's Motion re Memorandum in Opposition to Motion, (Alternative) Rule 56(f) Motion, Motion for Suspension of Reissue Proceedings, Motion to Amend/Correct for Leave From and Modification to the Protective Order, Motion for Partial Summary Judgment Regarding Integration of the Research Agreement, Dated Aug. 1, 1991.
Order Re Hearing Set for July 2, 2009.
Defendants' Opposition to Plaintiffs' (Alternative) Rule 56(f) Motion Opposing Defendants' Motion for Partial Summary Judgment Regarding Integration of the Research Agreement Dated Aug. 1, 1991 (including exhibits 1-6).
Minute Order. Proceedings held before Magistrate Judge Brooke C. Wells. Motion Hearing held on Jul. 2, 2009 re Plaintiff's Motion to Strike Sealed Document, Motion for Leave to File Motion to Allow in Camera Submission of Affidavits Regarding Discovery Efforts filed by Pfizer and Plaintiff's Motion to Compel Preserve and Produce Evidence filed by Daniel L. Simmons, Brigham Young University.
Plaintiffs' Notice Regarding Jul. 22, 2009 Hearing (re 272 Order on Motion to Compel, Motion Hearing, 239 Notice of Hearing on Motion).
Exhibit 6—Letter from L. Schneider to K. Ricker.
Order granting Motion to Amend/Correct Scheduling Order.
Set/Reset Deadlines: Amended Pleadings due by: Plaintiffs Aug. 10, 2009, Defendants Aug. 23, 2009.
Order Granting in Part Pfizer's Motion to Allow in Camera Submission of Affidavits Regarding Discovery Efforts and Deeming Moot BYU's Motion to Strike.
Notice of Submission of Privilege Logs by Pfizer.
Exhibit 1—G. Haley Aff. Privilege Log.
Exhibit 2—D. Parkinson Aff. Privilege Log.
Exhibit 5—R. O'Malley Aff. Privilege Log.
Exhibit 6—L. Schneider Aff. Privilege Log.
Exhibit 7—N. Wyland Aff. Privilege Log.
Exhibit 9—J. Spanbauer Aff. Privilege Log.
Exhibit 10—N. Kopinski Aff. Privilege Log.
Exhibit 11—L. Friedlieb Aff. Privilege Log.
Defendants' Reply Memorandum in Support of Motion for Partial Summary Judgment Regarding Integration of the Research Agreement, Dated Aug. 1, 1991.
Order—Request for Courtesy Copies Pertaining to Aug. 18, 2009 Hearing.
Exhibit 76—Plaintiffs' Supplemental Response to Defendants' Interrogatory No. 4, served Jun. 27, 2008.
Exhibit 78—Research Agreement between Brigham Young University and Monsanto Company, effective as of Aug. 1, 1991 (BYU-11-0111-0127).
Notice of Filing of Official Transcript of Proceedings held on Aug. 18, 2009—Motion Hearing before Judge Dale A. Kimball.
Notice of Filing of Official Transcript of Proceedings held on Apr. 8, 2009—Motion Hearing before Judge Brooke Wells.
Aug. 18, 2009 Hearing Transcript.
Memorandum Decision and Order granting in part and denying in part Motion to Amend/Correct for Leave From and Modification to the Protective Order; denying Motion for Suspension of Reissue Proceedings; denying Motion for Partial Summary Judgment Regarding Integration of the Research Agreement, Dated Aug. 1, 1991; finding/denying as moot Motion re Memorandum in Opposition to Motion, (Alternative) Rule 56(f) Motion.
Order and Memorandum Decision Granting in Part Plaintiffs' Motion for Sanctions.
R. Soliman et al. *J. Pharm. Sci.,* 76, 626 (1987).
H. Mokhtar, Pak *J. Sci. Ind. Res.,* 31, 762 (1988).
H. Mokhtar et al. *Pak. J. Sci. Ind. Res.,* 34, 9 (1991).
M. Cocco et al. *Il Farmaco-Ed. Sci.,* 40, 272 (1985).
R. Soliman et al. *J. Pharm. Sci.,* 72, 1004 (1983).
H. Feid-Allah, *Pharmazie,* 36, 754 (1981).
R. Soliman et al. *J. Pharm. Sci.,* 70, (1981).
Maybridge Chemical Co./ *Ryan Scientific Catalog,* Compound No. BTB 06812 (No date available).
H. Mokhtar et al. *Pak. J. Sci. Ind. Res.,* 33:30-36 (1990).
H. Mokhtar et al. *J. Chem. Soc. Pak.,* 10:414-424 (1988).
R. Soliman et al. *J. Pharm. Sci.,* 72:999-1004 (1983).
M.S. I. Makki et al. *Chem. Abstracts,* 121:11 (1994).

R. Hamilton, *J. Heterocyclic Chem.,* 13, 545 (1976).
M. Hashem et al. *J. Med. Chem.,* 19, 229 (1976).
H. Feid-Allah, *J. Heterocyclic Chem.,* 18, 1561 (1981).
H. Mokhtar et al, *Pharmazie,* 33, 649 (1978).
R. Soliman et al. *Pharmazie,* 33, (1978).
Bandaru et al. Cancer Research, 56. pp. 4566-4569 (1996).

* cited by examiner

4-[5-(4-METHYLPHENYL)-3-(TRIFLUORO METHYL)-1H-PYRAZOL-1-YL]BENZENE SULFONAMIDE FOR THE TREATMENT OF INFLAMMATION OR AN INFLAMMATION-ASSOCIATED DISORDER

Matter enclosed in heavy brackets [ ] appears in the original patent but forms no part of this reissue specification; matter printed in italics indicates the additions made by reissue.

RELATED CASE

[This is an application under 35 USC §371 of International Application PCT/US 94/12720, with an international filing date of Nov. 14, 1994, which is a continuation-in-part of U.S. patent application Ser. No. 08/223,629, filed Apr. 6, 1994, now issued as U.S. Pat. No. 5,521,207, which is a continuation-in-part of U.S. patent application Ser. No. 08/160,594, filed Nov. 30, 1993, now issued as U.S. Pat. No. 5,466,823.] *This application is a reissue of U.S. Pat. No. 5,760,068, which issued from U.S. application Ser. No. 08/648,113 filed on Sep. 6, 1996, which is a 35 USC §371 National Stage Application of PCT/US 94/12720 filed Nov. 14, 1994, and a divisional of U.S. application Ser. No. 08/160,594 filed Nov. 30, 1993* (*now issued as U.S. Pat. No. 5,466,823*).

FIELD OF THE INVENTION

This invention is in the field of anti-inflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of anti-inflammatory drug discovery. However, common non-steroidal anti-inflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

[Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase II (COX II)" or "prostaglandin G/H synthase II") provides a viable target of inhibition which more effectively reduces inflammation and produces fewer and less drastic side effects.]

Pyrazoles have been described for use in the treatment of inflammation. U.S. Pat. No. 5,134,142 to Matsuo et at described 1,5-diaryl pyrazoles, and specifically, 1-(4-fluorophenyl)-5-[4-(methylsulfonyl)phenyl]-3-trifluoromethyl pyrazole, as having anti-inflammatory activity.

[U.S. Pat. No. 3,940,418 to R. Hamilton described tricyclic 4,5-dihydrobenz[g]indazoles as antiinflammatory agents. In addition, R. Hamilton [J. Heterocyclic Chem., 13, 545 (1976)] describes tricyclic 4,5-dihydrobenz[g]indazoles as antiinflammatory agents. U.S. Pat. No. 5,134,155 describes fused tricyclic pyrazoles having a saturated ring bridging the pyrazole and a phenyl radical as HMG-CoA reductase inhibitors. European publication EP 477,049, published Mar. 25, 1992, described [4,5-dihydro-1-phenyl-1H-benz[g]indazol-3-yl]amides as having antipsychotic activity. European publication EP 347,773, published Dec. 27, 1989, describes [4,5-dihydro-1-phenyl-1H-benz[g]indazol-3yl]propanamides as immunostimulants. M. Hashem et al [J. Med. Chem., 19, 229 (1976)] describes fused tricyclic pyrazoles, having a saturated ring bridging the pyrazole and a phenyl radical, as antibiotics.]

Certain substituted pyrazolyl-benzenesulfonamides have been described in the literature as synthetic intermediates. Specifically, 4-[5-(4-chlorophenyl)-3-phenyl-1H-pyrazol-1yl]benzenesulfonamide has been prepared from a pyrazoline compound as an intermediate for compounds having hypoglycemic activity [R. Soliman et al, J. Pharm. Sci., 76, 626 (1987)]. 4-[5-[2-(4-Bromophenyl)-2H-1,2,3-triazol-4-yl]-3-methyl-1H-pyrazol-1-yl]benzenesulfonamide has been prepared from a pyrazoline compound and described as potentially having hypoglycemic activity [H. Mokhtar, Pak. J. Sci. Ind. Res., 31, 762 (1988)]. Similarly, 4-[4-bromo-5-[2-(4-chlorophenyl)-2H-1,2,3-triazol-4yl]-3-methyl-1H-pyrazol-1-yl]benzenesulfonamide has been prepared [H. Mokhtar et al, Pak. J. Sci. Ind. Res., 34, 9 (1991)].

The phytotoxicity of pyrazole derivatives is described [M. Cocco et al. Il. Farmaco-Ed. Sci., 40, 272 (1985)], specifically for 1-[4-(aminosulfonyl)phenyl]-5-phenyl-1H-pyrazole-3,4-dicarboxylic acid.

[The use of styryl pyrazole esters for antidiabetes drugs is described [H. Mokhtar et al, Pharmazie, 33, 649-651 (1978)]. The use of styryl pyrazole carboxylic acids for antidiabetes drugs is described [R. Soliman et al, Pharmazie, 33, 184-5 (1978)].] The use of 4-[3,4,5-trisubstituted-pyrazol-1-yl]benzenesulfonamides as intermediates for sulfonylurea anti-diabetes agents is described, and specifically, 1-[4-(aminosulfonyl)phenyl]-3-methyl-5-phenyl-1H-pyrazole-4-carboxylic acid [R. Soliman et al, J. Pharm. Sci., 72, 1004 (1983)]. A series of [443] *4,4,3*-substituted methyl-5-phenyl-1H-pyrazol-1-yl]benzenesulfonamides has been prepared as intermediates for anti-diabetes agents, and more specifically, 4-[3-methyl-5-phenyl-1H-pyrazol-1-yl]benzenesulfonamide [H. Feid-Allah, Pharmazie, 36, 754 (1981)]. In addition, 1-(4-[aminosulfonyl]phenyl)-5-phenylpyrazole-3-carboxylic acid has been prepared from the above described [443] *4,4,3*-methyl-5-phenyl-1H-pyrazol-1-yl]benzenesulfonamide compound [R. Soliman et al, J.[Par-m.] *Pharm.* Sci., 70, 602 (1981)].

DESCRIPTION OF THE INVENTION

[A class of compounds useful in treating inflammation-related disorders is defined by Formula I:

(I)

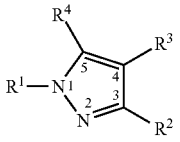

]

[wherein $R^1$ is selected from aryl and heteroaryl, wherein $R^1$ is substituted at a substitutable position with one or more radicals selected from sulfamyl, halo, alkyl, alkoxy, hydroxyl, haloalkyl and

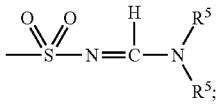

]

[wherein $R^2$ is selected from hydrido, halo, alkyl, haloalkyl, cyano, nitro, formyl, carboxyl, alkoxy, aminocarbonyl, alkoxycarbonyl, carboxyalkyl, alkoxycarbonylalkyl, amidino, cyanoamidino, cyanoalkyl, alkoxycarbonylcyanoalkenyl, aminocarbonylalkyl, N-alkylaminocarbonyl, N-arylaminocarbonyl, N,N-dialkylaminocarbonyl, N-alkyl-N-arylaminocarbonyl, cycloalkylaminocarbonyl, heterocyclicaminocarbonyl, carboxyalkylaminocarbonyl, aralkoxycarbonylalkylaminocarbonyl, alkylcarbonyl, alkylcarbonylalkyl, hydroxyalkyl, haloaralkyl, carboxyhaloalkyl, alkoxycarbonylhaloalkyl, aminocarbonylhaloalkyl, alkylaminocarbonylhaloalkyl, N-alkylamino, N,N-dialkylamino, N-arylamino, N-aralkylamino, N-alkyl-N-aralkylamino, N-alkyl-N-arylamino, aminoalkyl, N-alkylaminoalkyl, N,N-dialkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylthio, alkylsulfinyl, alkylsulfonyl, N-alkylaminosulfonyl, N-arylaminosulfonyl, arylsulfonyl, N,N-dialkylaminosulfonyl, N-alkyl-N-arylaminosulfonyl, heterocyclic,

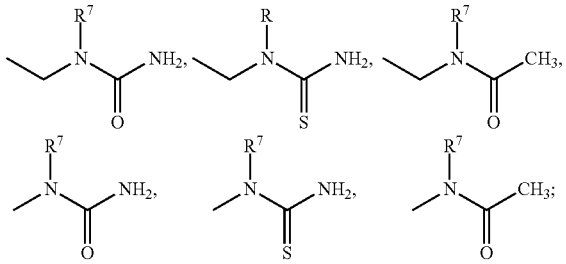

]

[wherein $R^3$ is selected from hydrido, alkyl, halo, haloalkyl, cyano, nitro, formyl, carboxyl, alkoxycarbonyl, carboxyalkyl, alkoxycarbonylalkyl, amidino, cyanoamidino, aminocarbonyl, alkoxy, N-alkylamino, N,N-dialkylamino, aminocarbonylalkyl, N-alkylaminocarbonyl, N-arylaminocarbonyl, N,N-dialkylaminocarbonyl, N-alkyl-N-arylaminocarbonyl, alkylcarbonyl, alkylcarbonylalkyl, hydroxyalkyl, alkylthio, alkylsulfinyl, alkylsulfonyl, N-alkylaminosulfonyl, N-arylaminosulfonyl, arylsulfonyl, N,N-dialkylaminosulfonyl, N-alkyl-N-arylaminosulfonyl, cycloalkyl, heterocyclic, heterocyclicalkyl and aralkyl;]

[wherein $R^4$ is selected from aralkenyl, aryl, cycloalkyl, cycloalkenyl and heterocyclic; wherein $R^4$ is optionally substituted at a substitutable position with one or more radicals selected from halo, alkylthio, alkylsulfinyl, alkyl, alkenyl, alkylsulfonyl, cyano, carboxyl, alkoxycarbonyl, aminocarbonyl, N-alkylaminocarbonyl, N-arylaminocarbonyl, N,N-dialkylaminocarbonyl, N-alkyl-N-arylaminocarbonyl, haloalkyl, hydroxyl, alkoxy, hydroxylakyl, haloalkoxy, sulfamyl, N-alkylaminosulfonyl, amino, N-alkylamino, N,N-dialkylamino, heterocyclic, cycloalkylalkyl, nitro, acylamino,

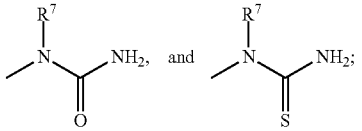

]

[or wherein $R^3$ and $R^4$ together form

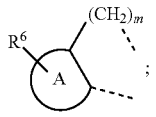

]

[wherein m is 1 to 3, inclusive;]

[wherein A is selected from phenyl and five or six membered heteroaryl;]

[wherein $R^5$ is alkyl;]

[wherein $R^6$ is one or more radicals selected from halo, alkylthio, alkylsulfinyl, alkylsulfonyl, cyano, carboxyl, alkoxycarbonyl, aminocarbonyl, N-alkylaminocarbonyl, N-arylaminocarbonyl, alkyl, alkenyl, N,N-dialkylaminocarbonyl, N-alkyl-N-arylaminocarbonyl, haloalkyl, hydrido, hydroxyl, alkoxy, hydroxyalkyl, haloalkoxy, sulfamyl, N-alkylaminosulfonyl, amino, N-alkylamino, N,N-dialkylamino, heterocyclic, cycloalkylalkyl, nitro and acylamino; and]

[wherein $R^7$ is selected from hydrido, alkyl, aryl and aralkyl;]

[provided $R^2$ and $R^3$ are not identical radicals selected from hydrido, carboxyl and ethoxycarbonyl; further provided that $R^2$ is not carboxyl or methyl when $R^3$ is hydrido and when $R^4$ is phenyl; further provided that $R^4$ is not triazolyl when $R^2$ is methyl; further provided that $R^4$ is not aralkenyl when $R^2$ is carboxyl, aminocarbonyl or ethoxycarbonyl; further provided that $R^4$ is not phenyl when $R^2$ is methyl and $R^3$ is carboxyl; further provided that $R^4$ is not unsubstituted thienyl when $R^2$ is trifluoromethyl; and further provided that $R^4$ is aryl substituted with sulfamyl or $R^6$ is sulfamyl, when $R^1$ is phenyl not substituted with sulfamyl; or a pharmaceutically-acceptable salt thereof.]

[The phrase "further provided", as used in the above description, is intended to mean that the denoted proviso is not to be considered conjunctive with any of the other provisos.]

Compounds of [Formula I] *the present invention* would be useful for[, but not limited to,] the treatment of inflammation in a subject, and for treatment of other inflammation-associated disorders, such as, as an analgesic in the treatment of pain and headaches, or as an antipyretic for the treatment of fever. For example, compounds of [Formula I] *the present invention* would be useful to treat arthritis, including but not limited to rheumatoid arthritis, spondyloarthropathies, gouty arthritis, osteoarthritis, systemic lupus erythematosus and juvenile arthritis. Such compounds of [Formula I] *the present invention* would be useful in the treatment of asthma, bronchitis, menstrual cramps, tendinitis, bursitis, and skin related conditions such as psoriasis, eczema, burns and dermatitis. Compounds of [Formula I] *the present invention* also would be useful to treat gastrointestinal conditions such as inflammatory bowel disease, Crohn's disease, gastritis, irritable bowel syndrome and ulcerative colitis [and for the prevention of colorectal cancer]. Compounds of [Formula I] *the present invention* would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as antiinflammatory agents, such as for the treatment of arthritis, with the additional benefit of having significantly less harmful side effects.

[The present invention preferably includes compounds which selectively inhibit cyclooxygenase II over cyclooxygenase I. Preferably, the compounds have a cyclooxygenase II $IC_{50}$ of less than about 0.2 μM, and also have a selectivity ratio of cyclooxygenase II inhibition over cyclooxygenase I inhibition of at least 50, and more preferably of at least 100. Even more preferably, the compounds have a cyclooxygenase I $IC_{50}$ of greater than about 1 μM, and more preferably of greater than 10 μM. Such preferred selectivity may indicate an ability to reduce the incidence of common NSAID-induced side effects.]

[A preferred class of compounds consists of those compounds of Formula I wherein $R^1$ is selected from aryl selected from phenyl, naphthyl and biphenyl, and five- or six-membered heteroaryl, wherein $R^1$ is substituted at a substitutable position with one or more radicals selected from sulfamyl, halo, lower alkyl, lower alkoxy, hydroxyl, lower haloalkyl and

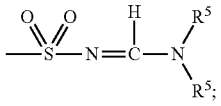

]

[wherein $R^2$ is selected from hydrido, halo, lower alkyl, lower haloalkyl, cyano, nitro, formyl, carboxyl, lower alkoxycarbonyl, lower carboxyalkyl, lower alkoxycarbonylalkyl, amidino, cyanoamidino, lower cyanoalkyl, lower alkoxycarbonylcyanoalkenyl, aminocarbonyl, lower alkoxy, lower aryloxy, lower aralkoxy, lower aminocarbonylalkyl, lower N-alkylaminocarbonyl, N-arylaminocarbonyl, lower N,N-dialkylaminocarbonyl, lower N-alkyl-N-arylaminocarbonyl, lower cycloalkylaminocarbonyl, lower heterocyclicaminocarbonyl, lower carboxyalkylaminocarbonyl, lower aralkoxycarbonylalkylaminocarbonyl, lower haloaralkyl, lower carboxyhaloalkyl, lower alkoxycarbonylhaloalkyl, lower aminocarbonylhaloalkyl, lower alkylaminocarbonylhaloalkyl, lower alkylcarbonyl, lower alkylcarbonylalkyl, lower alkylamino, lower N,N-dialkylamino, N-arylamino, lower N-aralkylamino, lower N-alkyl-N-aralkylamino, lower N-alkyl-N-arylamino, lower aminoalkyl, lower N-alkylaminoalkyl, lower N,N-dialkylaminoalkyl, lower N-arylaminoalkyl, lower N-aralkylaminoalkyl, lower N-alkyl-N-aralkylaminoalkyl, lower N-alkyl-N-arylaminoalkyl, arylthio, lower aralkylthio, lower hydroxylakyl, lower alkylthio, lower alkylsulfinyl, lower alkylsulfonyl, lower N-alkylaminosulfonyl, N-arylaminosulfonyl, arylsulfonyl, lower N,N-dialkylaminosulfonyl, lower N-alkyl-N-arylaminosulfonyl, heterocyclic,

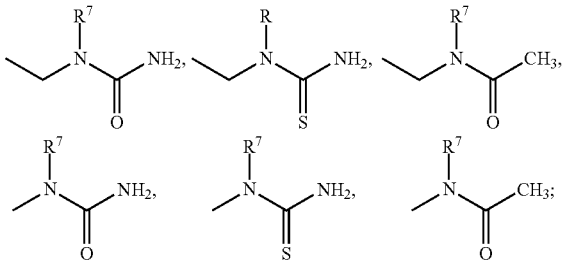

]

[wherein $R^3$ is selected from hydrido, lower alkyl, halo, lower haloalkyl, cyano, nitro, formyl, carboxyl, lower alkoxycarbonyl, lower carboxyalkyl, lower alkoxycarbonylalkyl, amidino, cyanoamidino, aminocarbonyl, lower alkoxy, lower N-alkylamino, lower N,N-dialkylamino, lower aminocarbonylalkyl, lower N-alkylaminocarbonyl, lower N-arylaminocarbonyl, lower N,N-dialkylaminocarbonyl, lower N-alkyl-N-arylaminocarbonyl, lower alkylcarbonyl, lower alkylcarbonylalkyl, lower hydroxyalkyl, lower alkylthio, lower alkylsulfinyl, lower alkylsulfonyl, lower N-alkylaminosulfonyl, N-arylaminosulfonyl, arylsulfonyl, lower N,N-dialkylaminosulfonyl, lower N-alkyl-N-arylaminosulfonyl, lower cycloalkyl, heterocyclic, lower heterocyclicalkyl and lower aralkyl;]

[wherein $R^4$ is selected from lower aralkenyl, aryl, lower cycloalkyl, lower cycloalkenyl and five to ten membered heterocyclic; wherein $R^4$ is optionally substituted at a substitutable position with one or more radicals selected from halo, lower alkylthio, lower alkylsulfinyl, lower alkyl, lower alkenyl, lower alkylsulfonyl, cyano, carboxyl, lower alkoxycarbonyl, aminocarbonyl, lower N-alkylaminocarbonyl, N-arylaminocarbonyl, lower N,N-dialkylaminocarbonyl, lower N-alkyl-N-arylaminocarbonyl, lower haloalkyl, hydroxyl, lower alkoxy, lower hydroxyalkyl, lower haloalkoxy, sulfamyl, lower N-alkylaminosulfonyl, amino, lower N-alkylamino, lower N,N-dialkylamino, five- or six-membered heterocyclic, lower cycloalkylalkyl, nitro, acylamino,

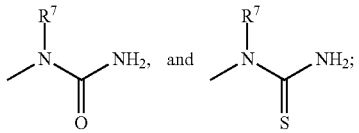

]

[or wherein $R^3$ and $R^4$ together form

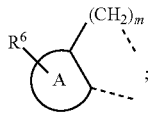

]

[wherein m is 1 to 3, inclusive;]

[wherein A is selected from phenyl and five or six membered heteroaryl;]

[wherein $R^5$ is lower alkyl;]

[wherein $R^6$ is one or more radicals selected from halo, lower alkylthio, lower alkylsulfinyl, lower alkylsulfonyl, cyano, carboxyl, lower alkoxycarbonyl, aminocarbonyl, lower N-alkylaminocarbonyl, N-arylaminocarbonyl, lower alkyl, lower alkenyl, lower N,N-dialkylaminocarbonyl, lower N-alkyl-N-arylaminocarbonyl, lower haloalkyl, hydrido, hydroxyl, lower alkoxy, lower hydroxyalkyl, lower haloalkoxy, sulfamyl, lower N-alkylaminosulfonyl, amino, lower N-alkylamino, lower N,N-dialkylamino, five- or six membered heterocyclic, lower cycloalkylalkyl, nitro and acylamino; and]

[wherein $R^7$ is selected from hydrido, lower alkyl, aryl and lower aralkyl;]

[or a pharmaceutically-acceptable salt thereof.]

[A more preferred class of compounds consists of those compounds of Formula I where $R^1$ is phenyl, wherein $R^1$ is substituted at a substitutable position with one or more radicals selected from sulfamyl, halo, lower alkyl, lower alkoxy, hydroxyl, lower haloalkyl and

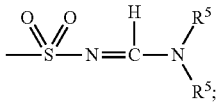

]

[wherein $R^2$ is selected from hydrido, lower alkyl, lower haloalkyl, cyano, carboxyl, lower alkoxycarbonyl, lower carboxyalkyl, lower cyanoalkyl, lower alkoxycarbonylcyanoalkenyl, lower haloaralkyl, lower carboxyhaloalkyl, lower alkoxycarbonylhaloalkyl, lower aminocarbonylhaloalkyl, lower alkylaminocarbonylhaloalkyl, lower N-alkylamino, lower N,N-dialkylamino, N-arylamino, lower N-aralkylamino, lower N-alkyl-N-aralkylamino, lower N-alkyl-N-arylamino, lower aminoalkyl, lower N-alkylaminoalkyl, lower N,N-dialkylaminoalkyl, lower N-arylaminoalkyl, lower N-aralkylaminoalkyl, lower N-alkyl-N-aralkylaminoalkyl, lower N-alkyl-N-arylaminoalkyl, aryloxy, lower aralkoxy, lower alkoxy, lower alkylthio, arylthio, lower aralkylthio, aminocarbonyl, lower aminocarbonylalkyl, lower N-alkylaminocarbonyl, N-arylaminocarbonyl, lower N,N-dialkylaminocarbonyl, lower N-alkyl-N-arylaminocarbonyl, lower cycloalkylaminocarbonyl, lower carboxyalkylaminocarbonyl, lower aralkoxycarbonylalkylaminocarbonyl, lower hydroxyalkyl,

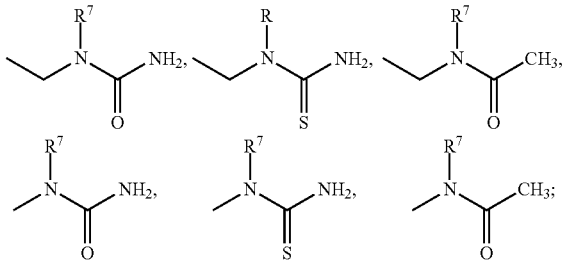

]

[wherein $R^3$ is selected from hydrido, lower alkyl, halo, cyano, lower hydroxyalkyl, lower alkylthio, lower alkylsulfinyl, lower alkylsulfonyl, lower alkoxy, lower N-alkylamino, lower N,N-dialkylamino, lower N-alkylaminosulfonyl, N-arylaminosulfonyl, arylsulfonyl, lower N,N-dialkylaminosulfonyl, lower N-alkyl-N-arylaminosulfonyl and lower cycloalkyl;]

[wherein $R^4$ is selected from lower aralkenyl, aryl, lower cycloalkyl, lower cycloalkenyl and five to ten membered heterocyclic; wherein $R^4$ is optionally substituted at a substitutable position with one or more radicals selected from halo, lower alkylthio, lower alkylsulfinyl, lower alkyl, lower alkenyl, lower alkylsulfonyl, cyano, carboxyl, lower alkoxycarbonyl, aminocarbonyl, lower haloalkyl, hydroxyl, lower alkoxy, lower hydroxyalkyl, lower haloalkoxy, sulfamyl, lower alkylaminosulfonyl, amino, lower N-alkylamino, lower N,N-dialkylamino, five or six membered heterocyclic, lower cycloalkylalkyl, nitro,

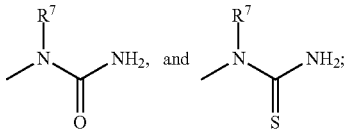

]

[or wherein $R^3$ and $R^4$ together form

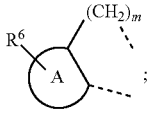

]

[wherein m is 2;]

[wherein A is selected from phenyl and five or six membered heteroaryl;]

[wherein $R^5$ is lower alkyl;]

[wherein $R^6$ is one or more radicals selected from halo, lower alkylthio, lower alkylsulfinyl, lower alkyl, lower alkenyl, lower alkylsulfonyl, cyano, carboxyl, lower alkoxycarbonyl, aminocarbonyl, lower haloalkyl, hydroxyl, lower alkoxy, lower hydroxyalkyl, lower haloalkoxy, sulfamyl, amino, lower N-alkylamino, lower N,N-dialkylamino, lower cycloalkylalkyl and nitro; and]

[wherein $R^7$ is selected from hydrido, lower alkyl, aryl and lower aralkyl;]

[or a pharmaceutically-acceptable salt thereof.]

[An even more preferred class of compounds consists of those compounds of Formula I wherein $R^1$ is phenyl, wherein $R^1$ is substituted at a substitutable position with one or more radicals selected from sulfamyl, halo, lower alkyl, lower alkoxy and

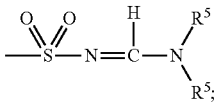

]

[wherein $R^2$ is selected from hydrido, lower alkyl, lower haloalkyl, cyano, carboxyl, lower alkoxycarbonyl, lower carboxyalkyl, lower cyanoalkyl, lower alkoxycarbonylcyanoalkenyl, lower haloaralkyl, lower carboxyhaloalkyl, lower alkoxycarbonylhaloalkyl, lower aminocarbonylhaloalkyl, lower alkylaminocarbonylhaloalkyl, lower N-alkylamino, lower N,N-dialkylamino, N-arylamino, lower N-aralkylamino, lower N-alkyl-N-aralkylamino, lower N-alkyl-N-arylamino, lower aminoalkyl, lower N-alkylaminoalkyl, lower N,N-dialkylaminoalkyl, lower N-arylaminoalkyl, lower N-aralkylaminoalkyl, lower N-alkyl-N-arylaminoalkyl, lower alkoxy, aryloxy, lower aralkoxy, lower alkylthio, arylthio, lower aralkylthio, aminocarbonyl, lower aminocarbonylalkyl, lower N-alkylaminocarbonyl, N-arylaminocarbonyl, lower N,N-dialkylaminocarbonyl, lower N-alkyl-N-arylaminocarbonyl, lower cycloalkylaminocarbonyl, lower carboxyalkylaminocarbonyl, lower heterocyclicaminocarbonyl, lower aralkoxycarbonylalkylaminocarbonyl, lower hydroxyalkyl,

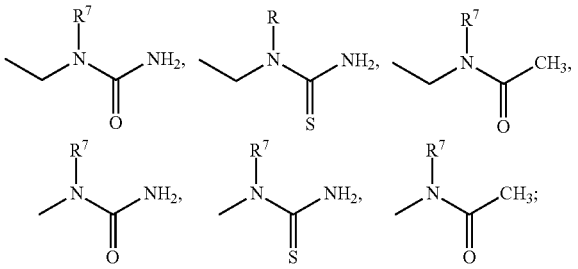

]

[wherein $R^3$ is selected from hydrido, lower alkyl, halo, cyano, lower hydroxyalkyl, lower alkoxy, lower N-alkylamino, lower N,N-dialkylamino, lower alkylthio, lower alkylsulfonyl and lower cycloalkyl;]

[wherein $R^4$ is selected from lower aralkenyl, aryl, lower cycloalkyl, lower cycloalkenyl and five to ten membered heterocyclic; wherein $R^4$ is optionally substituted at a substitutable position with one or more radicals selected from halo, lower alkylthio, lower alkylsulfinyl, lower alkyl, lower alkenyl, lower alkylsulfonyl, cyano, carboxyl, lower alkoxycarbonyl, aminocarbonyl, lower haloalkyl, hydroxyl, lower alkoxy, lower hydroxyalkyl, lower haloalkoxy, sulfamyl, amino, lower N-alkylamino, lower N,N-dialkylamino, five or six membered heterocyclic, lower cycloalkylalkyl, nitro,

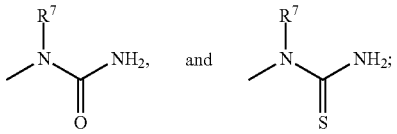

]

[or wherein $R^3$ and $R^4$ together form

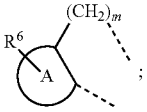

]

[wherein m is 2;]

[wherein A is selected from phenyl and five membered heteroaryl;]

[wherein $R^5$ is lower alkyl;]

[wherein $R^6$ is one or more radicals selected from halo, lower alkyl, lower alkylsulfonyl, lower haloalkyl, lower alkoxy, sulfamyl, amino and nitro; and]

[wherein $R^7$ is selected from hydrido, lower alkyl, aryl and lower aralkyl;]

[or a pharmaceutically-acceptable salt thereof.]

[Within Formula I there is a subclass of compounds which consists of compounds wherein $R^1$ is phenyl substituted at a substitutable position with one or more radicals selected from halo, lower alkyl, sulfamyl and

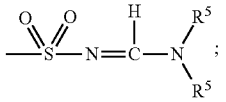

]

[wherein $R^2$ is selected from hydrido, lower alkyl, lower haloalkyl, cyano, carboxyl, lower alkoxycarbonyl, lower carboxyalkyl, lower cyanoalkyl, lower alkoxycarbonylcyanoalkenyl, lower haloaralkyl, lower carboxyhaloalkyl, lower alkoxycarbonylhaloalkyl, lower aminocarbonylhaloalkyl, lower alkylaminocarbonylhaloalkyl, lower N-alkylamino, lower N,N-dialkylamino, N-arylamino, lower N-aralkylamino, lower N-alkyl-N-aralkylamino, lower N-alkyl-N-arylamino, lower aminoalkyl, lower N-alkylaminoalkyl, lower N,N-dialkylaminoalkyl, lower N-arylaminoalkyl, lower N-aralkylaminoalkyl, lower N-alkyl-N-aralkylaminoalkyl, lower N-alkyl-N-arylaminoalkyl, lower alkoxy aryloxy, lower aralkoxy, lower alkylthio, arylthio, lower aralkylthio, aminocarbonyl, lower aminocarbonylalkyl, lower N-alkylaminocarbonyl, N-arylaminocarbonyl, lower N,N-dialkylaminocarbonyl, lower N-alkyl-N-arylaminocarbonyl, lower cycloalkylaminocarbonyl, lower carboxyalkylaminocarbonyl, lower aralkoxycarbonylalkylaminocarbonyl, lower hydroxyalkyl,

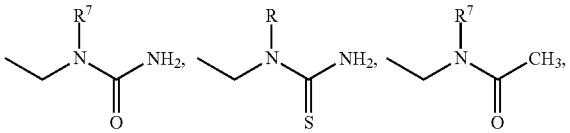

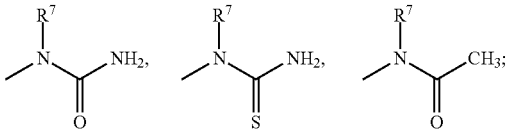

]

[wherein $R^3$ is selected from hydrido, lower alkyl, halo, cyano, lower hydroxyalkyl, lower alkoxy, lower alkylthio, lower N-alkylamino, lower N,N-dialkylamino, lower alkylsulfonyl and lower cycloalkyl;]

[wherein $R^4$ is selected from lower aralkenyl, aryl, lower cycloalkyl, lower cycloalkenyl and five to ten membered heterocyclic; wherein $R^4$ is optionally substituted at a substitutable position with one or more radicals selected from halo, lower alkylthio, lower alkylsulfinyl, lower alkyl, lower alkenyl, lower alkylsulfonyl, cyano, carboxyl, lower alkoxycarbonyl, aminocarbonyl, lower haloalkyl, hydroxyl, lower alkoxy, lower hydroxyalkyl, lower haloalkoxy, sulfamyl, lower alkylaminocarbonyl, amino, lower N-alkylamino, lower N,N-dialkylamino, five or six membered heterocyclic, lower cycloalkylalkyl, nitro,

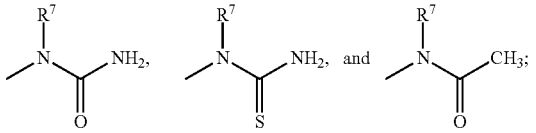

]

[wherein $R^5$ is lower alkyl; and]

[wherein $R^7$ is selected from hydrido, lower alkyl, aryl and lower aralkyl;]

[or a pharmaceutically-acceptable salt thereof.]

[A class of compounds of particular interest consists of those compounds of Formula I wherein $R^1$ is phenyl, substituted at a substitutable position with one or more radicals selected from fluoro, chloro, methyl, sulfamyl and

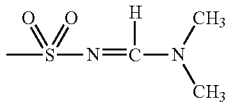

]

[wherein $R^2$ is selected from hydrido, methyl, ethyl, isopropyl, tert-butyl, isobutyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoromethyl, difluoropropyl, dichloroethyl, dichloropropyl, cyano, carboxyl methoxycarbonyl, ethoxycarbonyl, isopropoxycarbonyl, tert-butoxycarbonyl, propoxycarbonyl, butoxycarbonyl, isobutoxycarbonyl, pentoxycarbonyl, acetyl, propionyl, butyryl, isobutyryl, valeryl, isovaleryl, pivaloyl, hexanoyl, trifluoroacetyl, cyanomethyl, ethoxycarbonylcyanoethenyl, 1,1-difluoro-1-phenylmethyl, 1,1-difluoro-1-phenylethyl, difluoroacetyl, methoxycarbonyldifluoromethyl, difluoroacetamidyl, N,N-dimethyldifluoroacetamidyl, N-phenyldifluoroacetamidyl, N-ethylamino, N-methylamino, N,N-dimethylamino, N,N-diethylamino, N-phenylamino, N-benzylamino, N-phenylethylamino, N-methyl-N-benzylamino, N-ethyl-N-phenylamino, N-methyl-N-phenylamino, aminomethyl, N-methylaminomethyl, N,N-dimethylaminomethyl, N-phenylaminomethyl, N-benzylaminomethyl, N-methyl-N-benzylaminomethyl, N-methyl-N-phenylaminomethyl, methoxy, ethoxy, phenoxy, benzyloxy, methylthio, phenylthio, benzylthio, N-methylurea, N-methylthiourea, N-methylacetamidyl, urea, ureamethyl, thiourea, thioureamethyl, acetamidyl, N-phenylthioureamethyl, N-benzylthioureamethyl, N-methylthioureamethyl, N-phenylureamethyl, N-benzylureamethyl, N-methylureamethyl, N-phenylacetamidylmethyl, N-benzylacetamidylmethyl, N-methylacetamidylmethyl, aminocarbonyl, aminocarbonylmethyl, N-methylaminocarbonyl, N-ethylaminocarbonyl, N-isopropylaminocarbonyl, N-propylaminocarbonyl, N-butylaminocarbonyl, N-isobutylaminocarbonyl, N-tert-butylaminocarbonyl, N-pentylaminocarbonyl, N-phenylaminocarbonyl, N,N-dimethylaminocarbonyl, N-methyl-N-ethylaminocarbonyl, N-(3-fluorophenyl)aminocarbonyl, N-(4-methylphenyl)aminocarbonyl, N-(3-chlorophenyl) aminocarbonyl, N-methyl-N-(3-chlorophenyl)aminocarbonyl, N-(4-methoxyphenyl)aminocarbonyl, N-methyl-N-phenylaminocarbonyl, cyclopentylaminocarbonyl, cyclohexylaminocarbonyl, carboxymethylaminocarbonyl, benzyloxycarbonylmethylaminocarbonyl, hydroxypropyl, hydroxymethyl, and hydroxypropyl;]

[wherein $R^3$ is selected from hydrido, methyl, ethyl, isopropyl, tert-butyl, isobutyl, hexyl, fluoro, chloro, bromo, cyano, methoxy, methylthio, methylsulfonyl, N-methylamino, N-ethylamino, N,N-dimethylamino, N,N-diethylamino, cyclopropyl, cyclopentyl, hydroxypropyl, hydroxymethyl, and hydroxyethyl; and]

[wherein $R^4$ is selected from phenylethenyl, phenyl, naphthyl, biphenyl, cyclohexyl, cyclopentyl, cycloheptyl, 1-cyclohexenyl, 2-cyclohexenyl, 3-cyclohexenyl, 4-cyclohexenyl, 1-cyclopentenyl, 4-cyclopentenyl, benzofuryl, 2,3-dihydrobenzofuryl, 1,2,3,4-tetrahydronaphthyl, benzothienyl, indenyl, indanyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl and pyrazinyl; wherein $R^4$ is optionally substituted at a substitutable position with one or more radicals selected from fluoro, chloro, bromo, methylthio, methylsulfinyl, methyl, ethyl, propyl, isopropyl, tert-butyl, isobutyl, hexyl, ethylenyl, propenyl, methylsulfonyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, fluoromethyl, difluoromethyl, trifluoromethyl, chloromethyl, dichloromethyl, trichloromethyl, pentafluoroethyl, heptafluoropropyl, bromodifluoromethyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, sulfamyl, methylaminosulfonyl, hydroxypropyl, hydroxyisopropyl, hydroxymethyl, hydroxyethyl, trifluoromethoxy, amino, N-methylamino, N-ethylamino, N-ethyl-N-methylamino, N,N-dimethylamino, N,N-diethylamino, formylamino, methylcarbonylamino, trifluroracetamino, piperadinyl, piperazinyl, morpholino, cyclohexylmethyl, cyclopropylmethyl, cyclopentylethyl, nitro,

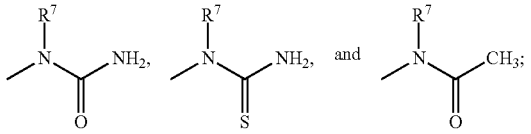

]

[and]

[wherein $R^7$ is selected from hydrido, methyl, ethyl, phenyl and benzyl;]

[or a pharmaceutically-acceptable salt thereof.]

[Within Formula I there is a second sub class of compounds of high interest wherein $R^1$ is phenyl substituted at a substitutable position with sulfamyl; wherein $R^2$ is selected from lower haloalkyl, cyano, carboxyl, lower alkoxycarbonyl, lower carboxyalkyl, aminocarbonyl, lower N-alkylaminocarbonyl, N-arylaminocarbonyl, lower N,N-dialkylaminocarbonyl, lower N-alkyl-N-arylaminocarbonyl, lower cycloalkylaminocarbonyl and lower hydroxyalkyl; wherein $R^3$ and $R^4$ together form

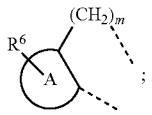

]

[wherein m is 2; wherein A is selected from phenyl and five membered heteroaryl; and where $R^6$ is one or more radicals selected from halo, lower alkyl, lower alkylsulfonyl, lower haloalkyl, lower alkoxy, amino and nitro; or a pharmaceutically-acceptable salt thereof.]

[A class of compounds of particular interest consists of those compounds of Formula I wherein $R^2$ is selected from fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxy, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, acetyl, propionyl, butyryl, isobutyryl, valeryl, isovaleryl, pivaloyl, hexanoyl, trifluoroacetyl, aminocarbonyl, N-methylaminocarbonyl, N-ethylaminocarbonyl, N-isopropylaminocarbonyl, N-propylaminocarbonyl, N-butylaminocarbonyl, N-isobutylaminocarbonyl, N-tert-butylaminocarbonyl, N-pentylaminocarbonyl, N-phenylaminocarbonyl, N,N-dimethylaminocarbonyl, N-methyl-N-ethylaminocarbonyl, N-(3-fluorophenyl)aminocarbonyl, N-(4-methylphenyl)aminocarbonyl, N-(3-chlorophenyl) aminocarbonyl, N-(4-methoxyphenyl)aminocarbonyl, N-methyl-N-phenylaminocarbonyl, cyclohexylaminocarbonyl, hydroxypropyl, hydroxymethyl and hydroxyethyl; wherein A is selected from phenyl, furyl and thienyl; and wherein $R^6$ is one or more radicals selected from fluoro, chloro, bromo, methylsulfonyl, methyl, ethyl, isopropyl, tert-butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, methylenedioxy, ethoxy, propoxy, n-butoxy, amino, and nitro; or a pharmaceutically-acceptable salt thereof.]

[Within Formula I there is a third subclass of compounds of high interest wherein $R^1$ is selected from phenyl, naphthyl, biphenyl, and five- or six-membered heteroaryl, wherein $R^1$ is substituted at a substitutable position with one or more radicals selected from halo, lower alkyl, lower alkoxy, hydroxyl and lower haloalkyl; wherein $R^2$ is selected from lower haloalkyl; wherein $R^3$ is hydrido; and wherein $R^4$ is aryl substituted at a substitutable position with sulfamyl; or a pharmaceutically-acceptable salt thereof.]

[A class of compounds of particular interest consists of those compounds of Formula I wherein $R^1$ is selected from phenyl, naphthyl, benzofuryl, benzothienyl, indolyl, benzodioxolyl, benzodioxanyl, pyridyl, thienyl, thiazolyl, oxazolyl, furyl and pyrazinyl; wherein $R^1$ is substituted at a substitutable position with one or more radicals selected from fluoro, chloro, bromo, fluoromethyl, difluoromethyl, trifluoromethyl, chloromethyl, dichloromethyl, trichloromethyl, pentafluoroethyl, heptafluoropropyl, difluorochloromethyl, dichloropropyl, dichlorofluoromethyl, difluoroethyl, difluoropropyl, dichloroethyl, methyl, ethyl, propyl, hydroxyl, methoxy, ethoxy, propoxy and n-butoxy; wherein $R^2$ is selected from fluoromethyl, difluoromethyl, trifluoromethyl, chloromethyl, dichloromethyl, trichloromethyl, pentafluoroethyl, heptafluoropropyl, difluorochloromethyl, difluoroethyl, dichlorofluoromethyl, difluoropropyl, dichloroethyl and dichloropropyl; wherein $R^3$ is hydrido; and wherein $R^4$ is phenyl substituted at a substitutable position with sulfamyl; or a pharmaceutically-acceptable salt thereof.]

[Within Formula I there is a subclass of compounds of high interest represented by Formula II:

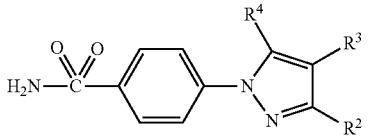

]

[wherein $R^2$ is selected from hydrido, alkyl, haloalkyl, alkoxycarbonyl, cyano, cyanoalkyl, carboxyl, aminocarbonyl, alkylaminocarbonyl, cycloalkylaminocarbonyl, arylaminocarbonyl, carboxyalkylaminocarbonyl, carboxyalkyl, aralkoxycarbonylalkylaminocarbonyl, aminocarbonylalkyl, alkoxycarbonylcyanoalkenyl and hydroxyalkyl;]

[wherein $R^3$ is selected from hydrido, alkyl, cyano, hydroxyalkyl, cycloalkyl, alkylsulfonyl and halo; and]

[wherein $R^4$ is selected from aralkenyl, aryl, cycloalkyl, cycloalkenyl and heterocyclic; wherein $R^4$ is optionally substituted at a substitutable position with one or more radicals selected from halo, alkylthio, alkylsulfonyl, cyano, nitro, haloalkyl, alkyl, hydroxyl, alkenyl, hydroxyalkyl, carboxyl, cycloalkyl, alkylamino, dialkylamino, alkoxycarbonyl, aminocarbonyl, alkoxy, haloalkoxy, sulfanyl, heterocyclic and amino;]

[provided $R^2$ and $R^3$ are not both hydrido; further provided that $R^2$ is not carboxyl or methyl when $R^3$ is hydrido and when $R^4$ is phenyl; further provided that $R^4$ is not triazolyl when $R^2$ is methyl; further provided that $R^4$ is not aralkenyl when $R^2$ is carboxyl, aminocarbonyl or ethoxycarbonyl; further provided that $R^4$ is not phenyl when $R^2$ is methyl and $R^3$ is carboxyl; and further provided that $R^4$ is not unsubstituted thienyl when $R^2$ is trifluoromethyl;]

[or a pharmaceutically-acceptable salt thereof.]

[A class of compounds of particular interest consists of those compounds of Formula II wherein $R^2$ is selected from hydrido, lower alkyl, lower haloalkyl, lower alkoxycarbonyl, cyano, lower cyanoalkyl, carboxyl, aminocarbonyl, lower alkylaminocarbonyl, lower cycloalkylaminocarbonyl, arylaminocarbonyl, lower carboxyalkylaminocarbonyl, lower aralkoxycarbonylalkylaminocarbonyl, lower aminocarbonylalkyl, lower carboxyalkyl, lower alkoxycarbonylcyanoalkenyl and lower hydroxyalkyl;]

[wherein $R^3$ is selected from hydrido, lower alkyl, cyano, lower hydroxyalkyl, lower cycloalkyl, lower alkylsulfonyl and halo; and]

[wherein $R^4$ is selected from aralkenyl, aryl, cycloalkyl, cycloalkenyl and heterocyclic; wherein $R^4$ is optionally substituted at a substitutable position with one or more radicals selected from halo, lower alkylthio, lower alkylsulfonyl, cyano, nitro, lower haloalkyl, lower alkyl, hydroxyl, lower alkenyl, lower hydroxyalkyl, carboxyl, lower cycloalkyl, lower alkylamino, lower dialkylamino, lower alkoxycarbonyl, aminocarbonyl, lower alkoxy, lower haloalkoxy, sulfamyl, five or six membered heterocyclic and amino; or a pharmaceutically-acceptable salt thereof.]

[A family of specific compounds of particular interest within Formula I consists of compounds and pharmaceutically-acceptable salts thereof as follows:]

[4-[5-(4-(N-ethylamino)phenyl)-3-(trifluoromethyl)-1H-pyrazol-1-yl]benzenesulfonamide;]

[4-[5-(4-(N-ethyl-N-methylamino)phenyl)-3-(trifluoromethyl)-1H-pyrazol-1-yl]benzenesulfonamide;]

[4-[5-(3-fluoro-4-(N-methylamino)phenyl)-3-(trifluoromethyl)-1H-pyrazol-1-yl]benzenesulfonamide;]

[4-[5-(3-chloro-4-(N-methylamino)phenyl)-3-(trifluoromethyl)-1H-pyrazol-1-yl]benzenesulfonamide;]

[4-[5-(3-methyl-4-(N-methylamino)phenyl)-3-(trifluoromethyl)-1H-pyrazol-1-yl]benzenesulfonamide;]

[4-[5-(4-(N,N-dimethylamino)-3-fluorophenyl)-3-(trifluoromethyl)-1H-pyrazol-1-yl]benzenesulfonamide;]

[4-[5-(3chloro-4-(N,N-dimethylamino)phenyl)-3-(trifluoromethyl)-1H-pyrazol-1-yl]benzenesulfonamide;]

[4-[5-(4-(N,N-dimethylamino)-3-methylphenyl)-3-(trifluoromethyl)-1H-pyrazol-1-yl]benzenesulfonamide;]

[4-[5-(4-(N-ethyl-N-methylamino)-3-fluorophenyl)-3-(trifluoromethyl)-1H-pyrazol-1-yl]benzenesulfonamide;]

[4-[5-(3-chloro-4-(N-ethyl-N-methylamino)phenyl)-3-(trifluoromethyl)-1H-pyrazol-1-yl]benzenesulfonamide;]

[4-[5-(4-(N-ethyl-N-methylamino)-3-methylphenyl)-3-3(trifluoromethyl)-1H-pyrazol-1-yl]benzenesulfonamide;]

[4-[5-(4-(N,N-diethylamino)-3-fluorophenyl)-3-3-(trifluoromethyl)-1H-pyrazol-1-yl]benzenesulfonamide;]

[4-[5-(4-(3-chloro-4-(N,N-diethylamino)phenyl)-3-(trifluoromethyl)-1H-pyrazol-1-yl]benzenesulfonamide;]

[4-[5-(4-(N,N-diethylamino)-3-methylphenyl)-3-(trifluoromethyl)-1H-pyrazol-1-yl]benzenesulfonamide;]

[N-[4-[1-[4-(aminosulfonyl)phenyl]-3-(trifluoromethyl)-1H-pyrazol-5-yl]-3-fluorophenyl]-N-methylacetamide;]

[N-[4-[1-[4-(aminosulfonyl)phenyl]-3-(trifluoromethyl)-1H-pyrazol-5-yl]-3-chlorophenyl]-N-methylacetamide;]

[N-[4-[1-[4-(aminosulfonyl)phenyl]-3-(trifluoromethyl)-1H-pyrazol-5-yl]-3-methylphenyl]-N-methylacetamide;]

[N-[4-[1-[4-(aminosulfonyl)phenyl]-3-(trifluoromethyl)-1H-pyrazol-5-yl]-3-fluorophenyl]-N-methylurea;]

[N-[4-[1-[4-(aminosulfonyl)phenyl]-3-(trifluoromethyl)-1H-pyrazol-5-yl]-3-chlorophenyl]-N-methylurea;]

[N-[4-[1-[4-(aminosulfonyl)phenyl]-3-(trifluoromethyl)-1H-pyrazol-5-yl]-3-methylphenyl]-N-methylurea;]

[N-[4-[1-[4-(aminosulfonyl)phenyl]-3-(trifluoromethyl)-1H-pyrazol-5-yl]-3-fluorophenyl]-N-methylthiourea;]

[N-[4-[1-[4-(aminosulfonyl)phenyl]-3-(trifluoromethyl)-1H-pyrazol-5-yl]-3-chlorophenyl]-N-methylthiourea;]

[N-[4-[1-[4-(aminosulfonyl)phenyl]-3-(trifluoromethyl)-1H-pyrazol-5-yl]-3-methylphenyl]-N-methylthiourea;]

[4-[5-(3-(N,N-dimethylamino)phenyl)-3-(trifluoromethyl)-1H-pyrazol-1-yl]benzenesulfonamide;]

[4-[5-(3-(N-ethyl-N-methylamino)phenyl)-3-(trifluoromethyl)-1H-pyrazol-1-yl]benzenesulfonamide;]

[4-[5-(4-chloro-3-(N-methylamino)phenyl)-3-(trifluoromethyl-1H-pyrazol-1-yl]benzenesulfonamide;]

[4-[5-(4-methyl-3-(N-methylamino)phenyl)-3-(trifluoromethyl)-1H-pyrazol-1-yl]benzenesulfonamide;]

[N-[3-[1-[4-(aminosulfonyl)phenyl]-3-(trifluoromethyl)-1H-pyrazol-5-yl]phenyl]-N-methylacetamide;]

[N-[3-[1-[4-(aminosulfonyl)phenyl]-3-(trifluoromethyl)-1H-pyrazol-5-yl]-4-fluorophenyl]-N-methylacetamide;]

[N-[3-[1-[4-(aminosulfonyl)phenyl]-3-(trifluoromethyl)-1H-pyrazol-5-yl]-4-methylphenyl]-N-methylurea;]

[N-[3-[1-[4-(aminosulfonyl)phenyl]-3-(trifluoromethyl)-1H-pyrazol-5-yl]-4-fluorophenyl]-N-methylthiourea;]

[4-[5-(2-(N-ethyl-N-methylamino)-4-methylphenyl)-3-(trifluoromethyl)-1H-pyrazol-1-yl]benzenesulfonamide;]

[N-[2-[1-[4-(aminosulfonyl)phenyl]-3-(trifluoromethyl)-1H-pyrazol-5-yl]-4-methylphenyl]-N-methylurea;]

[N-[2-[1-[4-(aminosulfonyl)phenyl]-3-(trifluoromethyl)-1H-pyrazol-5-yl]-4-fluorophenyl]-N-methylthiourea;]

[4-[5-(1H-indol-5-yl)-3-trifluoromethyl)-1H-pyrazol-1-yl]benzenesulfonamide;]

[4-[5-(7-fluoro-1H-indol-5-yl)-3-(trifluoromethyl)-1H-pyrazol-1-yl]benzenesulfonamide;]

[4-[4-(1-ethyl-1H-indol-5-yl)-3-(trifluoromethyl)1H-pyrazol-1-yl]benzenesulfonamide;]

[4-[5-(7-methyl-1H-indol-5-yl)-3-(trifluoromethyl)-1H-pyrazol-1-yl]benzenesulfonamide;]

[4-[5-(7-chloro-1-methyl-1H-indol-5-yl)-3-(trifluoromethyl)-1H-pyrazol-1-yl]benzenesulfonamide;]

[4-[5-(2,3-dihydro-1H-indol-5-yl)-3-(trifluoromethyl)-1H-pyrazol-1-yl]benzenesulfonamide;]

[4-[5-(7-fluoro-1-methyl-2,3-dihydro-1H-indol-5-yl)-3-(trifluoromethyl)-1H-pyrazol-1-yl]benzenesulfonamide;]

[4-[3-aminomethyl-5-phenyl-1H-pyrazol-1-yl]benzenesulfonamide;]

[4-[3-(N-methylamino)methyl-5-phenyl-1H-pyrazol-1-yl]benzenesulfonamide;]

[4-[3-(N,N-dimethylamino)methyl-5-phenyl-1H-pyrazol-1-yl]benzenesulfonamide;]

[4-[5-phenyl-3-(N-phenylamino)methyl-1H-pyrazol-1-yl]benzenesulfonamide;]

[4-[3-(N-benzylamino)methyl-5-phenyl-1H-pyrazol-1-yl]benzenesulfonamide;]

[4-[3-(N-benzyl-N-methylamino)methyl-5-phenyl-1H-pyrazol-1-yl]benzenesulfonamide;]

[4-[3-(N-methyl-N-phenylamino)methyl-5-phenyl-1H-pyrazol-1-yl]benzenesulfonamide;]

[N-[[1-[4-(aminosulfonyl)phenyl]-5-phenyl-1H-pyrazol-3-yl]methyl]acetamide;]

[N-[[1-[4-(aminosulfonyl)phenyl]-5-phenyl-1H-pyrazol-3-yl]methyl]-N-methylacetamide;]

[N-[[1-[4-(aminosulfonyl)phenyl]-5-phenyl-1H-pyrazol-3-yl]methyl]-N-phenylacetamide;]

[N-[[1-[4-(aminosulfonyl)phenyl]-5-phenyl-1H-pyrazol-3-yl]methyl]-N-benzylacetamide;]

[N-[[1-[4-(aminosulfonyl)phenyl]-5-phenyl-1H-pyrazol-3-yl]methyl]urea;]

[N-[[1-[4-(aminosulfonyl)phenyl]-5-phenyl-1H-pyrazol-3-yl]methyl]-N-methylurea;]

[N-[[1-[4-(aminosulfonyl)phenyl]-5-phenyl-1H-pyrazol-3-yl]methyl]-N-phenylurea;]

[N-[[1-[4-(aminosulfonyl)phenyl]-5-phenyl-1H-pyrazol-3-yl]methyl]-N-benzylurea;]

[N-[[1-[4-(aminosulfonyl)phenyl]-5-phenyl-1H-pyrazol-3-yl]methyl]thiourea;]

[N-[[1-[4-(aminosulfonyl)phenyl]-5-phenyl-1H-pyrazol-3-yl]methyl]-N-methylthiourea;]

[N-[[1-[4-(aminosulfonyl)phenyl]-5-phenyl-1H-pyrazol-3-yl]methyl]-N-phenylthiourea;]

[N-[[1-[4-(aminosulfonyl)phenyl]-5-phenyl-1H-pyrazol-3-yl]methyl]-N-benzylthiourea;]

[4-[4-methoxy-5-phenyl-3-(trifluoromethyl)-1H-pyrazol-1-yl]benzenesulfonamide;]

[4-[4-methylthio-5-phenyl-3-(trifluoromethyl)-1H-pyrazol-1-yl]benzenesulfonamide;]

[4-[4-(N-methylamino)-5-phenyl-3-(trifluoromethyl)-1H-pyrazol-1-yl]benzenesulfonamide;]

[4-[4-(N,N-dimethylamino)-5-phenyl-3-(trifluoromethyl)-1H-pyrazol-1-yl]benzenesulfonamide;]

[4-[3-methoxy-5-phenyl-1H-pyrazol-1-yl]benzenesulfonamide;]

[4-[3-ethoxy-5-phenyl-1H-pyrazol-1-yl]benzenesulfonamide;]

[4-[3-phenoxy-5-phenyl-1H-pyrazol-1-yl]benzenesulfonamide;]

[4-[3-benzyloxy-5-phenyl-1H-pyrazol-1-yl]benzenesulfonamide;]

[4-[3-methylthio-5-phenyl-1H-pyrazol-1-yl]benzenesulfonamide;]

[4-[3-benzylthio-5-phenyl-1H-pyrazol-1-yl]benzenesulfonamide;]

[4-[3-(N-methylamino)-5-phenyl-1H-pyrazol-1-yl]benzenesulfonamide;]

[4-[3-(N,N-dimethylamino)-5-phenyl-1H-pyrazol-1-yl]benzenesulfonamide;]

[4-[3-(N-benzyl-N-methylamino)-5-phenyl-1H-pyrazol-1-yl]benzenesulfonamide;]

[N-[1-[4-(aminosulfonyl)phenyl]-5-phenyl-1H-pyrazol-3-yl]acetamide;]

[N-[1-[4-(aminosulfonyl)phenyl]-5-phenyl-1H-pyrazol-3-yl]-N-methylacetamide;]

[N-[1-[4-(aminosulfonyl)phenyl]-5-phenyl-1H-pyrazol-3-yl]-N-benzylacetamide;]

[N-[1-[4-(aminosulfonyl)phenyl]-5-phenyl-1H-pyrazol-3-yl]urea;]

[N-[1-[4-(aminosulfonyl)phenyl]-5-phenyl-1H-pyrazol-3-yl]-N-methylurea;]

[N-[1-[4-(aminosulfonyl)phenyl]-5-phenyl-1H-pyrazol-3-yl]-N-benzylurea;]

[N-[1-[4-(aminosulfonyl)phenyl]-5-phenyl-1H-pyrazol-3-yl]thiourea;]

[N-[1-[4-(aminosulfonyl)phenyl]-5-phenyl-1H-pyrazol-3-yl]-N-methylthiourea;]

[N-[1-[4-(aminosulfonyl)phenyl]-5-phenyl-1H-pyrazol-3-yl]-N-benzylthiourea;]

[4-[5-phenyl-3-(1,1-difluoro-1-phenylmethyl)-1H-pyrazol-1-yl]benzenesulfonamide;]

[4-[5-phenyl-3-(1,1-difluoro-2-phenylethyl)-1H-pyrazol-1-yl]benzenesulfonamide;]

[1-[4-(aminosulfonyl)phenyl]-5-phenyl-1H-pyrazole-3-difluoroacetic acid;]

[methyl 1-[4-(aminosulfonyl)phenyl]-5-phenyl-1H-pyrazole-3-difluoroacetate;]

[1-[4-(aminosulfonyl)phenyl]-5-phenyl-1H-pyrazole-3-difluoroacetamide;]

[N,N-dimethyl-1-[4-(aminosulfonyl)phenyl]-5-phenyl-1H-pyrazole-3-difluoroacetamide;]

[N-phenyl-1-[4-(aminosulfonyl)phenyl]-5-phenyl-1H-pyrazole-3-difluoroacetamide;]

[1-[4-(aminosulfonyl)phenyl]-5-phenyl-1H-pyrazole-5-acetic acid;]

[1-[4-(aminosulfonyl)phenyl]-4-chloro-5-phenyl-1H-pyrazole-3-difluoroacetic acid;]

[1-[4-(aminosulfonyl)phenyl]-4-bromo-5-phenyl-1H-pyrazole-3-difluoroacetic acid;]

[1-[4-(aminosulfonyl)phenyl]-4-chloro-5-(4-chlorophenyl)-1H-pyrazole-3-acetic acid;]

[1-[4-(aminosulfonyl)phenyl]-4-bromo-5-phenyl-1H-pyrazole-3-acetic acid;]

[(R)-2-[1-[4-(aminosulfonyl)phenyl]-5-phenyl-1H-pyrazol-3-yl]propanoic acid;]

[(S)-2-[1-[4-(aminosulfonyl)phenyl]-5-phenyl-1H-pyrazole-3-yl]propanoic acid;]

[(R)-2-[1-[4-(aminosulfonyl)phenyl]-4-chloro-5-phenyl-1H-pyrazole-3-yl]propanoic acid;]

[(S)-2-[1-[4-(aminosulfonyl)phenyl]-4-chloro-5-phenyl-1H-pyrazole-3-yl]propanoic acid;]

[(R)-2-[1-[4-(aminosulfonyl)phenyl]-4-bromo-5-phenyl-1H-pyrazole-3-yl]propanoic acid;]

[(S)-2-[1-[4-(aminosulfonyl)phenyl]-4-bromo-5-phenyl-1H-pyrazol-3-yl]propanoic acid;]

[2-[1-[4-(aminosulfonyl)phenyl]-5-phenyl-1H-pyrazol-3-yl]-2-methylpropanoic acid;]

[2-[1-[4-(aminosulfonyl)phenyl]-4-chloro-5-phenyl-1H-pyrazol-3-yl]-2-methylpropanoic acid;]

[2-[1-[4-(aminosulfonyl)phenyl]-4-bromo-5-phenyl-1H-pyrazol-3-yl]-2-methylpropanoic acid;]

[2-fluoro-4-[5-phenyl-3-(trifluoromethyl)-1H-pyrazol-1-yl]benzenesulfonamide;]

[3-fluoro-4-[5-phenyl-3-(trifluoromethyl)-1H-pyrazol-1-yl]benzenesulfonamide;]

[2-methyl-4-[5-phenyl-3-(trifluoromethyl-1H-pyrazol-1-yl]benzenesulfonamide;]

[3-methyl-4-[5-phenyl-3-(trifluoromethyl)-1H-pyrazol-1-yl]benzenesulfonamide;]

[ethyl 1-[4-(aminosulfonyl)phenyl]-5-(4-chlorophenyl)-1H-pyrazole-3-carboxylate;]

[ethyl 1-[4-(aminosulfonyl)phenyl]-5-(4-methylphenyl)-1H-pyrazole-3-carboxylate;]

[isopropyl 1-[4-(aminosulfonyl)phenyl]-5-(4-chlorophenyl)-1H-pyrazole-3-carboxylate;]

[methyl 1-[4-(aminosulfonyl)phenyl]-5-(4-aminophenyl)-1H-pyrazole-3-carboxylate;]

[1-[4-(aminosulfonyl)phenyl]-5-(4-chlorophenyl)-1H-pyrazole-3-carboxylic acid;]

[tert-butyl-1-[4-(aminosulfonyl)phenyl]-5-(4-chlorophenyl)-1H-pyrazole-3-carboxylate;]

[propyl-1-[4-(aminosulfonyl)phenyl]-5-(4-chlorophenyl)-1H-pyrazole-3-carboxylate;]

[butyl-1-[4-(aminosulfonyl)phenyl]-5-(4-chlorophenyl)-1H-pyrazole-3-carboxylate;]

[isobutyl-1-[4-(aminosulfonyl)phenyl]-5-(4-chlorophenyl)-1H-pyrazole-3-carboxylate;]

[pentyl-1-[4-aminosulfonyl)phenyl]-5-(4-chlorophenyl)-1H-pyrazole-3-carboxylate;]

[methyl-1-[4-aminosulfonyl)phenyl]-5-(4-chlorophenyl)-1H-pyrazole-3-carboxylate;]

[methyl-1-[4-aminosulfonyl)phenyl]-5-(4-methylphenyl)-1H-pyrazole-3-carboxylate;]

[methyl-1-[4-aminosulfonyl)phenyl]-5-(4-methoxyphenyl)-1H-pyrazole-3-carboxylate;]

[methyl-1-[4-aminosulfonyl)phenyl]-5-(4-bromophenyl)-1H-pyrazole-3-carboxylate;]

[methyl-1-[4-aminosulfonyl)phenyl]-5-(4-nitrophenyl)-1H-pyrazole-3-carboxylate;]

[methyl-1-[4-aminosulfonyl)phenyl]-5-(4-fluorophenyl)-1H-pyrazole-3-carboxylate;]

[methyl-1-[4-aminosulfonyl)phenyl]-5-(3,5-dichloro-4-methoxyphenyl)-1H-pyrazole-3-carboxylate;]

[methyl-1-[4-aminosulfonyl)phenyl]-5-(3,5-difluoro-4-methoxyphenyl)-1H-pyrazole-3-carboxylate;]

[N-[4-methylphenyl]-1-[4-(aminosulfonyl)phenyl]-5-(4-fluorophenyl)-1H-pyrazole-3-carboxamide;]

[N-[3-chlorophenyl]-1-[4-(aminosulfonyl)phenyl]-5-(4-fluorophenyl)-1H-pyrazole-3-carboxamide;]

[N-[3-fluorophenyl]-1-[4-(aminosulfonyl)phenyl]-5-(4-fluorophenyl)-1H-pyrazole-3-carboxamide;]

[N-[3-fluorophenyl]-1-[4-(aminosulfonyl)phenyl]-5-(4-chlorophenyl)-1H-pyrazole-3-carboxamide;]

[phenylmethyl N-[[1-[4-(aminosulfonyl)phenyl]-5-(4-chlorophenyl)-1H-pyrazol-3-yl]carbonyl]glycinate;]

[1-[4-(aminosulfonyl)phenyl]-5-(4-bromophenyl)-1H-pyrazole-3-carboxamide;]

[1-[4-(aminosulfonyl)phenyl]-5-(4-chlorophenyl)-1H-pyrazole-3-carboxamide;]

[N-phenyl-1-[4-(aminosulfonyl)phenyl]-5-(4-fluorophenyl)-1H-pyrazole-3-carboxamide;]

[N-(4-methoxyphenyl)-1-[4-(aminosulfonyl)phenyl]-5-(4-fluorophenyl)-1H-pyrazole-3-carboxamide;]

[N-(4-methylphenyl)-1-[4-(aminosulfonyl)phenyl]-5-(4-chlorophenyl)-1H-pyrazole-3-carboxamide;]

[N-N-dimethyl-1-[4-(aminosulfonyl)phenyl]-5-(4-chlorophenyl)-1H-pyrazole-3-carboxamide;]

[N-methyl-1-[4-(aminosulfonyl)phenyl]-5-(4-chlorophenyl)-1H-pyrazole-3-carboxamide;]

[N-methyl-N-ethyl-1-[4-aminosulfonyl)phenyl]-5-(4-chlorophenyl)-1H-pyrazole-3-carboxamide;]

[N-phenyl-1-[4-(aminosulfonyl)phenyl]-5-(4chlorophenyl)-1H-pyrazole-3-carboxamide;]

[N-methyl-N-phenyl-1-[4-(aminosulfonyl)phenyl]-5-(4-chlorophenyl)-1H-pyrazole-3-carboxamide;]

[N-ethyl-1-[4-(aminosulfonyl)phenyl]-5-(4-chlorophenyl)-1H-pyrazole-3-carboxamide;]

[N-isopropyl-1-[4-(aminosulfonyl)phenyl]-5-(4-chlorophenyl)-1H-pyrazole-3-carboxamide;]

[N-propyl-1-[4-(aminosulfonyl)phenyl]-5-(4-chlorophenyl)-1H-pyrazole-3-carboxamide;]

[N-butyl-1-[4-(aminosulfonyl)phenyl]-5-(4-chlorophenyl)-1H-pyrazole-3-carboxamide;]

[N-isobutyl-1-[4-(aminosulfonyl)phenyl]-5-(4-chlorophenyl)-1H-pyrazole-3-carboxamide;]

[N-tert-butyl-1-[4-(aminosulfonyl)phenyl]-5-(4-chlorophenyl)-1H-pyrazole-3-carboxamide;]

[N-pentyl-1-[4-(aminosulfonyl)phenyl]-5-(4-chlorophenyl)-1H-pyrazole-3-carboxamide;]

[N-cyclohexyl-1-[4-(aminosulfonyl)phenyl]-5-(4-fluorophenyl)-1H-pyrazole-3-carboxamide;]

[N-cyclopentyl-1-[4-(aminosulfonyl)phenyl]-5-(4-chlorophenyl)-1H-pyrazole-3-carboxamide;]

[4-[5-(4-chlorophenyl)-3-(piperidinocarboxamide)-1H-pyrazol-1-yl]benzenesulfonamide;]

[N-(3-chlorophenyl)-1-[4-(aminosulfonyl)phenyl]-5-(4-chlorophenyl)-1H-pyrazole-3-carboxamide;]

[N-(2-pyridyl)-1-[4-(aminosulfonyl)phenyl]-5-(4-chlorophenyl)-1H-pyrazole-3-carboxamide;]

[N-methyl-N-(3-chlorophenyl)-1-[4-(aminosulfonyl)phenyl]-5-(4-chlorophenyl)-1H-pyrazole-3-carboxamide;]

[1-[4-(aminosulfonyl)phenyl]-5-(4-nitrophenyl)-1H-pyrazole-3-carboxamide;]

[1-[4-(aminosulfonyl)phenyl]-5-(4-fluorophenyl)-1H-pyrazole-3-carboxamide;]

[1-[4-(aminosulfonyl)phenyl]-5-phenyl-1H-pyrazole-3-carboxamide;]

[1-[4-(aminosulfonyl)phenyl]-5-(3-chloro-4-methoxyphenyl)-1H-pyrazole-3-carboxamide;]

[1-[4-(aminosulfonyl)phenyl]-5-(4-methylthiophenyl)-1H-pyrazole-3-carboxamide;]

[1-[4-(aminosulfonyl)phenyl]-5-(4-methoxyphenyl)-1H-pyrazole-3-carboxamide;]

[1-[4-(aminosulfonyl)phenyl]-5-(4-methylphenyl)-1H-pyrazole-3-carboxamide;]

[N-methyl 1-[4-(aminosulfonyl)phenyl]-5-(4-methoxyphenyl)-1H-pyrazole-3-carboxamide;]

[N-[[1-[4-(aminosulfonyl)phenyl]-5-(4-chlorophenyl)-1H-pyrazol-3-yl]carbonyl]glycine;]

[1-[4-(aminosulfonyl)phenyl]-5-(3-bromo-4-methoxyphenyl)-1H-pyrazole-3-carboxamide;]

[1-[4-(aminosulfonyl)phenyl]-5-(3,5-dichloro-4-methoxyl)-1H-pyrazole-3-carboxamide;]

[4-[5-(4-bromophenyl)3-cyano-1H-pyrazol-1-yl]benzenesulfonamide;]

[4-[3-cyano-5-(4-fluorophenyl)-1H-pyrazol-1-yl]benzenesulfonamide;]

[4-[5-(4-chlorophenyl)-3-cyano-1H-pyrazol-1-yl]benzenesulfonamide;]

[4-[3-cyano-5-(4-methoxyphenyl)-1H-pyrazol-1-yl]benzenesulfonamide;]

[4-[3-cyano-5-(4-methylphenyl)-1H-pyrazol-1-yl]benzenesulfonamide;]

[4-[3-cyano-5-(4-methylthiophenyl)-1H-pyrazol-1-yl]benzenesulfonamide;]

[4-[5-(3-chloro-4-methoxyphenyl)3-cyano-1H-pyrazol-1-yl]benzenesulfonamide;]

[4-[5-(3,5-dichloro-4-methoxyphenyl)-3-cyano-1H-pyrazol-1-yl]benzenesulfonamide;]

[4-[5-(3-bromo-4-methoxyphenyl)-3-cyano-1H-pyrazol-1-yl]benzenesulfonamide;]

[4-[3-cyano-5-phenyl-1H-pyrazol-1-yl]benzenesulfonamide;]

[4-[5-(4-nitrophenyl)-3-(cyano)-1H-pyrazol-1-yl]benzenesulfonamide;]

[4-[4-chloro-5-(4-fluorophenyl)-1H-pyrazol-1-yl]benzenesulfonamide;]

[4-[4-chloro-5-(4-chlorophenyl)-1H-pyrazol-1-yl]benzenesulfonamide;]

[4-[4-chloro-5-(4-chlorophenyl)-1H-pyrazol-1-yl]benzenesulfonamide;]

[4-[4-bromo-5-(4-chlorophenyl)-1H-pyrazol-1-yl]benzenesulfonamide;]

[4-[4-chloro-5-phenyl-1H-pyrazol-1-yl]benzenesulfonamide;]

[4-[4-chloro-5-(3,5-dichloro-4-methoxyphenyl)-1H-pyrazol-1-yl]benzenesulfonamide;]

[4-[4-bromo-5-(4-methylphenyl)-1H-pyrazol-1-yl]benzenesulfonamide;]

[4-[4-chloro-5-(4-methylphenyl)-1H-pyrazol-1-yl]benzenesulfonamide;]

[4-[4-chloro-5-(3-chloro-4-methoxyphenyl)-1H-pyrazol-1-yl]benzenesulfonamide;]

[4-[4-chloro-5-(4-methoxyphenyl)-1H-pyrazol-1-yl]benzenesulfonamide;]

[4-[4-bromo-5-(4-methoxyphenyl)-1H-pyrazol-1-yl]benzenesulfonamide;]

[4-[4-cyano-5-(4-methoxyphenyl)-1H-pyrazol-1-yl]benzenesulfonamide;]

[4-[4-chloro-5-(3,5-difluoro-4-methoxyphenyl)-1H-pyrazol-1-yl]benzenesulfonamide;]

[4-[4-methyl-5-phenyl-1H-pyrazol-1-yl]benzenesulfonamide;]

[4-[4-fluoro-5-phenyl-1H-pyrazol-1-yl]benzenesulfonamide;]

[4-[5-(4-chlorophenyl)-4-methylsulfonyl-1H-pyrazol-1-yl]benzenesulfonamide;]

[4-[4-chloro-5-(4-chlorophenyl)-3-(trifluoromethyl)-1H-pyrazol-1-yl]benzenesulfonamide;]

[4-[4-ethyl-5-phenyl-3-(trifluoromethyl)-1H-pyrazol-1-yl]benzenesulfonamide;]

[4-[4-methyl-5-phenyl-3-(trifluoromethyl)-1H-pyrazol-1-yl]benzenesulfonamide;]

[4-[5-(4-methoxyphenyl)-4-methyl-3-(trifluoromethyl)-1H-pyrazol-1-yl]benzenesulfonamide;]

[4-[5-(4-chlorophenyl)-4-methyl-3-(trifluoromethyl)-1H-pyrazol-1-yl]benzenesulfonamide;]

[4-[5-(4-chlorophenyl)-4-ethyl-3-(trifluoromethyl)-1H-pyrazol-1-yl]benzenesulfonamide;]

[4-[4-ethyl-5-(4-methylphenyl)-3-(trifluoromethyl)-1H-pyrazol-1-yl]benzenesulfonamide;]

[4-[4-ethyl-5-(4-methoxy-3-methylphenyl)-3-(trifluoromethyl)-1H-pyrazol-1-yl]benzenesulfonamide;]

[4-[4-ethyl-5-(4-methoxyphenyl)-3-(trifluoromethyl)-1H-pyrazol-1-yl]benzenesulfonamide;]

[4-[4-cyclopropyl-5-phenyl-3-(trifluoromethyl)-1H-pyrazol-1-yl]benzenesulfonamide;]

[4-[4-ethyl-5-(3-fluoro-4-chlorophenyl)-3-(trifluoromethyl)-1H-pyrazol-1-yl]benzenesulfonamide;]

[4-[4-hydroxymethyl-5-phenyl-3-(trifluoromethyl)-1H-pyrazol-1-yl]benzenesulfonamide;]

[4-[5-(4-fluorophenyl)-4-methyl-3-(trifluoromethyl)-1H-pyrazol-1-yl]benzenesulfonamide;]

[4-[4-methyl-5-(4-methylphenyl)-3-(trifluoromethyl)-1H-pyrazol-1-yl]benzenesulfonamide;]

[4-[4-fluoro-5-phenyl-3-(trifluoromethyl)-1H-pyrazol-1-yl]benzenesulfonamide;]

[4-[4-bromo-5-(4-chlorophenyl)-3-(difluoromethyl)-1H-pyrazol-1-yl]benzenesulfonamide;]

[4-[4-chloro-5-(3,5-dichloro-4-methoxyphenyl)-3-(difluoromethyl)-1H-pyrazol-1-yl]benzenesulfonamide;]

[4-[4-chloro-3-(difluoromethyl)-5-phenyl-1H-pyrazol-1-yl]benzenesulfonamide;]

[4-[4-bromo-3-(difluoromethyl)-5-phenyl-1H-pyrazol-1-yl]benzenesulfonamide;]

[4-[4-chloro-3-(difluoromethyl)-5-(4-methoxyphenyl)-1H-pyrazol-1-yl]benzenesulfonamide;]

[4-[4-chloro-3-cyano-5-phenyl-1H-pyrazol-1-yl]benzenesulfonamide;]

[4-[3-chloro-5-(4-chlorophenyl)-3-cyano-1H-pyrazol-1-yl]benzenesulfonamide;]

[4-[4-chloro-3-cyano-5-(4-fluorophenyl)-1H-pyrazol-1-yl]benzenesulfonamide;]

[4-[4-bromo-3-cyano-5-(4-fluorophenyl)-1H-pyrazol-1-yl]benzenesulfonamide;]

[4-[4-bromo-3-cyano-5-phenyl-1H-pyrazol-1-yl]benzenesulfonamide;]

[ethyl [1-(4-aminosulfonylphenyl)-4-bromo-5-(4-chlorophenyl)-1H-pyrazol-3-yl]carboxylate;]

[methyl [1-(4-aminosulfonylphenyl)-4-chloro-5-(4-chlorophenyl)-1H-pyrazol-3-yl]carboxylate;]

[ethyl [1-(4-aminosulfonylphenyl)-4-chloro-5-(4-chlorophenyl)-1H-pyrazol-3-yl]carboxylate;]

[methyl [1-(4-aminosulfonylphenyl)-4-chloro-5-(4-fluorophenyl)-1H-pyrazol-3-yl]carboxylate;]

[methyl [1-(4-aminosulfonylphenyl)-4-bromo-5-(4-fluorophenyl)-1H-pyrazol-3-yl]carboxylate;]

[methyl [1-(4-aminosulfonylphenyl)-4-chloro-5-(3-chloro-4-methoxyphenyl)-1H-pyrazol-3-yl]carboxylate;]

[methyl [1-(4-aminosulfonylphenyl)-4-chloro-5-(3,5-dichloro-4-methoxyphenyl)-1H-pyrazol-3-yl]carboxylate;]

[methyl [1-(4-aminosulfonylphenyl)-5-(3-bromo-4-methoxyphenyl)-4-chloro-1H-pyrazol-3-yl]carboxylate;]

[[1-(4-aminosulfonylphenyl)-4-chloro-5-phenyl-1H-pyrazol-3-yl]carboxamide;]

[[1-(4-aminosulfonylphenyl)-4-chloro-5-(4-chlorophenyl)-1H-pyrazol-3-yl]carboxamide;]

[[1-(4-aminosulfonylphenyl)-4-chloro-5-(4-fluorophenyl)-1H-pyrazol-3-yl]carboxamide;]

[[1-(4-aminosulfonylphenyl)-4-bromo-5-(4-chlorophenyl)-1H-pyrazol-3-yl]carboxamide;]

[[1-(4-aminosulfonylphenyl)-4-bromo-5-phenyl-1H-pyrazol-3yl]carboxamide;]

[[1-(4-aminosulfonylphenyl)-4-chloro-5-(4-chlorophenyl)-1H-pyrazol-3-yl]carboxylic acid;]

[[1-(4-aminosulfonylphenyl)-4-chloro-5-phenyl-1H-pyrazol-3-yl]carboxylic acid;]

[[1-(4-aminosulfonylphenyl)-4-chloro-5-(3,5-dichloro-4-methoxyphenyl)-1H-pyrazol-3-yl]carboxylic acid;]

[4-[4-chloro-3-isopropyl-5-phenyl-1H-pyrazol-1-yl]benzenesulfonamide;]

[4-[4-chloro-3-methyl-5-phenyl-1H-pyrazol-1-yl]benzenesulfonamide;]

[4-[4-chloro-3-hydroxymethyl-5-phenyl-1H-pyrazol-1-yl]benzenesulfonamide;]

[4-[4-chloro-5-(4-chlorophenyl)-3-hydroxymethyl-1H-pyrazol-1-yl]benzenesulfonamide;]

[[1-(4-aminosulfonylphenyl)-4-chloro-5-(4-chlorophenyl)-1H-pyrazol-3-yl]propanoic acid;]

[4-[5-(4-chlorophenyl)-3-(trifluoromethyl)-1H-pyrazol-1-yl]benzenesulfonamide;]

[4-[4-phenyl-3-(trifluoromethyl)-1H-pyrazol-1-yl]benzenesulfonamide;]

[4-[5-(4-fluorophenyl)-3-(trifluoromethyl)-1H-pyrazol-1-yl]benzenesulfonamide;]

[4-[5-(4-cyanophenyl)-3-(trifluoromethyl)-1H-pyrazol-1-yl]benzenesulfonamide;]

[4-[5-(2,4-difluorophenyl)-3-(trifluoromethyl)-1H-pyrazol-1-yl]benzenesulfonamide;]

[4-[5-(2,6-difluorophenyl)-3-(trifluoromethyl)-1H-pyrazol-1-yl]benzenesulfonamide;]

[4-[5-(4-methoxyphenyl)-3-(trifluoromethyl)-1H-pyrazol-1-yl]benzenesulfonamide;]

[4-[5-(3,4-dichlorophenyl)-3-(trifluoromethyl)-1H-pyrazol-1-yl]benzenesulfonamide;]

[4-[5-(4-bromophenyl)-3-(trifluoromethyl)-1H-pyrazol-1-yl]benzenesulfonamide;]

[4-[5-(2,4-dichlorophenyl)-3-(trifluoromethyl)-1H-pyrazol-1-yl]benzenesulfonamide;]

[4-[5-(3-chlorophenyl)-3-(trifluoromethyl)-1H-pyrazol-1-yl]benzenesulfonamide;]

[4-[5-(4-methylphenyl)-3-(trifluoromethyl)-1H-pyrazol-1-yl]benzenesulfonamide;]

[4-[5-(4-trifluoromethylphenyl)-3-(trifluoromethyl)-1H-pyrazol-1-yl]benzenesulfonamide;]

[4-[5-(4-trifluoromethoxyphenyl)-3-(trifluoromethyl)-1H-pyrazol-1-yl]benzenesulfonamide;]

[4-[5-(4-nitrophenyl)-3-(trifluoromethyl)-1H-pyrazol-1-yl]benzenesulfonamide;]

[4-[5-(2-chlorophenyl)-3-(trifluoromethyl)-1H-pyrazol-1-yl]benzenesulfonamide;]

[4-[5-(2-fluorophenyl)-3-(trifluoromethyl)-1H-pyrazol-1-yl]benzenesulfonamide;]

[4-[5-(4-aminophenyl)-3-(trifluoromethyl)-1H-pyrazol-1-yl]benzenesulfonamide;]

[4-[5-(2-methylphenyl)-3-(trifluoromethyl)-1H-pyrazol-1-yl]benzenesulfonamide;]

[4-[5-(4-fluoro-2-methylphenyl)-3-(trifluoromethyl)-1H-pyrazol-1-yl]benzenesulfonamide;]

[4-[5-(3-methylphenyl)-3-(trifluoromethyl)-1H-pyrazol-1-yl]benzenesulfonamide;]

[4-[5-(4-ethoxyphenyl)-3-(trifluoromethyl)-1H-pyrazol-1-yl]benzenesulfonamide;]

[4-[5-(3,5-dimethyl-4-methoxyphenyl)-3-(trifluoromethyl)-1H-pyrazol-1-yl]benzenesulfonamide;]

[4-[5-(3-fluorophenyl)-3-(trifluoromethyl)-1H-pyrazol-1-yl]benzenesulfonamide;]

[4-[5-(3-fluoro-4-methoxyphenyl)-3-(trifluoromethyl)-1H-pyrazol-1-yl]benzenesulfonamide;]

[4-[5-(4-methylthiophenyl)-3-(trifluoromethyl)-1H-pyrazol-1-yl]benzenesulfonamide;]

[4-[5-(4-chloro-3-methylphenyl)-3-(trifluoromethyl)-1H-pyrazol-1-yl]benzenesulfonamide;]

[4-[5-(4-ethylphenyl)-3-(trifluoromethyl)-1H-pyrazol-1-yl]benzenesulfonamide;]

[4-[5-(2,4-dimethylphenyl)-3-(trifluoromethyl)-1H-pyrazol-1-yl]benzenesulfonamide;]

[4-[5-(2-methoxyphenyl)-3-(trifluoromethyl)-1H-pyrazol-1-yl]benzenesulfonamide;]

[4-[5-(4-methoxy-3-methylphenyl)-3-(trifluoromethyl)-1H-pyrazol-1-yl]benzenesulfonamide;]

[4-[5-(3-bromo-4-methylthiophenyl)-3-(trifluoromethyl)-1H-pyrazol-1-yl]benzenesulfonamide;]

[4-[5-(4-hydroxy-3-methylphenyl)-3-(trifluoromethyl)-1H-pyrazol-1-yl]benzenesulfonamide;]

[4-[5-(3-chloro-4-methylphenyl)-3-(trifluoromethyl)-1H-pyrazol-1-yl]benzenesulfonamide;]

[4-[5-(3,4-dimethoxyphenyl)-3-(trifluoromethyl)-1H-pyrazol-1-yl]benzenesulfonamide;]

[4-[5-(3-chloro-4-methoxyphenyl)-3-(trifluoromethyl-1H-pyrazol-1-yl]benzenesulfonamide;]

[4-[5-(3-chloro-4-methoxy-5-methylphenyl)-3-(trifluoromethyl)-1H-pyrazol-1-yl]benzenesulfonamide;]

[4-[5-(3-ethyl-4-methoxyphenyl)-3-(trifluoromethyl)-1H-pyrazol-1-yl]benzenesulfonamide;]

[4-[5-(4-fluoro-2-methoxyphenyl)-3-(trifluoromethyl)-1H-pyrazol-1-yl]benzenesulfonamide;]

[4-[5-(4-hydroxymethylphenyl)-3-(trifluoromethyl)-1H-pyrazol-1-yl]benzenesulfonamide;]

[4-[5-(4-methoxy-3-(1-propenyl)phenyl)-3-(trifluoromethyl)-1H-pyrazol-1-yl]benzenesulfonamide;]

[4-[5-(3,5-dichloro-4-methoxyphenyl)-3-(trifluoromethyl)-1H-pyrazol-1-yl]benzenesulfonamide;]

[4-[5-(2,4-dimethoxyphenyl)-3-(trifluoromethyl)-1H-pyrazol-1-yl]benzenesulfonamide;]

[4-[5-(3-chloro-4-fluorophenyl)-3-(trifluoromethyl)-1H-pyrazol-1-yl]benzenesulfonamide;]

[4-[5-(4-methoxy-3-propylphenyl)-3-(trifluoromethyl)-1H-pyrazol-1-yl]benzenesulfonamide;]

[4-[5-(3,5-difluoro-4-methoxyphenyl)-3-(trifluoromethyl)-1H-pyrazol-1-yl]benzenesulfonamide;]

[4-[5-(3-fluoro-4-methylthiophenyl)-3-(trifluoromethyl)-1H-pyrazol-1-yl]benzenesulfonamide;]

[4-[5-(3-cyclopropylmethyl-4-methoxyphenyl)-3-(trifluoromethyl)-1H-pyrazol-1-yl]benzenesulfonamide;]

[4-[5-[4-(aminosulfonyl)phenyl]-3-(trifluoromethyl)-1H-pyrazol-5-yl]benzoic acid;]

[4-[5-(3-methyl-4-methylthiophenyl)-3-(trifluoromethyl)-1H-pyrazol-1-yl]benzenesulfonamide;]

[4-[5-(3-chloro-4-methylthiophenyl)-3-(trifluoromethyl)-1H-pyrazol-1-yl]benzenesulfonamide;]

[4-[5-(4-(N,N-dimethylamino)phenyl)-3-(trifluoromethyl)-1H-pyrazol-1-yl]benzenesulfonamide;]

[4-[5-(4-methyl-3-nitrophenyl)-3-(trifluoromethyl)-1 H-pyrazol-1-yl]benzenesulfonamide;]

[4-[5-(4-(N-methylamino)phenyl)-3-(trifluoromethyl)-1H-pyrazol-1-yl]benzenesulfonamide;]

[4-[5-(3-amino-4-methylphenyl)-3-(trifluoromethyl)-1H-pyrazol-1-yl]benzenesulfonamide;]

[methyl-4-[1-[4-(aminosulfonyl)phenyl]-3-(trifluoromethyl)-1H-pyrazol-5yl]benzoate;]

[4-[1-[4-(aminosulfonyl)phenyl]-3-(trifluoromethyl)-1H-pyrazol-5-yl]benzamide;]

[4-[5-(3,5-difluorophenyl)-3-(trifluoromethyl)-1H-pyrazol-1-yl]benzenesulfonamide;]

[4-[5-(2,4,6-trifluorophenyl)-3-(trifluoromethyl)-1H-pyrazol-1-yl]benzenesulfonamide;]

[4-[5-(2,6-dichlorophenyl)-3-(trifluoromethyl)-1H-pyrazol-1-yl]benzenesulfonamide;]

[4-[5-(2,4,6-trichlorophenyl)-3-(trifluoromethyl)-1H-pyrazol-1-yl]benzenesulfonamide;]

[4-[5-(3-methoxyphenyl)-3-(trifluoromethyl)-1H-pyrazol-1-yl]benzenesulfonamide;]

[4-[5-(3,4-dimethylphenyl)-3-(trifluoromethyl)-1H-pyrazol-1-yl]benzenesulfonamide;]

[4-[5-(1,3-benzodioxol-5-yl)-3-(trifluoromethyl)-1H-pyrazol-1-yl]benzenesulfonamide;]

[4-[5-(2-fluoro-4-methoxyphenyl)-3-(trifluoromethyl)-1H-pyrazol-1-yl]benzenesulfonamide;]

[4-[5-(2-chloro-4-methoxyphenyl)-3-(trifluoromethyl)-1H-pyrazol-1-yl]benzenesulfonamide;]

[4-[5-(4-chloro-2-methoxyphenyl)-3-(trifluoromethyl)-1H-pyrazol-1-yl]benzenesulfonamide;]

[4-[5-(2-methylthiophenyl)-3-(trifluoromethyl)-1H-pyrazol-1-yl]benzenesulfonamide;]

[4-[5-(3-methylthiophenyl)-3-(trifluoromethyl)-1H-pyrazol-1-yl]benzenesulfonamide;]

[4-[5-(2-methylsulfinylphenyl)-3-(trifluoromethyl)-1H-pyrazol-1-yl]benzenesulfonamide;]

[4-[5-(3-methylsulfinylphenyl)-3-(trifluoromethyl-1H-pyrazol-1-yl]benzenesulfonamide;]

[4-[5-(4-methylsulfinylphenyl)-3-(trifluoromethyl)-1H-pyrazol-1-yl]benzenesulfonamide;]

[4-[5-(2-fluoro-4-methylphenyl)-3-(trifluoromethyl)-1H-pyrazol-1-yl]benzenesulfonamide;]

[4-[5-(4-fluoro-3-methylphenyl)-3-(trifluoromethyl)-1H-pyrazol-1-yl]benzenesulfonamide;]

[4-[5-(2-chloro-4-methylphenyl)-3-(trifluoromethyl)-1H-pyrazol-1-yl]benzenesulfonamide;]

[4-[5-(4-chloro-2-methylphenyl)-3-(trifluoromethyl)-1H-pyrazol-1-yl]benzenesulfonamide;]

[4-[5-(4-hydroxyphenyl)-3-(trifluoromethyl)-1H-pyrazol-1-yl]benzenesulfonamide;]

[4-[5-(3,4-dihydroxyphenyl)-3-(trifluoromethyl)-1H-pyrazol-1-yl]benzenesulfonamide;]

[4-[5-(4-isopropylphenyl)-3-(trifluoromethyl)-1H-pyrazol-1-yl]benzenesulfonamide;]

[N-[4-[1-[4-(aminosulfonyl)phenyl]-3-trifluoromethyl-1H-pyrazol-5-yl]phenyl]acetamide;]

[N-[4-[1-[4-(aminosulfonyl)phenyl]-3-trifluoromethyl-1H-pyrazol-5-yl]phenyl]formamide;]

[N-[4-[1-[4-(aminosulfonyl)phenyl]-3-trifluoromethyl-1H-pyrazol-5-yl]phenyl]trifluoroacetamide;]

[4-[5-(4-[N-methylaminosulfonyl]phenyl)-3-(trifluoromethyl)-1H-pyrazol-1-yl]benzenesulfonamide;]

[4-[5-(2,5-dichlorophenyl)-3-(trifluoromethyl)-1H-pyrazol-1-yl]benzenesulfonamide;]

[4-[5-(4-n-butoxyphenyl)-3-(trifluoromethyl)-1H-pyrazol-1-yl]benzenesulfonamide;]

[4-[5-(4-[aminosulfonyl]phenyl)-3-(trifluoromethyl)-1H-pyrazol-1-yl]benzenesulfonamide;]

[4-[5-(2,3-difluorophenyl)-3-(trifluoromethyl)-1H-pyrazol-1-yl]benzenesulfonamide;]

[4-[5-(2,5-difluorophenyl)-3-(trifluoromethyl)-1H-pyrazol-1-yl]benzenesulfonamide;]

[4-[5-(2,3,4-trifluorophenyl)-3-(trifluoromethyl)-1H-pyrazol-1-yl]benzenesulfonamide;]

[4-[5-(3,4,5-trifluorophenyl)-3-(trifluoromethyl)-1H-pyrazol-1-yl]benzenesulfonamide;]

[4-[5-(2,4,5-trifluorophenyl)-3-(trifluoromethyl)-1H-pyrazol-1-yl]benzenesulfonamide;]

[4-[5-(2,5,6-trifluorophenyl)-3-(trifluoromethyl)-1H-pyrazol-1-yl]benzenesulfonamide;]

[4-[5-(2,3,4,5-tetrafluorophenyl)-3-(trifluoromethyl)-1H-pyrazol-1-yl]benzenesulfonamide;]

[4-[5-(2,3,4,6-tetrafluorophenyl)-3-(trifluoromethyl)-1H-pyrazol-1-yl]benzenesulfonamide;]

[4-[5-(2,3,5,6-tetrafluorophenyl)-3-(trifluoromethyl)-1H-pyrazol-1-yl]benzenesulfonamide;]

[4-[5-(pentafluorophenyl)-3-(trifluoromethyl)-1H-pyrazol-1-yl]benzenesulfonamide;]

[4-[5-(2,3,4-trichlorophenyl)-3-(trifluoromethyl)-1H-pyrazol-1-yl]benzenesulfonamide;]

[4-[5-(3,4,5-trichlorophenyl)-3-(trifluoromethyl)-1H-pyrazol-1-yl]benzenesulfonamide;]

[4-[5-(2,4,5-trichlorophenyl)-3-(trifluoromethyl)-1H-pyrazol-1-yl]benzenesulfonamide;]

[4-[5-(2,5,6-trichlorophenyl)3-(trifluoromethyl)-1H-pyrazol-1-yl]benzenesulfonamide;]

[4-[5-(2,3,4,5-tetrachlorophenyl)-3-(trifluoromethyl)-1H-pyrazol-1-yl]benzenesulfonamide;]

[4-[5-(2,3,4,6-tetrachlorophenyl)-3-(trifluoromethyl)-1H-pyrazol-1-yl]benzenesulfonamide;]

[4-[5-(2,3,5,6-tetrachlorophenyl)-3-(trifluoromethyl)-1H-pyrazol-1-yl]benzenesulfonamide;]

[4-[5-(2,3,4,5,6-pentachlorophenyl)-3-(trifluoromethyl)-1H-pyrazol-1-yl]benzenesulfonamide;]

[4-[5-(4-tert-butylphenyl)-3-(trifluoromethyl)-1H-pyrazol-1-yl]benzenesulfonamide;]

[4-[5-(4-isobutylphenyl)-3-(trifluoromethyl)-1H-pyrazol-1-yl]benzenesulfonamide;]

[4-[5-(4-chlorophenyl)-3-(difluoromethyl)-1H-pyrazol-1-yl]benzenesulfonamide;]

[4-[5-(4-trifluoromethylphenyl)-3-(difluoromethyl)-1H-pyrazol-1-yl]benzenesulfonamide;]

[4-[5-(4-methylthiophenyl)-3-(difluoromethyl)-1H-pyrazol-1-yl]benzenesulfonamide;]

[4-[5-(4-(1-morpholino)phenyl)-3-(difluoromethyl)-1H-pyrazol-1-yl]benzenesulfonamide;]

[4-[5-(4-methylphenyl)-3-(difluoromethyl)-1H-pyrazol-1-yl]benzenesulfonamide;]

[4-[5-phenyl-3-(difluoromethyl)-1H-pyrazol-1-yl]benzenesulfonamide;]

[4-[5-(4-methoxyphenyl)-3-(trifluoromethyl)-1H-pyrazol-1-yl]benzenesulfonamide;]

[4-[5-(3,4-dimethylphenyl)-3-(difluoromethyl)-1H-pyrazol-1-yl]benzenesulfonamide;]

[4-[5-(3-fluoro-4-methoxyphenyl)-3-(trifluoromethyl)-1H-pyrazol-1-yl]benzenesulfonamide;]

[4-[1-[4-(aminosulfonyl)phenyl]-3-(difluoromethyl)-1H-pyrazol-5yl]benzoic acid;]

[methyl 4-[1-[4-(aminosulfonyl)phenyl]-3-(difluoromethyl)-1H-pyrazol-5-yl]benzoate;]

[4-[1-(4-aminosulfonylphenyl)-3-(difluoromethyl)-1H-pyrazol-5-yl]benzamide;]

[4-[5-(2-fluoro-4-methoxyphenyl)-3-(difluoromethyl)-1H-pyrazol-1-yl]benzenesulfonamide;]

[4-[5-(4-cyanophenyl)-3-(difluoromethyl)-1H-pyrazol-1-yl]benzenesulfonamide;]

[4-[5-(3-chloro-4-methylphenyl)-3-(difluoromethyl)-1H-pyrazol-1-yl]benzenesulfonamide;]

[4-[5-(3-chloro-4-methoxyphenyl)-3-(difluoromethyl)-1H-pyrazol-1-yl]benzenesulfonamide;]

[4-[5-(4-chloro-3-methylphenyl)-3-(difluoromethyl)-1H-pyrazol-1-yl]benzenesulfonamide;]

[4-[5-(3,4-dimethoxyphenyl)-3-(difluoromethyl)-1H-pyrazol-1-yl]benzenesulfonamide;]

[4-[5-(3,5-dichloro-4-methoxyphenyl)-3-(difluoromethyl)-1H-pyrazol-1-yl]benzenesulfonamide;]

[4-[5-(3,5-difluoro-4-methoxyphenyl)-3-(difluoromethyl)-1H-pyrazol-1-yl]benzenesulfonamide;]

[4-[5-(2-methoxyphenyl)-3-(difluoromethyl)-1H-pyrazol-1-yl]benzenesulfonamide;]

[4-[5-(3-bromo-4-methoxyphenyl)-3-(difluoromethyl)-1H-pyrazol-1-yl]benzenesulfonamide;]

[4-[5-(4-methylsulfonylphenyl)-3-(difluoromethyl)-1H-pyrazol-1-yl]benzenesulfonamide;]

[4-[5-(5-bromo-2-thienyl)-3-(difluoromethyl)-1H-pyrazol-1-yl]benzenesulfonamide;]

[4-[5-(5-chloro-2-thienyl)-3-(difluoromethyl)-1H-pyrazol-1-yl]benzenesulfonamide;]

[4-[5-(1-cyclohexenyl)-3-(difluoromethyl)-1H-pyrazol-1-yl]benzenesulfonamide;]

[4-[5-(cyclohexyl)-3-(difluoromethyl)-1H-pyrazol-1-yl]benzenesulfonamide;]

[4-[5-(biphenyl)-3-(difluoromethyl)-1H-pyrazol-1-yl]benzenesulfonamide;]

[4-[5-(1,4-benzodioxan-6-yl)-3-(difluoromethyl)-1H-pyrazol-1-yl]benzenesulfonamide;]

[4-[3-(difluoromethyl)-5-(4-methylcyclohexyl)-1H-pyrazol-1-yl]benzenesulfonamide;]

[4-[5-(methyl-1-cyclohexenyl)-3-(difluoromethyl)-1H-pyrazol-1-yl]benzenesulfonamide;]

[4-[5-(2-methyl-1-cyclopentenyl)-3-(difluoromethyl)-1H-pyrazol-1-yl]benzenesulfonamide;]

[4-[5-(benzofuran-2-yl)-3-(difluoromethyl)-1H-pyrazol-1-yl]benzenesulfonamide;]

[4-[5-(1,3-benzodioxol-5-yl)-3-(difluoromethyl)-1H-pyrazol-1-yl]benzenesulfonamide;]

[4-[5-(2-pyrazinyl)-3-(difluoromethyl)-1H-pyrazol-1-yl]benzenesulfonamide;]

[4-[5-(4-(morpholino)phenyl)-3-(difluoromethyl)-1H-pyrazol-1-yl]benzenesulfonamide;]

[4-[5-(2,5-dimethyl-3-furyl)-3-(difluoromethyl)-1H-pyrazol-1-yl]benzenesulfonamide;]

[4-[5-(5-methyl-2-furyl)-3-(difluoromethyl)-1H-pyrazol-1-yl]benzenesulfonamide;]

[4-[5-(1-chloro-1-methyl-4-cyclohexyl)-3-(difluoromethyl)-1H-pyrazol-1-yl]benzenesulfonamide;]

[4-[5-(3,4-dibromo-4-methylcyclohexyl)-3-(difluoromethyl)-1H-pyrazol-1-yl]benzenesulfonamide;]

[4-[5-(2-methoxycyclohexyl)-3-(difluoromethyl)-1H-pyrazol-1-yl]benzenesulfonamide;]

[4-[5-(2-thienyl)-3-(difluoromethyl)-1H-pyrazol-1-yl]benzenesulfonamide;]

[4-[5-(2,4-dimethyl-3-thienyl)-3-(difluoromethyl)-1H-pyrazol-1-yl]benzenesulfonamide;]

[4-[5-(2,5-dichloro-3-thienyl)-3-(difluoromethyl)-1H-pyrazol-1-yl]benzenesulfonamide;]

[4-[5-()benzofuran-5-yl)-3-(trifluoromethyl)-1H-pyrazol-1-yl]benzenesulfonamide;]

[4-[5-(4-bromo-2-thienyl)-3-(trifluoromethyl)-1H-pyrazol-1-yl]benzenesulfonamide;]

[4-[5-(5-chloro-2-thienyl)-3-(trifluoromethyl)-1H-pyrazol-1-yl]benzenesulfonamide;]

[4-[5-(5-indanyl)-3-(trifluoromethyl)-1H-pyrazol-1-yl]benzenesulfonamide;]

[4-[5-(5-methyl-2-thienyl)-3-(trifluoromethyl)-1H-pyrazol-1-yl]benzenesulfonamide;]

[4-[5-(2,3-dihydrobenzofuran-5-yl)-3-(trifluoromethyl)-1H-pyrazol-1-yl]benzenesulfonamide;]

[4-[5-(1-cyclohexenyl)-3-(trifluoromethyl)-1H-pyrazol-1-yl]benzenesulfonamide;]

[4-[5-(5-benzothienyl)-3-(trifluoromethyl)-1H-pyrazol-1-yl]benzenesulfonamide;]

[4-[5-(3,4-dihydro-2H-1-benzopyran-6-yl)-3-(trifluoromethyl)-1H-pyrazol-1-yl]benzenesulfonamide;]

[4-[5-(3,4-dihydro-2H-1-benzothiopyran-6-yl)-3-(trifluoromethyl)-1H-pyrazol-1-yl]benzenesulfonamide;]

[4-[5-(2-phenylethenyl)-3-(trifluoromethyl)-1H-pyrazol-1-yl]benzenesulfonamide;]

[4-[5-(4-methyl-1,3-benzodioxol-6-yl)-3-(trifluoromethyl)-1H-pyrazol-1-yl]benzenesulfonamide;]

[4-[5-(4-methyl-1,3-benzodioxol-5-yl)-3-(trifluoromethyl)-1H-pyrazol-1-yl]benzenesulfonamide;]

[4-[5-(2-pyrazinyl)-3-(trifluoromethyl)-1H-pyrazol-1-yl]benzenesulfonamide;]

[4-[5-(biphenyl)-3-(trifluoromethyl)-1H-pyrazol-1-yl]benzenesulfonamide;]

[4-[5-(1,2,3,4-tetrahydronaphth-6-yl])-3-(trifluoromethyl)-1H-pyrazol-1-yl]benzenesulfonamide;]

[4-[5-(2-naphthyl)-3-(trifluoromethyl)-1H-pyrazol-1-yl]benzenesulfonamide;]

[4-[5-(2-thioazolyl)-3-(trifluoromethyl)-1H-pyrazol-1-yl]benzenesulfonamide;]

[4-[5-(2-oxazolyl)-3-(trifluoromethyl)-1H-pyrazol-1-yl]benzenesulfonamide;]

[4-[5-(cyclohexyl)-3-(trifluoromethyl)-1H-pyrazol-1-yl]benzenesulfonamide;]

[4-[5-(cyclopentyl)-3-trifluoromethyl)-1H-pyrazol-1-yl]benzenesulfonamide;]

[4-[5-(cycloheptyl)-3-(trifluoromethyl)-1H-pyrazol-1-yl]benzenesulfonamide;]

[4-[5-(1-cyclopentenyl)-3-(trifluoromethyl)-1H-pyrazol-1-yl]benzenesulfonamide;]

[4-[5-(2-furyl)-3-(trifluoromethyl)-1H-pyrazol-1-yl]benzenesulfonamide;]

[4-[5-(2-pyridyl)-3-(trifluoromethyl)-1H-pyrazol-1-yl]benzenesulfonamide;]

[4-[5-(3-pyridyl)-3-(trifluoromethyl)-1H-pyrazol-1-yl]benzenesulfonamide;]

[4-[5-(6-methyl-3-pyridyl)-3-(trifluoromethyl)-1H-pyrazol-1-yl]benzenesulfonamide;]

[4-[5-(4-pyridyl)-3-(trifluoromethyl)-1H-pyrazol-1-yl]benzenesulfonamide;]

[4-[5-(3-cyclohexenyl)-3-(trifluoromethyl)-1H-pyrazol-1-yl]benzenesulfonamide;]

[4-[5-(4-cyclohexenyl)-3-(trifluoromethyl)-1H-pyrazol-1-yl]benzenesulfonamide;]

[4-[5-(4-methylcyclohex-4-ene-1-yl)-3-(trifluoromethyl)-1H-pyrazol-1-yl]benzenesulfonamide;]

[4-[5-(5-chloro-2-furyl)-3-(trifluoromethyl)-1H-pyrazol-1-yl]benzenesulfonamide;]

[4-[5-(5-bromo-2-furyl)-3-(trifluoromethyl)-1H-pyrazol-1-yl]benzenesulfonamide;]

[4-[5-(6-methoxy-2-naphthyl)-3-(trifluoromethyl)-1H-pyrazol-1-yl]benzenesulfonamide;]

[4-[5-(6-methoxy-2-naphthyl)-3-(trifluoromethyl)-1H-pyrazol-1-yl]benzenesulfonamide;]

[4-[5-(4-chlorophenyl)-3-(heptafluoropropyl)-1H-pyrazol-1-yl]benzenesulfonamide;]

[4-[5-(4-chlorophenyl)-3-(chlorodifluoromethyl)-1H-pyrazol-1-yl]benzenesulfonamide;]

[4-[5-(4-chlorophenyl)-3-(pentafluoroethyl)-1H-pyrazol-1-yl]benzenesulfonamide;]

[4-[5-(3-chloro-4-methoxyphenyl)-3-(chloromethyl)-1H-pyrazol-1-yl]benzenesulfonamide;]

[4-[3-(chlorodifluoromethyl)-5-(3-fluoro-4-methoxyphenyl)-1H-pyrazol-1-yl]benzenesulfonamide;]

[4-[5-(phenyl)-3-(fluoromethyl)-1H-pyrazol-1-yl]benzenesulfonamide;]

[4-[3-(dichloromethyl)-5-(3-fluoro-4-methoxyphenyl)-1H-pyrazol-1-yl]benzenesulfonamide;]

[4-[3-(bromodifluoromethyl)-5-(3-fluoro-4-methoxyphenyl)-1H-pyrazol-1-yl]benzenesulfonamide;]

[4-[5-(4-chlorophenyl)-3-(fluoromethyl)-1H-pyrazol-1-yl]benzenesulfonamide;]

[4-[5-(4-chlorophenyl)-3-(chloromethyl)-1H-pyrazol-1-yl]benzenesulfonamide;]

[4-[5-(4-chlorophenyl)-3-(dichloromethyl)-1H-pyrazol-1-yl]benzenesulfonamide;]

[4-[5-(4-chlorophenyl)-3-(dichlorofluoromethyl)-1H-pyrazol-1-yl]benzene sulfonamide;]

[4-[5-(4-fluorophenyl)-3-(trichloromethyl)-1H-pyrazol-1-yl]benzenesulfonamide;]

[4-[5-(4-chlorophenyl)-3-(1,1-difluoroethyl)-1H-pyrazol-1-yl]benzenesulfonamide;]

[4-[5-(4-chlorophenyl)-3-(1,1-difluoropropyl)-1H-pyrazol-1-yl]benzenesulfonamide;]

[4-[5-(4-chlorophenyl)-3-(1,1-dichloroethyl)-1H-pyrazol-1-yl]benzenesulfonamide;]

[4-[5-(4-chlorophenyl)-3-(1,1-dichloropropyl)-1H-pyrazol-1-yl]benzenesulfonamide;]

[4-[5-(4-chlorophenyl)-3-nitro-1H-pyrazol-1-yl]benzenesulfonamide;]

[4-[5-(4-chlorophenyl)-3-(amidino)-1H-pyrazol-1-yl]benzenesulfonamide;]

[4-[5-(4-chlorophenyl)-3-(methylsulfonyl)-1H-pyrazol-1-yl]benzenesulfonamide;]

[4-[5-(4-chlorophenyl)-3-(N-methyl-aminosulfonyl)-1H-pyrazol-1-yl]benzenesulfonamide;]

[4-[5-(4-fluorophenyl)-3-(imidazolyl)-1H-pyrazol-1-yl]benzenesulfonamide;]

[4-[5-(4-fluorophenyl)-3-(2-pyridyl)-1H-pyrazol-1-yl]benzenesulfonamide;]

[4-[5-(4-chlorophenyl)-3-(N-cyanoamidino)-1H-pyrazol-1-yl]benzenesulfonamide;]

[4-[5-(4-chlorophenyl)-3-(tetrazolyl)-1H-pyrazol-1-yl]benzenesulfonamide;]

[4-[5-(4-chlorophenyl)-3-(phenylsulfonyl)-1H-pyrazol-1-yl]benzenesulfonamide;]

[4-[5-(4-chlorophenyl)-3-(N-phenylaminosulfonyl)-1H-pyrazol-1-yl]benzenesulfonamide;]

[4-[5-(4-chlorophenyl)-3-(N,N-dimethylaminosulfonyl)-1H-pyrazol-1-yl]benzenesulfonamide;]

[4-[5-(4-chlorophenyl)-3-(N-methyl-N-phenylaminosulfonyl)-1H-pyrazol-1-yl]benzenesulfonamide;]

[4-[5-(4-chlorophenyl)-3-(N-ethylaminosulfonyl)-1H-pyrazol-1-yl]benzenesulfonamide;]

[4-[5-(4-chlorophenyl)-3-(N-isopropylaminosulfonyl)-1H-pyrazol-1-yl]benzenesulfonamide;]

[4-[5-(4-chlorophenyl)-3-(N-methyl-N-ethylaminosulfonyl)-1H-pyrazol-1yl]benzenesulfonamide;]

[4-[5-(4-chlorophenyl)-3-(N-methyl-N-(3-chlorophenyl) aminosulfonyl)-1H-pyrazol-1-yl]benzenesulfonamide;]

[4-[5-(4-chlorophenyl)-3-(N-methyl-N-(2-pyridyl)aminosulfonyl)-1H-pyrazol-1-yl]benzenesulfonamide;]

[4-[3-methyl-5-phenyl-1H-pyrazol-1-yl]benzenesulfonamide;]

[4-[3-isobutyl-5-phenyl-1H-pyrazol-1-yl]benzenesulfonamide;]

[4-[3-(3-hydroxypropyl)-5-phenyl-1H-pyrazol-1-yl]benzenesulfonamide;]

[4-[5-(4-fluorophenyl)-3-(3-hydroxypropyl)-1H-pyrazol-1-yl]benzenesulfonamide;]

[4-[5-(3,5-dichloro-4-methoxyphenyl)-3-(3-hydroxypropyl)-1H-pyrazol-1-yl]benzenesulfonamide;]

[4-[5-(4-methylphenyl)-3-(2-hydroxyisopropyl)-1H-pyrazol-1-yl]benzenesulfonamide;]

[1-[4-(aminosulfonyl)phenyl]-5-(4-fluorophenyl)-1H-pyrazol-3-propanoic acid;]

[1-[4-(aminosulfonyl)phenyl]-5-(4-chlorophenyl)-1H-pyrazol-3-propanoic acid;]

[1-[4-(aminosulfonyl)phenyl]-5-(4-chlorophenyl)-1H-pyrazol-3-propanamide;]

[methyl 1-[4-(aminosulfonyl)phenyl]-5-(4-fluorophenyl)-1H-pyrazol-3-propanoate;]

[4-[3-(3-hydroxymethyl)-5-phenyl-1H-pyrazol-1-yl]benzenesulfonamide;]

[4-[5-(4-chlorophenyl)-3-(3-hydroxymethyl)-1H-pyrazol-1-yl]benzenesulfonamide;]

[4-[3-(3-hydroxymethyl)-5-(4-methoxyphenyl)-1H-pyrazol-1-yl]benzenesulfonamide;]

[4-[5-(3,5-dichloro-4-methoxyphenyl)-3-(3-hydroxymethyl)-1H-pyrazol-1-yl]benzenesulfonamide;]

[4-[5-(3-chloro-4-methoxyphenyl)-3-(3-hydroxymethyl)-1H-pyrazol-1yl]benzenesulfonamide;]

[ethyl 3-[1-(4-aminosulfonylphenyl)-5-(phenyl)-1H-pyrazol-3-yl]-2-cyano-2-propenoate;]

[4-[5-(4-chlorophenyl)-3-(chloro)-1H-pyrazol-1-yl]benzenesulfonamide;]

[4-[5-(4-chlorophenyl)-3-(bromo)-1H-pyrazol-1-yl]benzenesulfonamide;]

[4-[5-(4-chlorophenyl)-3-(fluoro)-1H-pyrazol-1-yl]benzenesulfonamide;]

[4-[3-(difluoromethyl)-4,5-dihydro-7-methoxy-1H-benz[g]indazol-1yl]benzenesulfonamide;]

[4-[3-(difluoromethyl)-4,5-dihydro-7-methyl-1H-benz[g]indazol-1yl]benzenesulfonamide;]

[4-[4,5-dihydro-7-methoxy-3-(trifluoromethyl)-1H-benz[g]indazol-1-yl]benzenesulfonamide;]

[4-[4,5-dihydro-3-(trifluoromethyl)-1H-benz[g]indazol-1yl]benzenesulfonamide;]

[4-[4,5-dihydro-7-methyl-3-(trifluoromethyl)-1H-benz[g]indazol-1-yl]benzenesulfonamide;]

[4-[4,5-dihydro-6,8-dimethyl-3-(trifluoromethyl)-1 H-benz[g]indazol-1yl]benzenesulfonamide;]

[4-[4,5-dihydro-6,8-dimethoxy-3(trifluoromethyl)-1H-benz[g]indazol-1yl]benzenesulfonamide;]

[methyl[1-(4-aminosulfonylphenyl)-4,5-dihydro-7-methoxy-1H-benz[g]indazol-3yl]carboxylate;]

[4-[4,5-dihydro-3-trifluoromethyl-1H-thieno[3,2g]indazol-1-yl]benzenesulfonamide;]

[4-[1-phenyl-3-(difluoromethyl)-1H-pyrazol-5-yl]benzenesulfonamide;]

[4-[1-(4-chlorophenyl)-3-(difluoromethyl)-1H-pyrazol-5-yl]benzenesulfonamide;]

[4-[1-(4-fluorophenyl)-3-(difluoromethyl)-1H-pyrazol-5-yl]benzenesulfonamide;]

[4-[1-(4-methoxyphenyl)-3-(difluoromethyl)-1H-pyrazol-5-yl]benzenesulfonamide;]

[4-[1-phenyl-3-(trifluoromethyl)-1H-pyrazol-5-yl]benzenesulfonamide;]

[4-[1-(4-chlorophenyl)-3-(trifluoromethyl)-1H-pyrazol-5-yl]benzenesulfonamide;]

[4-[1-(4-fluorophenyl)-3-(trifluoromethyl)-1H-pyrazol-5-yl]benzenesulfonamide; and]

[4-[1-(4-methoxyphenyl)-3-(trifluoromethyl)-1H-pyrazol-5-yl]benzenesulfonamide.]

[A family of specific compounds of particular interest within Formula II consists of compounds and pharmaceutically-acceptable salts thereof as follows:]

[4-[5-(4-chlorophenyl)-3-(trifluoromethyl)-1H-pyrazol-1-yl]benzenesulfonamide;]

[4-[5-phenyl-3-(trifluoromethyl)-1H-pyrazol-1-yl]benzenesulfonamide;]

[4-[5-(4-fluorophenyl)-3-(trifluoromethyl)-1H-pyrazol-1-yl]benzenesulfonamide;]

[4-[5-(4-methoxyphenyl)-3-(trifluoromethyl)-1H-pyrazol-1-yl]benzenesulfonamide;]

[4-[5-(4-chlorophenyl)-3-(difluoromethyl)-1H-pyrazol-1-yl]benzenesulfonamide;]

[4-[5-(4-methylphenyl)-3-(trifluoromethyl)-1H-pyrazol-1-yl]benzenesulfonamide;]

[4-[4-chloro-5-(4-chlorophenyl)-3-(trifluoromethyl)-1H-pyrazol-1-yl]benzenesulfonamide;]

[4-[3-(difluoromethyl)-5-(4-methylphenyl)-1H-pyrazol-1-yl]benzenesulfonamide;]

[4-[3-(difluoromethyl)-5-phenyl-1H-pyrazol-1-yl]benzenesulfonamide;]

[4-[3-(difluoromethyl)-5-(4--methoxyphenyl)-1H-pyrazol-1-yl]benzenesulfonamide;]

[4-[3-cyano-5-(4-fluorophenyl)-1H-pyrazol-1-yl]benzenesulfonamide;]

[4-[3-(difluoromethyl)-5-(3-fluoro-4-methoxyphenyl)-1H-pyrazol-1-yl]benzenesulfonamide;]

[4-[5-(3-fluoro-4-methoxyphenyl)-3-(trifluoromethyl)-1H-pyrazol-1-yl]benzenesulfonamide;]

[4-[4-chloro-5-phenyl-1H-pyrazol-1-yl]benzenesulfonamide;]

[4-[5-(4-chlorophenyl)-3-(hydroxymethyl)-1H-pyrazol-1-yl]benzenesulfonamide; and]

[4-[5-(4-(N,N-dimethylamino)phenyl)-3-(trifluoromethyl)-1H-pyrazol-1yl]benzenesulfonamide.]

*One compound of the present invention is 4-[5-(4-chlorophenyl)-3-(trifluoromethyl)-1H-pyrazol-1-yl]benzenesulfonamide, and pharmaceutically acceptable salts thereof.*

*Another compound of the present invention is 4-[5-phenyl-3-(trifluoromethyl)-1H-pyrazol-1-yl]benzenesulfonamide, and pharmaceutically acceptable salts thereof.*

*Another compound of the present invention is 4-[5-(4-fluorophenyl)-3-(trifluoromethyl)-1H-pyrazol-1-yl]benzenesulfonamide, and pharmaceutically acceptable salts thereof.*

*Another compound of the present invention is 4-[5-(4-methoxyphenyl)-3-(trifluoromethyl)-1H-pyrazol-1-yl]benzenesulfonamide, and pharmaceutically acceptable salts thereof.*

*Another compound of the present invention is 4-[5-(4-chlorophenyl)-3-(difluoromethyl)-1H-pyrazol-1-yl]benzenesulfonamide, and pharmaceutically acceptable salts thereof.*

*Another compound of the present invention is 4-[5-(4-methylphenyl)-3-(trifluoromethyl)-1H-pyrazol-1-yl]benzenesulfonamide, and pharmaceutically acceptable salts thereof.*

[The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. Where the term "alkyl" is used, either alone or within other terms such as "haloalkyl" and "alkylsulfonyl", it embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon-carbon double bond of two to about twenty carbon atoms or, preferably, two to about twelve carbon atoms. More preferred alkyl radicals are "lower alkenyl" radicals having two to about six carbon atoms. Examples of such radicals include ethyl, n-propenyl, butenyl, and the like. The term "halo" means halogens such as fluorine, chlorine, bromine or iodine atoms. The term "haloalkyl" embraces radicals wherein any one or more of the alkyl carbon atoms is substituted with halo as defined above. Specifically embraced are amonohaloalkyl, dihaloalkyl and polyhaloalkyl radicals. A monohaloalkyl radical, or one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxylalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkoxyalkyl" embrace linear or branched oxy-containing radicals each having alkyl portions of one to about ten carbon atoms, such as methoxy radical. More preferred alkoxy radicals are "lower alkoxy" radicals having one to six carbon atoms. Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. More preferred alkoxyalkyl radicals are "lower alkoxyalkyl" radicals having one to six carbon atoms and one or two alkoxy radicals. Examples of such radicals include methoxymethyl, methoxyethyl, ethoxyethyl, methoxybutyl and methoxypropyl. The "alkoxy" or "alkoxyalkyl" radicals may be further substituted with one or more halo atoms, such as fluoro, chloro or bromo, to provide "haloalkoxy" or "haloalkoxyalkyl" radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. The term "heterocyclic" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocyclic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. The term "heteroaryl" embraces unsaturated hetereocyclic radicals. Examples of unsaturated heterocyclic radicals, also termed "heteroaryl" radicals include unsaturated 5 to 6 membered heteromonocyclic group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotraizolyl, tetrazolopyridazinyl [e.g., tetrazolo [1,5-b]pyridinzinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, triazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl, hydroxy, oxo, amino and lower alkylamino. Preferred heterocyclic radicals include five to ten membered fused or unfused radicals. More preferred examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl, and pyrazinyl. The term "sulfonyl", whether used alone or linked to other terms such as alkylsulfonyl, denotes respectively divalent radicals —$SO_2$—.]

["Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The term "arylsulfonyl" embraces aryl radicals as defined above, attached to a sulfonyl radical. Examples of such radicals include phenylsulfonyl. The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—$SO_2NH_2$). The terms "N-alkylaminosulfonyl" and "N,N-dialkylaminosulfonyl" denote sulfamyl radicals substituted, respectively, with one alkyl radical, or two alkyl radicals. More preferred alkylaminosulfonyl radicals are "lower alkylaminosulfonyl" radicals having one to six carbon atoms. Examples of such lower alkylaminosulfonyl radicals include N-methylaminosulfonyl, N-ethylaminosulfonyl and N-methyl-N-ethylaminosulfonyl. The terms "N-arylaminosulfonyl" and "N-alkyl-N-arylaminosulfonyl" denote sulfamyl radicals substituted, respectively, with one aryl radical, or one alkyl and one aryl radical. More preferred N-alkyl-N-arylaminosulfonyl radicals are "lower N-alkyl-N-arylsulfonyl" radicals having alkyl radicals of one to six carbon atoms. Examples of such lower N-alkyl-N-aryl aminosulfonyl radicals include N-methyl-phenylaminosulfonyl and N-ethyl-phenylaminosulfonyl The terms "carboxy" or "carboxyl", whether used alone or with other terms, such as "carboxyalkyl", denotes —$CO_2H$. The terms "alkanoyl" or "carboxyalkyl" embrace radicals having a carboxy radical as defined above, attached to an alkyl radical. The alkanoyl radicals may be substituted or unsubstituted, such as formyl, acetyl, propionyl (propanoyl), butanoyl (butyryl), isobutanoyl (isobutyryl), valeryl (pentanoyl), isovaleryl, pivaloyl, hexanoyl or the like. The term "carbonyl", whether used alone or with other terms, such as "alkylcarbonyl", denotes —(C═O)—. The term "alkylcarbonyl" embraces radicals having a carbonyl radical substituted with an alkyl radical. More preferred alkylcarbonyl radicals are "lower alkylcarbonyl" radicals having one to six carbon atoms. Examples of such radicals include methylcarbonyl and ethylcarbonyl. The term "alkylcarbonylalkyl", denotes an alkyl radical substituted with an "alkylcarbonyl" radical. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl. The term "alkoxycarbonylalkyl" embraces radicals having "alkoxycarbonyl", as defined above substituted to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl, tert-butoxycarbonylethyl, and methoxycarbonylethyl. The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula —C(═O)$NH_2$. The terms "N-alkylaminocarbonyl" and "N,N-dialkylaminocarbonyl" denote aminocarbonyl radicals which have been substitute with one alkyl radical and with two alkyl radicals, respectively. More preferred are "lower alkylaminocarbonyl" having lower alkyl radicals as described above attached to an aminocarbonyl radical. The terms "N-arylaminocarbonyl" and "N-alkyl-N-arylaminocarbonyl" denote aminocarbonyl radicals substituted, respectively, with one aryl radical, or one alkyl and one aryl radical. The term "aminocarbonylalkyl" embraces alkyl radicals substituted with aminocarbonyl radicals. The term "N-cycloalkylaminocarbonyl" denoted aminocarbonyl radicals which have been substituted with at least one cycloalkyl radical. More preferred are "lower cycloalkylaminocarbonyl" having lower cycloalkyl radicals of three to seven carbon atoms, attached to an aminocarbonyl radical. The term "aminoalkyl" embraces alkyl radicals substituted with amino radicals. The term "alkylaminoalkyl" embraces aminoalkyl radicals having the nitrogen atom substituted with an alkyl radical. The term "amidino" denotes an —C(═NH)—$NH_2$ radical. The term "cyanoamidino" denotes an —C(═N—CN)—$NH_2$ radical. The term "heterocyclicalkyl" embraces heterocyclic-substituted alkyl radicals. More preferred heterocyclicalkyl radicals are "lower heterocyclicalkyl" radicals having one to six carbon atoms and a heterocyclic radical. Examples include such radicals as pyrrolidinylmethyl, pyridylmethyl and thienylmethyl. The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The aryl in said aralkyl may be additionally substituted with halo, alkyl, alkoxy, halkoalkyl and haloalkoxy. The terms benzyl and phenylmethyl are interchangeable. The term "cycloalkyl" embraces radicals having three to ten carbon atoms. More preferred cycloalkyl radicals are "lower cycloalkyl" radicals having three to seven carbon atoms. Examples include radicals such as cyclopropyl, cyclobutyl, cyclopentyl, cyclohexyl and cycloheptyl. The term "cycloalkenyl" embraces unsaturated cyclic radicals having three to ten carbon atoms, such as cyclobutenyl, cyclopentenyl, cyclohexenyl and cycloheptenyl. The term "alkylthio" embraces radicals containing a linear or branched alkyl radical, of one to ten carbon atoms, attached to a divalent sulfur atom. An example of "alkylthio" is methylthio, ($CH_3$—S—). The term "alkylsulfinyl" embraces radicals containing a linear or branched alkyl radical, of one to ten carbon atoms, attached to a divalent —S(═O)— atom. The term "aminoalkyl" embraces alkyl radicals substituted with amino radicals. More preferred aminoalkyl radicals are "lower aminoalkyl" having one to six carbon atoms. Examples include aminomethyl, aminoethyl and aminobutyl. The term "alkylaminoalkyl" embraces aminoalkyl radicals having the nitrogen atom substituted with at least one alkyl radical. More preferred alkylaminoalkyl radicals are "lower alkylaminoalkyl" having one to six carbon atoms attached to a lower aminoalkyl radical as described above. The terms "N-alkylamino" and "N,N-dialkylamino" denote amino groups which have been substituted with one alkyl radical and with two alkyl radicals, respectively. More preferred alkylamino radicals are "lower alkylamino" radicals having one or two alkyl radicals of one to six carbon atoms, attached to a nitrogen atom. Suitable "alkylamino" may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical. The term "aralkylamino" denotes amino groups which have been substituted with one or two aralkyl radicals, such as N-benzylamino. The "aralkylamino" radicals may be further substituted on the aryl ring portion of the radical. The terms "N-alkyl-N-arylamino" and "N-aralkyl-N-alkylamino" denote amino groups which have been substituted with one aralkyl and one alkyl radical, or one aryl and one alkyl radical, respectively, to an amino group. The terms "N-arylaminoalkyl" and "N-aralkylaminoalkyl" denote amino groups which have been substituted with one aryl radical or one aralkyl radical, respectively, and having the amino group attached to an alkyl radical. More preferred arylaminoalkyl radicals are "lower arylaminoalkyl" having the arylamino radical attached to one to six carbon atoms. Examples of such radicals include N-phenylaminomethyl and N-phenyl-N-methylaminomethyl. The terms "N-alkyl-N-arylaminoalkyl" and "N-aralkyl-N-alkylaminoalkyl" denote N-alkyl-N-arylamino and N-alkyl-N-aralkylamino groups, respectively, and having the amino group attached to alkyl radicals. The term "acyl", whether used alone, or within a term such as "acylamino", denotes a radical provided by the residue after removal of hydroxyl from an organic acid. The term "acylamino" embraces an amino radical substituted with an acyl group. An examples of an "acylamino" radical is acetylamino or acetamido ($CH_3$C(═O)—NH—) where the amine may be further substituted with alkyl, aryl or aralyl. The term "arylthio" embraces aryl radicals of six to ten carbon atoms, attached to a divalent sulfur atom. An example of "arylthio" is phenylthio. The term "aralkylthio" embraces aralkyl radicals as described above, attached to a divalent sulfur atom. An example of "aralkylthio" is benzylthio. The term "aryloxy" embraces aryl radicals, as defined above, attached to an oxygen atom. Examples of such radicals include phenoxy. The term "aralkoxy" embraces oxy-containing aralkyl radicals attached through an oxygen atom to other radicals. More preferred aralkoxy radicals are "lower aralkoxy" radicals having phenyl radicals attached to lower alkoxy radical as described above. The term "haloaralkyl" embraces aryl radicals as defined above attached to haloalkyl radicals. The term "carboxyhaloalkyl" embraces carboxyalkyl radicals as defined above having halo radicals attached to the alkyl portion. The term "alkoxycarbonylhaloalkyl" embraces alkoxycarbonyl radicals as defined above substituted on a haloalkyl radical. The term "aminocarbonylhaloalkyl" embraces aminocarbonyl radicals as defined above substituted on a haloalkyl radical. The term "alkylaminocarbonylhaloalkyl" embraces alkylaminocarbonyl radicals as defined above substituted on a haloalkyl radical. The term "alkoxycarbonylcyanoalkenyl" embraces alkoxycarbonyl radicals as defined above, and a cyano radical, both substituted on an alkenyl radical. The term "carboxyalkylaminocarbonyl" embraces aminocarbonyl radicals substituted with carboxyalkyl radicals, as defined above. The term "aralkoxycarbonylalkylaminocarbonyl" embraces aminocarbonyl radicals substituted with aryl-substituted alkoxycarbonyl radicals, as defined above. The term "cycloalkylalkyl" embraces cycloalkyl radicals having three to ten carbon atoms attached to an alkyl radical, as defined above. More preferred cycloalkylalkyl radicals are "lower cycloalkylalkyl" radicals having cycloalkyl radicals attached to lower alkyl radicals as defined above. Examples include radicals such as cyclopropylmethyl, cyclobutylmethyl, and cyclohexylethyl. The term "aralkenyl" embraces aryl radicals attached to alkenyl radicals having two to ten carbon atoms, such as phenylbutenyl, and phenylethenyl or styryl.]

The present invention comprises a pharmaceutical composition for the treatment of inflammation and inflammation-associated disorders, such as arthritis, comprising a therapeutically-effective amount of a compound of [Formula I] *the present invention* in association with at least one pharmaceutically-acceptable carrier, adjuvant or diluent.

The present invention also comprises a therapeutic method of treating inflammation or inflammation-associated disorders in a subject, the method comprising administering to a subject having such inflammation or disorder a therapeutically-effective amount of a compound of [Formula I] *the present invention*.

Also included in the family of compounds of [Formula I] *the present invention* are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of [Formula I] *the present invention* may be prepared from an inorganic acid or from an organic Acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of [Formula I] *the present invention* by reacting, for example, the appropriate acid or base with the compound of [Formula I] *the present invention*.

[GENERAL SYNTHETIC PROCEDURES]

[The compounds of the invention can be synthesized according to the following procedures of Schemes I-VIII, wherein the $R^1$-$R^7$ substituents are as defined for Formula I, above, except where further noted.

SCHEME I

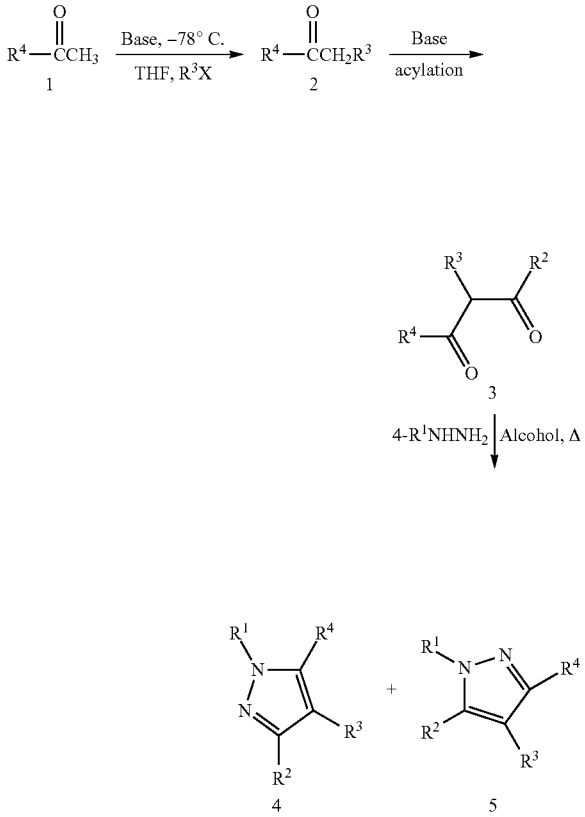

]

[Synthetic Scheme I shows the preparation of tetrasubstituted pyrazoles from starting material 1. In step 1 of synthetic Scheme I, the phenyl-methyl ketone (1) is treated with a base and an alkylating reagent ($R^3X$, where X represents a leaving group such as tosyl) to give the substituted ketone (2). In step 2, the substituted ketone (2) is treated with base, such as sodium methoxide, and an acylating reagent such as an ester ($R^2CO_2CH_3$), or ester equivalent ($R^2CO$-imidazole, to give the intermediate diketone (3) in a procedure similar to that developed by Reid and Calvin, J. Amer. Chem. Soc., 72, 2948-2952 (1950). In step 3, the diketone (3) is reacted with a substituted hydrazine in acetic acid or an alcoholic solvent to give a mixture of pyrazoles (4) and (5). Separation of the desired pyrazole (4) can be achieved by chromatography or recrystallization.

SCHEME II

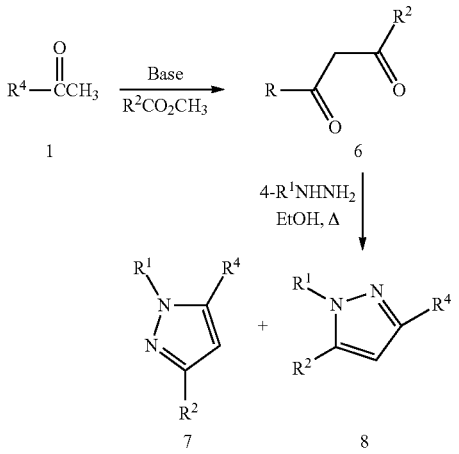

]

[Synthetic Scheme II shows the preparation of compounds embraced by Formula I, where $R^3$ is a hydrogen atom. In step 1, ketone (1) is treated with a base, preferably NaOMe or NaH, and an ester, or ester equivalent, to form the intermediate diketone (6) which is used without further purification. In step 2, diketone (6) in an anhydrous protic solvent, such as absolute ethanol or acetic acid, is treated with the hydrochloride salt or the free base of a substituted hydrazine at reflux for 10 to 24 hours to afford a mixture of pyrazoles (7) and (8). Recrystallization from diethyl ether/hexane or chromatography affords (7), usually as a light yellow or tan solid.

SCHEME III

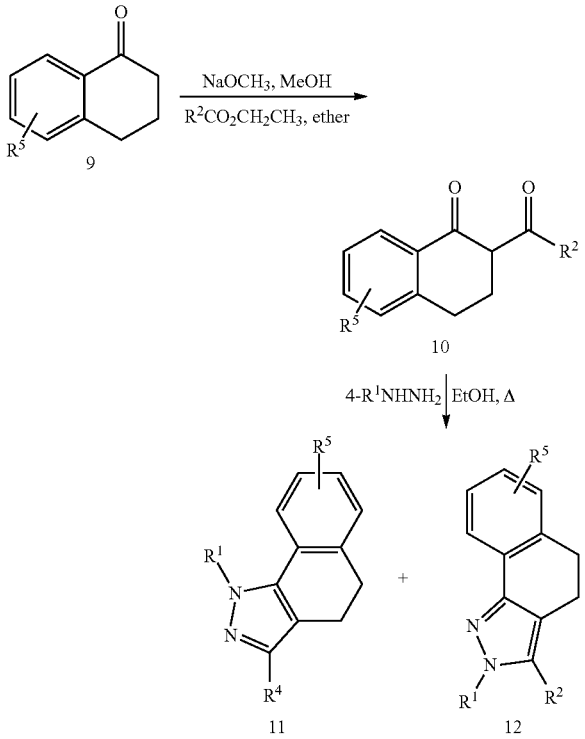

]

[Synthetic Scheme III shows the procedure for preparation of 4,5-dihydrobenz[g]indazole compounds embraced by Formula I. In step 1, ethyl trifluoroacetate is reacted with base, such as 25% sodium methoxide in a protic solvent, such as methanol, and a 1-tetralone derivative (9) to give the intermediate diketone (10). In step 2, the diketone (10) in an anhydrous protic solvent, such as absolute ethanol or acetic acid, is treated with the free base or hydrochloride salt of a substituted hydrazine at reflux for 24 hours to afford a mixture of pyrazoles (11) and (12). Recrystallization gives the 4,5-dihydro benz[g]indazolyl-benzenesulfonamide (11).

SCHEME IV

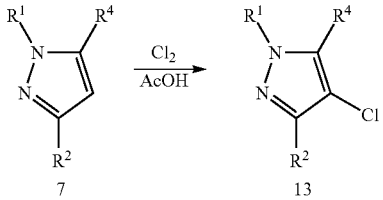

]

[Synthetic Scheme IV shows the preparation of pyrazole compounds (13), where $R^3$ is chlorine, from the available pyrazole compounds (7), where $R^3$ is hydrogen. Chlorination results from passing a stream of chlorine gas at room temperature through a solution containing (7).

Scheme V

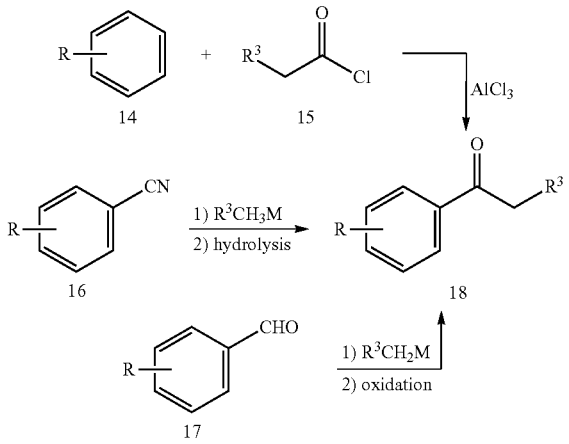

]

[Synthetic Scheme V shows the preparation of substituted ketones 18 which are not commercially available as used in Scheme I. The ketones can be prepared by standard Friedel-Craft acylation of the starting substituted benzenes 14 with acid chlorides or anhydrides 15. Alternatively, the ketones can be prepared from phenylcarbonitriles 16 by standard organometallic techniques where M represents metals such as lithium, magnesium, and the like. An alternative organometallic route is shown from the aldehydes 17 where M represents metals such as lithium, magnesium, and the like. Oxidation with a suitable oxidizing agent, such as $CrO_3$, follows to produce the ketones.

Scheme VI

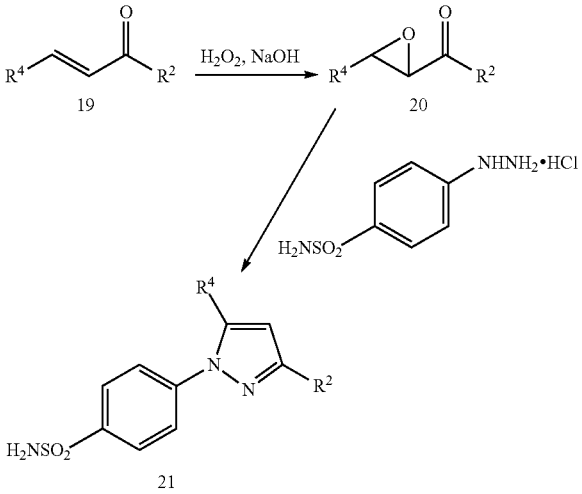

]

[Synthetic Scheme VI shows an alternative regioselective method of constructing the pyrazole 21. Commercially available enones 19 can be epoxidized to give epoxyketones 20, which are treated with 4-sulfonamidophenylhydrazine hydrochloride to provide the pyrazole 21.

Scheme VII

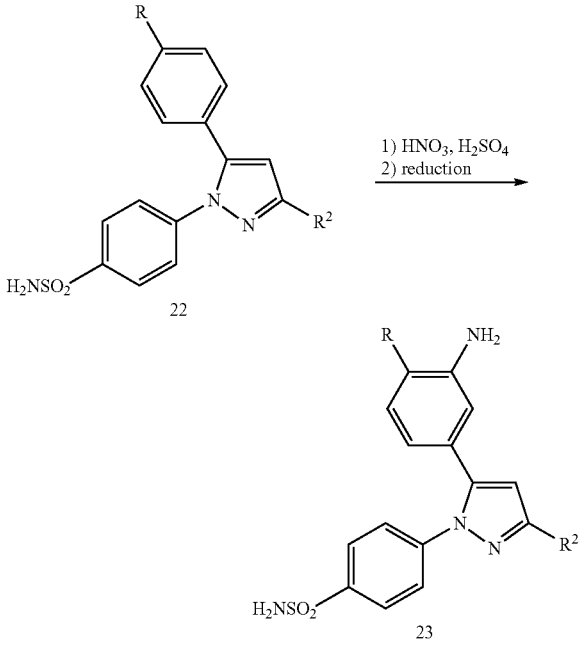

]

[Synthetic Scheme VII shows the preparation of pyrazoles 23 (where $R^4$ is 3-amino-4-substituted phenyl) from starting material 22. Appropriate 5-(4-substituted aryl)pyrazoles can be nitrated next to the R-group under standard nitration conditions and the nitro group reduced to the amino group, preferably with hydrazine and Pd/C. The amino compounds can be further manipulated by alkylation of the amino group.

Scheme VIII

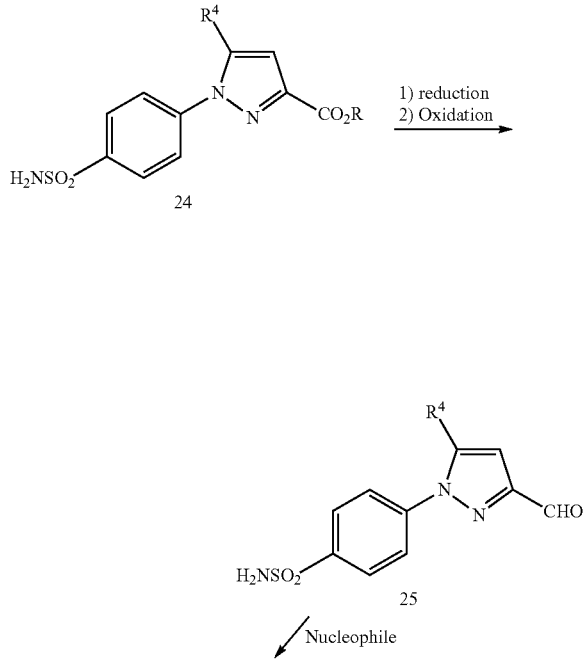

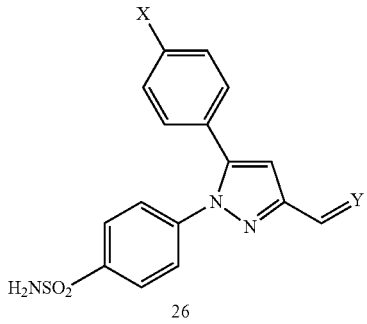

]

[Synthetic Scheme VIII shows the preparation of pyrazoles 26 from esters 24. Reduction of the ester 24 to the alcohol, preferably with lithium aluminum hydride (LAH) followed by oxidation, preferably with $MnO_2$, gives the aldehyde 25. Various nucleophiles (such as hydroxamates and 1,3-dicarbonyl compounds) can be condensed with the aldehyde to give the desired oximines or olefins 26.]

The following examples [containing] *provide* detailed description of the methods of preparation of compounds of [Formulas I-II] *the present invention*. [These detailed descriptions fall within the scope, and serve to exemplify, the above described General Synthetic Procedures which form part of the invention] *the present invention*. These detailed descriptions are presented for illustrative purposes only and are not intended as a restriction on the scope of the invention. All parts are by weight and temperatures are in Degrees centrigrade unless otherwise indicated. [HRMS is an abbreviation for High resolution mass spectrometry. In the following tables, "ND" represents "not determined".]

EXAMPLE 1

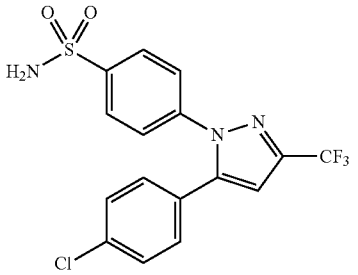

4-[5-(4-Chlorophenyl)-3-(trifluoromethyl)-1H-pyrazol-1-yl]benzenesulfonamide

Step 1: Preparation of 4,4,4-trifluoro-1-[4-(chloro) phenyl]-butane-1,3-dione

Ethyl trifluoroacetate (23.52 g, 166 mmol) was placed in a 500 mL three-necked round bottom flask, and dissolved in methyl tert-butyl ether (75 mL). To the stirred solution was added 25% sodium methoxide (40 mL, 177 mmol) via an addition funnel over a 2 minute period. Next 4'-chloroacetophenone (23.21 g, 150 mmol) was dissolved in methyl tert-butyl ether (20 mL), and added to the reaction dropwise over 5 minutes. After stirring overnight (15.75 hours), 3N HCl (70 mL) was added. The organic layer was collected, washed with brine (75 mL), dried over $MgSO_4$, filtered, and concentrated in vacuo to give a 35.09 g of yellow-orange solid. The solid was recrystallized from iso-octane to give 31.96 g (85%) of the dione: mp66°-67° C.

Step 2: Preparation of 4-[5-(4-chlorophenyl)-3-(trifluoromethyl)-1H-pyrazol-1-yl]benzenesulfonamide.

4-Sulphonamidophenylhydrazine hydrochloride (982 mg, 4.4 mmol 1.1 equivalent) was added to a stirred solution of 4,4,4-trifluoro-1-[4-(chloro)phenyl]-butane-1,3-dione [from Step 1] (1.00 g, 4.0 mmol) in ethanol (50 mL). The reaction was heated to reflux and stirred for 20 hours. (HPLC area percent showed a 96:3 ratio of 4-[5-(4-chlorophenyl)-3-(trifluoromethyl)-1H-pyrazol-1-yl]benzenesulfonamide to its regioisomer (4-[3-(4-chlorophenyl)-5-(trifluoromethyl)-1H-pyrazol-1-yl]benzenesulfonamide). After cooling to room temperature, the reaction mixture was concentrated in vacuo. The residue was taken up in ethyl acetate, washed with water and with brine, dried over $MgSO_4$, filtered, and concentrated in vacuo to give a light brown solid which was recrystallized from ethyl acetate and iso-octane to give the pyrazole (1.28 g, 80%, mp 143°-145° C.). HPLC showed that the purified material was a 99.5:0.5 mixture of 4-[5-(4-chlorophenyl)-3-(trifluoromethyl)-1H-pyrazol-1-yl]benzenesulfonamide to its regioisomer. $^1H$ NMR ($CDCl_3/CD_3OD$ 10/1) d 5.2 (s, 2H), 6.8 (s, 1H), 7.16 (d, j=8.5 Hz, 2H), 7.35 (d, j=8.5 Hz, 2H), 7.44 (d, j=8.66, 2H), 7.91 (d, j=8.66, 2H); $^{13}C$ NMR ($CDCl_3/CD_3OD$ 10/1) d 106.42 (d, j=0.03 Hz), 121.0 (q, j=276 Hz), 125.5, 126.9, 127.3, 129.2, 130.1, 135.7, 141.5, 143.0, 143.9 (q, j=37 Hz), 144.0; $^{19}F$ NMR ($CDCl_3OD$ 10/1) d -62.9; EI GC-MS M+=401

*Example 2 was prepared in a similar manner using the appropriate acetophenone.* .

EXAMPLE 2

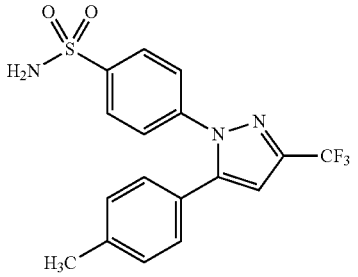

4-[5-(4-Methylphenyl)-3-(trifluoromethyl)-1H-pyrazol-1-yl]benzenesulfonamide

[Step 1: Preparation of 1-(4-methylphenyl)-4,4,4-trifluorobutane-1,3-dione]

[4'-Methylacetophenone (5.26 g, 39.2 mmol) was dissolved in 25 mL of methanol under argon and 12 mL (52.5 mmol) sodium methoxide in methanol (25%) was added. The mixture was stirred for 5 minutes and 5.5 mL (46.2 mmol) ethyl trifluoroacetate was added. After refluxing for 24 hours, the mixture was cooled to room temperature and concentrated. 100 mL 10% HCl was added and the mixture extracted with 4×75 mL ethyl acetate. The extracts were dried over $MgSO_4$, filtered and concentrated to afford 8.47 g (94%) of a brown oil which was carried on without further purification.]

[Step 2: Preparation of 4-[5-(4-methylphenyl)-3-(trifluoromethyl)-1H-pyrazol-1-yl]benzenesulfonamide]

[To the dione from Step 1 (4.14 g, 18.0 mmol) in 75 mL absolute ethanol was added 4.26 g (19.0 mmol) 4-sulphonamidophenylhydrazine hydrochloride. The reaction was refluxed under argon for 24 hours. After cooling to room temperature and filtering, the reaction mixture was concentrated to afford 6.13 g of an orange solid. The solid was recrystallized from methylene chloride/hexane to give 3.11 g (8.2 mmol, 46%) of the product as a pale yellow] *Yellow* solid: mp 157°-159° C.; Anal. calc'd for $C_{17}H_{14}N_3O_2SF_3$: C, 53.54; H, 3.70; N, 11.02. Found: C, 53.17; H, 3.81; N, 10.90.

[EXAMPLE 3

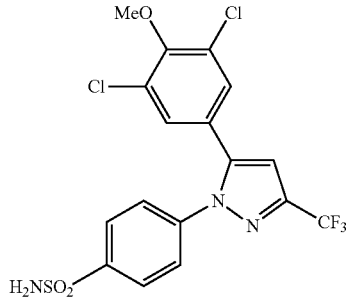

4-[5-(3,5-Dichloro-4-methoxyphenyl)-3-(trifluoromethyl)-1H-pyrazol-1-yl]benzensulfonamide

]

[Step 1: Preparation of 3,5-dichloro-4-methoxyacetophenone]

[To a cooled solution (0° C.) of 7.44 g (55.8 mmol) $AlCl_3$ in 25 mL of $CH_2Cl_2$ under argon was added 2.5 mL of acetic anhydride dropwise. After stirring for 0.5 hours, 4.18 g (23.6 mmol) of 2,6-dichloroanisole was added dropwise. The reaction was stirred at 0° C. for 1 hour, warmed to room temperature and stirred for 12 hours. The reaction was poured into 6 mL conc. hydrochloric acid/80 mL ice water. The aqueous phase was extracted with ethyl acetate (3×75 mL). The combined organic washes were dried over $MgSO_4$, filtered, and stripped to afford the crude product as a yellow oil. NMR analysis showed that acylation only occured para to the methoxy. The crude oil was used without any further purification.]

[Steps 2 and 3: Preparation of 4-[5-(3,5-dichloro-4-methoxyphenyl)-3-(trifluoromethyl)-1H-pyrazol-1-yl]benzenesulfonamide]

[The title compound was prepared in the same manner as Example 2, Steps 1 and 2 and was purified on a prep plate eluting with 10:1 hexane/ethyl acetate to afford a yellow solid: Anal. cal'd for $C_{17}H_{12}N_3O_3SF_3Cl_2.H_2O$: C, 42.16; H, 2.91; N, 8.68. Found: C, 42.03; H, 2.54; N, 8.45.]

[EXAMPLE 4

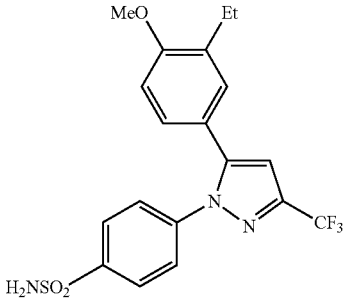

4-[5-(3-Ethyl-4-methoxyphenyl)-3-(trifluoromethyl)-1H-pyrazol-1-yl]benzenesulfonamide

]

[Step 1: Preparation of 3-ethyl-4-methoxyacetophenone]

[$AlCl_3$ (4.9 g, 36.8 mmol) was added to a solution of 2-ethylanisole (2.5 g, 18.4 mmol) in methylene chloride (50 mL). Acetyl chloride (1.3 mL, 18.4 mmol) was added dropwise to the reaction mixture, which was then stirred at reflux for 0.5 hours. After cooling to room temperature, the reaction was poured over crushed ice and followed up with a methylene chloride/water extraction. The organic layer was dried over magnesium sulfate, filtered and concentrated. The crude product was chromatographed on a 4000 micron chromatotron plate with 10% ethyl acetate/90% hexane as eluant to afford 2.3 g of desired material.]

[Steps 2 and 3: Preparation of 4-[5-(3-ethyl-4-methoxyphenyl)-3-(trifluoromethyl)-1H-pyrazol-1-yl] benzenesulfonamide]

[The title compound was prepared using the procedure describe din Example 2, Steps 1 and 2: Anal. calcd for $C_{19}H_{18}N_3O_3SF_3$: C, 53.64; H, 4.26; N, 9.88. Found: C, 53.69; H, 4.36; N, 9.88.]

[EXAMPLE 5

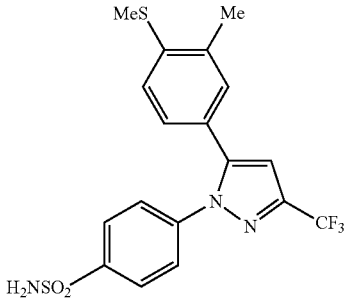

4-[5-(3-Methyl-4-methylthiophenyl)-3-(trifluoromethyl)-1H-pyrazol-1-yl]benzensulfonamide

]

[Step 1: Preparation of 2-methylthioanisole]

[Methyl iodide (0.5 mL, 8.1 mmol) and potassium carbonate (1.1 g, 8.1 mmol) were added to a solution of o-thiocresol (1.0 g, 8.1 mmol) in 10 mL of DMF. The reaction was stirred at 50° C., for 4 hours and poured into hexane and water. The organic layer was separated, dried over magnesium sulfate and concentrated to afford 1.1 g of desired material.]

[Steps 2, 3 and 4: Preparation of 4-[5-(3-methyl-4-methylthiophenyl)-3-(trifluoromethyl)-1H-pyrazol-1-yl]benzenesulfonamide]

[The title compound was prepared using the procedures found in Example 4, Steps 1, 2 and 3: Anal. calcd. for $C_{18}H_{16}N_3O_2S_2F_3$: C, 50.58; H, 3.77; N, 9.83. Found: C, 50.84; H, 3.62; N, 9.62.]

[EXAMPLE 6

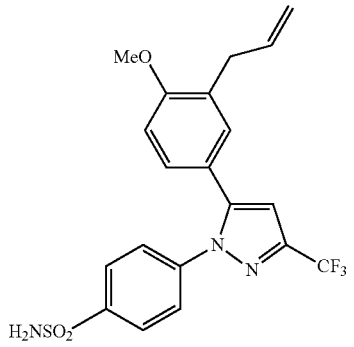

4-[5-(3-(3-Propenyl)-4-methoxyphenyl)-3-(trifluoromethyl)-1H-pyrazol-1-yl]benzenesulfonamide

]

[Step 1: Preparation of 3-allyl-4-methoxyacetophenone]

[Potassium hydroxide (3.2 g, 56.8 mmol) was added to a solution of 3-allyl-4-hydroxyacetophenone (10 g, 56.8) in 125 mL THF. Dimethyl sulfate (excess) was added and the reaction was stirred at 50° C. for 16 hours. The reaction was cooled, concentrated and poured into EtOAc and water. The organic layer was separated and washed with dilute sodium hydroxide to get rid of unreacted starting material. The ethyl acetate layer was dried and concentrated to afford 9.2 g of 3-allyl-4-methoxy acetophenone.]

[Steps 2 and 3: Preparation of 4-[5-(3-propenyl)-4-methoxyphenyl)-3-(trifluoromethyl)-1H-pyrazol-1-yl]benzenesulfonamide]

[The title compound was prepared using the procedures described in Example 2, Steps 1 and 2: Anal. calc'd for $C_{20}H_{18}N_3F_3O_3S$: C, 54.92; H, 4.15; N, 9.61. Found: C, 54.70; H, 4.12; N, 9.43.]

[EXAMPLE 7

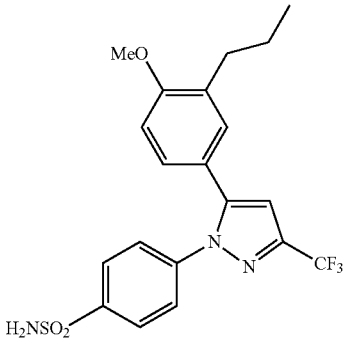

4-[5-(3-Propyl)-4-methoxyphenyl)-3-(trifluoromethyl)-1H-pyrazol-1-yl]benzenesulfonamide

]

[Step 1: Preparation of 3-n-propyl-4-methoxyacetophenone]

[To a solution of the product in Example 6, Step 1 (3 g, 17.0 mmol) in 50 mL of ethanol was added a catalytic amount of 4% Pd/C. The reaction mixture was stirred in a Parr shaker at room temperature at 5 psi hydrogen for 0.5 hours. The reaction was filtered and concentrated to afford 4 g of pure 3-propyl-4-methoxy acetophenone.]

[Steps 2 and 3: Preparation of 4-[5-(3-n-propyl-4-methoxyphenyl)-3-(trifluoromethyl)-1H-pyrazol-1-yl]benzenesulfonamide]

[The title compound was prepared using the procedures described in Example 2, Steps 1 and 2: Anal. calcd. for $C_{20}H_{20}N_3F_3O_3S$: C, 54.66; H, 4.59; N, 9.56. Found: C, 54.84; H, 4.65; N, 9.52.]

[EXAMPLE 8

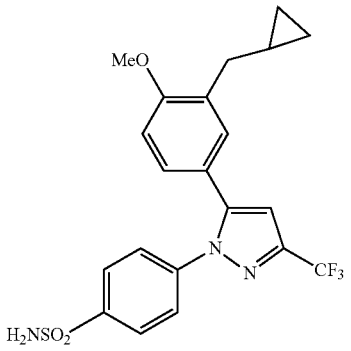

4-[5-(3-Cyclopropylmethyl-4-methoxyphenyl)-3-(trifluoromethyl)-1H-pyrazol-1-yl]benzensulfonamide

]

[Step 1: Preparation of 3-cyclopropylmethyl-4-methoxyacetophenone]

[To a solution of the product in Example 6, Step 1 (3 g, 17.0 mmol) and catalytic $Pd(OAc)_2$ in 20 mL $Et_2O$ was added ethereal diazomethane until starting material was consumed. The reaction was filtered, concentrated and chromatographed on a 4000 micron chromatotron plate (20% EA/80% hexane as eluant) to afford 2.5 g of desired ketone.]

[Steps 2 and 3: Preparation of 4-[5-(3-cyclopropylmethy-4-methoxyphenyl)-3-(trifluoromethyl)-1H-pyrazol-1-yl]benzenesulfonamide]

[The title compound was prepared using the procedures described in Example 2, Steps 1 and 2: Anal. calc'd. for $C_{21}H_{20}N_3F_3SO_3$: C, 55.87; H, 4.47; N, 9.31. Found: C, 55.85; H, 4.27; N, 9.30.]

[EXAMPLE 9

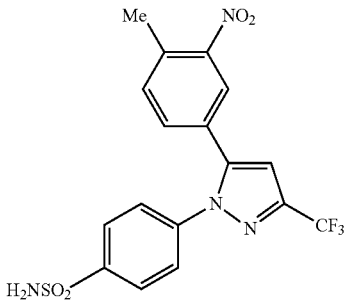

4-[4-Methyl-3-nitrophenyl)-3-(trifluoromethyl)-1H-pyrazol-1-yl]benzensulfonamide

]

[To a solution of the product of Example 2 (500 mg, 1.31 mmol) in 5 mL of sulfuric acid was added nitric acid (0.6 mL, 1.31 mmol) and the reaction was stirred at room temperature for 0.5 hours. The mixture was poured over ice, the solid precipitate was filtered and chromatographed on a 4000 micron plate (20% EtOAc/80% hexane as eluant) to afford 410 mg of desired material: Anal. calc'd for $C_{17}H_{13}N_4O_4SF_3$: C, 47.89; H, 3.07; N, 13.14. Found: C, 47.86; H, 2.81; N, 13.15.]

[EXAMPLE 10

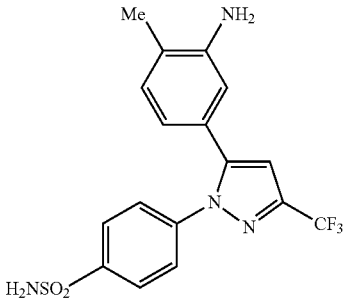

4-[5-(3-Amino-4-methylphenyl)-3-(trifluoromethyl)-1H-pyrazol-1-yl]benzenesulfonamide

]

[A catalytic amount of 10% Pd/C was added to a solution of hydrazine hydrate (0.022 mL, 0.7 mmol) in 10 mL of ethanol. The reaction mixture was refluxed for 15 minutes before the addition of the compound from Example 9 (100 mg, 0.23 mmol), and the resulting reaction mixture was refluxed for another 2 hours. The reaction was cooled, filtered through Celite and concentrated to afford 100 mg of title compound: Anal. calc'd for $C_{17}H_{15}N_4O_2SF_3.0.5\,CO_2$: C, 50.24; H, 3.61; N, 13.39. Found: C, 50.49; H, 3.44; N, 13.37.]

[EXAMPLE 11

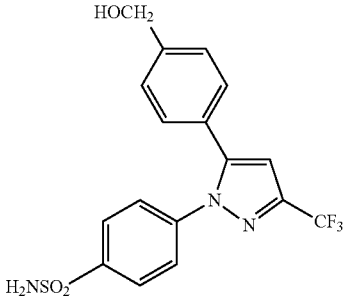

4-[5-(4-Hydroxymethylphenyl)-3-(trifluoromethyl)-1H-pyrazol-1-yl]benzenesulfonamide

]

[Step 1: Preparation of 4-[5-(4-bromomethylphenyl)-3-(trifluoromethyl)-1H-pyrazol-1-yl]benzenesulfonamide]

[The product from Example 2 (1.13 g, 3.0 mmol) and N-bromosuccinimide (NBS, 0.64 g, 3.6 mmol) were dissolved in 40 mL of benzene and irradiated with a UV lamp for 3 hours. The reaction was cooled to room temperature and poured into 50 mL of $H_2O$. The organic phase was separated, washed with brine and dried over $MgSO_4$. The crude pyrazole was obtained as an amber oil. The oil was purified via radical band chromatography eluting with 30% ethyl acetate/70% hexane to afford the 4-bromomethyl compound as a yellow oil which crystallized upon standing.]

[Step 2: Preparation of 4-[5-(4-hydroxymethylphenyl)-3-(trifluoromethyl)-1H-pyrazol-1-yl]benzenesulfonamide]

[The bromo methyl compound from Step 1 was dissolved in 30 mL of acetone/4 mL of $H_2O$ and refluxed for 120 hours. The reaction was concentrated and the residue dissolve in 50 mL of ethyl acetate and dried over $MgSO_4$. The crude product was obtained as an amber oil. The oil was purified via radial band chromatography eluting with 30% ethyl acetate/70% hexane to afford the title compound as a yellow solid: Anal. calc'd for $C_{17}H_{14}N_3O_3SF_3$: C, 51.38; H, 3.55; N, 10.57. Found: C, 51.28; H, 3.59; N, 10.31.]

[EXAMPLE 12

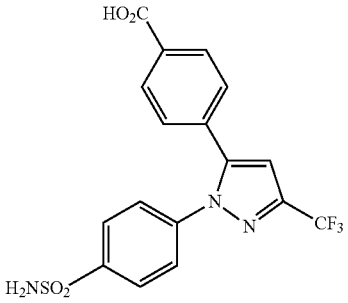

4-[1-(4-Aminosulfonyl)phenyl)-3-(trifluoromethyl)-1H-pyrazol-5-yl]benzoic acid

]

[To the product from Example 11 in 2 mL of acetone was added 1.33M Jones reagent until an orange color persisted. The reaction was poured into 20 mL of ethyl acetate and 20 mL of $H_2O$ and the organic layer separated, washed with saturated sodium bisulfite and dried over $MgSO_4$. The crude product was filtered through silica gel/Celite to afford the title compound as a yellow solid: HRMS m/z 411.0507 (calc'd for $C_{17}H_{12}N_3O_4SF_3$, 411.0500).]

The following compounds in Table I were prepared [according to procedures similar to that exemplified in Examples 1-12, with the substitution of] *in a similar manner using* the appropriate acetophenone.

TABLE I

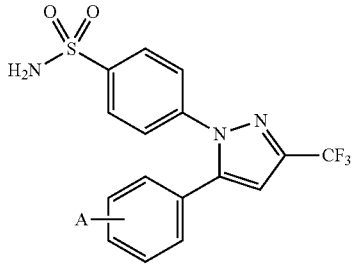

| Ex. | A | M.P.(° C.) | Analytical |
|---|---|---|---|
| 13 | 4-Br | 137-139 | Calc. C, 43.07; H, 2.48; N, 9.42; Br, 17.91<br>Obs. C, 43.01; H, 2.32; N, 9.39; Br, 17.62 |
| 14 | 3-Cl | 154-155 | Calc. C, 47.83; H, 2.76; N, 10.46; Cl, 8.82<br>Obs. C, 47.61; H, 2.85; N, 10.31; Cl, 8.43 |
| 15 | 2-Cl | 159-160 | Calc. C, 47.83; H, 2.76; H, 10.46<br>Obs. C, 47.47; H, 2.65; N, 10.31 |
| 16 | 4-$CF_3$ | 144-145 | Calc. C, 46.90; H, 2.55; N, 9.65<br>Found: C, 46.98; H, 2.57; N, 9.61 |
| 17 | 4-F | 168-169 | Calc. C, 49.87; H, 2.88; N, 10.90<br>Found: C, 49.83; H, 2.89; N, 10.86 |
| 18 | H | 164-165 | Calc. C, 52.31; H, 3.29; N, 11.43<br>Found: C, 52.14; H, 3.07; N, 11.34 |
| 19 | 4-$OCH_3$ | 153-154 | Calc. C, 51.38; H, 3.55; N, 10.57<br>Found: C, 51.00; H, 3.48; N, 10.24 |
| 20 | 4-$OCF_3$ | 101-103 | Calc. C, 45.24; H, 2.46; N, 9.31<br>Found: C, 45.22; H, 2.37; N, 9.29 |
| 21 | 2-$CH_3$ | 126-128 | Calc. C, 53.54; H, 3.70; N, 11.02<br>Found: C, 53.52; H, 3.55; N, 11.06 |
| 22 | 2,4-di-F | 127-130 | M + H 404 |
| 23 | 2,6-di-F | 178-180 | M + H 404 |
| 24 | 4-CN | 196-197.5 | |
| 25 | 3,4-di-Cl | 145-147 | Calc. C, 44.05; H, 2.31; N, 9.63; Cl, 16.25<br>Found: C, 44.00; H, 2.20; N, 9.63; Cl, 16.46 |
| 26 | 2,4-di-Cl | 153-155 | Calc. C, 43.87; H, 2.35; N, 9.59<br>Found: C, 43.78; H, 2.13; N, 9.56 |
| [27 | 4-$NO_2$ | 169-172 (dec) | Calc. C, 46.61; H, 2.69; N, 13.59; S, 7.78<br>Obs.: C, 46.52; H, 2.67; N, 13.51; S, 7.84 |
| 28 | 2-F | 165-166 | Calc. C, 49.87; H, 2.88; N, 10.90<br>Found: C, 49.49; H, 2.62; N, 10.79 |
| 29 | 4-$NH_2$ | 124-127 (dec) | HRMS: 382.0671 |
| 30 | 4-F, 2-$CH_3$ | 170-171 | Calc. C, 51.13; H, 3.28; N, 10.52<br>Found: C, 50.83, H, 2.98; N, 10.55 |
| 31 | 3-$CH_3$ | 135-137 | Calc. C, 53.54; H, 3.70; N, 11.02<br>Found: C, 53.15; H, 3.58; N, 10.96 |
| 32 | 4-$OCH_2CH_3$ | 141-142 | Calc. C, 51.43; H, 4.08; N, 9.99<br>Found: C, 51.49; H, 3.80; N, 10.08 |
| 33 | 4-$OCH_3$, 3,5-di-$CH_3$ | 143-144 | Calc. C, 53.64; H, 4.26; N, 9.87<br>Found: C, 53.49; H, 4.39; N, 9.64 |
| 34 | 3-F | 143-144 | Calc. C, 49.87; H, 2.88; N, 10.90<br>Found: C, 49.80; H, 2.80; N, 10.84 |
| 35 | 4-OCH, 3-F | 155-156 | Calc. C, 49.16; H, 3.15; N, 10.11<br>Found: C, 48.77; H, 2.93; N, 9.96 |
| 36 | 4-$SCH_3$ | 165-166 | Calc. C, 49.39; H, 3.41; N, 10.16<br>Found: C, 49.48; H, 3.46; N, 10.26 |
| 37 | 4-Cl, 3-$CH_3$ | ND | Calc. C, 49.10; H, 3.15; N, 10.11<br>Found: C, 49.00; H, 3.00; N, 10.10 |
| 38 | 4-$CH_2CH_3$ | ND | Calc. C, 54.68; H, 4.08; N, 10.63<br>Found: C, 54.54; H, 3.73; N, 10.67 |
| 39 | 2,4-di-$CH_3$ | ND | Calc. C, 54.68; H, 4.08; N, 10.63<br>Found: C, 54.31; H, 4.32; N, 10.39 |
| 40 | 2-$OCH_3$ | 167-168 | Calc. C, 51.38; H, 3.55; N, 10.57<br>Found: C, 51.29; H, 3.34; N, 10.52 |
| 41 | 4-$OCH_3$, 3-$CH_3$ | 146-147 | |
| 42 | 4-$SCH_3$, 3-Br | 141-144 | HRMS: 490.9595 |

TABLE I-continued

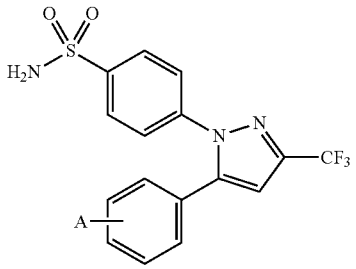

| Ex. | A | M.P.(° C.) | Analytical |
|---|---|---|---|
| 43 | 4-$CH_3$, 3-Cl | 186-190 | Calc. C, 49.10; H, 3.15; N, 10.11<br>Found: C, 49.21; H, 3.17; N, 10.10 |
| 44 | 3,4-di-$OCH_3$ | 192-193 | Calc. C, 50.58; H, 3.77; N, 9.83<br>Found: C, 50.58; H, 3.83; N, 9.72 |
| 45 | 4-$OCH_3$, 3-Cl | 166-168 | Calc. C, 47.29; H, 3.03; N, 9.73<br>Found: C, 47.21; H, 2.91; N, 9.55 |
| 46 | 4-$OCH_3$, 3-Cl, 5-$CH_3$ | ND | Calc. C, 48.49; H, 3.39; N, 9.42<br>Found: C, 48.27; H, 3.42; N, 9.22 |
| 47 | 2-$OCH_3$, 4-F | 163-164 | Calc. C, 49.16; H, 3.15; N, 10.12<br>Found: C, 49.32; H, 3.27; N, 10.18 |
| 48 | 2,4-di-$OCH_3$ | ND | Calc. C, 50.58; H, 3.77; N, 9.83<br>Found: C, 50.40; H, 3.78; N, 9.83 |
| 49 | 4-F, 3-Cl | ND | Calc. C, 45.78; H, 2.40; N, 10.01<br>Found: C, 45.75; H, 2.34; N, 10.15 |
| 50 | 4-$OCH_3$, 3,5-di-F | ND | Calc. C, 47.12; H, 2.79; N, 9.70<br>Found: C, 46.72; H, 2.75; N, 9.54 |
| 51 | 4-$SCH_3$, 3-F | ND | Calc. C, 47.33; H, 3.04; N, 9.74<br>Found: C, 47.25; H, 3.39; N, 9.45 |
| 52 | 4-$SCH_3$, 3-Cl | ND | Calc. C, 45.59; H, 2.93; N, 9.38<br>Found: C, 45.56; H, 2.76; N, 9.52 |
| 53 | 4-$N(CH_3)_2$ | ND | HRMS: 410.1016 |
| 54 | 4-$N(CH_2CH_3)_2$ | ND | HRMS: 438.1353] |

[EXAMPLE 55

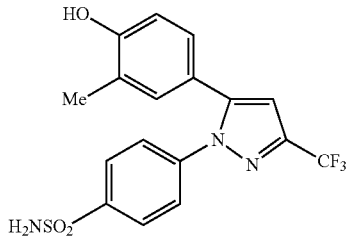

4-[5-(4-Hydroxy-3-methylphenyl)-3-(trifluoromethyl)-1H-pyrazol-1-yl]benzensulfonamide

]

[To a solution of the product of Example 41 (240 mg, 0.58 mmol) in DMF (3 mL) was added NaSMe (205 mg, 2.9 mmol) and the mixture heated to reflux for 2 hours. The mixture was cooled, poured into 0.1N HCl and extracted with EtOAc (3×). The combined extracts were dried over $MgSO_4$ and concentrated. Flash chromatography using 1:1 hexane/ethyl acetate provided 31 mg of the title compound: Anal.

calc'd for $C_{17}H_{14}N_3O_3SF_3$.0.25 $H_2O$: C, 50.80; H, 3.64; N, 10.45. Found: C, 50.71; H, 3.47; N, 10.39.]

[EXAMPLE 56

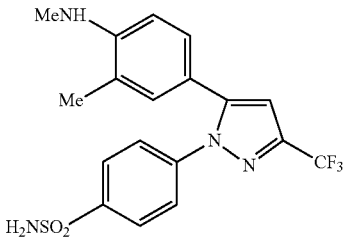

4-[5-(4-Methylamino)phenyl)-3-(trifluoromethyl)-1H-pyrazol-1-yl]benzenesulfonamide

]

[To a solution of the product from Example 53 (431 mg, 1.0 mmol) in 10 ml methanol was added 36 mg (0.17 mmol) ruthenium, (III) chloride hydrate, followed by 1.5 mL 30% hydrogen peroxide (14.7 mmol) over 2 hours. The reaction was quenched with 25 mL of 1M KOH in methanol and concentrated to give 1.24 g of a brown solid. The solid was purified on a prep plate eluting with 2/97/1 methanol/methylene chloride/ammonium chloride to give 52 mg (0.14 mmol, 12%) of the product as a yellow solid.]

[EXAMPLE 57

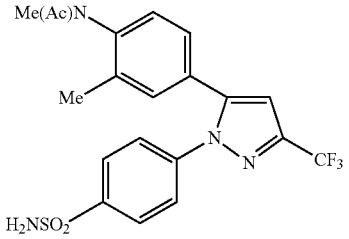

N-[4-[1-[4-(Aminosulfonyl)phenyl]-3-(trifluoromethyl)-1H-pyrazol-5-yl]phenyl]-N-methylacetamide

]

[19 mg (0.051 mmol) of the product from Example 56 was treated with 0.03 mL acetic anhydride (0.32 mmol) and 0.03 mL triethylamine (0.22 mmol) in 3 mL methylene chloride at room temperature for 12 hours. The reaction matured was concentrated and the residue dissolved in 10 mL ethyl acetate. After washing with brine (2×10 mL), the solution was dried over $MgSO_4$, filtered and concentrated to afford the title compound (18.4 mg, 74%) as a yellow solid: HRMS m/e 438.0976 (calc'd for $C_{19}H_{17}N_4O_3SF_3$, 438.0974).]

EXAMPLE 58

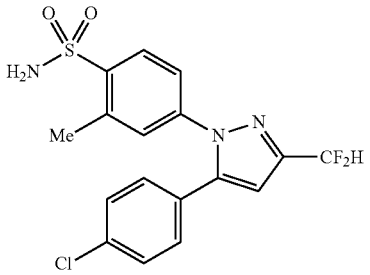

4-[5-(4-Chlorophenyl)-3-(difluoromethyl)-1H-pyrazol-1-yl]benzensulfonamide

Step 1: Preparation of 4,4-difluoro-1-[4-(chloro)phenyl]-butane-1,3-dione

Ethyl difluoroacetate (24.82 g, 200 mmol) was placed in a 500 mL three-necked round bottom flash, and dissolved in diethyl ether (200 mL). To the stirred solution was added 25% sodium methoxide in methanol (48 mL, 210 mmol) via an addition funnel over a 2 minute period. Next, 4'-chloroacetophenone (25.94 g, 200 mmol) was dissolved in diethyl ether (50 mL), and added to the reaction dropwise over 5 minutes. After stirring overnight (18 hours), 1N HCl (250 mL) and ether (250 mL) were added. The organic layer was collected, washed with brine (250 mL), dried over $MgSO_4$, filtered, and concentrated in vacuo to give 46.3 g of a yellow solid. The solid was recrystallized from methylene chloride and iso-octane to give 31.96 g (69%) of the dione: mp 65°-66.5° C.

Step 2: Preparation of 4-[5-(4-chlorophenyl)-3-(difluoromethyl)-1H-pyrazol-1-yl]benzenesulfonamide 4-Sulphonamidophenylhydrazine hydrochloride (1.45 g, 6.5 mmol 1.3 equivalent) and 4,4-difluoro-1-[4-(chloro)phenyl]butane-1,3-dione [from Step 1] (1.16 g, 5 mmol) were dissolved in ethanol (10 mL). The reaction was heated to reflux and stirred for 20 hours. After cooling to room temperature, the reaction mixture was concentrated in vacuo. The residue was taken up in ethyl acetate (100 mL) and washed with water (100 mL) and with brine (100 mL), dried over $MgSO_4$, filtered, and concentrated in vacuo to give 1.97 g of a light brown solid which was recrystallized from ethanol and water to give 4-[5-(4-chlorophenyl)-3-(difluoromethyl)-1H-pyrazol-1-yl]benzenesulfonamide (1.6 g, [93% yield,]): mp 185°-186° C.

[EXAMPLE 59

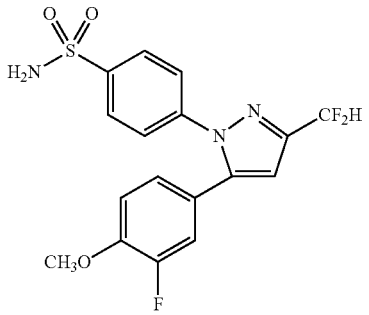

4-[5-(3-Fluoro-4-methoxyphenyl)-3-(difluoromethyl)-1H-pyrazol-1-yl]benzensulfonamide

]

[Step 1: Preparation of 3'-fluoro-4'-methoxyacetophenone]

[Aluminum chloride, (80.0 g, 0.6 mol) and chloroform (750 mL) were placed in a 2 L three-necked round bottom flask fitted with a mechanical stirrer and cooled by means of an ice bath. To the stirred solution acetyl chloride (51.0 g, 0.65 mol) was added dropwise, maintaining the temperature between 5°-10° C. The mixture was stirred for 10 minutes at 5° C. before the dropwise addition at 5°-10° C. of 2-fluoroanisole (62.6 g, 0.5 mol). The mixture was stirred at 0°-10° C. for 1 hour and poured into ice (1 L). The resultant layers were separated and the aqueous layer was extracted with dichloromethane (2×250 mL). The combined organic layers were washed with water (2×150 mL), dried over anhydrous $MgSO_4$, filtered and concentrated in vacuo to a volume of 300 mL. Hexanes were added and a white solid formed which was isolated by filtration and air dried. This material was recrystallized from a mixture of dichloromethane and hexanes to afford (77.2 g, 92%) of material suitable for use in the next step: mp 92°-94° C.; $^1$H NMR (DMSO-$d_6$) 7.8 (m, 2H), 7.3 (t, 1H), 3.9 (s, 3H), 2.5 (s, 3H).]

[Step 2: Preparation of 4,4-difluoro-1-(3-fluoro-4-methoxyphenyl)-butane-1,3-dione]

[Ethyl difluoroacetate (4.06 g, 32.7 mmol) was placed in a 250 mL Erlenmeyer flask, and dissolved in methyl tert-butyl ether (50 mL). To the stirred solution was added 25% sodium methoxide (7.07 g, 32.7 mmol) followed by 3'-fluoro-4'-methoxyacetophenone from Step 1 (5.0 g, 29.7 mmol). After stirring for 16 hours, 1N HCl (50 mL) was added. The organic layer was collected, washed with water (2×50 mL), dried over anhydrous $MgSO_4$, filtered, and added to hexanes to precipitate a tan solid (7.0 g, 96%): mp 70°-72° C.; $^1$H NMR (DMSO-$d_6$) 8.0 (m, 3H), 7.3 (t, 1H), 6.9 (s, 1H), 6.5 (t, 1H), 3.9 (s, 3H).]

[Step 3: Preparation of 4-[5-(3-fluoro-4-methoxyphenyl)-3-(difluoromethyl)-1H-pyrazol-1-yl]benzenesulfonamide]

[4,4-Difluoro-1-(3-fluoro-4-methoxyphenyl)-butane-1,3-dione from Step 2 (7.0 g, 28.4 mmol) was dissolved in ethanol (150 mL). To the stirred mixture was added 4-sulphonamidophenylhydrazine hydrochloride (7.4 g, 33 mmol) and stirred at reflux overnight (16 hours). The mixture was cooled and water was added until crystals slowly appeared. The product was isolated by filtration and air dried to provide the desired product as a light tan solid (9.8 g, 87%): mp 159°-161° C.; $^1$H NMR (DMSO-$d_6$) 7.85 (d, 2H), 7.5 (m, 6H), 7.3-6.9 (m, 5H), 3.8 (s 3H). Anal. Calc'd for $C_{17}H_{14}N_3SO_3F_3$: C, 51.38; H, 3.55; N, 10.57. Found: C, 51.46; H, 3.52; N, 10.63.]

[EXAMPLE 60

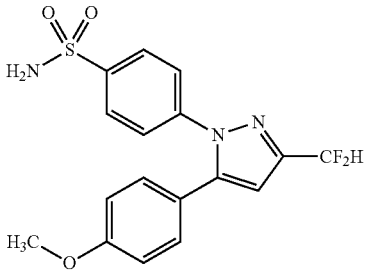

4-[3-Difluoromethyl)-5-(4-methoxyphenyl)-1-H-pyrazol-1-yl]benzenesulfonamide

]

[Step 1: Preparation of 4,4,4-trifluoromethyl-1-(4-methoxyphenyl)butane-1,3-dione]

[To a stirred solution of 4-methoxyacetophenone (11.43 g, 76.11 mmol) and ethyl difluoroacetate (8.4 mL, 10.4 g, 83.72 mmol) in diethyl ether (300 mL) in a 500 mL round bottomed flask was added sodium methoxide in methanol (18.2 mL of a 25% solution, 79.91 mmol). The solution became a dark lavender color within thirty minutes, and then a gray suspension within 1.5 hours. The reaction was stirred for 60 hours. Diethyl ether (300 mL) was added and the mixture was acidified (pH 2) with 1N HCl. The mixture was transferred to a separatory funnel, mixed and separated. The ethereal phase was washed with water, dried over magnesium sulfate, and filtered. Hexane was added causing precipitation of an orange solid 5.25 g of 4,4,4-trifluoromethyl-1-(4-methoxyphenyl) butane-1,3-dione. An additional 3.43 g of product was obtained by recrystallization of the concentrated mother liquor from hexane: $^1$H NMR ($CDCl_3$) 400 mHz 15.58 (br s, 1H), 7.94 (d, J=8.87 Hz, 2H), 6.98 (d, J=8.87 Hz, 2H), 6.49 (s, 1H), 6.00 (t, J=54.55 Hz, 1H), 3.89 (s, 3H).]

[Step 2: Preparation of 4-[5-(4-methoxyphenyl)-3-difluoromethyl-1-H-pyrazol-1-yl]benzenesulfonamide]

[A mixture of 4,4,4-trifluoromethyl-1-(4-methoxyphenyl) butane-1,3-dione from Step 1 (2.006 g, 8.79 (mmol) and 4-sulfonamidophenylhydrazine hydrochloride salt (2.065 g, 9.23 mmol) dissolved in ethanol (25 mL) was heated to reflux for 16 hours. The reaction was cooled to room temperature, was concentrated and recrystallized from methanol yielding 4-[5-(4-methoxyphenyl)-3-difluoromethyl-1-H-pyrazol-1-yl]benzenesulfonamide as fluffy tan crystals (1.49 g, 45%): mp 133°-135° C.; $^1$H NMR ($CDCl_3$) 300 mHz 7.90 (d, J=8.863 Hz, 2H), 7.45 (d, J=8.863 Hz, 2H), 7.14 (d, J=8.863 Hz, 2H), 6.88 (d, J=8.863 Hz, 2H), 6.77 (t, J=56.47 Hz, 1H), 6.68 (s, 1H), 4.96 (br s, 2H), 3.83 (s, 3 H); $^{19}$NMR ($CDCl_3$) 300 mHz −112.70 (d, J=57.9 Hz). High resolution mass spectrum Calc'd for $C_{17}H_{15}F_2N_3O_3S$: 379.0802. Found: 379.0839. Elemental analysis calc'd for $C_{17}H_{15}F_2N_3O_3S$: C, 53.82; H, 3.99; N, 11.08. Found: C, 53.75; H, 3.99; N, 11.04.]

The following compounds in Table II were obtained [according to procedures similar to that exemplified in Examples 58-60, with the substitution of] *in a similar manner using* the appropriate acetophenone.

TABLE II

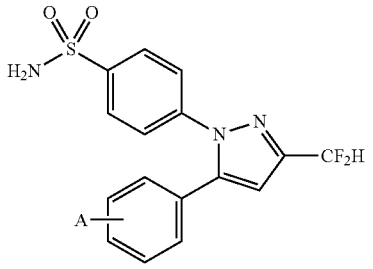

| Ex. | A | M.P.(° C.) | Anal. |
|---|---|---|---|
| 61 | 4-$CF_3$ | 202-205 | M + H 418 |
| 62 | 4-$SCH_3$ | 157-158 | |
| 63 | 4-(1-morpholino) | 167-171 | M + 434 |
| [64 | 4-$CH_3$ | 158-159 | Calc. C, 56.19; H, 4.16; N, 11.56<br>Obs. C, 56.25; H, 4.17; N, 11.61 |
| 65 | 3,4-di—$CH_3$ | 168-171 | Calc. C, 57.28; H, 4.54; N, 11.13<br>Obs. C, 57.34; H, 4.59; N, 11.16 |
| 66 | 4-$CO_2CH_3$ | 157-158 | Calc. C, 53.56; H, 3.09; N, 15.61<br>Obs. C, 53.45; H, 3.11; N, 15.62 |
| 67 | 4-$CONH_2$ | 235-236 | HRMS: 393.0833 |
| 68 | 4-$CO_2H$ | 258-260 (dec) | HRMS: 394.0662 |
| 69 | 2-F, 4-$OCH_3$ | 138-140 | Calc. C, 51.38; H, 3.55; N, 10.57<br>Obs. C, 51.14; H, 3.48; N, 10.40 |
| 70 | 4-CN | 222-224 | Calc. C, 54.54; H, 3.23; N, 14.97<br>Obs.: C, 54.58; H, 3.21; N, 15.06 |
| 71 | 3-Cl, 4-$CH_3$ | 156-158 | Calc. C, 51.32; H, 3.55; N, 10.56<br>Obs: C, 51.46; H, 3.53; N, 10.53 |
| 72 | 3-Cl, 4-$OCH_3$ | 160 | Calc. C, 49.34; H, 3.41; N, 10.15; Cl, 8.57; S, 7.75<br>Obs.: C, 49.41; H, 3.37; N, 10.17; Cl, 8.62; S, 7.67 |
| 73 | 4-Cl, 3-$CH_3$ | 163-165 | Calc. C, 51.32; H, 3.55; N, 10.56<br>Obs.: C, 51.42; H, 3.57; N, 10.53 |
| 74 | 3,4-di-$OCH_3$ | 181-185 | Calc. C, 52.81; H, 4.19; N, 10.26<br>Obs.: C, 52.86; H, 4.19; N, 10.20 |
| 75 | 3,5-di-Cl, 4-$OCH_3$ | 170-173 | Calc. C, 45.55; H, 2.92; N, 9.37<br>Obs.: C, 45.83; H, 3.05; N, 9.31 |
| 76 | 3,5-di-F, 4-$OCH_3$ | 149-150 | Calc. C, 49.16; H, 3.15; N, 10.12<br>Obs.: C, 49.24; H, 3.16; N, 10.13 |
| 77 | 2-$OCH_3$ | 129-132 | Calc. C, 53.82; H, 3.99; N, 11.08<br>Obs.: C, 53.82; H, 3.97; N, 11.15 |
| 78 | 3-Br, 4-$OCH_3$ | 164 | HRMS: 456.9883] |
| 79 | 4-$SO_2CH_3$ | 209-210 | |
| [80 | 4-$C_6H_5$ | 167-170 | M + 425 |
| 81 | H | 171-172 | HRMS: 349.0737] |

[EXAMPLE 82

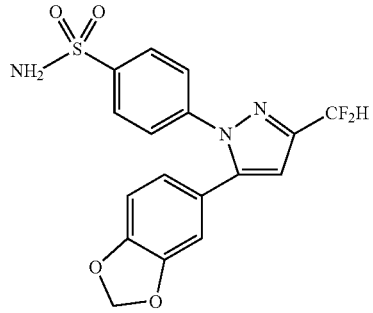

4-[5-(1,3-Benzodioxol-5-yl)-3-(difluoromethyl)-1H-pyrazol-1-yl]benzensulfonamide

]

[Step 1. Preparation of 1-(1,3-benzodioxol-5-yl)-4,4-difluorobutane-1,3-dione]

[Ethyl difluoroacetate (1.72 g, 11 mmol) was dissolved in ether (25 mL). To the stirred solution was added 25% sodium methoxide (2.38 g, 11 mmol) followed by 3',4'-(methylenedioxy)acetoxyphenone (1.64 g, 10 mmol). After stirring 16 hours, 1N HCl (25 mL) was added. The organic layer was collected and washed with water (2×25 mL), dried over magnesium sulfate, filtered, and concentrated. The resulting crude dione was used in the next step without further purification or characterization.]

[Step 2. Preparation of 5-(1,3-benzodioxol-5-yl)-4-[3-(difluoromethyl)-1H-pyrazol-1-yl]benzenesulfonamide]

[1-(1,3-Benzodioxol-5-yl)-4,4-difluorobutane-1,3-dione from Step 1 (2.4 g, 10 mmol) was dissolved in ethanol (100 mL). To the stirred mixture was added 4-sulfonamidophenylhydrazine hydrochloride (2.46 g, 11 mmol) and heated to reflux for 16 hours. The mixture was cooled and water was added until crystals slowly appeared. Filtration yielded a light tan solid (3.3 g, 84%): mp 214°-218° C. $^1$H NMR ($D_6$-DMSO): 7.86 (d, J=8.7Hz, 2H), 7.51 (d, J=8.7Hz, 2H), 7.49 (brs, 2H), 7.3-6.7 (m, 5H), 6.06(s, 2H). Anal. Calc'd for $C_{17}H_{13}N_3SO_4F_2$: C, 51.91; H, 3.33; N, 10.68. Found: C, 51.90; H, 3.25; N, 10.65.]

EXAMPLE 83

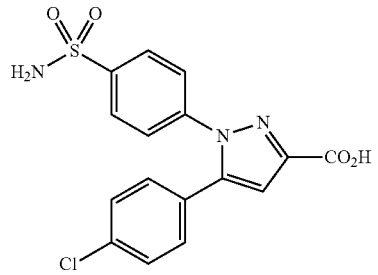

4-[4-(Aminosulfonyl)phenyl]-5-(4-chlorophenyl)-1H-pyrazole-3-carboxylic acid

Step 1: Preparation of Methyl-4-[4-(chloro)phenyl]-2,4-dioxobutanoate

Dimethyl oxalate (23.6 g, 200 mmol) was placed in a 500 mL three-necked round bottom flask, and dissolved in diethyl ether (200 mL). To the stirred solution was added 25% sodium methoxide in methanol (48 mL, 210 mmol) via an addition funnel over a 2 minute period. Next, 4'-chloroacetophenone (25.94 g, 200 mmol) was dissolved in diethyl ether (50 mL), and added to the reaction dropwise over 3 minutes. After stirring overnight (18 hours), 1N HCl (400 mL) and ethyl acetate (750 mL) were added. The organic layer was collected, washed with brine (350 mL), dried over $MgSO_4$, filtered, and concentrated in vacuo to give 45.7 g of a yellow solid. The solid was recrystallized from ethyl acetate and iso-octane to give 23 g (48%) of the dione: mp 108.5°-110.5° C.

Step 2: Preparation of 4-[4-(aminosulfonyl)phenyl]-5-(4-chlorophenyl)-1H-pyrazole-3-carboxylic Acid 4-Sulphonamidophenylhydrazine hydrochloride (1.45 g, 6.5 mmol, 1.3 equivalent) and methyl-4-[4-(chloro)phenyl]-2,4-dioxobutanoate (1.2 g, 5 mmol) were dissolved in ethanol (50 mL). The reaction was heated to reflux and stirred for 20 hours. After cooling to room temperature, the reaction mixture was concentrated in vacuo. The residue was taken up in ethyl acetate (200 mL) and washed with water (100 mL) and brine (100 mL), dried over $MgSO_4$, filtered and concentrated in vacuo to give 1.7 g of a light brown solid which was recrystallized from methanol and water to yield 1.6 g (85%) of a white solid. This material was dissolved in methanol (150 mL) and 3N NaOH (75 mL) and stirred at reflux for 3 hours. The methanol was removed in vacuo and the aqueous solution acidified with concentrated HCl. The product was extracted into ethyl acetate (200 mL), which was washed with brine (100 mL), dried over $MgSO_4$ filtered and concentrated to give 4-[4-(aminosulfonyl)phenyl]-5-(4-chlorophenyl)-1H-pyrazole-3-carboxylic acid, 1.4 g (74%): mp 135° C. (dec).

[EXAMPLE 84

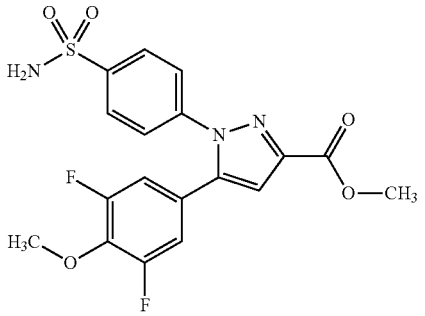

Methyl 1-(4-aminosulfonylphenyl)-5-(3,5-difluoro-4-methoxyphenyl)-1-H-pyrazole-3-carboxylate

]

[Step 1. Preparation of 3,5-difluoro-4-methoxyacetophenone]

[To a stirred suspension of $AlCl_3$ (24.05 g, 180.40 mmol) in chloroform (300 mL, dried by passage through alumina) at 4° C. (ice bath) under nitrogen was added acetyl chloride (11.0 mL, 152.65 mmol) over 20 minutes. This chilled suspension was stirred at 0° C. for 30 minutes and 2,6-difluoro anisole was added dropwise over 30 minutes. The resulting suspension was warmed to room temperature and stirred overnight. The reaction was quenched by slowly pouring it into a rapidly stirred ice/water mixture. The water layer was extracted with methylene chloride (2×50 mL) and the organic phases were combined and concentrated in vacuo yielding a clear mobile oil. In a 50 mL round bottomed flask was added the above clear oil, DMF (25 mL), $K_2CO_3$ (15 g). Methyl iodide (6 mL) was added and the suspension stirred at 45° C. under nitrogen overnight. Water (1 mL) was added and the mixture was heated for an additional 14 hours. The crude reaction mixture was cooled to room temperature, diluted with water (250 mL) and extracted with diethyl ether (3×100 mL). The ether phase was washed with sodium bicarbonate saturated solution, potassium bisulfate (0.1N solution), dried over $MgSO_4$, filtered and concentrated in vacuo yielding a clear mobile liquid. This liquid was distilled (30° C., 1 mm) yielding 12.5 g of a clear liquid which was a mixture of 3,5-difluoro-4-methoxyacetophenone and 3,5-difluoro-4-acetoxyacetophenone in an 85:15 ratio. The yield based upon this ratio was 41%. This ketone was used as is.]

[Step 2. Preparation of Methyl 1-(4-aminosulfonylphenyl)-5-(3,5-difluoro-4-methoxyphenyl)-1-H-pyrazole-3-carboxylate]

[To a stirred solution of 3,5-fluoro-4-methoxyacetophenone from Step 1 (6.46 g, 34.70 mmol) and dimethyl oxalate (6.15 g, 52.05 mmol) in methanol (80 mL), was added sodium methoxide solution (13.4 mL of 25% solution, 58.99 mmol) in one portion and the reaction stirred overnight. The crude reaction was diluted with methylene chloride, washed with potassium bisulfate (0.1N solution), brine, dried over $MgSO_4$, filtered, and concentrated in vacuo yielding methyl 4-(3,5-difluoro-4-methoxyphenyl)-2,4-dioxo-butanoate as an off white crystalline solid which was used as is. A mixture of 4-(3,5-difluoro-4-methoxyphenyl)-2,4-dioxo-butanoate and 4-sulfonamidophenylhydrazine hydrochloride salt (7.76 g, 34.70 mmol) dissolved in methanol was warmed to reflux for 9 hours. Upon allowing the clear reaction to cool to room temperature, a crystalline precipitate formed which was collected by vacuum filtration yielding 5.45 g, (37% based upon the 3,5-difluoro-4-methoxyacetophenone) of methyl 1-(4-aminosulfonylphenyl)-5-(3,5-difluoro-4-methoxyphenyl)-1-H-pyrazole-3-carboxylate as an off-white solid: mp 185°-190° C.; $^1H$ NMR ($CDCl_3$/300 mHz) 7.95 (d, J=8.86, 2H), 7.49 (d, J=8.86, 2H), 7.02 (s, 1H), 6.77 (m, 2H), 4.99 (s, 2H, 4.04 (s, 3H), 3.98 (s, 3H); $^{19}F$ NMR ($CDCl_3$/300 mHz) −126.66. Anal. Calc'd for $C_{17}H_{13}F_2N_3O_3S$: C, 51.06; H, 3.57; N, 9.92. Found: C, 51.06; H, 3.54, N, 9.99.]

[EXAMPLE 85

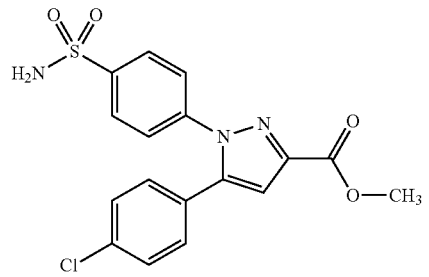

Methyl [1-(4-aminosulfonylphenyl)-5-(4-chlorophenyl)-1-H-pyrazole-3-yl-]carboxylate

]

[Step 1. Preparation of Methyl 4-[4-(chloro)phenyl]-2,4-dioxobutanoate]

[Dimethyl oxalate (15.27 g, 0.129 mol) and 4'-chloroacetophenone (20.0 g, 0.129 mol) were charged to a 500 mL round-bottom flask, with provisions made for magnetic stirring, and diluted with methanol (300 mL). Sodium methoxide (25% in methanol, 70 mL) was added in one portion. The reaction was stirred at room temperature for 16 hours. The reaction became an insoluble mass during this time. The solid was mechanically broken up, then concentrated hydrochloric acid (70 mL) was added, and the white suspension was stirred vigorously at room temperature for sixty minutes. The suspension was cooled to 0° C. and held for 30 minutes. The solid was filtered, and the filter cake was washed with cold water (100 mL). Upon drying, methyl 4-[4-(chloro)phenyl]-2,4-dioxobutanoate was obtained (16.94 g, 54.4%) as the enol: $^1$H NMR ($CDCl_3$/300 MHz) 7.94 (d, J=8.66 Hz, 2H), 7.48 (d, J=8.66 Hz, 2H), 7.04 (s, 1H), 3.95 (s, 3H), 3.48 (s, 1H).]

[Step 2. Preparation of Methyl [1-(4-aminosulfonylphenyl)-5-(4-chlorophenyl)-1H-pyrazole-3yl] carboxylate]

[A 100 mL round-bottomed flask equipped with magnetic stirrer and nitrogen inlet was charged with methyl 4-[4-(chloro)phenyl]-2,4-dioxobutanoate from Step 1 (5.0 g, 20.78 mmol), 4-sulfonamidylphenylhydrazine hydrochloride (5.11 g, 22.86 mmol) and methanol (50 mL). The reaction vessel was heated to reflux and held for 16 hours. A precipitate formed overnight. The suspension was cooled to 0° C., held for 0.5 hour, filtered and washed with cold water to provide, after air-drying, 7.91 g (91%) of crude product. Recrystallized 3.50 g from boiling ethanol to yield 3.14 g (97%) of pure methyl [1-(4-aminosulfonylphenyl)-5-(4-chlorophenyl)-1H-pyrazole-3-yl]carboxylate: mp 227° C.; $^1$H NMR ($CDCl_3$/300 MHz) 7.91 (d, J=8.86 Hz, 2H), 7.44 (d, J=8.86 Hz, 2H), 7.33 (d, J=8.66 Hz, 2H), 7.14 (d, J=8.66 Hz, 2H), 7.03 (s, 1H), 3.96 (s, 3H). Mass Spectrum, MH+=392. Anal. Calc'd for $C_{17}H_{14}N_3O_4ClS$: C, 52.11; H, 3.60; N, 10.72; Cl, 9.05; S, 8.18. Found: C, 52.07; H, 3.57; N, 10.76; Cl, 9.11; S, 8.27.]

[EXAMPLE 86

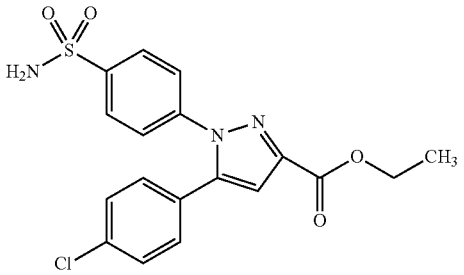

Ethyl [1-(4-aminosulfonylphenyl)-5-(4-chlorophenyl)-1-H-pyrazole-3-yl-]carboxylate

]

[Methyl [1-(4-aminosulfonylphenyl)-5-(4-chlorophenyl)-1H-pyrazole-3-yl]carboxylate (Example 85) (0.10 g) was dissolved in absolute ethanol (10 mL) and a catalytic amount of 21% NaOEt/EtOH was added. The reaction was stirred without temperature control for 72 hours, then water (10 mL) was added. The product crystallized, the suspension was cooled to 0° C. and held for 30 minutes. The product was filtered, washed with water (5 mL) and dried to yield 0.071 g (70%) of a white solid: Mass Spectrum: MH+=406. Anal. Calc'd for $C_{18}H_{16}N_3O_4ClS$: C, 53.27; H, 3.97; N, 10.35; Cl, 8.74; S, 7.90. Found: C, 53.04; H, 4.00; N, 10.27; Cl, 8.69; S, 7.97.]

[The following compounds in Table III were prepared according to procedures similar to that exemplified in Examples 83-86, with the substitution of the appropriate reagents.

TABLE III

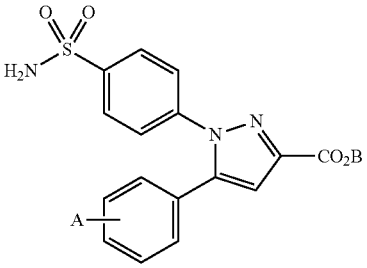

| Ex. | A | B | M.P. (° C.) | Analytical. |
|---|---|---|---|---|
| 87 | 4-$NO_2$ | —$CH_3$ | 216-220 | MH+ = 403 |
| 88 | 4-F | —$CH_3$ | ND | Calc. C, 54.40; H, 3.76; N, 11.19; S, 8.54<br>Obs. C, 54.49; H, 3.70; N, 11.25; S, 8.50 |
| 89 | 4-$NH_2$ | —$CH_3$ | 267-269(dec) | MH+ = 373 |
| 90 | 4-Br | —$CH_3$ | 221-224 | MH+ = 438 |
| 91 | 4-$OCH_3$ | —$CH_3$ | 169-171 | HRMS: 387.0930 |
| 92 | 4-$CH_3$ | —$CH_3$ | 213-215 | HRMS: 371.0965 |
| 93 | 4-$CH_3$ | —$CH_2CH_3$ | 219-220 | Calc. C, 59.21; H, 4.97; N, 10.90<br>Obs. C, 58.73; H, 4.96; N, 10.78 |
| 94 | 4-Cl | —$CH_2CH_2CH_3$ | ND | Calc. C, 54.35; H, 4.32; N, 10.01; Cl, 8.44; S, 7.64<br>Obs. C, 54.11; H, 4.28; N, 10.14; Cl, 8.54; S, 7.64 |
| 95 | 3,5-di-Cl, 4-$OCH_3$ | —$CH_3$ | 225-229 | |

]

EXAMPLE 96

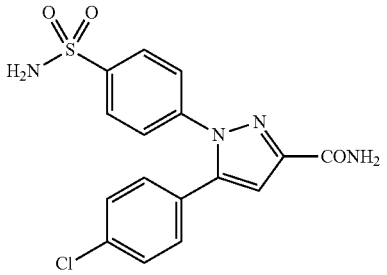

4-[4-(Aminosulfonyl)phenyl]-5-(4-chlorophenyl)-1H-pyrazole-3-carboxamide

4-[4-(Aminosulfonyl)phenyl]-5-(4-chlorophenyl)-1H-pyrazole-3-carboxylic acid [(Example 83)] (1.08 g, 2.86 mmol), HOBt (0.66 g, 4.3 mmol) and EDC (0.66 g, 3.4 mmol) were dissolved in dimethylformamide (DMF) (20 mL) and stirred at ambient temperature for 5 minutes. To this solution was added $NH_4OH$ (30%, 2.9 mL) and the reaction stirred for an additional 18 hours. This solution was then poured into ethyl acetate (200 mL) and 1N HCl (200 mL), shaken and separated. The organic layer was washed with saturated $NaHCO_3$ (150 mL) and brine (150 mL), dried over $MgSO_4$, filtered and concentrated to yield 0.9 g of a white solid which was recrystallized from ethyl acetate and iso-octane to yield 4-[4-(aminosulfonyl)phenyl]-5-(4-chlorophenyl)-1H-pyrazole-3-carboxamide (0.85 g, 79%): mp 108°-110° C.

[

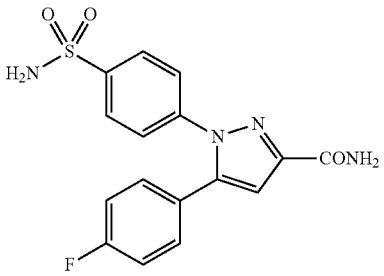

[1-(Aminosulfonylphenyl)-5-(4-fluorophenyl)-1H-pyrazol-3-yl]carboxamide

]

[A 250 mL three-neck round-bottom flask, equipped with a thermometer, gas sparging tube, reflux condenser and provisions for magnetic stirring, was charged with methyl [1-(4-aminosulfonylphenyl)-5-(4-fluorophenyl)-1H-pyrazol-3-yl] carboxylate (Example 88) (3.0 g, 7.99 mmol), methanol (100 mL), and a catalytic amount of sodium cyanide. Anhydrous ammonia gas was sparged through the reaction vessel for 16 hours without temperature control. The suspension turned a deep red during this time. The reaction was sparged with anhydrous nitrogen at room temperature for 20 minutes, cooled to 0° C. and held for 30 minutes. The solid was filtered and washed with cold water (50 mL) to yield, upon drying, 1.87 g (65%) of [1-(4-aminosulfonylphenyl)-5-(4-fluorophenyl)-1H-pyrazol-3-yl]carboxamide as a white solid: mp 214°-216° C.; $^1H$ NMR ($CDCl_3/CD_3OD$/300 MHz) 7.64 (d, J=8.66 Hz, 2H), 7.14 (d, J=8.66 Hz, 2H), 6.95 (m, 2H), 6.82-6.67 (m,6H), 6.39(s, 1H); $^{19}F$ NMR ($CDCl_3/CD_3OD$/282.2 MHz) −112.00(m). Mass spectrum, MH+=361. Anal. Calc'd for $C_{16}H_{13}N_4O_3FS$: C, 53.33; H, 3.64; N, 15.55; S, 8.90. Found: C, 53.41; H, 3.69; N, 15.52; S, 8.96.]

[EXAMPLE 98

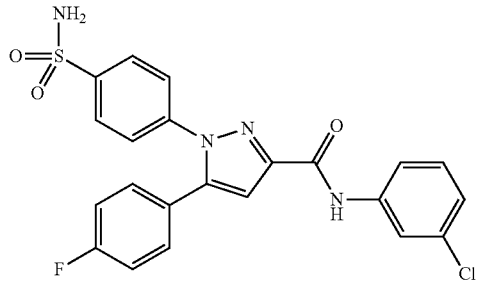

N-(3-Chlorophenyl)-[1-(4-aminosulfonylphenyl)-5-(4-fluorophenyl)-1H-pyrazol-3-yl-]carboxamide

]

[Step 1. Preparation of Methyl 4-[4-fluorophenyl]-2,4-dioxobutanoate]

[Dimethyl oxalate (18.80 g, 0.159 mol) and 4'-fluoroacetophenone (20.0 g, 0.145 mol) were charged to a 1000 mL round-bottom flask and diluted with methanol (400 mL). The reaction flask was placed in a sonication bath (Bransonic 1200), and sodium methoxide (25% in methanol, 70 mL) was added over 25 minutes. The reaction was sonicated at 45° C. for 16 hours. The reaction became an insoluble mass during this time. The solid was mechanically broken up, then poured into a hydrochloric acid solution (1N, 500 mL). A magnetic stirrer was added, and the white suspension was stirred vigorously at room temperature for 60 minutes. The suspension was cooled to 0° C. and held for 30 minutes. The solid was filtered, and the filter cake was then washed with cold water (100 mL). Upon drying, methyl 4-[4-fluorophenyl]-2,4-diketobutanoate was obtained (22.91 g, 70.6%) as the enol: $^1H$ NMR ($CDCl_3$/300 MHz) 8.03 (ddd, J=8.86 Hz, J=8.66 Hz, J=5.03 Hz, 2H), 7.19 (dd, J=8.86 Hz, J=8.66 Hz, 2H), 7.04 (s, 1H), 3.95 (s, 3H). $^{19}F$ NMR ($CDCl_3$/282.2 MHz) −103.9(m).]

[Step 2. Preparation of Methyl 4-[1-(4-aminosulfonylphenyl)-5-(4-fluorophenyl)-1H-pyrazol-3-yl]carboxylate]

[A 500 mL one-neck round-bottom flask equipped for magnetic stirring was charged with methyl 4-[4-fluorophenyl]-2,4-diketobutanoate from Step 1 (1.00 mg, 44.61 mmol), 4-sulfonamidylphenylhyrazine hydrochloride (10.98 g, 49.07 mmol) and methanol (200 mL). The suspension was heated and held at reflux for three hours, then cooled to room temperature. The suspension was cooled to 0° C., held for 30 minutes, filtered, washed with water (100 mL), and dried to yield 14.4 g (86%) of methyl 4-[1-(4-aminosulfonylphenyl)-5-(4-fluorophenyl)-1H-pyrazol-3-yl]carboxylate as a white solid: $^1H$ NMR ($CDCl_3$/300 MHz) 7.85 (d, J=8.66 Hz, 2H), 7.36 (d, J=8.66 Hz, 2H), 7.18 (ddd, J=8.66 Hz, J=8.46 Hz, J=4.85 Hz, 2H), 7.00 (dd, J=8.66 Hz, J=8.46 Hz, 2H), 6.28 (s, 1H), 3.90 (s, 3H). $^{19}F$ NMR ($CDCl_3$/282.2 MHz: −111.4(m).

Mass spectrum. MH+=376. Anal. Calc'd for $C_{17}N_{14}N_3O_4FS$: C, 54.40; H, 3.76; N, 11.19; S, 8.54. Found: C, 54.49; H, 3.70; N, 11.25; S, 8.50.]

[Step 3. Preparation of [1-(4-aminosulfonylphenyl)-5-(4-fluorophenyl)-1H-pyrazol-3-yl]carboxylic Acid]

[A 500 mL one-neck round-bottom flask, equipped with provisions for magnetic stirring, was charged with methyl 4-[1-(4-aminosulfonylphenyl)-5-(4-fluorophenyl)-1H-pyrazol-3-yl]carboxylate from Step 2 (10.0 g, 26.64 mmol) and tetrahydrofuran (200 mL). Aqueous sodium hydroxide (2.5N, 27 mL) and water (25 mL) were added, and the suspension was heated to reflux and held for 16 hours. The solids all dissolved during this time. The reaction was cooled to room temperature, and hydrochloric acid solution (1N, 110 mL) was added. The aqueous suspension was extracted with methylene chloride (2×200 mL). The combined organic solution was dried over anhydrous magnesium sulfate, filtered, and concentrated in vacuo to an oil. Trituration with 300 mL of methylene chloride yielded, upon filtration and drying, 9.0 g, (94%) of [1-(4-aminosulfonylphenyl)-5-(4-fluorophenyl)-1H-pyrazol-3-yl]carboxylic acid as a white solid: mp 138°-142° C. (dec); $^1$H NMR ($CD_3OD$/300 MHz) 7.93 (d, J=8.66 Hz, 2H), 7.51 (d, J=8.66 Hz, 2H), 7.31 (ddd, J=8.86 Hz, J=8.66 Hz, J=4.83 Hz, 2H), 7.11 (dd, J=8.86 Hz, J=8.66 Hz, 2H), 7.06 (s, 1H). $^{19}$F NMR ($CD_3OD$/282.2 MHz): −114.01 (m).]

[Step 4. Preparation of N-(3-chlorophenyl)-[1-(4-aminosulfonylphenyl)-5-(4-fluorophenyl)-1H-pyrazol-3-yl]carboxamide]

[A 100 mL one-neck round-bottom flask, equipped with provisions for magnetic stirring, was charged with [1-(4-aminosulfonylphenyl)-5-(4-fluorophenyl)-1H-pyrazol-3-yl]carboxylic acid from Step 3 (0.500 g, 1.38 mmol), 1-hydroxybenzotriazole hydrate (0.206 g, 1.522 mmol), 1-(3-dimethylaminopropyl)-3-ethylcarbodiimide hydrochloride (0.318 g, 1.66 mmol) and N,N-dimethylformamide (30 mL). The solution was stirred at room temperature for forty minutes, then 3-chloroaniline (0.154 mL, 1.453 mmol) was added. The reaction was held at room temperature for sixteen hours, then poured into an aqueous solution of citric acid (5%, 100 mL). The aqueous solution was extracted with ethyl acetate (2×60 mL), and the combined organic solutions were washed with aqueous citric acid (60 mL), saturated sodium bicarbonate solution (2×60 mL) and 50% saturated sodium chloride solution (2×60 mL). The organic solution was dried over anhydrous magnesium sulfate, filtered, and concentrated in vacuo to an oil. Trituration with 20 mL of dichloromethane yielded, upon filtration and drying, 0.439 g (67%) of N-(3-chlorophenyl)-[1-(4-aminosulfonylphenyl)-5-(4-fluorophenyl)-1H-pyrazol-3-yl]carboxamide as a white solid: mp 207°-212° C.; $^1$H NMR ($CDCl_3$/$CD_3OD$/300 MHz) 8.90 (s, 1H), 7.86 (d, J=8.66 Hz, 2H), 7.79 (t, J=2.01 Hz, 1H), 7.46 (dd, J=7.05 Hz, J=2.01 Hz, 1H), 7.33 (d, J=8.86 Hz, 2H), 7.21-7.11 (m, 3H), 7.02-6.94 (m, 4H). $^{19}$F NMR ($CDCl_3$/$CD_3OD$/282.2 MHz): −111.38(m). Mass spectrum, MH+=470. Anal. Calc'd for $C_{22}H_{16}N_4O_3ClFS$: C, 56.11; H, 3.42; N, 11.90; Cl, 6.81; S, 7.53. Found: C, 55.95; H, 3.50; N, 11.85; Cl, 6.82; S, 7.50.]

[The following compounds in Table IV were prepared according to procedures similar to that exemplified in Examples 96-98, with substitution of the appropriate starting material.

TABLE IV

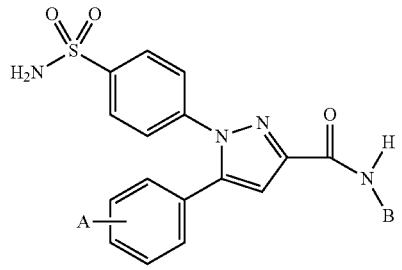

| Ex. | A | B | MP. ° C. | Analytical |
|---|---|---|---|---|
| 99 | 4-Br | H | 143-145 | MH+ = 421 |
| 100 | 4-F | phenyl- | 233-236 | MH+ = 436 |
| 101 | 4-$NO_2$ | H | 278-281 | MH+ = 387 |
| 102 | 4-F | 4-$CH_3O$-phenyl- | 209-211 | MH+ = 466 |
| 103 | 4-F | 4-$CH_3$-phenyl- | 222-225 | MH+ = 451 |
| 104 | 4-F | cyclohexyl- | 224-227 | MH+ = 442 |
| 105 | 4-F | 3-F-phenyl- | 227 | MH+ = 454 |
| 106 | 4-Cl | 3-F-phenyl- | 174-176(dec) | MH+ = 471 |
| 107 | H | H | ND | MH+ = 343 |
| 108 | 4-$OCH_3$, 3-Cl | H | ND | MH+ = 408 |
| 109 | 4-$SCH_3$ | H | 115(dec) | HRMS: 389.0743 |
| 110 | 4-$OCH_3$ | H | 115-140 | Calc. C, 54.83; H, 4.33; N, 15.04<br>Obs. C, 54.76; H, 4.34; N, 14.98 |
| 111 | 4-$CH_3$ | H | 139-140 | HRMS•H2O: 356.0939 |
| 112 | 4-$OCH_3$ | —$CH_3$ | 209 | MH+ = 387 |
| 113 | 4-Cl | glycine benzyl ester | 136 | MH+ = 525 |
| 114 | 4-Cl | glycine | 124-130 | MH+ = 435 |
| 115 | 4-$OCH_3$, 3-Br | H | ND | M + Li = 457/459 |
| 116 | 4-$OCH_3$, 3,5-di-Cl | H | 185(dec) | HRMS: 440.0113 |

]

[EXAMPLE 117

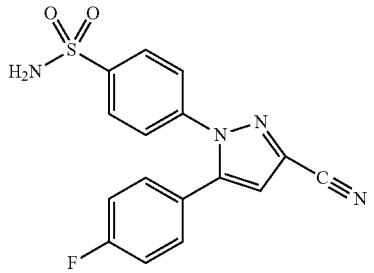

4-[3-Cyano-5-(4-fluorophenyl-1H-pyrazol-1-yl] benzenesulfonamide

]

[A dry 100 ml three-neck flask, equipped with a reflux condenser, thermometer, pressure-equalizing addition funnel and provisions for magnetic stirring was charged with anhydrous DMF (20 mL) and cooled to 0° C. Oxalyl chloride (0.530 mL, 6.105 mmol) was added over twenty seconds, causing a 5° C. exotherm. The white precipitate formed dissolved as the reaction cooled to 0° C. The reaction was held at 0° C. for ten minutes, then a solution of [1-(4-aminosulfonylphenyl)-5-(4-fluorophenyl)-1H-pyrazol-3-yl]carboxamide (Example 97) in anhydrous DMF was added to the vigorously stirring solution over approximately two minutes. After fifteen minutes, pyridine (1.0 mL, 12.21 mmol) was added to quench the reaction. The mixture was poured into dilute hydrochloric acid (1N, 100 mL) and extracted with ethyl acetate (2×75 mL). The combined organic solution was washed with 1N HCl (2×100 mL) and with 50% saturated NaCl (3×100 mL). The organic solution was dried over magnesium sulfate, filtered and concentrated in vacuo to a crude oil. The oil was applied to a column of silica gel and eluted with ethyl acetate and hexane (40% ethyl acetate) to obtain, upon concentration of the appropriate fractions, 0.66 g (69%) of 4-[3-cyano-5-(4-fluorophenyl-1H-pyrazol-1-yl]benzenesulfonamide as a white solid: mp 184°-185° C.; $^{1}$H NMR ($CDCl_3$/300 MHz) 7.94 (d, J=8.86 Hz, 2H), 7.44 (d, J=8.86 Hz, 2H), 7.23-7.07 (m, 4H), 6.87 (s, 1H), 4.88 (brs, 2H); $^{19}$F NMR ($CDCl_3$/282.2 MHz) −109.90(m). Mass spectrum, MH+=343. Anal. Calc'd for $C_{16}H_{11}N_4O_2FS$: C, 56.14; H, 3.24; N, 16.37; S, 9.36. Found: C, 56.19; H, 3.16; N, 16.39; S, 9.41.]

[The following compounds in Table V were prepared according to procedures similar to that exemplified in Example 117, with the substitution of the appropriate starting material.

TABLE V

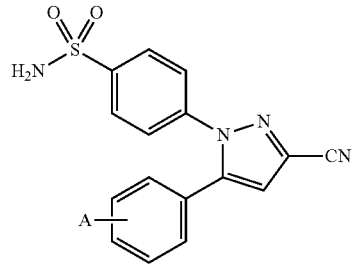

| Ex. | A | M.P. (° C.) | Anal. |
|---|---|---|---|
| 118 | 4-Br | 156-157 | HRMS: 401.9833 |
| 119 | 4-Cl | 142-143 | |
| 120 | 4-$OCH_3$ | ND | HRMS: 354.0774 |
| 121 | 4-$CH_3$ | 90-95 | HRMS: 338.0849 |
| 122 | 4-$SCH_3$ | 192-193 | |
| 123 | 4-$OCH_3$, 3-Cl | 179 | MH+ = 389 |
| 124 | 4-$OCH_3$, 3,5-di-Cl | 121-125 | HRMS: 422.0051 |
| 125 | 4-$OCH_3$, 3-Br | 213 | MH+ = 433 |
| 126 | 4-$NO_2$ | 230-232 | MH+ = 370 |
| 127 | H | ND | MH+ = 325 |

]

[EXAMPLE 108

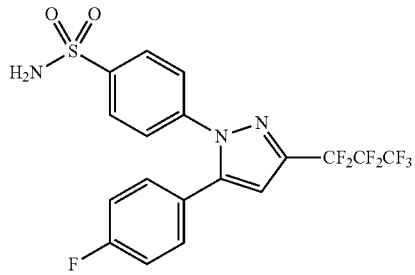

4-[5-(4-Chlorophenyl)-3-(heptafluoropropyl)-1H-pyrazol-1-yl] benzenesulfonamide

]

[Step 1: Preparation of 4,4,5,5,6,6,6-heptafluoro-1-[4-(chloro)phenyl]hexane-1,3-dione]

[Ethyl heptafluorobutyrate (5.23 g, 21.6 mmol) was placed in a 100 mL round bottom flask, and dissolved in ether (20 mL). To the stirred solution was added 25% sodium methoxide (4.85 g, 22.4 mmol) followed by 4-chloroacetophenone (3.04 g, 19.7 mmol). The reaction was stirred at room temperature overnight (15.9 hours) and treated with 3N HCl (17 mL). The organic layer was collected, washed with brine, dried over $MgSO_4$, concentrated in vacuo, and recrystallized from iso-octane to give the diketone as a white solid (4.27 g, 62%): mp 27°-30° C.; $^{1}$H NMR ($CDCl_3$) 300 MHz 15.20 (br s, 1H), 7.89 (d, J=8.7 Hz, 2H), 7.51 (d, J=8.7 Hz, 2H), 6.58 (S, 1H); $^{19}$F NMR ($CDCl_3$) 300 MHz: −80.94 (t), −121.01 (t), −127.17 (s); M+H 351.]

[Step 2: Preparation of 4-[5-(4-chlorophenyl)-3-(heptafluoropropyl)-1H-pyrazol-1-yl]benzenesulfonamide]

[The 4-sulfonamidophenylhydrazine hydrochloride (290 mg, 1.30 mmol) was added to a stirred solution of the diketone from Step 1 (400 mg, 1.14 mmol) in ethanol (5 mL). The reaction was heated to reflux and stirred overnight (23.8 hours). The ethanol was removed in vacuo, and the residue was dissolved in ethyl acetate, washed with water and brine, dried over $MgSO_4$, and concentrated in vacuo to give a white solid which was passed through a column of silica gel with ethyl acetate/hexane (40%) and recrystallized from ethyl acetate/isooctane to give the pyrazole as a white solid (0.24 g, 42%): mp 168°-71° C.; $^1H$ NMR ($CDCl_3$) 300 MHz 7.90 (d, J=8.7 Hz, 2H), 7.45 (d, J=8.7 Hz, 2H), 7.34 (d, J=8.5 Hz, 2H), 7.19 (d, J=8.5 Hz, 2H), 6.79 (s, 1H), 5.20 (br s, 2H); $^{19}F$ NMR ($CDCl_3$) 300 MHz: −80.48 (t), −111.54 (t), −127.07 (s).]

EXAMPLE 129

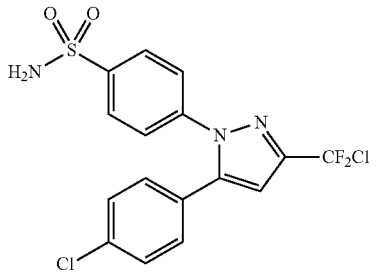

4-[5-(4-Chlorophenyl)-3-(chloro-difluoromethyl)-1H-pyrazol-1-yl] benzenesulfonamide Step 1: Preparation of 4-chloro-4,4-difluoro-1-[4-(chloro)phenyl]-butane-1,3-dione Methyl 2-chloro-2,2-difluoroacetate (4.20 g, 29 mmol) was placed in a 100 mL round bottom flask, and dissolved in ether (10 mL). To the stirred solution was added 25% sodium methoxide (6.37 g, 29 mmol) followed by 4'-chloroacetophenone (4.10 g, 26.5 mmol). The reaction was stirred at room temperature overnight (20.4 hours), then poured into a separatory funnel and washed with 3N HCl (15 mL), brine (20 mL), dried over $MgSO_4$, and concentrated in vacuo and recrystallized from iso-octane to give the diketone as a yellow solid (3.78 g, 53%): mp 53°-55° C.; $^1H$ NMR ($CDCl_3$) 300 MHz 14.80 (br s, 1H), 7.87 (d, J=8.7 Hz, 2H), 7.50 (d, J=8.7 Hz, 2H), 6.49 (S, 1H); $^{19}F$ NMR ($CDCl_3$) 300 MHz: −66.03 (s); M+ 267.

Step 2: Preparation of 4-[5-(4-chlorophenyl)-3-(chloro-difluoromethyl)-1H-pyrazol-1-yl]benzene-sulfonamide 4-Sulfonamidophenylhydrazine hydrochloride (1.39 g, 6.2 mmol) was added to a stirred solution of the diketone from Step 1 (1.43 g, 5.7 mmol) in ethanol (10 mL). The reaction was heated to reflux and stirred overnight (15.75 hours). The ethanol was removed in vacuo, and the residue was dissolved in ethyl acetate, washed with water and brine, dried over $MgSO_4$, and concentrated in vacuo to give a white solid which was recrystallized from ethyl acetate/isooctane to give the pyrazole as a white solid (0.32 g, 41%): mp 130°-33° C.; $^1H$ NMR ($CDCl_3$) 300 MHz 7.90 (d, J≦8.9 Hz, 2H), 7.47 (d, J=8.7 Hz, 2H), 7.35 (d, J=8.5 Hz, 2H), 7.19 (d, J=8.7 Hz, 2H), 6.76 (s, 1 H), 5.13 (br s, 2H); $^{19}F$ NMR ($CDCl_3$) 300 MHz: −48.44 (s); M+ 417/419.

[EXAMPLE 130

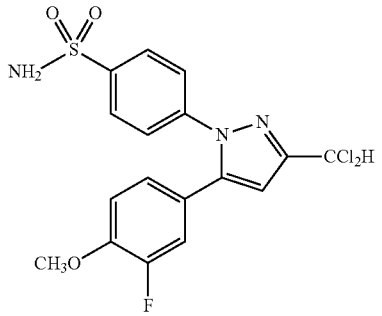

4-[3-(Dichloromethyl)-5-(3-fluoro-4-methoxyphenyl)-1H-pyrazol-1-yl] benzenesulfonamide

]

[Step 1. Preparation of 3'-fluoro-4'-methoxyacetophenone]

[Aluminum chloride (80.0 g, 0.6 mol) and chloroform (750 mL) were placed in a 2 L three-necked round bottom flask fitted with a mechanical stirrer and cooled by means of an ice bath. To the stirred solution was added acetyl chloride (51.0 g, 0.65 mol) dropwise, maintaining the temperature between 5°-10° C. The mixture was allowed to stir for 10 minutes at 5° C. before the dropwise addition at 5°-10° C. of 2-fluoroanisole (63.06 g, 0.5 mol. The mixture was stirred at 0°-10° C. for 1 hour and poured into ice (1 L). The resultant layers were separated and the aqueous layer was extracted with methylene chloride (2×250 mL). The combined organic layers were washed with water (2×150 mL), dried over magnesium sulfate, and concentrated to 300 mL. Hexanes crystallized from the mixture: mp 92°-94° C.; $^1H$ NMR ($d_6$-DMSO) 7.8 (m, 2H), 7.3 (t, J=8.7Hz, 1H), 3.9 (s, 3H), 2.5 (s, 3H).]

[Step 2. Preparation of 4,4-dichloro-1-(3-fluoro-4-methoxyphenyl)-butene-1,3-dione]

[Methyl dichloroacetate (1.57 g, 11 mmol) was dissolved ether (25 mL). To the stirred solution was added 25% sodium methoxide (2.38 g, 11 mmol) followed by 3'-fluoro-4'-methoxyacetophenone from Step 1 (1.68 g, 10 mmol). After stirring 16 hours 1N HCl (25 mL) was added. The organic layer was collected and washed with water (2×25 mL), dried over magnesium sulfate, filtered, and concentrated. The resulting crude dione was used in the next step without further purification or characterization.]

[Step 3. Preparation of 4-[3-(dichloromethyl)-5-(3-fluoro-4-methoxyphenyl)-1H-pyrazol-1-yl]benzene-sulfonamide]

[4,4-Dichloro-1-(3-fluoro-4-methoxyphenyl)-butane-1,3-dione from Step 2 (2.8 g, 10 mmol) was dissolved in ethanol (100 mL). To the stirred mixture was added 4-sulfonamidophenylhydrazine hydrochloride (2.46 g, 11 mmol) and heated to reflux for 16 hours. The mixture was cooled and water was added until crystals slowly appeared. Filtration yielded a light tan solid (2.7 g, 63%): mp 190°-193° C.: $^1$H NMR (DMSO-$d_6$) 7.84 (d, J=8.4Hz, 2H), 7.53 (s, 1H), 7.48 (d, J=8.4Hz, 2H), 7.47 (brs, 2H), 7.3-7.0 (m, 3H), 6.95 (s, 1H), 3.85 (s, 3H). Anal. Calc'd for $C_{17}H_{14}N_3SO_3FCl_2$: C, 47.45; H, 3.28; N, 9.76. Found: C, 47.68; H, 3.42; N, 10.04.]

[EXAMPLE 131

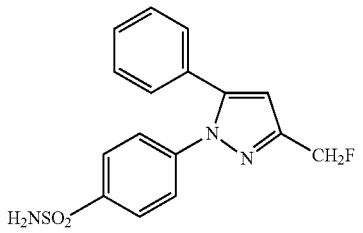

4-[3-Fluoromethyl-5-phenyl-1H-pyrazol-1-yl] benzenesulfonamide

]

[Step 1: Preparation Methyl 4-phenyl-2,4-dioxobutanoate]

[To a solution of dimethyl oxalate (11.81 g, 100 mmol) in ether (200 mL) is added 24 mL of 25% sodium methoxide in methanol, followed by a solution of acetophenone (12.02 g, 100 mmol) in ether (20 mL) and the mixture stirred overnight at room temperature. The mixture was partitioned between 1N HCl and EtOAc and the organic layer was washed with brine, dried over $MgSO_4$ and concentrated to give 18.4 g of crude butanoate.]

[Step 2. Preparation of Methyl 1-[(4-(aminosulfonyl) phenyl]-5-phenyl-1H-pyrazole 3-carboxylate]

[The ester was prepared from the butanoate in Step 1 using the procedure described in Example 2, Step 2.]

[Step 3. Preparation of 4-[3-hydroxymethyl-5-phenyl-1H-pyrazol-1-yl]benzene Sulfonamide]

[To a solution of ester in Step 2 (4.0 g, 10.4 mmol) in 50 mL THF was added $LiAlH_4$ (0.592 g, 15.6 mmol) in portions and the mixture refluxed overnight. The reaction was cooled and quenched with 1N $NaHSO_4$ and extracted with ether (3×). The combined extracts were dried over $MgSO_4$ and concentrated to give 3.5 g crude alcohol. Flash chromatography using 1:1 hexane/EtOAc provided the title compound.]

[Step 4: Preparation 4-[3-fluoromethyl-5-phenyl-1H-pyrazol-1-yl]benzenesulfonamide]

[To a mixture of the alcohol from Step 3 (212 mg, 0.64 mmol) in dichloromethane (4 mL) was added diethylaminosulfur trifluoride (0.13 mL, 1.0 mmol). The reaction mixture was stirred at room temperature for 3 hours and partitioned between water and dichloromethane. The organic solution was washed with brine and concentrated. The residue was chromatographed on silica (72 mg, 34%): mp 162°-163° C.; Anal. calc'd for $C_{16}H_{14}N_3O_2SF$: C, 58.00; H, 4.26; N, 12.68. Found: C, 57.95; H, 4.03; N, 12.58.]

[The following compounds in Table VI were prepared according to procedures similar to that exemplified in Examples 128-131, with the substitution of the appropriate substituted acetyl and acetate starting materials.

TABLE VI

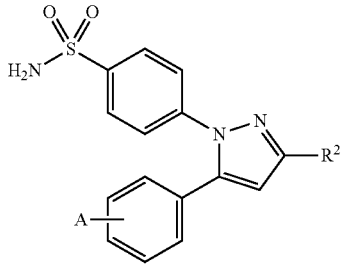

| Ex. | A | $R^2$ | M.P. (° C.) | Anal. |
|---|---|---|---|---|
| 132 | 4-Cl | —$CF_2CF_3$ | 145.5-150 | |
| 133 | 4-Cl | —$CH_2Cl$ | 198-201 | Calc. C, 50.27; H, 3.43; N, 10.99<br>Found C, 50.34; H, 3.43; N, 10.96 |
| 134 | 3- F, 4-$OCH_3$ | —$CF_2Cl$ | 120-124 | Calc. C, 47.29; H, 3.04; N, 9.74<br>Found C, 47.28; H, 3.37; N, 9.88 |
| 135 | 3- F, 4-$OCH_3$ | —$CBrF_2$ | 120-122 | Calc. C, 42.87; H, 2.75; N, 8.82<br>Found C, 42.99; H, 3.81; N, 9.92 |
| 136 | 3- Cl, 4-$OCH_3$ | —$CH_2Cl$ | ND | Calc. C, 49.53; H, 2.84; N, 8.66<br>Found C, 50.03; H, 3.81; N, 9.92 |

]

EXAMPLE 137

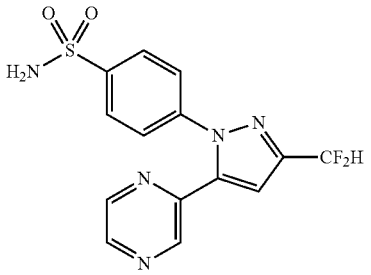

4-[5-(2-Pyrazinyl)-3-(difluoromethyl)-1H-pyrazol-1-yl] benzenesulfonamide

Step 1: Preparation of 4,4-difluoro-1-(2-pyrazinyl)-butane-1,3-dione

Ethyl difluoroacetate (2.23 g, 18 mmol) was placed in a 100 mL round bottom flask and dissolved in ether (10 mL). To the stirred solution was added 25% sodium methoxide (4.68 g, 22 mmol) followed by acetylpyrazine (2.00 g, 16 mmol). After two hours stirring at room temperature, a precipitate formed and THF (10 mL) was added to the reaction. The reaction was stirred an additional 25.9 hours, then treated with 3N HCl (10 mL). The organic layer was collected, washed with brine (20 mL), dried over $MgSO_4$, and concentrated in vacuo and recrystallized from methylene chloride/iso-octane to give the diketone as a brown solid (2.23 g, 68%); mp 103°-110° C.; $^1$H NMR ($CDCl_3$) 300 MHz 14.00 (br s, 1H), 9.31 (d, J=1.4 Hz, 1H), 8.76 (d, J=2.4 Hz, 1H), 8.68 (dd, J=1.4 Hz 2.4 Hz, 1H), 7.20 (s, 1H), 6.03 (t, J=54.0 Hz, 1H); $^{19}F$ NMR ($CDCl_3$) 300 MHz: −127.16 (d); M+ 200.

Step 2: Preparation of 4-[5-(2-pyrazinyl)-3-(difluoromethyl)-1H-pyrazol-1-yl]benzenesulfonamide 4-Sulfonamidophenylhydrazine hydrochloride (0.37 g, 1.65 mmol) was added to a stirred suspension of the diketone [from Step 1] (0.30 g, 1.50 mmol) in ethanol (10 mL). The reaction was heated to reflux and stirred for 5.3 hours. The ethanol was removed in vacuo, and the residue was dissolved in ethyl acetate, washed with water (20 mL), brine (20 mL), dried over $MgSO_4$, and concentrated in vacuo to give a brown solid (0.36 g) which was recrystallized from ethyl acetate/ethanol/isooctane to give the pyrazole as a brown solid (0.20 g, 38%): mp 191°-94° C.; $^1H$ NMR (acetone $d_6$) 300 MHz 8.94(d, J=1.4 Hz, 1H), 8.62 (d, J=2.4 Hz, 1H), 8.52 (dd, J=1.4 Hz, 2.4 Hz, 1H), 7.95 (d, J=8.7 Hz, 2H), 7.61 (d, J=8.7 Hz, 2H), 7.30 (s, 1H), 7.02 (t, J=54.6 Hz, 1H), 6.73 (br s, 2 H); $^{19}F$ NMR (acetone $d_6$) 300 MHz: −113.67 (d): M+351.

[EXAMPLE 138

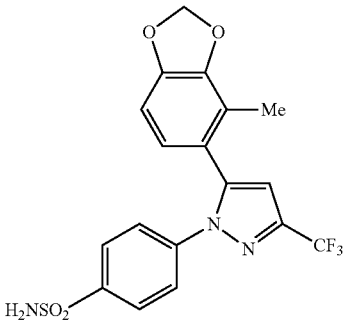

4-[5-(4-methyl-1,3-benzodioxol-5-yl)-3-(trifluoromethyl)-1H-pyrazol-1-yl] benzenesulfonamide

]

[Step 1: Preparation of 4-methyl-1,3-benzodioxole]

[11.6 g Adogen 464 and 7 mL of dibromomethane were refluxed in 50 mL of $H_2O$ for 0.5 hours under argon. 3-Methylcatechol (8.89 g, 71.6 mmol) was added over 2 hours and the mixture refluxed for an additional 1 hour. Distillation of the product from the reaction mixture afforded the title compound as a yellow oil: HRMS m/e 136.0524 (calc'd for $C_8H_8O_2$, 136.0524).]

[Step 2: Preparation of 5-acetyl-4-methyl-1,3-benzodioxole (A) and 6-acetyl-4-methyl-1,3-benzodioxole (B)]

[13.8 g of polyphosphoric acid and 5 mL of acetic anhydride were heated to 45° C. under a drying tube of $CaSO_4$ until liquified. The product from Step 1 was added and the reaction was stirred at 45° C. for 4.5 hours. The reaction was cooled to room temperature and quenched with 150 mL of ice water. The aqueous phase was washed with ethyl acetate (4×50 mL). The combined organic extracts were dried over $MgSO_4$ and filtered to give the crude product as a red oil. The oil was chromatographed on silica gel eluting with 10% ethyl acetate/90% hexane to afford two products: A: Anal. calcd for $C_{10}H_{10}O_3$: C, 67.07; H, 5.66. Found: C, 67.41; H, 5.75, and B: MS, M+ 178.]

[Steps 3 and 4: 4-[5-(4-methyl-1,3-benzodioxol-5yl)-3-(trifluoromethyl)-1H-pyrazol-1-yl]benzenesulfonamide]

[The title compound was prepared from product A using the procedures described in Example 2, Steps 1 and 2: White solid: Anal. calcd for $C_{18}H_{14}N_3O_4SF_3$: C, 50.82; H, 3.22; N, 9.88. Found: C, 50.71; H, 3.34; N, 9.55.]

The following compounds in Table VII were prepared [according to procedures similar to that exemplified in Examples 137-138, with the substitution of] *in a similar manner using* the appropriate starting material.

TABLE VII

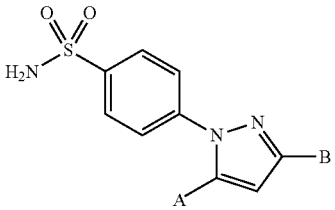

| Ex. | A | B | M.P.(° C.) | Anal. |
|---|---|---|---|---|
| 139 | 5-bromo-2-thienyl | $CF_2H$ | 168-169 | M + Li 440/442 |
| 140 | 2-thienyl | $CF_2H$ | 190-191 | M + Li 367 |
| 141 | 5-chloro-2-thienyl | $CF_2H$ | 168-170 | M + 389/391 |
| 142 | 1-cyclohexenyl | $CF_2H$ | 160-161 | M + 353. |
| [143 | 1,4-benzodioxan | $CF_2H$ | 115-119 | Calc. C, 53.06; H, 3.71; N, 10.32<br>Obs. C, 52.40; H, 3.98; N, 9.96 |
| 144 | 4-methylcyclohex-3-ene-1-yl | $CF_2H$ | 164-168 | HRMS: 367.1194 |
| 145 | 2-methylcyclopenten-1-yl | $CF_2H$ | 165-166 | HRMS: 353.1033 |

TABLE VII-continued

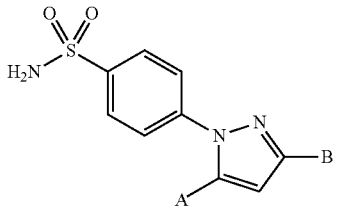

| Ex. | A | B | M.P.(° C.) | Anal. |
|---|---|---|---|---|
| 146 | 2,5-dimethyl-3-thienyl | $CF_2H$ | 125-127 | Calc. C, 50.12; H, 3.94; N, 10.96<br>Obs. C, 50.21; H, 3.92; N, 11.00 |
| 147 | 2,5-dimethyl-3-furyl | $CF_2H$ | 139-142 | Calc. C, 52.31; H, 4.12; N, 11.44<br>Obs. C, 52.07; H, 4.16; N, 11.37 |
| 148 | 5-methyl-2-furyl | $CF_2H$ | 177-179 | Calc C, 50.99; H, 3.71; N, 11.89<br>Obs. C, 51.08; H, 3.68; N, 11.95 |
| 149 | 4-bromo-4-methylcyclohex-1-yl | $CF_2H$ | 175-178(dec) | HRMS: 448.0520 |
| 150 | 4-methylcyclohex-1-yl | $CF_2H$ | 190-192 | HRMS: 369.1341 |
| 151 | 4-chloro-4-methylcyclohex-1-yl | $CF_2H$ | 197-199 | HRMS: 403.095 |
| 152 | 3,4-dibromo-4-methylcyclohex-1-yl | $CF_2H$ | 172-173] | |
| 153 | 2-methoxycyclohex-1-yl | $CF_2H$ | 177-179 | HRMS: 386.1357 |
| 154 | 2-benzofuryl | $CF_2H$ | 215-217 | Calc C, 55.52; H, 3.37; N, 10.79<br>Obs. C, 55.52; H, 3.32; N, 10.85 |
| 155 | 2,5-dichloro-3-thien-yl | $CF_2H$ | 154-156 | Calc. C, 39.63; H, 2.14; N, 9.90<br>Obs. C, 39.63; H, 2.13; N, 9.89 |
| 156 | 2-benzofuryl | $CF_3$ | 227-228 | Calc. C, 53.07; H, 2.97; N, 10.31<br>Obs. C, 53.02; H, 2.96; N, 10.39 |
| 157 | 5-chloro-2-thienyl | $CF_3$ | 161-165 | HRMS: 406.9784] |
| 158 | 5-bromo-2-thienyl | $CF_3$ | ND | Calc: C, 37.18; H, 2.01; N, 9.29; Br, 17.67<br>Found: C, 37.25; H, 1.93; N, 9.45; Br, 17.40 |
| 159 | 5-indanyl | $CF_3$ | 118-120 | Calc: C, 56.01; H, 3.96; N, 10.31<br>Found: C, 56.02; H, 4.06; N, 10.22 |
| 160 | 5-methylthien-2-yl | $CF_3$ | 188-190 | Calc. C, 46.51; H, 3.12; N, 10.85<br>Found: C, 46.17; H, 3.10; N, 10.75 |
| 161 | 2,3-dihydrobenzofuryl | $CF_3$ | 152-153 | Calc. C, 52.81; H, 3.45; N, 10.26<br>Found: C, 52.67; H, 3.78; N, 10.13 |
| 162 | 1-cyclohexenyl | $CF_3$ | [135-138 | HRMS: 371.0918 |
| 163 | 6-tetrahydronaphthyl | $CF_3$ | 143-145 | Calc. C, 57.00; H, 4.31; N, 9.97<br>Found: C, 56.72; H, 4.27; N, 9.90 |
| 164 | 3-benzothienyl | $CF_3$ | 164-165 | Calc. C, 51.06; H, 2.86; N, 9.92<br>Obs. C, 50.96; H, 2.73; N, 9.78 |
| 165 | 3,4-dihydrobenzopyranyl | $CF_3$ | ND | HRMS: 423.0855 |
| 166 | styryl | $CF_3$ | 166-167 | Calc. C, 54.96; H, 3.59; N, 10.68<br>Obs. C, 54.77; H, 3.59; N, 10.47 |
| 167 | 4-methyl-1,3-benzodioxol-6-yl | $CF_3$ | ND | Calc. C, 50.82; H, 3.22; N, 9.88<br>Obs. C, 50.64; H, 3.35; N, 9.72 |
| 168 | 3-pyridyl | $CF_3$ | 202-204 | Calc. C, 48.91; H, 3.01; N, 15.21<br>Obs. C, 48.97; H, 3.16; N, 14.96 |
| 169 | 3,4-dihydrobenzothiopyranyl | $CF_3$ | ND | Calc. C, 51.95; H, 3.67; N, 9.56<br>Obs. C, 51.98; H, 3.78; N, 9.48] |

EXAMPLE 170

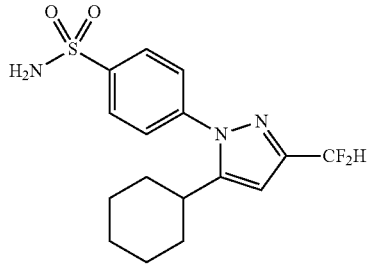

4-[5-(1-Cyclohexyl)-3-(difluoromethyl)-1H-pyrazol-1-yl] benzenesulfonamide

4-[5-(1-Cyclohexenyl)-3-(difluoromethyl)-1H-pyrazol-1-yl]benzenesulfonamide [(Example 142)] (0.31 g, 0.88 mmol) was dissolved in ethanol (15 mL), 10% palladium on charcoal was added, and the suspension was stirred at room temperature under hydrogen (36 psi) for 18.25 hours. The reaction was filtered through celite, and the ethanol removed in vacuo to give a white solid, which was recrystallized from methylene chloride/isooctane (0.31 g, 99%); mp 199°-203° C.; $^1$H NMR (acetone-$d_6$) 300 MHz 8.05 (d, J=8.7 Hz, 2H), 7.60 (d, J=8.5 Hz, 2H), 6.69 (t, J=55.0 Hz 1H), 6.47 (s, 1H), 5.02 (br s, 2H), 2.67 (m, 1H), 1.71-1.88(m, 5H), 1.24-1.43 (m, 5H); $^{19}$F NMR (acetone-$d_6$) 300 MHz: −112.86 (d).

[EXAMPLE 171

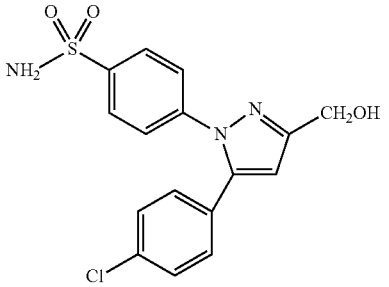

4-[5-(4-Chlorophenyl)-3-hydroxymethyl-1H-pyrazol-1-yl] benzenesulfonamide

]

[4-[4-(Aminosulfonyl)phenyl-5-(4-chlorophenyl)-1H-pyrazol-3-carboxylic acid (Example 83) (3.8 g, 10 mmol) and tetrahydrofuran (100 mL) were stirred at room temperature during the dropwise addition of 1.0M borane-tetrahydrofuran complex (30 mL, 30 mmol). The mixture was heated to reflux for 16 hours. The solution was cooled and methanol was added dropwise until gas evolution ceased. Ethyl acetate (100 mL) was added and the mixture was washed successively with 1N hydrochloric acid, brine, sat. aq. sodium bicarbonate solution, and water, dried over magnesium sulfate, filtered and concentrated. The resultant product was recrystallized from ethanol:water to yield 2.6 g (71%) of a white solid: mp 192°-194° C.; $^1$H NMR ($d_6$-DMSO/300 MHz) 7.81 (d, J=8.7Hz, 2H, 7.46 (d, J=8.4Hz, 2H), 7.42 (brs, 2H), 7.40 (d, J=8.7Hz, 2H), 7.26 (d, J=8.4Hz, 2H), 6.63 (s, 1H), 5.35 (t, J=8.0Hz, 1H), 4.50 (d, J=8.0Hz, 2H). Anal. Calc'd for $C_{16}H_{14}N_6SO_2Cl$: C, 52.82; H, 3.88; N, 11.55. Found: C, 52.91; H, 3.88; N, 11.50.]

EXAMPLE 172

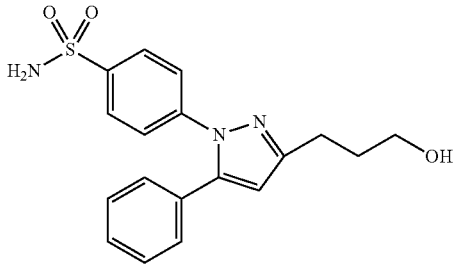

4-[5-Phenyl-3-(3-hydroxypropyl)-1H-pyrazol-1-yl] benzenesulfonamide

A 60% dispersion of sodium hydride in mineral oil (4.0 g, 100 mmol) was twice washed with hexane (100 mL each) and dried under a stream of nitrogen. Ether (300 mL) was added followed by dropwise addition of ethanol (0.25 mL) and γ-butyrolactone (4.0 mL, 52 mmol). The mixture was cooled to 10° C. and acetophenone (5.8 mL, 50 mmol) in ether (40 mL) was added dropwise over 1 hour. The mixture was warmed to 25° C. and stirred overnight. The mixture was cooled to 0° C. and quenched with ethanol (5 mL) followed by 10% aqueous ammonium sulfate (100 mL). The organic solution was separated, dried over $Na_2SO_4$ and concentrated. The residue was chromatographed on silica gel with 1:1 hexane/ethyl acetate to give the desired diketone (3.4 g) as an oil. Pyridine (0.34 mL, 4.2 mmol) and the diketone (700 mg, 3.4 mmol) in methanol (3 mL) were added to a slurry of 4-sulfonamidophenylhydrazine-HCl (750 mg, 3.4 mmol) in methanol (8 mL). The mixture was stirred at 25° C. overnight and concentrated in vacuo. The residue was dissolved in methylene chloride and the solution washed with 1N HCl. The organic solution was separated, dried and concentrated. The residue was chromatographed on silica gel using ethyl acetate to give the desired pyrazole (435 mg) as a solid: Anal. calc'd for $C_{18}H_{19}N_3O_3S$: C, 60.49; H, 5.36; N, 11.75. Found: C, 60.22; H, 5.63; N, 11.54.

EXAMPLE 173

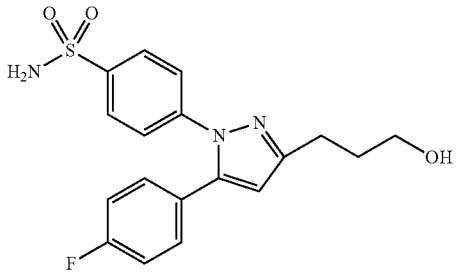

4-[5-(4-Fluorophenyl)-3-(3-hydroxypropyl)-1H-pyrazol-1-yl] benzenesulfonamide

Following the procedure of Example 172, but substituting 4-fluoroacetophenone for acetophenone afforded 4-[5-(4-fluorophenyl)-3-(3-hydroxypropyl)-1H-pyrazol-1-yl]benzenesulfonamide. Anal. calc'd for $C_{18}H_{18}N_3O_3SF.0.25\ H_2O$: C, 56.90; H, 4.91; N, 11.05. Found: C, 56.80; H, 4.67; N, 11.02.

EXAMPLE 174

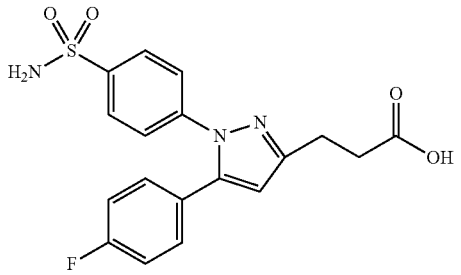

4-[4-(Aminosulfonyl)phenyl]-5-(4-fluorophenyl)-1H-pyrazol]-3-propanoic acid

Jones reagent (0.64 mL of a 2.67M solution) was added dropwise to a solution of 4-[5-(4-fluorophenyl)-3-(3-hydroxypropyl)-1H-pyrazol-1-yl]benzenesulfonamide from Example 173 (295 mg, 0.78 mmol) in acetone (8 mL). The mixture was stirred at 25° C. for 2 hours. The solution was filtered and the filtrate concentrated in vacuo. The residue was dissolved in ethyl acetate and washed with water (3×). The organic solution was dried over $MgSO_4$ and concentrated. The residual oil was crystallized from ether/hexane to give the desired acid (149 mg): mp 180°-182° C.; Anal. calc'd for $C_{18}H_{16}N_3O_4SF$: C, 55.52; H, 4.14; N, 10.79. Found: C, 55.47; H, 4.22; N, 10.50.

[EXAMPLE 175

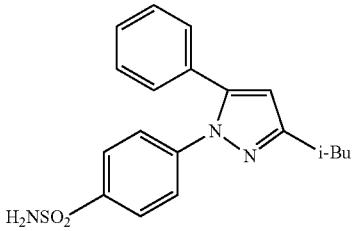

4-(3-Isobutyl]-5-phenyl-1H-pyrazol-1-yl) benzensulfonamide

]

[Step 1: Preparation of 2,3-epoxy-5-methyl-1-phenyl-3-hexanone]

[To a solution of 5-methyl-1-phenyl-1-hexan-3-one (2.0 g, 10.6 mmol) in 15 mL EtOH and 5 mL acetone was added a mixture of 30% hydrogen peroxide (2 mL) and 4N NaOH (1.5 mL) dropwise and the mixture stirred at 25° C. for 1-3 hours. Water (50 mL) was added and the precipitate filtered and dried at 40° C. in vacuo to provide 1.9 g of the epoxide as a white solid: Anal. calc'd for $C_{13}H_{16}O_2.0.1\ H_2O$: C, 75.77; H, 7.92; Found: C, 75.47; H, 7.56.]

[Step 2: Preparation of 4-(3-isobutyl-5-phenyl-1H-pyrazol-1-yl)benzenesulfonamide]

[The epoxide prepared above in Step 1 (1.26 g, 6.11 mmol) and 4-sulfonamidophenylhydrazine hydrochloride (1.38 g, 6.17 mmol) were stirred in 20 mL EtOH with AcOH (0.5 mL) and the mixture refluxed for 3 hours, cooled and quenched with 50 mL $H_2O$. The aqueous layer was extracted with ethyl acetate (3×50 mL), the combined extracts were dried over $MgSO_4$ and concentrated. Flash chromatography using 70:30 hexane/ethyl acetate provided the title compound (0.41 g, 19%) as a white solid: Calc'd for $C_{19}H_{21}N_3O_2S$: C, 64.20; H, 5.96; N, 11.82. Found: C, 64.31; H, 6.29; N, 11.73.]

[EXAMPLE 176

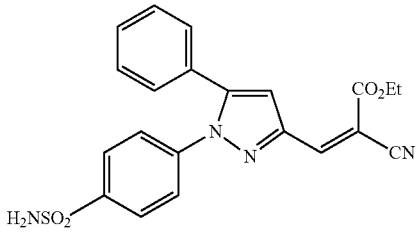

Ethyl 3-[1-[4-(aminosulfonyl)phenyl]-5-phenyl-1H-pyrazol-3-yl]-2-cyano-2-propenoate

]

[Step 1: Preparation of 4-[3-formyl-5-phenyl-1H-pyrazol-1-yl]benzenesulfonamide]

[To a solution of the alcohol prepared in Example 131, Step 3 (1.1 g, 3.3 mmol) in ethyl acetate (20 mL) was added $MnO_2$ (5 g, 60 mmol) and the mixture stirred at room temperature overnight. The mixture was filtered through Celite and the solution was concentrated to provide the crude aldehyde.]

[Step 2: Preparation of Ethyl 3-[1-[4-(aminosulfonyl)phenyl]-5-phenyl-1H-pyrazol-3-yl]-2-cyano-2-propenoate]

[To a solution of the aldehyde from Step 1 (1.2 g, 3.6 mmol) in benzene (18 mL) was added ethyl cyanoacetate (0.38 mL, 3.6 mmol), ammonium acetate (50 mg, 0.7 mmol) and glacial acetic acid (0.17 mL, 2.8 mmol). The solution was heated at reflux for 18 hours, cooled, and partitioned between water and ethyl acetate. The organic solution was washed with a saturated aqueous sodium bicarbonate solution, water and brine. The organic solution was dried and concentrated. The residue was chromatographed on silica (40% hexane in ethyl acetate) to give the desired product (1.0 g, 66%): Anal. calc'd for $C_{21}H_{18}N_4O_4S$: C, 59.82; H, 4.30; N, 13.22. Found: C, 59.70; H, 4.29; N, 13.26.]

[EXAMPLE 177

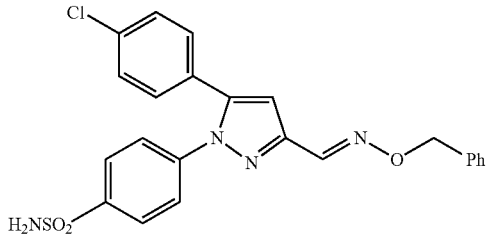

4-[5-(4-Chlorophenyl)-3-[[(phenylmethoxy)imino]methyl]-1H-pyrazol-1-yl] benzenesulfonamide

]

[To a suspension of 220 mg (0.58 mmol) 4-[5-(4-chlorophenyl)-3-formyl-1H-pyrazol-1-yl]benzenesulfonamide (prepared as described in Example 176, Step 1) in dichloromethane (3 mL) was added pyridine (0.12 mL, 1.3 mmol) and O-benzylhyroxylamine hydrochloride (110 mg, 0.68 mmol) and the reaction stirred at room temperature for 18 hours. The mixture was partitioned between pH 7 buffer and dichloromethane and the organic layer was washed with water, dried and concentrated. Flash chromatography on silica gel (2:1 hexane/EtOAc) provided the title compound (151 mg, 56%): mp 158°-159° C.; Anal. calc'd for $C_{23}H_{19}N_4O_3SCl.0.25\ H_2O$: C, 58.59; H, 4.17; N, 11.88. Found: C, 58.43; H, 4.03; N, 11.85.]

[The following compounds in Table VIII were prepared according to procedures similar to that exemplified in Examples 171-177, with the substitution of the appropriate starting material.

TABLE VIII

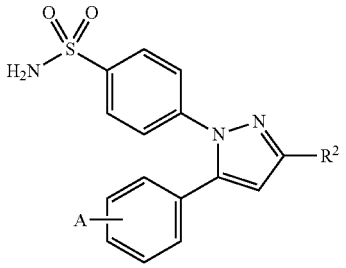

| Ex | A | $R^2$ | M.P. (° C.) | Anal. |
|---|---|---|---|---|
| 178 | H | —$CH_2OH$ | 183-184 | HRMS: 329.0845 |
| 179 | 4-$OCH_3$ | —$CH_2OH$ | 140-142 | Calc. C, 56.81; H, 4.77; N, 11.69<br>Found: C, 56.92; H, 4.76; N, 11.64 |
| 180 | 3,5-di-Cl, 4-$OCH_3$ | —$CH_2OH$ | 191-193 | HRMS 427.0199 |
| 181 | 3-Cl, 4-$OCH_3$ | —$CH_2OH$ | ND | Calc. C, 51.84; H, 4.09; N, 10.67 Cl, 9.00; S,8.14<br>Found: C, 51.77; H, 4.02; N, 10.73; Cl, 9.11; S, 8.03 |
| 182 | 4-$CH_3$ | —$C(CH_3)_2OH$ | 178-179 | |
| 183 | 4-Cl | —$(CH_3)_2CO_2H$ | 156-159 | |
| 184 | 4-Cl | —$CH_2CONH_2$ | 198-200 | |
| 185 | H | —$CH_3$ | ND | Calc. C, 60.46; H, 5.07; N, 13.21<br>Found: C, 60.48; H, 4.95; N, 13.19 |
| 186 | 4-Cl | —$CH_2CN$ | 212-214 | Calc. C, 54.77; H, 3.51 N, 15.03<br>Found: C, 54.94; H, 3.61; N, 14.88 |

]

EXAMPLE 187

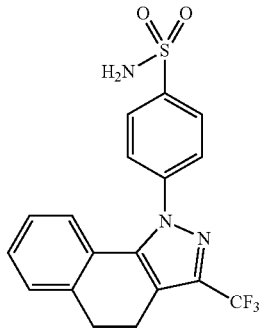

4-[4,5-Dihydro-3-(trifluoromethyl)-1H-benz[g]indazol-1-yl] benzenesulfonamide

Step 1: Preparation of 2-trifluoroacetyl-1-tetralone

A 250 mL one necked round bottom flask equipped with a reflux condenser, nitrogen inlet and provisions for magnetic stirring was charged with ethyl trifluoroacetate (28.4 g, 0.2 mol) and 75 mL of ether. To this solution was added 48 mL of 25% sodium methoxide in methanol (0.21 mol). A solution of 1-tetralone (29.2 g, 0.2 mol) in 50 mL of ether was added over about 5 minutes. The reaction mixture was stirred at room temperature for 14 hours and was diluted with 100 mL of 3N HCl. The phases were separated and the organic layer was washed with 3N HCl, and with brine, dried over anhydrous $MgSO_4$, filtered and concentrated in vacuo. The residue was taken up in 70 mL of boiling ethanol/water and cooled to room temperature, whereupon crystals of 2-trifluoroacetyl-1-tetralone formed which were isolated by filtration and air dried to give pure compound (32 g, 81%): mp 48°-49° C.; $^1$H NMR $CDCl_3$ δ 2.8 (m, 2H), 2.9 (m, 2H), 7.2 (d, j=3.0 Hz, 1H), 7.36 (m, 1H), 7.50 (m, 1H), 7.98 (m, 1H), $^{19}$F NMR $CDCl_3$ δ −72.0. EI GC-MS M+=242.

Step 2: Preparation of 4-[4,5-dihydro-3-(trifluoromethyl)-1H)-benz[g]indazol-1-yl]benzenesulfonamide A 100 mL one necked round bottomed flask equipped with reflux condenser, nitrogen inlet and provisions for magnetic stirring was charged with 2-trifluoroacetyl-1-tetralone [from Step 1] (1.21 g, 5.0 mmol), 4-sulfonamidophenylhydrazine hydrochloride (1.12 g, 5.0 mmol) and 25 mL of absolute ethanol. The solution was warmed to reflux for 15 hours and concentrated in vacuo. The residue was dissolved in ethyl acetate[,] *and then* washed with water, and with brine, dried over anhydrous $MgSO_4$, filtered and concentrated in vacuo. The residue was recrystallized from a mixture of ethyl acetate and isooctane to give 1.40 g, 71% of pure product: mp 257°-258° C.; $^1$H NMR ($CDCl_3/CD_3OD$, 4:1) δ 2.7 (m, 2H), 2.9 (m, 2H), 6.6 (m, 1H), 6.9 (m, 1H), 7.1 (m, 1H), 7.16 (m, 1H), 7.53 (m, 2H), 7.92 (m, 2H); $^{19}$F NMR ($CDCl_3$) δ −62.5. [(] FAB-MS M+H=394.

[EXAMPLE 188

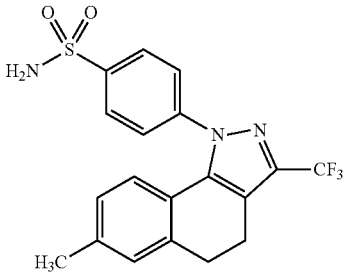

4-[4,5-Dihydro-7-methyl-3-(trifluoromethyl)-1H-benz[g]indazol-1-yl] benzenesulfonamide

]

[Step 1. Preparation of 6-methyl-2-(trifluoroacetyl) tetralone]

[Ethyl trifluoroacetate (5.33 g, 37.5 mmol) was dissolved in ether (50 mL) and treated with a sodium methoxide solution (25% in methanol, 9.92 g, 45.9 mmol) followed by 6-methyltetralone (5.94 g, 37.1 mmol). The reaction was stirred at room temperature for 6.1 hours then treated with 1N HCl (20 mL). The organic layer was collected, washed with brine, dried over $MgSO_4$, and concentrated in vacuo to give a brown oil (8.09 g) that was used in the next step without further purification.]

[Step 2. Preparation of 4-[4,5-dihydro-7-methyl-3-(trifluoromethyl)-1H-benz[g]indazol-1-yl]benzenesulfonamide]

[4-Sulfonamidophenylhydrazine hydrochloride (1.80 g, 8.0 mmol) was added to a stirred solution of the diketone from Step 1 (1.86 g, 7.3 mmol) in ethanol (10 mL). The reaction was heated to reflux and stirred for 14.8 hours. The reaction mixture was cooled and filtered. The filtrate was concentrated in vacuo, dissolved in ethyl acetate, washed with water and with brine, dried over $MgSO_4$ and reconcentrated in vacuo to give the pyrazole as a brown solid (1.90 g, 64%): mp 215°-218° C. $^1$H NMR (acetone-$d_6$) 300 MHz 8.10 (d, 2H), 7.80 (d, 2H), 7.24 (s, 1H), 6.92 (d, 1H), 6.79 (br s, 2H), 6.88 (d,1H), 3.02 (m, 2H), 2.85 (m, 2H), 2.30 (s, 3H). $^{19}$F NMR (acetone-$d_6$) 282 MHz −62.46 (s). High resolution mass spectrum Calc'd. for $C_{19}H_{17}F_3O_2S$: 408.0994. Found: 408.0989.]

[The following compounds in Table IX were prepared according to procedures similar to that exemplified in Examples 187-188, with the substitution of the appropriate ester.

TABLE IX

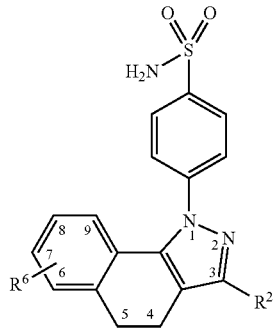

| Ex. | $R^2$ | $R^6$ | M.P. (° C.) | Anal. |
|---|---|---|---|---|
| 189 | —$CHF_2$ | 6-$OCH_3$ | 275-277 | HRMS: 405.0961 |
| 190 | —$CHF_2$ | 7-$CH_3$ | 240-241 | HRMS: 390.1122 |
| 191 | —$CF_3$ | 6,8-$CH_3$ | 284-288 | HRMS: 422.1089 |
| 192 | —$CF_3$ | 7-$OCH_3$ | 277-278 | HRMS: 423.0838 |
| 193 | —$CF_3$ | 7,8-$OCH_3$ | 269-275 | HRMS: 453.1011 |
| 194 | —$CHF_2$ | 7-$OCH_3$ | 256-257 | |
| 195 | —$CO_2CH_3$ | 7-$OCH_3$ | 274-276 | HRMS: 414.1117 |

]

[EXAMPLE 196

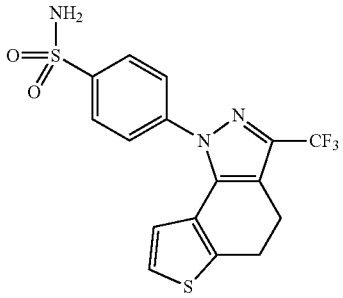

4-[4,5-Dihydro-3-(trifluoromethyl)-1H thieno[3,2-g] indazol-1-yl] benzenesulfonamide

]

[Step 1. Preparation of 4-keto-4,5,6,7-tetrahydrothianaphthene]

[4-(2-Thienyl)butyric acid (28.42 g, 167 mmol) was placed in a round bottom flask with acetic anhydride (30 mL) and phosphoric acid (0.6 mL), and heated to reflux for 3.2 hours. The reaction mixture was poured into 100 mL of water, extracted with ethyl acetate, washed with brine, dried over $MgSO_4$, and concentrated in vacuo to give a brown oil (22.60 g) which was vacuum distilled (1 mm Hg, 107°-115° C.) to give a white solid (13.08 g, 51%): mp 34°-40° C.); $^1$H NMR ($CDCl_3$) 300 MHz 7.29 (d, J=5.2 Hz, 1H), 6.99 (d, J=5.2 Hz, 1H, 2.95 (t, J=6.0 Hz, 2H), 2.47(m, 2H), 2.13(m, 2H). M+H=153.]

[Step 2. Preparation of 4-keto-4,5,6,7-tetrahydro-5-(trifluoroacetyl)thianaphthene]

[Ethyl trifluoroacetate (11.81 g, 83.1 mmol) was dissolved in ether (50 mL) and treated with a sodium methoxide solution (25% in methanol, 18.35 g, 84.9 mmol) followed by 4-keto-4,5,6,7-tetrahydrothianaphthene from Step 1 (12.57 g, 82.6 mmol) dissolved in ether (25 mL). The reaction was stirred for 69.4 hours at room temperature, then treated with 3N HCl (40 mL). The organic layer was collected, washed with brine, dried over $MgSO_4$, and concentrated in vacuo to give a brown solid which was recrystallized from ether/hexane to give the diketone (10.77 g, 52%) as brown needles; mp 54°-64° C.; $^1$H NMR ($CDCl_3$) 300 MHz 15.80 (s, 1H), 7.41 (d, J=5.2 Hz, 1H), 7.17 (d, J=5.2 Hz, 1H), 3.04 (m, 2H), 2.91 (m, 2H), $^{19}$F NMR ($CDCl_3$) 282 MHz −70.37 (s). M+H=249.]

[Step 3. Preparation of 4-[4,5-dihydro-3-(trifluoromethyl)-1H thieno[3,2-g]indazol-1-yl]benzenesulfonamide]

[4-Sulfonamidophenylhydrazine hydrochloride (2.36 g, 10.6 mmol) was added to a stirred solution of the diketone from Step 2 (2.24 g, 9.0 mmol) in ethanol (20 mL). The reaction was heated to reflux and stirred 14.7 hours. The reaction mixture was filtered and washed with ethanol and with water to give the desired pyrazole as a white solid (2.69 g, 75%): mp 288°-290° C.; $^1$H NMR (acetone-$d_6$) 300 MHz 8.12 (d, J=8.7 Hz, 2H), 7.83 (d, J=8.7 Hz, 2H), 7.27 (d, J=5.2 Hz, 1H), 6.81 (br s, 2H), 6.59 (s, J=5.4 Hz, 1H), 3.18 (m, 2H), 3.01 (m, 2H); $^{19}$F NMR (acetone-$d_6$) 282 MHz −62.46 (s). High resolution mass spectrum Calc'd. for $C_{16}H_{12}F_3N_3O_2S_2$: 399.0323. Found: 399.0280.]

EXAMPLE 197

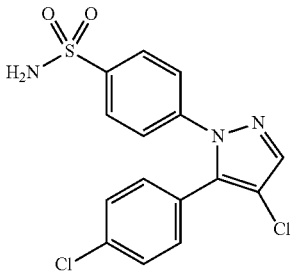

4-[5-(4-Chlorophenyl)-4-chloro-1H-pyrazol-1-yl] benzenesulfonamide

[Step 1. Preparation of 3-[4-(chloro)phenyl]-propane-1,3-dione]

[Ethyl formate (8.15 g, 0.11 mol) and 4'-chloroacetophenone (15.4 g, 0.1 mol) were stirred in ether (150 mL) at room temperature. Sodium methoxide (25%) (23.77 g, 0.11 mol) was added dropwise. The mixture was stirred at room temperature for 16 hours and was then treated with 150 mL of 1N hydrochloric acid. The phases were separated and the ethereal solution washed with brine, dried over magnesium sulfate, filtered and concentrated in vacuo to afford 18.3 g of a yellow oil. The resulting crude mixture was used directly in the next step without purification.]

[Step 2. Preparation of 4-[5-(4-chlorophenyl)-1H-pyrazol-1-yl]benzenesulfonamide]

[3-[4-(Chloro)phenyl]-propane-1,3-dione from Step 1 (18.3 g, 0.1 mol) and 4-sulfonamidophenylhydrazine hydrochloride (22.4 g, 0.1 mol) were dissolved in 150 mL of absolute ethanol and heated to reflux for 16 hours. The solution was cooled to room temperature, diluted with 100 mL of water and let stand, whereupon crystals of pyrazole formed that were isolated by filtration to provide 8.4 g (25%) of a white solid: mp 185°-187° C.; $^1$H NMR ($CDCl_3$/300 MHz) 7.89 (d, J=8.7Hz, 2H), 7.76 (d, J=1.8Hz, 1H), 7.43 (d,J=8.7Hz, 2H), 7.34 (d, J=8.7Hz, 2H), 7.17 (d, J=8.7Hz, 2H), 6.53 (d, J=1.8Hz, 1H), 4.93 (brs 2H). Anal. Calc'd for $C_{15}H_{12}N_3SO_2Cl$: C, 53.97; H, 3.62; N, 12.59. Found: C, 54.08; H, 3.57; N, 12.64.]

[Step 3. Preparation of 4-[5-(4-chlorophenyl)-4-chloro-1H-pyrazol-1-yl]benzenesulfonamide]

[4-[5-(4-Chlorophenyl)-1H-pyrazol-1-yl]benzenesulfonamide from Step 2 (3.0 g, 9 mmol) was dissolved in 50 mL of acetic acid, and 9 mL of 1M chlorine in acetic acid was added dropwise. The mixture was stirred for 16 hours when sat. aq. sodium bicarbonate solution was slowly added until the mixture was neutral to pH paper. The mixture was extracted with ethyl acetate (3×50 mL), combined and washed with sat. aq. sodium bicarbonate and with brine, dried over magnesium sulfate, filtered, and concentrated. The resultant product was recrystallized from isopropanol to yield 2.6 g (78%) of a white solid: mp 168°-171° C. (dec); $^1$H NMR (DMSO-$D_6$/300 MHz) 8.08 (s, 1H), 7.83 (d, J=8.7Hz, 2H), 7.55 (d, J=8.7Hz, 2H), 7.46 (brs, 2H), 7.44 (d, J=8.7Hz, 2H), 7.35 (d, J=8.7Hz, 2H). Anal. Calc'd for $C_{15}H_{11}N_3SO_2Cl_2$: C, 48.93; H, 3.01; N, 11.41. Found: C, 49.01; H, 2.97; N, 11.41.]

[EXAMPLE 198

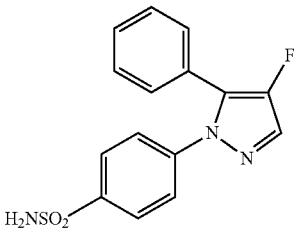

4-(4-Fluoro-5-phenyl]-1H-pyrazol-1-yl) benzenesulfonamide

]

[Step 1: Preparation of 2-fluoroacetophenone]

[To a solution of 2-hydroxyacetophenone (2.5 g, 18.4 mmol) in 100 mL $CH_2Cl_2$ at −78° C., was added triflic anhydride (10 g, 35.4 mmol) followed by 2,6-lutidine (4.1 mL, 35.4 mmol) and the mixture stirred at −78° C. for 50 minutes. The mixture was poured into $CH_2Cl_2$ and water and the $CH_2Cl_2$ layer separated, washed with brine, dried over $Na_2SO_4$ and concentrated to a peach solid. To a solution of the crude triflate in 100 mL THF was added 35 mL of 1N tetrabutylammonium fluoride in THF. The mixture was refluxed for 15 minutes, cooled and poured into ether and water. The ether layer was separated, washed with brine, dried over $Na_2SO_4$ and concentrated. Flash chromatography on silica gel using 20:1 hexane/EtOAc furnished the α-fluoroketone (0.852 g, 33.5%).]

[Step 2: Preparation of 4-(4-fluoro-5-phenyl-1H-pyrazol-1-yl)benzenesulfonamide]

[A solution of 2-fluoroacetophenone (200 mg, 1.45 mmol) in 2 mL dimethylformamide-dimethylacetal was refluxed for 18 hours. The mixture was cooled and concentrated to give the crude enaminoketone. Without further purification, the enaminoketone was treated with 4-sulfonamidophenyl hydrazine hydrochloride (0.34 g, 1.52 mmol) in 10 mL EtOH at reflux for 17 hours. The mixture was cooled, filtered and the filtrate concentrated to a yellow gum. Flash chromatography using a gradient of 5:1 to 2:1 hexane/EtOAc provided 0.11 g of a yellow solid: Recrystallization from ether/hexane gave the product as a pale yellow solid. mp 194°-194.5° C.; Anal. calc'd for $C_{15}H_{12}N_3O_2SF.0.2\ H_2O$: C, 56.14; H, 3.89; N, 13.09. Found: C, 55.99; H, 3.65; N, 12.92.]

EXAMPLE 199

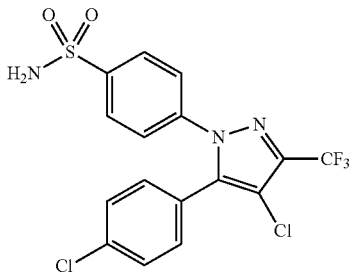

4-[5-(4-Chlorophenyl)-3-(trifluoromethyl)-4-chloro-1H-pyrazol-1-yl]benzenesulfonamide A 100 mL three-necked round-bottomed flask equipped with reflux condenser, gas dispersion tube and provisions for magnetic stirring was charged with 4-[5-(4-chlorophenyl)-3-trifluoromethyl-1H-pyrazol-1-yl]benzenesulfonamide (Example 1) (500 mg, 1.2 mmol) and 50 mL of glacial acetic acid. The solution was stirred at room temperature and treated with a stream of chlorine gas for a period of 15 minutes. The solution was then stirred at room temperature for 1.25 hours and then diluted with 100 mL of water. The solution was then extracted three times with ether and the combined ethereal phase washed with brine, dried over $MgSO_4$, filtered, and concentrated in vacuo to give a white solid that was recrystallized from ether/petroleum ether to provide 390 mg (75%) of 4-[5-(4-chlorophenyl)-4-chloro-3-trifluoromethyl-1H-pyrazol-1-yl]benzenesulfonamide: mp 180°-182° C.; $^1H$ NMR ($CDCl_3$/300 MHz) 7.97 (d, J=6.6Hz, 2H, 7.49 (d, 2H), 7.45 (d, J=6.3Hz, 2H), 7.25 (d, J=6.6Hz, 2H), 5.78 (brs, 2H).

[EXAMPLE 200

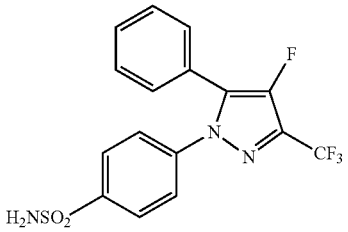

4-[4-Fluoro-5-phenyl-3-(trifluoromethyl)-1H-pyrazol-1-yl]benzenesulfonamide

]

[Step 1: Preparation of 4,4,4-trifluoro-1-phenylbutane-1,3-dione]

[To a solution of 2-fluoroacetophenone from Step 1 of Example 198 (0.48 g, 3.4 mmol) in 25 mL THF at −78° C., was added 1N lithium bis(trimethylsilyl)amide (4 mL) and the mixture stirred at −78° C. for 45 minutes. 1-(Trifluoroacetyl)imidazole (0.65 mL, 5.7 mmol) was added and the mixture stirred at −78° C. for 30 minutes and at 0° C. for 30 minutes. The mixture was quenched with 0.5N HCl, poured into ether and water, and the ether layer separated, washed with brine, dried over $Na_2SO_4$ and concentrated. Flash chromatography on silica gel using a gradient of 10:1 to 4:1 hexane/EtOAc furnished the 1,3-diketone (0.34 g, 43%).]

[Step 2: Preparation of 4-[4-fluoro-5-phenyl-3-trifluoromethyl-1H-pyrazol-1-yl]benzenesulfonamide]

[The diketone from Step 1 (0.34 g, 1.45 mmol) was treated with 4-sulfonamidophenyl hydrazine hydrochloride (0.35 g, 1.56 mmol) in 15 mL EtOH at reflux for 15 hours. The mixture was cooled, filtered and the filtrate concentrated to a yellow gum. Flash chromatography using 3:1 hexane/EtOAc provided 0.28 g of a yellow solid. Recrystallization from $CH_2Cl_2$/hexane gave the product as a pale yellow solid: Anal. calc'd for $C_{16}H_{11}N_3O_2SF_4$: C, 49.87; H, 2.88; N, 10.90. Found: C, 49.79; H, 2.88; N, 10.81.]

[EXAMPLE 201

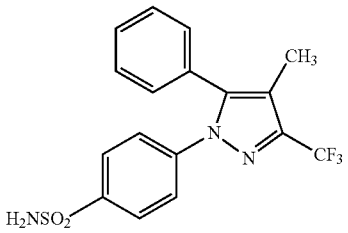

4-[4-Methyl-5-phenyl]-3-(trifluoromethyl)-1H-pyrazol-1-yl]benezenesulfonamide

]

[Step 1: Preparation of 2-methyl-1-phenyl-4,4,4-trifluorobutane-1,3-dione]

[To a solution of propiophenone (965 mg, 7.2 mmol) in THF (20 mL) at −78° C. was added sodium bis(trimethylsilyl) amide (7.9 mL of a 1M solution in THF). The solution was kept at −78° C. for 0.5 hour and then warmed to −20° C. over 1 hour. The solution was cooled to −78° C. and 1-(trifluoroacetyl)imidazole (1.5 g, 9.1 mmol) in THF (4 mL) was added via cannula. The solution was warmed to room temperature and stirred overnight. The mixture was partitioned between 1N HCl and ether. The organic solution was dried ($Na_2SO_4$) and concentrated to give the crude diketone (1.9 g).]

[Step 2: Preparation of 4-[4-methyl-5-phenyl-3-(trifluoromethyl)-1H-pyrazol-1-yl]benzenesulfonamide]

[The diketone from Step 1 was dissolved in absolute ethanol (25 mL) and 4-sulfonamidophenylhydrazine hydrochloride (2.0 g, 9.0 mmol) was added. The mixture was heated at reflux for 19 hours. Volatiles were removed in vacuo and the residue dissolved in ethyl acetate. The organic solution was washed with water and brine, dried and concentrated. The residue was chromatographed on silica (2:1 hexane/ethyl acetate) to give the title pyrazol (1.52 g, 49%): mp 145°-146° C.; Calc'd for $C_{17}H_{14}N_3O_2SF_3$: C, 53.54; H, 3.70; N, 11.01. Found: C, 53.41; H, 3.66; N, 10.92.]

[EXAMPLE 202

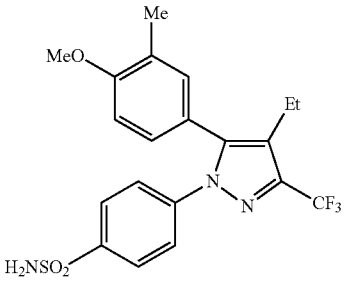

4-[4-Ethyl-5-(3-methyl-4-methoxyphenyl)-3-(trifluoromethyl)-1H-pyrazol-1-yl]benzenesulfonamide

]

[Step 1: Preparation of 4-methoxy-3-methylbutyrophenone]

[To a suspension of aluminum chloride (10.3 g, 77.2 mmol) in dichloromethane (40 mL) at 0° C. was added dropwise a solution of 2-methylanisole (5.0 mL, 35.3 mmol) and butyric anhydride (5.8 mL, 35.3 mmol). The reaction solution was kept at 0° C. for 2 hours and then warmed to room temperature and stirred overnight. The reaction solution was poured into conc. HCl (9 mL) and ice water (80 mL). The reaction was extracted with dichloromethane and the organic layer was washed with 2N NaOH and brine, dried and concentrated. The residue was chromatographed on silica (9:1 hexane:ethyl acetate) to give the desired product (5.2 g, 77%).]

[Steps 2 and 3: Preparation of 4-[4-ethyl-5-(3-methyl-4-methoxyphenyl)-3-(trifluoromethyl)-1H-pyrazol-1-yl]benzenesulfonamide]

[The title compound was prepared from the butyrophenone in Step 1 using the procedure described in Example 201, Steps 1 and 2: mp 135°-136° C.; Calc'd for $C_{20}H_{20}N_3O_3SF_3$: C, 54.66; H, 4.59; N, 9.56. Found: C, 54.11; H, 4.38; N, 9.43.]

[EXAMPLE 203

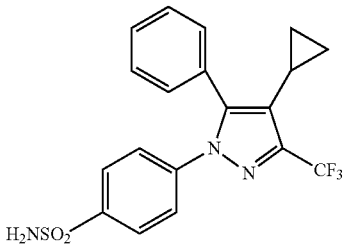

4-[4-Cyclopropyl-5-phenyl-3-(trifluoromethyl)-1H-pyrazol-1-yl]benzenesulfonamide

]

[Step 1: Preparation of 2-cyclopropylacetophenone]

[To a suspension of sodium cyanide (1.8 g, 37.0 mmol) in dimethyl sulfoxide (20 mL) at 60° C. was added dropwise (bromomethyl)cyclopropane (5.0 g, 37.0 mmol). The addition was done at such a rate to keep the temperature of the reaction at 60° C. After the addition was completed, the reaction mixture was heated at 80° C. for 15 minutes. The mixture was cooled and partitioned between ether and water. The organic solution was washed with 1N HCl and water, dried and concentrated. The residue was dissolved in ether (5 mL) and added to a solution of phenyl magnesium bromide (25 mL of a 3M solution in ether) in ether (20 mL) and benzene (25 mL). The reaction mixture was stirred at room temperature for 20 hours, then poured into a 1N HCl solution and stirred for 1.5 hours. The organic solution was separated and the aqueous solution extracted with dichloromethane. The organic solution was dried and concentrated. The residue was chromatographed on silica (9:1 hexane:ethyl acetate) to give the desired product (2.0 g, 34%).]

[Steps 2 and 3: Preparation of 4-[4-cyclopropyl-5-phenyl-3-(trifluoromethyl)-1H-pyrazol-1-yl]benzenesulfonamide]

[The title compound was prepared from the acetophenone in Step 1 using the procedure described in Example 201), Steps 1 and 2: mp 173°-174° C.; Calc'd for $C_{19}H_{16}N_3O_2SF_3$: C, 56.01; H, 3.96; N, 10.31. Found: C, 55.85; H, 3.78; N, 10.19.]

[EXAMPLE 204

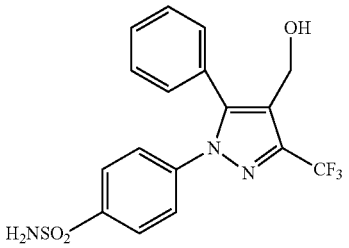

4-[4-hydroxymethyl-5-phenyl-3-(trifluoromethyl)-1H-pyrazol-1-yl]benzenesulfonamide

]

[Step 1: Preparation of 4-[4-bromomethyl-5-phenyl-3-(trifluoromethyl)-1H-pyrazol-1-yl]benzenesulfonamide]

[To a solution of 4-[4-methyl-5-phenyl-3-(trifluoromethyl)-1H-pyrazol-1-yl]benzenesulfonamide prepared in Example 201 (500 mg, 1.3 mmol) in carbon tetrachloride (9 mL) and benzene (4 mL) was added N-bromosuccinimide (285 mg, 1.6 mmol). The mixture was irradiated with a sunlamp for 3.5 hours. The reaction mixture was partitioned between dichloromethane and water and the organic solution was dried and concentrated to give the desired product, 412 mg (69%).]

[Step 2: Preparation of 4-[4-formyl-5-phenyl-3-(trifluoromethyl)-1H-pyrazol-1-yl]benzenesulfonamide]

[To a solution of the compound prepared in Step 1 (362 mg, 0.79 mmol) in dimethyl sulfoxide (7 mL) was added collidine (0.14 mL, 1.0 mmol). The solution was heated at 120° C. for 3 hours and then kept at overnight at room temperature. The reaction solution was partitioned between ethyl acetate and water and the organic solution was washed with water, dried and concentrated. The residue was chromatographed (1:1 hexane:ethyl acetate) to give the desired product (205 mg, 66%).]

[Step 3: Preparation of 4-[4-hydroxymethyl-5-phenyl-3-(trifluoromethyl)-1H-pyrazol-1-yl]benzenesulfonamide]

[To a solution of the aldehyde prepared in Step 2 (165 mg, 0.41 mmol) in methanol (3.5 mL) at 0° C. was added sodium borohydride (16 mg, 0.41 mmol). The reaction solution was kept at 0° C. for 2.5 hours. The reaction was quenched with the addition of an aqueous 1M $KHSO_4$ solution (3 mL). The mixture was extracted with dichloromethane and the organic solution dried and concentrated. The residue was chromatographed on silica (1:1 hexane:ethyl acetate) to give the desired product (36 mg, 46%): m.p. 179°-180° C.; $^1$H NMR d 7.91 (m, 2H), 7.53-7.40 (m, 5H), 6.75 (s, 2H), 4.53 (d, 2h, J=5.0 Hz), 4.30 (t, 1H, J=5.0 Hz).]

[EXAMPLE 205

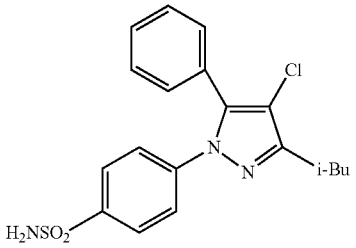

4-(4-Chloro-3-isobutyl-5-phenyl]-1H-pyrazol-1-yl)benzenesulfonamide

]

[To a solution of the pyrazole prepared in Example 175 (0.15 g, 0.42 mmol) in $CH_2Cl_2$ (10 mL) was added an excess of sulfuryl chloride slowly at room temperature. The mixture was stirred at room temperature for 2 hours, quenched with water and the aqueous layer extracted three time with methylene chloride. The combined organic layers were dried over $MgSO_4$ and concentrated to give an oil which was purified by flash chromatography on silica gel using 70:30 hexane/ethyl acetate as eluent to give the desired compound: HRMS m/z 389.0970 (calc'd for $C_{19}H_{20}ClN_3SO_2$, 389.0965).]

[The following compounds in Table X were prepared according to procedures similar to that exemplified in Examples 197-205, with the substitution of the appropriate starting material.

TABLE X

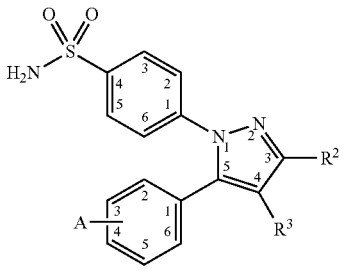

| Ex. | $R^3$ | $R^2$ | A | MP (° C.) | Analytical |
|---|---|---|---|---|---|
| 206 | Cl | H | 4-F | 175-178 | Calc C, 51.22; H, 3.15; N, 11.94<br>Obs. C, 51.43; H, 3.10; N, 11.82 |

TABLE X-continued

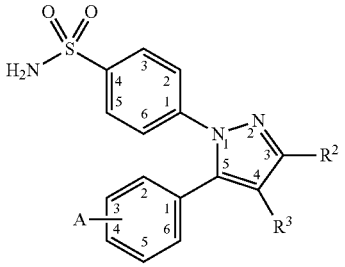

| Ex. | $R^3$ | $R^2$ | A | MP (° C.) | Analytical |
|---|---|---|---|---|---|
| 207 | Br | H | 4-Cl | 209-210 | Calc. C, 43.66; H, 2.69; N, 10.18<br>Obs. C, 43.74; H, 2.70; N, 10.23 |
| 208 | Cl | H | H | 172-174 | Calc. C, 53.98; H, 3.62; N, 12.59 Cl, 10.62; S, 9.60<br>Obs. C, 54.17; H, 3.64, N, 12.45 Cl, 10.46; S, 9.42 |
| 209 | Cl | H | 3-di-Cl, 4-$OCH_3$ | 211-212 | Calc. C, 44.41; H, 2.80; N, 9.71<br>Obs. C, 44.72; H, 3.04, N, 9.72 |
| 210 | Br | H | 4-$CH_3$ | ND | HRMS: 391.0003 |
| 211 | Cl | H | 4-$CH_3$ | 160-163 | Calc. C, 55.25; H, 4.06; N, 12.08<br>Obs. C, 55.06; H, 4.03. N, 12.02 |
| 212 | Cl | H | 3-Cl, 4-$OCH_3$ | ND | Calc. C, 48.25; H, 3.29; N, 10.55 Cl, 17.80; S, 8.05<br>Obs. C, 48.10; H, 3.31. N, 10.52 Cl, 17.70; S, 7.98 |
| 213 | Cl | H | 4-$OCH_3$ | 155-156 | Calc. C, 52.82; H, 3.88; N, 11.55<br>Obs. C, 52.18;H, 3.93, N, 11.41 |
| 214 | Br | H | 4-$OCH_3$ | 130-132 | |
| 215 | CN | H | 4-$OCH_3$ | 216-219 | HRMS: 355.0860 |
| 216 | Cl | H | 3,5-di-F, 4-$OCH_3$ | 196-199 | Calc. C, 48.07; H, 3.03; N, 10.51<br>Obs. C, 48.45; H, 355, N, 10.10 |
| 217 | $SO_2CH_3$ | H | Cl | 182-185 | Calc. C, 46.66; H, 3.43; N, 10.20<br>Obs. C, 46.57; H, 3.49, N, 10.39 |
| 218 | $C_2H_5$ | $CF_3$ | H | 177-178 | Calc. C, 54.68; H, 4.08; N, 10.62<br>Obs. C, 54.61; H, 4.10; N, 1054 |
| 219 | $CH_3$ | $CF_3$ | 4-$OCH_3$ | 158-159 | Calc. C, 52.55; H, 3.92; N, 10.21<br>Obs. C, 52.27; H, 4.00; N, 10.16 |
| 220 | $CH_3$ | $CF_3$ | 4-Cl | 154-155 | Calc. C, 49.10; H, 3.15; N, 10.10<br>Obs. C, 49.05; H, 3.02; N, 9.96 |
| 221 | $CH_3$ | $CF_3$ | 44 | 103-104 | Calc. C, 51.13; H, 3.28; N, 10.52<br>Obs. C, 51.09; H, 3.26; N, 1034 |
| 222 | $C_2H_5$ | $CF_3$ | 4-Cl | ND | Calc. C, 50.30; H, 3.52; N, 9.77<br>Obs. C, 50.40; H, 3.51; N, 9.72 |
| 223 | $CH_3$ | $CF_3$ | 4-$CH_3$ | 144-145 | Calc. C, 54.68; H, 4.08; N, 10.62<br>Obs. C, 5438; H, 3.87; N, 1031 |
| 224 | $C_2H_5$ | $CF_3$ | 4-$CH_3$ | 142-143 | Calc. C, 55.74; H, 4.43; N, 10.26<br>Obs. C, 55.60; H, 4.37; N, 10.17 |
| 225 | $C_2H_5$ | $CF_3$ | 4-$OCH_3$ | 160-161 | Calc. C, 53.64; H, 4.26; N, 9.87<br>Obs. C, 53.55; 4.23; N, 9.65 |
| 226 | $C_2H_5$ | $CF_3$ | 3-F, 4-$OCH_3$ | 156-157 | Calc. C, 51.46; H, 3-86; N, 9.47<br>Obs. C, 51.27; H, 3.75; N, 9.33 |
| 227 | Br | $CHF_2$ | 4-Cl | 224-226 | Calc. C, 41.53; H, 2.40; N, 9.08<br>Obs. C, 41.50; H, 238; N, 9.00 |
| 228 | Cl | $CHF_2$ | 3,5-di-Cl, 4-$OCH_3$ | 92-102(dec) | Calc C, 42.30; H, 2.51; N, 8.70<br>Obs. C, 42.50; H, 2.67, N, 8.56 |
| 229 | Cl | $CHF_2$ | H | 174-176 | Calc. C, 50.07; H, 3.15; N, 10.95<br>Obs. C, 50.07; H, 3.18, N, 10.98 |
| 230 | Br | $CHF_2$ | H | 184-186 | Calc. C, 44.87; H, 2.82; N, 9.81<br>Obs. C, 44.98; H, 2.81, N, 9.64 |
| 231 | Cl | $CHF_2$ | 4-$OCH_3$ | 171-172 | HRMS: 413.0351 |
| 232 | Cl | CN | H | 174-l77(sub) | Calc. C, 53.56; H, 3.09; N, 15.61;<br>Cl, 9.98; S, 8.94<br>Obs. C, 53.81; H, 3.18; N, 15.43;<br>Cl, 9.78; S, 8.91 |
| 233 | Cl | CN | 4-Cl | ND | Calc. C, 48.87; H, 2.56; N, 14.25;<br>Cl, 18.03; S, 8.15<br>Obs. C, 48.99; H, 2.55; N, 14.30;<br>Cl, 17.96; S, 8.08 |
| 234 | Cl | CN | 4-F | ND | Calc. C, 51.00; H, 2.68; N, 14.87;<br>Cl, 9.41; S, 8.51<br>Obs. C, 51.19; H, 2.73; N, 14.98;<br>Cl, 9.22; S, 8.56 |
| 235 | Br | CN | 4-F | ND | Calc. C, 45.62; H, 239; N, 13.30;<br>Br, 18.97; S, 7.61<br>Obs. C, 45.51; H, 2.36; N, 13.21;<br>Br, 19.09; S, 7.51 |

TABLE X-continued

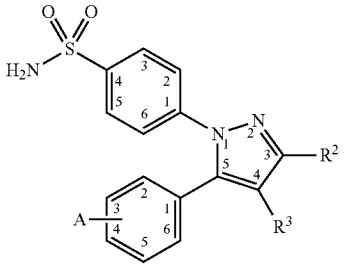

| Ex. | $R^3$ | $R^2$ | A | MP (° C.) | Analytical |
|---|---|---|---|---|---|
| 236 | Br | CN | H | ND | Calc. C, 47.66; H, 2.75; N, 13.89; Br, 19.81; S, 7.95 Obs. C, 47.62; H, 2.77; N, 13.77; Br, 19.74; S, 8.04 |
| 237 | Br | $CO_2C_2H_5$ | 4-Cl | ND | HRMS: 482.9707 |
| 238 | Cl | $CO_2CH_3$ | H | ND | HRMS: 342.0495 |
| 239 | Cl | $CO_2CH_3$ | 4-Cl | ND | HRMS: 426.0128 |
| 240 | Cl | $CO_2C_2H_5$ | 4-Cl | ND | HRMS: 440.0207 |
| 241 | Cl | $CO_2CH_3$ | 4-F | ND | HRMS: 410.0391 |
| 242 | Br | $CO_2CH_3$ | 4-F | ND | HRMS: 453.9880 |
| 243 | Cl | $CO_2CH_3$ | 4-$OCH_3$, 3-Cl | ND | Calc. C, 47.38; H, 331; N, 9.21; Cl, 15.54; S, 7.03 Obs. C, 47.10; H, 3.26; N, 9.01; Cl, 15.74; S, 6.92 |
| 244 | Cl | $CO_2CH_3$ | 4-$OCH_3$, 3,5-di-Cl | 198-199 | Calc. C, 44.06; H, 2.88; N, 8.56 Obs. C, 43.59; H, 2.77; N, 8.44 |
| 245 | Cl | $CO_2CH_3$ | 4-$OCH_3$, 3-Br | ND | Calc. C, 43.18, H, 3.02; N, 839; S, 6.40 Obs. C, 43.25; H, 257; N, 8.40; S, 6.59 |
| 246 | Cl | $CONH_2$ | H | ND | HRMS: 377.0539 |
| 247 | Cl | $CONH_2$ | 4-Cl | ND | HRMS: 411.0115 |
| 248 | Cl | $CONH_2$ | 4-F | ND | HRMS: 395.0397 |
| 249 | Br | $CONH_2$ | 4-F | ND | Calc. C, 43.75, H, 2.75; N, 12.75; Br, 18.19; S, 7.30 Obs. C, 43.65; H, 2.78; N, 12.66; Br, 18.13; S, 7.21 |
| 250 | Br | $CONH_2$ | H | ND | HRMS: 419.9920 |
| 251 | Cl | $CO_2H$ | H | ND | HRMS: 377.0249 |
| 252 | Cl | $CO_2H$ | 4-Cl | ND | Calc. C, 46.62, H, 2,69; N, 10.19; Cl, 17.20; S, 7.78 Obs. C, 46.59, H, 2.68; N, 10.21; Cl, 17.25; S, 7.73 |
| 253 | Cl | $CO_2H$ | 4-$OCH_3$, 3,5-di-Cl | 220(dec) | Calc. C, 42.83: H, 2.54; N, 8.81 Obs. C, 43.65; H, 2.52; N, 8.78 |
| 254 | Cl | $CH_3$ | H | ND | Calc. C, 55.25; H, 4.06; N, 12.08 Obs. C, 55.24; H, 4.26; N, 12.17 |
| 255 | Cl | $CH_2OH$ | H | 195-197 | HRMS: 363.0431 |
| 256 | Cl | $CH_2OH$ | 4-Cl | 203-204 | Calc. C, 48.25; H, 3.29; N, 10.55 Obs. C, 48.36; H, 3.27; N, 10.50 |
| 257 | Cl | $(CH_2)_2CO_2H$ | 4-Cl | 212-214 | Calc. C, 49.10; H, 3.43; N, 9.54 Obs. C, 49.23; H, 3.45; N, 9.49 |
| 258 | $OCH_3$ | $CF_3$ | H | 137-138 | Calc. C, 51.38; H, 3.55; N, 10.57 Obs. C, 51.40; H, 3.47; N, 10.47 |

]

[EXAMPLE 259

]

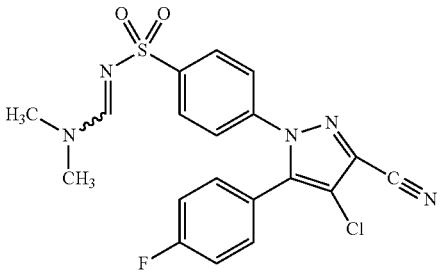

4-[4-chloro-3-cyano-5-[4-(fluoro)phenyl])-1H-pyrazol-1-yl]-N[(dimethylamino)methylene] benzenesulfonamide

[Increasing the polarity of the eluant used in the purification in Example 234 to 60% ethyl acetate, upon concentration of the appropriate fractions, yielded 4-[4-chloro-3-cyano-5-[4-(fluoro)phenyl])-1H-pyrazol-1-yl]-N-[(dimethylamino) methylene]benzenesulfonamide (0.485 g, 15%): High Resolution Mass Spectrum (MLi+) calc'd: 438.0779. Found: 438.0714. Elemental analysis calc'd for $C_{19}H_{15}N_5O_2FClS$: C, 52.84; H, 3.50: N, 16.22; Cl, 8.21; S, 7.42. Found: C, 52.76; H, 3.52; N, 16.12; Cl, 8.11; S, 7.35.]

[EXAMPLE 260

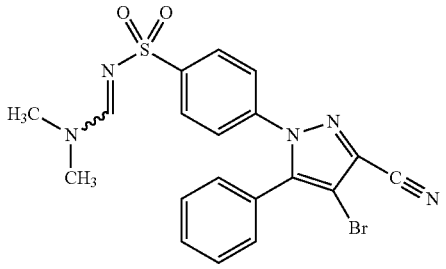

4-[4-Bromo-3-cyano-5-phenyl-1H-pyrazol-1-yl]-N-[(dimethylamino)methylene]benzenesulfonamide

]

[Similarly, 4-[4-bromo-3-cyano-5-phenyl-1H-pyrazol-1-yl]-N-[(dimethylamino)methylene]benzenesulfonamide was isolated from the purification of Example 235 (0.153 g, 28%): High Resolution Mass Spectrum (M+) calc'd: 457.0208. Found: 457.0157. Elemental analysis calc'd for $C_{19}H_{16}N_5O_2BrS$: 49.79; H, 3.52: N, 15.28; Br, 17.43; S, 6.99. Found: C, 49.85; H, 3.56; N, 15.10; Br, 17.52; S, 6.87.]

EXAMPLE 261

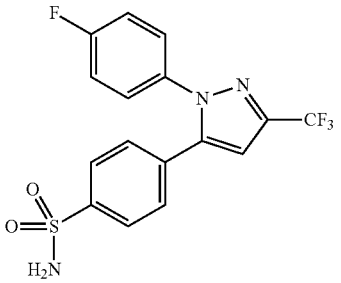

4-[1-(4-Fluorophenyl)-3-(trifluoromethyl)-1H-pyrazol-5-yl]benzenesulfonamide

[Step 1: Preparation of N,N-bis(4-methoxybenzyl)-4-(aminosulfonyl)acetophenone]

[To a solution of 4-(aminosulfonyl)acetophenone (2.0 g, 9.0 mmol) in dimethylsulfoxide (25 mL) was added sodium hydride (450 mg, 19.0 mmol). The reaction mixture was stirred for 45 minutes and then 4-methoxybenzyl bromide (3.5 g, 19.0 mmol) in dimethylsulfoxide (5 mL) was added via cannula. The mixture was stirred at room temperature for 24 hours and partitioned between ethyl acetate and pH 7 buffer. The aqueous solution was extracted with ethyl acetate. The organic solution was dried ($MgSO_4$) and concentrated. The residue was chromatographed on silica (2:1 hexane:ethyl acetate) to give the desired product (815 mg, 21%).]

[Step 2: Preparation of N,N-bis(4-methoxybenzyl)-4-[1-(4-fluorophenyl)-3-trifluoromethyl-1H-pyrazol-5-yl]benzenesulfonamide]

[To a 25% sodium methoxide solution in methanol (0.2 mL) was added ethyl trifluoroacetate (75 mg, 0.53 mmol) and the protected acetophenone from Step 1 (235 mg, 0.53 mmol). THF (0.5 mL) was added and the reaction mixture was heated at reflux for 2 hours and then stirred at room temperature overnight. The mixture was partitioned between ether and 1N HCl solution. The organic solution was dried and concentrated to give the crude diketone (279 mg), which was diluted with absolute ethanol (2.5 mL). To this slurry was added pyridine (49 mg, 0.62 mmol) and 4-fluorophenylhydrazine hydrochloride (80 mg, 0.50 mmol). The mixture was stirred at room temperature for 24 hours and concentrated in vacuo. The residue was dissolved in methylene chloride and washed with 1N HCl. The organic solution was dried and concentrated. The residue was chromatographed on silica (3:1 hexane:ethyl acetate) to give the protected pyrazole (159 mg, 51%).]

[Step 3: Preparation of 4-[1-(4-fluorophenyl)-3-trifluoromethyl-1H-pyrazol-5-yl]benzenesulfonamide]

[To a solution of the protected pyrazole (50 mg, 0.08 mmol) in acetonitrile (1 mL) and water (0.3 mL) was added ceric ammonium nitrate (360 mg, 0.65 mmol). The reaction solution was kept at room temperature for 16 hours. The solution was poured into water (15 mL) and extracted with ethyl acetate (2×25 mL). The combined extracts were dried ($MgSO_4$) and concentrated. The residue was chromatographed on silica (2:1 hexane:ethyl acetate) to give the desired product (13 mg, 42%): $^1H$ NMR ($CD_3OD$) 7.88 (d,2H), 7.46 (d, 2H), 7.39 (dd, 2H), 7.21 (t, 2H), 7.06 (s, 1H).]

[EXAMPLE 262

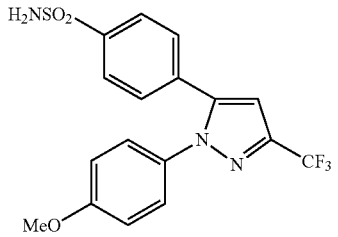

4-[1-(4-methoxyphenyl)-3-(trifluoromethyl)-1H-pyrazol-5-yl]benzenesulfonamide

]

[The title compound was prepared using the procedure described in Example 261: HRMS m/z 397.0702 (calc'd for $C_{17}H_{14}N_3O_3SF_3$. 397.0708).]

BIOLOGICAL EVALUATION

Rat Carrageenan Foot Pad Edema Test

The carrageenan foot edema test was performed with materials, reagents and procedures essentially as described by Winter, et al., (Proc. Soc. Exp. Biol. Med., 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, Laboratory Models for Testing NSAIDS, in Non-steroidal Anti-Inflammatory Drugs, (J. Lombardino, ed. 1985)). [The % inhibition shows the % decrease from control paw volume determined in this procedure and the data for selected compounds in this invention are summarized] *Results are shown* in Table I.

Rat Carrageenan-induced Analgesia Test

The analgesia test using rat carrageenan was performed with materials, reagents and procedures essentially as described by Hargreaves, et al., (Pain, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. [Results are shown in Table XI.]

TABLE XI

| [Examples] *Example* | RAT PAW EDEMA % Inhibition @ 10 mg/kg body weight | ANALGESIA % Inhibition @ 30 mg/kg body Weight |
|---|---|---|
| 1 | 44 | [94] |
| [2] | [35] | [38] |
| [58] | [36] | [65] |
| [59] | [25] | [41] |
| [60] | [49] | [39] |
| [82] | [22*] | |
| [86] | [42*] | |
| [98] | [2*] | |
| [117] | [32] | |
| [129] | [47*] | |
| [170] | [18*] | |
| [171] | [14] | [37] |
| [188] | [32*] | [27] |
| [197] | [45*] | |
| [199] | [35] | |

[*Assay Performed At 30 Mg/Kg Body Weight]

[Evaluation of COX I and COX II activity in vitro]

[The compounds of this invention exhibited inhibition in vitro of COX II. The COX II inhibition activity of the compounds of this invention illustrated in the Examples was determined by the following methods.]

[a. Preparation of recombinant COX baculoviruses]

[A 2.0 kb fragment containing the coding region of either human or murine COX-I or human or murine COX-II was cloned into a BamHI site of the baculovirus transfer vector pVL1393 (Invitrogen) to generate the baculovirus transfer vectors for COX-I and COX-II in a manner similar to the method of D. R. O'Reilly et al (Baculovirus Expression Vectors: A Laboratory Manual (1992)). Recombinant baculoviruses were isolated by transfecting 4 μg of baculovirus transfer vector DNA into SF9 insect cells (2×10 e8) along with 200 ng of linearized baculovirus plasmid DNA by the calcium phosphate method. See M. D. Summers and G. E. Smith, A Manual of Methods for Baculovirus Vectors and Insect Cell Culture Procedures, Texas Agric. Exp. Station Bull. 1555 (1987). Recombinant viruses were purified by three rounds of plaque purification and high titer (10E7-10E8 pfu/ml) stocks of virus were prepared. For large scale production, SF9 insect cells were infected in 10 liter fermentors ($0.5\times10^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.]

[b. Assay for COX I and COX II activity]

[COX activity was assayed as $PGE_2$ formed/μg protein/time using an ELISA to detect the prostaglandin released, CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10-20 minutes prior to the addition of arachidonic acid. Any reaction between the arachidonic add and the enzyme was stopped after ten minutes at 37° C./room temperature by transferring 40 μl of reaction mix into 160 μl ELISA buffer and 25 μM indomethacin. The $PGE_2$ formed was measured by standard ELISA technology (Cayman Chemical). Results are shown in Table XII.

[TABLE XII

| Example | Human COX II $ID_{50}$ μM | Human COX I $ID_{50}$ μM |
|---|---|---|
| 1 | <.1 | 18 |
| 2 | <.1 | 15.0 |
| 3 | <.1 | >100 |
| 4 | .6 | 37.5 |
| 5 | <.1 | 6.3 |
| 6 | .2 | 78.7 |
| 7 | 14 | >100 |
| 8 | 37.7 | >100 |
| 9 | .1 | 55.2 |
| 10 | 2.7 | >100 |
| 12 | 20 | >100 |
| 55 | 22 | 77.9 |
| 56 | <.1 | 11.7 |
| 57 | 47.9 | >100 |
| 58 | <.1 | 5.7 |
| 59 | <.1 | 26.8 |
| 60 | <.1 | .8 |
| 82 | <.1 | 1.1 |
| 84 | <.1 | 65.5 |
| 85 | 73.6 | >100 |
| 86 | .5 | >100 |
| 96 | 6.5 | >100 |
| 97 | 96 | >100 |
| 98 | <.1 | 1.7 |
| 117 | .3 | >100 |
| 128 | 1.1 | >100 |
| 129 | <.1 | 13.5 |
| 130 | 3.6 | 12.5 |

[TABLE XII-continued

| Example | Human COX II $ID_{50}$ μM | Human COX I $ID_{50}$ μM |
|---|---|---|
| 131 | .2 | >100 |
| 138 | .6 | <.1 |
| 170 | .1 | >100 |
| 171 | .8 | >100 |
| 172 | 4.2 | >100 |
| 173 | 4.7 | >100 |
| 174 | 3.5 | 100 |
| 175 | 66.9 | >100 |
| 176 | .3 | >100 |
| 187 | 1.1 | 13.6 |
| 188 | .2 | 19.8 |
| 196 | .6 | 4.1 |
| 197 | <.1 | 3.4 |
| 198 | 4.2 | 56.5 |
| 199 | <.1 | <.1 |
| 200 | <.1 | .5 |
| 201 | <.1 | 2.2 |
| 202 | <.1 | 91 |
| 203 | 27 | >100 |
| 204 | 6.7 | >100 |
| 205 | <.1 | 2.1 |
| 259 | 1.1 | >100 |
| 260 | 1.1 | >100 |
| 261 | <.1 | <.1 |
| 262 | <.1 | <.1] |

]

Also embraced within this invention is a class of pharmaceutical compositions comprising one or more compounds of [Formula I] *the present invention* in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regiment for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably from about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers of diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

[1. A method of treating inflammation or an inflammation-associated disorder in a subject, said method comprising administering to the subject having or susceptible to such inflammation or inflammation-associated disorder, a therapeutically-effective amount of a compound of Formula I (I)

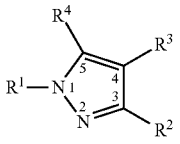

wherein $R^1$ is phenyl substituted at a substitutable position with one or more radicals selected from halo, $C_1$-$C_{10}$-alkyl, and sulfamyl wherein $R^2$ is selected from hydrido, $C_1$-$C_6$-haloalkyl, cyano, carboxy, $C_1$-$C_6$-alkoxycarbonyl, $C_1$-$C_6$-carboxyalkyl, $C_1$-$C_6$-alkoxy, $C_1$-$C_6$-alkylthio, aminocarbonyl, aminocarbonyl-$C_1$-$C_6$-alkyl, $C_1$-$C_6$-N-alkylaminocarbonyl, N-arylaminocarbonyl, $C_1$-$C_6$-N,N-dialkylaminocarbonyl, $C_1$-$C_6$-N-alkyl-N-arylaminocarbonyl, and $C_1$-$C_6$-hydroxyalkyl;

wherein $R^3$ is selected from hydrido, $C_1$-$C_{10}$-alkyl, halo, cyano, $C_1$-$C_6$-alkoxy, $C_1$-$C_6$-hydroxyalkyl, $C_1$-$C_6$-alkylthio, and $C_1$-$C_6$-alkylsulfonyl;

wherein $R^4$ is selected from aryl-$C_2$-$C_6$-alkenyl, aryl, $C_3$-$C_7$-cycloalkyl, $C_3$-$C_7$-cycloalkenyl and five to ten membered heterocyclic; wherein $R^4$ is optionally substituted at a substitutable position with one or more radicals selected from halo, $C_1$-$C_6$-alkylthio, $C_1$-$C_6$-alkylsulfinyl, $C_1$-$C_{10}$-alkyl, $C_1$-$C_6$-alkylsulfonyl, cyano, carboxyl, $C_1$-$C_6$-alkoxycarbonyl, aminocarbonyl, $C_1$-$C_6$-haloalkyl, hydroxyl, $C_1$-$C_6$-alkoxy, $C_1$-$C_6$-hydroxyalkyl, $C_1$-$C_6$-haloalkoxy, sulfamyl, $C_1$-$C_6$-N-alkylaminocrbonyl, amino, $C_1$-$C_6$-N-alkylamino, $C_1$-$C_6$-N,N-dialkylamino, five or six membered heterocyclic, nitro, and

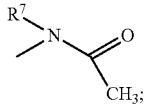

and wherein $R^7$ is hydrido;

wherein aryl wherever occurring means phenyl, naphthyl, tetrahydronaphthyl, indene, biphenyl, provided $R^2$ and $R^3$ are not identical radicals selected from hydrido, carboxyl and ethoxycarbonyl; further provided that $R^2$ is not carboxyl or methyl when $R^3$ is hydrido and when $R^4$ is phenyl; further provided that $R^4$ is not triazolyl when $R^2$ is methyl; further provided that $R^4$ is not aralkenyl when $R^2$ is carboxyl, aminocarbonyl or ethoxycarbonyl; further provided that $R^4$ is not phenyl when $R^2$ is methyl and $R^3$ is carboxyl; further provided that $R^4$ is not 4-chlorophenyl when $R^2$ is methyl and $R^3$ is bromo; further provided that $R^4$ is not unsubstituted thienyl when $R^2$ is trifluoromethyl; and further provided that $R^4$ is aryl substituted with sulfamyl when $R^1$ is phenyl not substituted with sulfamyl; and further provided the compound is not 4-[5-(3-fluoro-4-methoxyphenyl)-3-(difluoromethyl)-1H-pyrazol-1yl]benzenesulfonamide; or a pharmaceutically-acceptable salt thereof.]

[2. The method of claim 1 wherein $R^1$ is phenyl, substituted at a substitutable position with one or more radicals selected from fluoro, chloro, methyl, and sulfamyl;

wherein $R^2$ is selected from hydrido, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, acetyl, propionyl, butyryl, isobutyryl, valeryl, isovaleryl, pivaloyl, and hexanoyl, methoxy, ethoxy, methylthio, aminocarbonyl, aminocarbonylmethyl, N-methylaminocarbonyl, N-ethylaminocarbonyl, N-isopropylaminocarbonyl, N-propylaminocarbonyl, N-butylaminocarbonyl, N-isobutylaminocarbonyl, N-tert-butylaminocarbonyl, N-pentylaminocarbonyl, N-phenylaminocarbonyl, N,N-dimethylaminocarbonyl, N-methyl-N-ethylaminocarbonyl, N-(3-fluorophenyl)aminocarbonyl, N-(4-methylphenyl)aminocarbonyl, N-(3-chlorophenyl)aminocarbonyl, N-methyl-N-(3-chlorophenyl)aminocarbonyl, N-(4-methoxyphenyl)aminocarbonyl, N-methyl-N-phenylaminocarbonyl, hydroxymethyl, and hydroxypropyl;

wherein $R^3$ is selected from hydrido, methyl, ethyl, isopropyl, tert-butyl, isobutyl, hexyl, fluoro, chloro, bromo, cyano, methoxy, methylthio, methylsulfonyl, hydroxypropyl, hydroxymethyl, and hydroxyethyl; and wherein $R^4$ is selected from phenyl, naphthyl, biphenyl, cyclohexyl, cyclopentyl, cycloheptyl, 1-cyclohexenyl, 2-cyclohexenyl, 3-cyclohexenyl, 4-cyclohexenyl, 1-cyclopentenyl, 4-cyclopentenyl, benzofuryl, 2,3-dihydrobenzofuryl, 1,2,3,4-tetrahydronaphthyl, benzothienyl, indenyl, indanyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl and pyrazinyl; wherein $R^4$ is optionally substituted at a substitutable position with one or more radicals selected from fluoro, chloro, bromo, methylthio, methylsulfinyl, methyl, ethyl, propyl, isopropyl, tert-butyl, isobutyl, hexyl, methylsulfonyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, fluoromethyl, difluoromethyl, trifluoromethyl, chloromethyl, dichloromethyl, trichloromethyl, pentafluoroethyl, heptafluoropropyl, bromodifluoromethyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, sulfamyl, methylaminosulfonyl, hydroxypropyl, hydroxyisopropyl, hydroxymethyl, hydroxyethyl, trifluoromethoxy, amino, N-methylamino, N-ethylamino, N-ethyl-N-methylamino, N,N-dimethylamino, N,N-diethylamino, formylamino, methylcarbonylamino, trifluoroacetamino, piperadinyl, piperazinyl, morpholino, nitro, and

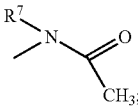

and wherein $R^7$ is hydrido;

or a pharmaceutically-acceptable salt thereof.]

[3. The method of claim 2 selected from compounds, and their pharmaceutically acceptable salts, of the group consisting of ethyl 1-[4-(aminosulfonyl)phenyl]-5-(4-chlorophenyl)-1H-pyrazole-3-carboxylate;

ethyl 1-[4-(aminosulfonyl)phenyl]-5-(4-methylphenyl)-1H-pyrazole-3-carboxylate;

isopropyl 1-[4-(aminosulfonyl)phenyl]-5-(4-chlorophenyl)-1H-pyrazole-3-carboxylate;

N-[4-methylphenyl]-1-[4-(aminosulfonyl)phenyl]-5-(4-fluorophenyl)-1H-pyrazole-3-carboxamide;

N-[3-chlorophenyl]-1-[4-(aminosulfonyl)phenyl]-5-(4-fluorophenyl)-1H-pyrazole-3-carboxamide;

N-[3-fluorophenyl]-1-[4-(aminosulfonyl)phenyl]-5-(4-fluorophenyl)-1H-pyrazole-3-carboxamide;

N-[3-fluorophenyl]-1-[4-(aminosulfonyl)phenyl]-5-(4-chlorophenyl)-1H-pyrazole-3-carboxamide;

phenylmethyl N-[[1-[4-(aminosulfonyl)phenyl]-5-(4-chlorophenyl)-1H-pyrazol-3-yl]carbonyl]glycinate;

4-[5-(4-bromophenyl)-3-cyano-1H-pyrazol-1-yl]benzenesulfonamide;

4-[3-cyano-5-(4-fluorophenyl)-1H-pyrazol-1-yl]benzenesulfonamide;

4-[5-(4-chlorophenyl)-3-cyano-1H-pyrazol-1-yl]benzenesulfonamide;

4-[3-cyano-5-(4-methoxyphenyl)-1H-pyrazol-1-yl]benzenesulfonamide;

4-[3-cyano-5-(4-methylphenyl)-1H-pyrazol-1-yl]benzenesulfonamide;

4-[3-cyano-5-(4-methylthiophenyl)-1H-pyrazol-1-yl]benzenesulfonamide;

4-[5-(5-chloro-4-methoxyphenyl)-3-cyano-1H-pyrazol-1-yl]benzenesulfonamide;

4-[5-(5-bromo-4-methoxyphenyl)-3-cyano-1H-pyrazol-1-yl]benzenesulfonamide;

4-[3-cyano-5-phenyl-1H-pyrazol-1-yl]benzenesulfonamide;

4-[4-chloro-5-(4-fluorophenyl)-1H-pyrazol-1-yl]benzenesulfonamide;
4-[4-chloro-5-(4-chlorophenyl)-1H-pyrazol-1-yl]benzenesulfonamide;
4-[4-bromo-5-(4-chlorophenyl)-1H-pyrazol-1-yl]benzenesulfonamide;
4-[4-chloro-5-phenyl-1H-pyrazol-1-yl]benzenesulfonamide;
4-[4-chloro-5-(3,5-dichloro-4-methoxyphenyl)-1H-pyrazol-1-yl]benzenesulfonamide;
4-[4-bromo-5-(4-methylphenyl)-1H-pyrazol-1-yl]benzenesulfonamide;
4-[4-chloro-5-(4-methylphenyl)-1H-pyrazol-1-yl]benzenesulfonamide;
4-[4-chloro-5-(3-chloro-4-methoxyphenyl)-1H-pyrazol-1-yl]benzenesulfonamide;
4-[4-chloro-5-(4-methoxyphenyl)-1H-pyrazol-1-yl]benzenesulfonamide;
4-[4-bromo-5-(4-methoxyphenyl)-1H-pyrazol-1-yl]benzenesulfonamide;
4-[4-cyano-5-(4-methoxyphenyl)-1H-pyrazol-1-yl]benzenesulfonamide;
4-[4-chloro-5-(4-chlorophenyl)-3-(trifluoromethyl)-1H-pyrazol-1-yl]benzenesulfonamide;
4-[4-ethyl-5-phenyl-3-(trifluoromethyl)-1H-pyrazol-1-yl]benzenesulfonamide;
4-[4-methyl-5-phenyl-3-(trifluoromethyl)-1H-pyrazol-1-yl]benzenesulfonamide;
4-[5-(4-methoxyphenyl)-4-methyl-3-(trifluoromethyl)-1H-pyrazol-1-yl]benzenesulfonamide;
4-[5-(4-chlorophenyl)-4-methyl-3-(trifluoromethyl)-1H-pyrazol-1-yl]benzenesulfonamide;
4-[5-(4-chlorophenyl)-4-ethyl-3-(trifluoromethyl)-1H-pyrazol-1-yl]benzenesulfonamide;
4-[4-ethyl-5-(4-methylphenyl)-3-(trifluoromethyl)-1H-pyrazol-1-yl]benzenesulfonamide;
4-[4-ethyl-5-(4-methoxy-3-methylphenyl)-3-(trifluoromethyl)-1H-pyrazol-1-yl]benzenesulfonamide;
4-[4-ethyl-5-(4-methoxyphenyl)-3-(trifluoromethyl)-1H-pyrazol-1-yl]benzenesulfonamide;
4-[4-ethyl-5-(3-fluoro-4-chlorophenyl)-3-(trifluoromethyl)-1H-pyrazol-1-yl]benzenesulfonamide;
4-[5-(4-fluorophenyl)-4-methyl-3-(trifluoromethyl)-1H-pyrazol-1-yl]benzenesulfonamide;
4-[4-methyl-5-(4-methylphenyl)-3-(trifluoromethyl)-1H-pyrazol-1-yl]benzenesulfonamide;
4-[4-fluoro-5-phenyl-3-(trifluoromethyl)-1H-pyrazol-1-yl]benzenesulfonamide;
4-[4-bromo-5-(4-chlorophenyl)-3-(difluoromethyl)-1H-pyrazol-1-yl]benzenesulfonamide;
4-[4-chloro-5-(3,5-dichloro-4-methoxyphenyl)-3-(difluoromethyl)-1H-pyrazol-1-yl]benzenesulfonamide;
4-[4-chloro-3-(difluoromethyl)-5-phenyl-1H-pyrazol-1-yl]benzenesulfonamide;
4-[4-bromo-3-(difluoromethyl)-5-phenyl-1H-pyrazol-1-yl]benzenesulfonamide;
4-[4-chloro-3-difluoromethyl)-5-(4-methoxyphenyl)-1H-pyrazol-1-yl]benzenesulfonamide;
4-[4-chloro-3-cyano-5-phenyl-1H-pyrazol-1-yl]benzenesulfonamide;
4-[4-chloro-5-(4-chlorophenyl)-3-cyano-1H-pyrazol-1-yl]benzenesulfonamide;
4-[4-chloro-3-cyano-5-(4-fluorophenyl)-1H-pyrazol-1-yl]benzenesulfonamide;
4-[4-bromo-3-cyano-5-(4-fluorophenyl)-1H-pyrazol-1-yl]benzenesulfonamide;
4-[4-bromo-3-cyano-5-phenyl-1H-pyrazol-1-yl]benzenesulfonamide;
ethyl [1-(4-aminosulfonylphenyl)-4-bromo-5-(4-chlorophenyl)-1H-pyrazol-3-yl]carboxylate;
methyl [1-(4-aminosulfonylphenyl)-4-chloro-5-phenyl-1H-pyrazol-3-yl]carboxylate;
methyl [1-(4-aminosulfonylphenyl)-4-chloro-5-(4-chlorophenyl)-1H-pyrazol-3yl]carboxylate;
ethyl [1-(4-aminosulfonylphenyl)-4-chloro-5-(4-chlorophenyl)-1H-pyrazol-3-yl]carboxylate;
methyl [1-(4-aminosulfonylphenyl)-4-chloro-5-(4-fluorophenyl)-1H-pyrazol-3-yl]carboxylate;
methyl [1-(4-aminosulfonylphenyl)-4-bromo-5-(4-fluorophenyl)-1H-pyrazol-3-yl]carboxylate;
methyl [1-(4-aminosulfonylphenyl)-4-chloro-5-(3-chloro-4-methoxyphenyl)-1H-pyrazol-3-yl]carboxylate;
methyl [1-(4-aminosulfonylphenyl)-4-chloro-5-(3,5dichloro-4-methoxyphenyl)-1H-pyrazol-3-yl]carboxylate;
methyl [1-(4-aminosulfonylphenyl)-5-(3-bromo-4-methoxyphenyl)-4-chloro-1H-pyrazol-3-yl]carboxylate;
4-[4-chloro-3-hydroxymethyl-5-phenyl-1H-pyrazol-1-yl]benzenesulfonamide;
4-[4-chloro-5-(4-chlorophenyl)-3-hydroxymethyl-1H-pyrazol-1-yl]benzenesulfonamide;
4-[5-(4-chlorophenyl)-3-(trifluoromethyl)-1H-pyrazol-1-yl]benzenesulfonamide;
4-[5-phenyl-3-(trifluoromethyl)-1H-pyrazol-1-yl]benzenesulfonamide;
4-[5-(4-fluorophenyl)-3-(trifluoromethyl)-1H-pyrazol-1-yl]benzenesulfonamide;
4-[5-(4-cyanophenyl)-3-(trifluoromethyl)-1H-pyrazol-1-yl]benzenesulfonamide;
4-[5-(2,4-difluorophenyl)-3-(trifluoromethyl)-1H-pyrazol-1-yl]benzenesulfonamide;
4-[5-(4-methoxyphenyl)-3-(trifluoromethyl)-1H-pyrazol-1-yl]benzenesulfonamide;
4-[5-(3,4-dichlorophenyl)-3-(trifluoromethyl)-1H-pyrazol-1-yl]benzenesulfonamide;
4-[5-(4-bromophenyl)-3-(trifluoromethyl)-1H-pyrazol-1-yl]benzenesulfonamide;
4-[5-(2,4-dichlorophenyl)-3-(trifluoromethyl)-1H-pyrazol-1-yl]benzenesulfonamide;
4-[5-(3-chlorophenyl)-3-(trifluoromethyl)-1H-pyrazol-1-yl]benzenesulfonamide;
4-[5-(4-methylphenyl)-3-(trifluoromethyl)-1H-pyrazol-1-yl]benzenesulfonamide;
4-[5-(2-chlorophenyl)-3-(trifluoromethyl)-1H-pyrazol-1-yl]benzenesulfonamide;
4-[5-(2-fluorophenyl)-3-(trifluoromethyl)-1H-pyrazol-1-yl]benzenesulfonamide;
4-[5-(4-aminophenyl)-3-(trifluoromethyl)-1H-pyrazol-1-yl]benzenesulfonamide;
4-[5-(2-methylphenyl)-3-(trifluoromethyl)-1H-pyrazol-1-yl]benzenesulfonamide;
4-[5-(4-fluoro-2-methylphenyl)-3-(trifluoromethyl)-1H-pyrazol-1-yl]benzenesulfonamide;
4-[5-(3-methylphenyl)-3-(trifluoromethyl)-1H-pyrazol-1-yl]benzenesulfonamide;
4-[5-(4-ethoxyphenyl)-3-(trifluoromethyl)-1H-pyrazol-1-yl]benzenesulfonamide;
4-[5-(3,5-dimethylphenyl-4-methoxy)-3-(trifluoromethyl)-1H-pyrazol-1-yl]benzenesulfonamide;
4-[5-(3-fluorophenyl)-3-(trifluoromethyl)-1H-pyrazol-1-yl]benzenesulfonamide;
4-[5-(3-fluoro-4-methoxyphenyl)-3-(trifluoromethyl)-1H-pyrazol-1-yl]benzenesulfonamide;

4-[5-(4-methylthiophenyl)-3-(trifluoromethyl)-1H-pyrazol-1-yl]benzenesulfonamide;
4-[5-(4-chloro-3-methylphenyl)-3-(trifluoromethyl)-1H-pyrazol-1-yl]benzenesulfonamide;
4-[5-(4-ethylphenyl)-3-(trifluoromethyl)-1H-pyrazol-1-yl]benzenesulfonamide;
4-[5-(2,4-dimethylphenyl)-3-(trifluoromethyl)-1H-pyrazol-1-yl]benzenesulfonamide;
4-[5-(2-methoxyphenyl)-3-(trifluoromethyl)-1H-pyrazol-1-yl]benzenesulfonamide;
4-[5-(4-methoxy-3-methylphenyl)-3-(trifluoromethyl)-1H-pyrazol-1-yl]benzenesulfonamide;
4-[5-(3-bromo-4-methylthiophenyl)-3-(trifluoromethyl)-1H-pyrazol-1-yl]benzenesulfonamide;
4-[5-(3-chloro-4-methylphenyl)-3-(trifluoromethyl)-1H-pyrazol-1-yl]benzenesulfonamide;
4-[5-(3,4-dimethoxyphenyl)-3-(trifluoromethyl)-1H-pyrazol-1-yl]benzenesulfonamide;
4-[5-(3-chloro-4-methoxyphenyl)-3-(trifluoromethyl)-1H-pyrazol-1-yl]benzenesulfonamide;
4-[5-(3-chloro-4-methoxy-5-methylphenyl)-3-(trifluoromethyl)-1H-pyrazol-1-yl]benzenesulfonamide;
4-[5-(3-ethyl-4-methoxyphenyl)-3-(trifluoromethyl)-1H-pyrazol-1-yl]benzenesulfonamide;
4-[5-(4-fluoro-2-methoxyphenyl)-3-(trifluoromethyl)-1H-pyrazol-1-yl]benzenesulfonamide;
4-[5-(4-methoxy-3-(3-propenyl)phenyl)-3-(trifluoromethyl)-1H-pyrazol-1-yl]benzenesulfonamide;
4-[5-(3,5-dichloro-4-methoxyphenyl)-3-(trifluoromethyl)-1H-pyrazol-1-yl]benzenesulfonamide;
4-[5-(3-chloro-4-fluorophenyl)-3-(trifluoromethyl)-1H-pyrazol-1-yl]benzenesulfonamide;
4-[5-(3-fluoro-4-methylthiophenyl)-3-(trifluoromethyl)-1H-pyrazol-1-yl]benzenesulfonamide;
4-[5-(3-methyl-4-methylthiophenyl)-3-(trifluoromethyl)-1H-pyrazol-1-yl]benzenesulfonamide;
4-[5-(3-chloro-4-methylthiophenyl)-3-(trifluoromethyl)-1H-pyrazol-1-yl]benzenesulfonamide;
4-[5-(4-(N,N-dimethylamino)phenyl)-3-(trifluoromethyl)-1H-pyrazol-1-yl]benzenesulfonamide;
4-[5-(4-methyl-3-nitrophenyl)-3-(trifluoromethyl)-1H-pyrazol-1-yl]benzenesulfonamide;
4-[5-(4-(N-methylamino)phenyl)-3-(trifluoromethyl)-1H-pyrazol-1-yl]benzenesulfonamide;
4-[5-(3-amino-4-methylphenyl)-3-(trifluoromethyl)-1H-pyrazol-1-yl]benzenesulfonamide;
4-[5-(4-chlorophenyl)-3-(difluoromethyl)-1H-pyrazol-1-yl]benzenesulfonamide;
4-[5-(4-methylthiophenyl)-3-(difluoromethyl)-1H-pyrazol-1-yl]benzenesulfonamide;
4-[5-(4-methylphenyl)-3-(difluoromethyl)-1H-pyrazol-1-yl]benzenesulfonamide;
4-[5-phenyl-3-(difluoromethyl)-1H-pyrazol-1-yl]benzenesulfonamide;
4-[5-(4-methoxyphenyl)-3-(difluoromethyl)-1H-pyrazol-1-yl]benzenesulfonamide;
4-[5-(4-chlorophenyl)-3-(difluoromethyl)-1H-pyrazol-1-yl]benzenesulfonamide;
4-[5-(2-fluoro-4-methoxyphenyl)-3-(difluoromethyl)-1H-pyrazol-1-yl]benzenesulfonamide;
4-[5-(3-chloro-4-methylphenyl)-3-(difluoromethyl)-1H-pyrazol-1-yl]benzenesulfonamide;
4-[5-(3-chloro-4-methoxyphenyl)-3-(difluoromethyl)-1H-pyrazol-1-yl]benzenesulfonamide;
4-[5-(4-chloro-3-methylphenyl)-3-(difluoromethyl)-1H-pyrazol-1-yl]benzenesulfonamide;
4-[5-(3,4-dimethoxyphenyl)-3-(difluoromethyl)-1H-pyrazol-1-yl]benzenesulfonamide;
4-[5-(3,5-dichloro-4-methoxyphenyl)-3-(difluoromethyl)-1H-pyrazol-1-yl]benzenesulfonamide;
4-[5-(3,5-difluoro-4-methoxyphenyl)-3-(difluoromethyl)-1H-pyrazol-1-yl]benzenesulfonamide;
4-[5-(2-methoxyphenyl)-3-(difluoromethyl)-1H-pyrazol-1-yl]benzenesulfonamide;
4-[5-(3-bromo-4-methoxyphenyl)-3-(difluoromethyl)-1H-pyrazol-1-yl]benzenesulfonamide;
4-[5-(4-methylsulfonylphenyl)-3-(difluoromethyl)-1H-pyrazol-1-yl]benzenesulfonamide;
4-[5-(4-chlorophenyl)-3-(heptafluoropropyl)-1H-pyrazol-1-yl]benzenesulfonamide;
4-[5-(4-chlorophenyl)-3-(chloro-difluoromethyl)-1H-pyrazol-1-yl]benzenesulfonamide;
4-[5-(4-chlorophenyl)-3-(pentafluoroethyl)-1H-pyrazol-1-yl]benzenesulfonamide;
4-[5-(4-fluorophenyl)-3-(3-hydroxypropyl)-1H-pyrazol-1-yl]benzenesulfonamide;
4-[5-(3,5-dichloro-4-methoxyphenyl)-3-(3-hydroxypropyl)-1H-pyrazol-1-yl]benzenesulfonamide;
4-[5-(3-chloro-4-methoxyphenyl)-3-(chloromethyl)-1H-pyrazol-1-yl]benzenesulfonamide;
4-[3-(chloro-difluoromethyl)-5-(3-fluoro-4-methoxyphenyl)-1H-pyrazol-1-yl]benzenesulfonamide;
4-[5-(phenyl)-3-(fluoromethyl)-1H-pyrazol-1-yl]benzenesulfonamide;
4-[5-(5-bromo-2-thienyl)-3-(difluoromethyl)-1H-pyrazol-1-yl]benzenesulfonamide;
4-[5-(5-chloro-2-thienyl)-3-(difluoromethyl)-1H-pyrazol-1-yl]benzenesulfonamide;
4-[5-(1-cyclohexenyl)-3-(difluoromethyl)-1H-pyrazol-1-yl]benzenesulfonamide;
4-[5-(1-cyclohexyl)-3-(difluoromethyl)-1H-pyrazol-1-yl]benzenesulfonamide;
4-[5-(6-benzodioxanyl)-3-(difluoromethyl)-1H-pyrazol-1-yl]benzenesulfonamide;
4-[3-(difluoromethyl)-5-(4-methylcyclohexyl)-1H-pyrazol-1-yl]benzenesulfonamide;
4-[5-(2-benzofuranyl)-3-(difluoromethyl)-1H-pyrazol-1-yl]benzenesulfonamide;
4-[5-(1,3-benzodioxol-5-yl)-3-(difluoromethyl)-1H-pyrazol-1-yl]benzenesulfonamide;
4-[5-(2-benzofuryl)-3-(trifluoromethyl)-1H-pyrazol-1-yl]benzenesulfonamide;
4-[5-(5-bromo-2-thienyl)-3-(trifluoromethyl)-1H-pyrazol-1-yl]benzenesulfonamide;
4-[5-(5-chloro-2-thienyl)-3-(trifluoromethyl)-1H-pyrazol-1-yl]benzenesulfonamide;
4-[5-(5-indanyl)-3-(trifluoromethyl)-1H-pyrazol-1-yl]benzenesulfonamide;
4-[5-(5-methyl-2-thienyl)-3-(trifluoromethyl)-1H-pyrazol-1-yl]benzenesulfonamide;
4-[5-(2,3-dihydrobenzofuran-2-yl)-3-(trifluoromethyl)-1H-pyrazol-1-yl]benzenesulfonamide,
4-[5-(1-cyclohexenyl)-3-(trifluoromethyl)-1H-pyrazol-1-yl]benzenesulfonamide;
4-[5-(1,2,3,4-tetrahydronaphth-5-yl)-3-(trifluoromethyl)-1H-pyrazol-1-yl]benzenesulfonamide;
4-[5-(2-benzothienyl)-3-(trifluoromethyl)-1H-pyrazol-1-yl]benzenesulfonamide;
4-[5-(3,4-dihydro-2H-1-benzothiopyran-7-yl)-3-(trifluoromethyl)-1H-pyrazol-1-yl]benzenesulfonamide;
4-[5-(4-methyl-1,3-benzodioxol-6-yl)-3-(trifluoromethyl)-1H-pyrazol-1-yl]benzenesulfonamide; and 4-[5-(4-methyl-1,3-benzodioxol-5-yl)-3-(trifluoromethyl)-1H-pyrazol-1-yl]benzenesulfonamide.]

[4. The method of claim 3 where the compound is 4-[5-(4-methylphenyl)-3-(trifluoromethyl)-1H-pyrazol-1-yl]benzenesulfonamide, or a pharmaceutically-acceptable salt thereof.]

[5. The method of claim 3 where the compound is 4-[5-(4-chlorophenyl)-3-(difluoromethyl)-1H-pyrazol-1-yl]benzenesulfonamide, or a pharmaceutically-acceptable salt thereof.]

[6. A method of treating inflammation or an inflammation-associated disorder in a subject, said method comprising administering to the subject having or susceptible to such inflammation or inflammation-associated disorder, a therapeutically-effective amount of a compound of Formula I (I)

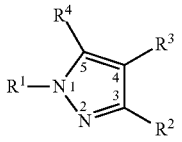

wherein $R^1$ is phenyl substituted at a substitutable position with sulfamyl;

wherein $R^2$ is selected from $C_1$-$C_5$-haloalkyl, cyano, carboxyl, $C_1$-$C_6$-alkoxycarbonyl, $C_1$-$C_5$-carboxyalkyl, aminocarbonyl, $C_1$-$C_6$-N-alkylaminocarbonyl, N-arylaminocarbonyl, $C_1$-$C_6$-N,N-dialkylaminocarbonyl, $C_1$-$C_6$-N-alkyl-N-arylaminocarbonyl, and $C_1$-$C_6$-hydroxyalkyl;

wherein $R^3$ and $R^4$ together form

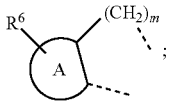

wherein m is 2;

wherein A is phenyl; and wherein $R^6$ is one or more radicals selected from halo, $C_1$-$C_{10}$-alkyl, $C_1$-$C_6$-alkylsulfonyl, $C_1$-$C_5$-haloalkyl, $C_1$-$C_6$-alkoxy, amino and nitro;

wherein aryl wherever occurring means phenyl, naphthyl, tetrahydronaphthyl, indane, biphenyl;

or a pharmaceutically-acceptable salt thereof.]

[7. The method of claim 6 wherein $R^2$ is selected from fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carbonyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, acetyl, propionyl, butyryl, isobutyryl, valeryl, isovaleryl, pivaloyl, hexanoyl, trifluoroacetyl, aminocarbonyl, N-methylaminocarbonyl, N-ethylaminocarbonyl, N-isopropylaminocarbonyl, N-propylaminocarbonyl, N-butylaminocarbonyl, N-isobutylaminocarbonyl, N-tert-butylaminocarbonyl, N-pentylaminocarbonyl, N-phenylaminocarbonyl, N,N-dimethylaminocarbonyl, N-methyl-N-ethylaminocarbonyl, N-(3-fluorophenyl)aminocarbonyl, N-(4-methylphenyl)aminocarbonyl, N-(3-chlorophenyl)aminocarbonyl, N-(4-methoxyphenyl)aminocarbonyl, N-methyl-N-phenylaminocarbonyl, hydroxypropyl, hydroxymethyl and hydroxyethyl; wherein A is phenyl; and wherein, $R^6$ is one or more radicals selected from fluoro, chloro, bromo, methylsulfonyl, methyl, ethyl, isopropyl, tert-butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, methylenedioxy, ethoxy, propoxy, n-butoxy, amino, and nitro;

or a pharmaceutically-acceptable salt thereof.]

[8. The method of claim 7 selected from compounds, and their pharmaceutically acceptable salts, of the group consisting of 4-[3-(difluoromethyl)-4,5-dihydro-7-methoxy-1H-benz[g]indazol-1-yl]benzenesulfonamide;

4-[3-(difluoromethyl)-4,5-dihydro-7-methyl-1H-benz[g]indazol-1-yl]benzenesulfonamide;

4-[4,5-dihydro-7-methoxy-3-(trifluoromethyl)-1H-benz[g]indazol-1-yl]benzenesulfonamide;

4-[4,5-dihydro-3-(trifluoromethyl)-1H-benz[g]indazol-1yl]benzenesulfonamide;

4-[4,5-dihydro-7-methyl-3-(trifluoromethyl)-1H-benz[g]indazol-1-yl]benzenesulfonamide;

methyl[1-(4-aminosulfonylphenyl)-4,5-dihydro-7-methoxy-1H-benz[g]indazol-3-yl]carboxylate; and 4-[4,5-dihydro-3-trifluoromethyl-1H-thieno[3,2,g]indazol-1-yl]benzenesulfonamide.]

[9. A method of treating inflammation or an inflammation-associated disorder in a subject, said method comprising administering to the subject having or susceptible to such inflammation or inflammation-associated disorder, a therapeutically-effective amount of a compound of Formula I (I)

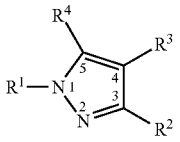

wherein $R^1$ is phenyl, wherein $R^1$ is substituted at a substitutable position with one or more radicals selected from halo, $C_1$-$C_{10}$-alkyl, $C_1$-$C_6$-alkoxy, hydroxyl and $C_1$-$C_6$-haloalkyl; wherein $R^2$ is selected from $C_1$-$C_6$-haloalkyl; wherein $R^3$ is hydrido; and wherein $R^4$ is aryl substituted at a substitutable position with sulfamyl; or a pharmaceutically-acceptable salt thereof;

wherein aryl wherever occurring means phenyl, naphthyl, tetrahydronaphthyl, indane, biphenyl;

or a pharmaceutically-acceptable salt thereof.]

[10. The method of claim 9 selected from compounds, and their pharmaceutically acceptable salts, of the group consisting of 4-[1-(4-fluorophenyl)-3-(trifluoromethyl)-1H-pyrazol-5-yl]benzenesulfonamide; and 4-[1-(4-methoxyphenyl)-3-(trifluoromethyl)-1H-pyrazol-5-yl]benzenesulfonamide.]

[11. A method of treating inflammation or an inflammation-associated disorder in a subject, said method comprising administering to the subject having or susceptible to such inflammation or inflammation-associated disorder, a therapeutically-effective amount of a compound of Formula II (II)

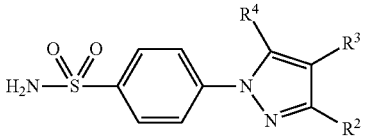

wherein $R^2$ is selected from hydrido, $C_1$-$C_6$-haloalkyl, $C_1$-$C_6$-alkoxycarbonyl, cyano, aminocarbonyl, arylaminocarbonyl, $C_1$-$C_6$-carboxyalkyl, and $C_1$-$C_6$-hydroxyalkyl;

wherein $R^3$ is selected from hydrido, and halo; and wherein $R^4$ is selected from aryl, $C_3$-$C_{10}$-cycloalkyl, $C_3$-$C_{10}$-cycloalkenyl and heterocyclic; wherein $R^4$ is optionally substituted at a substitutable position with one or more radicals selected from halo, $C_1$-$C_6$-alkylthio, $C_1$-$C_6$-alkylsulfonyl, cyano, nitro, $C_1$-$C_6$-haloalkyl, $C_1$-$C_{10}$-alkyl, $C_1$-$C_6$-alkoxy, $C_1$-$C_6$-haloalkoxy, sulfamyl, five or six membered heterocyclic and amino; wherein aryl wherever occurring means phenyl, naphthyl, tetrahydronaphthyl, indane, biphenyl;

provided $R^2$ and $R^3$ are not both hydrido; and further provided that $R^4$ is not unsubstituted thienyl when $R^2$ is trifluoromethyl; and further provided the compound is not 4-[5-(3-fluoro-4-methoxyphenyl)-3-(difluoromethyl)-1H-pyrazol-1-yl]benzenesulfonamide;

or a pharmaceutically-acceptable salt thereof.]

[12. The method of claim 11 wherein the compounds are selected from compounds, and their pharmaceutically acceptable salts, of the group consisting of 4-[5-(4-methoxyphenyl)-3-(trifluoromethyl)-1H-pyrazol-1-yl]benzenesulfonamide;

4-[5-(4-chlorophenyl)-3-(trifluoromethyl)-1H-pyrazol-1-yl]benzenesulfonamide;

4-[5-phenyl-3-(trifluoromethyl)-1H-pyrazol-1-yl]benzenesulfonamide;

4-[5-(4-fluorophenyl)-3-(trifluoromethyl)-1H-pyrazol-1-yl]benzenesulfonamide;

4-[5-(4-chlorophenyl)-3-(difluoromethyl)-1H-pyrazol-1-yl]benzenesulfonamide;

4-[5-(4-methylphenyl)-3-(trifluoromethyl)-1H-pyrazol-1-yl]benzenesulfonamide;

4-[4-chloro-5-(4-chlorophenyl)-3-(trifluoromethyl)-1H-pyrazol-1-yl]benzenesulfonamide;

4-[3-(difluoromethyl)-5-(4-methylphenyl)-1H-pyrazol-1-yl]benzenesulfonamide;

4-[3-(difluoromethyl)-5-phenyl-1H-pyrazol-1-yl]benzenesulfonamide;

4-[3-(difluoromethyl)-5-(4-methoxyphenyl)-1H-pyrazol-1-yl]benzenesulfonamide;

4-[3-cyano-5-(4-fluorophenyl)-1H-pyrazol-1-yl]benzenesulfonamide;

4-[5-(3-fluoro-4-methoxyphenyl)-3-trifluoromethyl)-1H-pyrazol-1-yl]benzenesulfonamide;

4-[4-chloro-5-phenyl-1H-pyrazol-1-yl]benzenesulfonamide;

4-[5-(4-chlorophenyl)-3-(hydroxymethyl)-1H-pyrazol-1-yl]benzenesulfonamide; and

4-[5-(4-(N,N-dimethylamino)phenyl)-3-(trifluoromethyl)-1H-pyrazol-1-yl]benzenesulfonamide.]

[13. The method of claim 1 for use in treatment of inflammation.]

[14. The method of claim 1 for use in treatment of an inflammation-associated disorder.]

[15. The method of claim 14 wherein the inflammation-associated disorder is arthritis.]

[16. The method of claim 14 wherein the inflammation-associated disorder is pain.]

[17. The method of claim 14 wherein the inflammation-associated disorder is fever.]

[18. The method of claim 1 for use in the prevention of colorectal cancer.]

*19. A method of treating arthritis in a subject, said method comprising administering to the subject having or susceptible to arthritis, a therapeutically-effective amount of 4-[5-(4-methylphenyl)-3-(trifluoromethyl)-1H-pyrazol-1-yl]benzenesulfonamide, or a pharmaceutically-acceptable salt thereof.*

*20. A method of treating pain in a subject, said method comprising administering to the subject having or susceptible to pain, a therapeutically-effective amount of 4-[5-(4-methylphenyl)-3-(trifluoromethyl)-1H-pyrazol-1-yl]benzenesulfonamide, or a pharmaceutically-acceptable salt thereof.*

*21. A method of treating osteoarthritis in a subject, said method comprising administering to the subject having or susceptible to osteoarthritis, a therapeutically-effective amount of 4-[5-(4-methylphenyl)-3-(trifluoromethyl)-1H-pyrazol-1-yl]benzenesulfonamide, or a pharmaceutically-acceptable salt thereof.*

*22. A method of treating rheumatoid arthritis in a subject, said method comprising administering to the subject having or susceptible to rheumatoid arthritis, a therapeutically-effective amount of 4-[5-(4-methylphenyl)-3-(trifluoromethyl)-1H-pyrazol-1-yl]benzenesulfonamide, or a pharmaceutically-acceptable salt thereof.*

*23. A method of treating juvenile arthritis in a subject, said method comprising administering to the subject having or susceptible to juvenile arthritis, a therapeutically-effective amount of 4-[5-(4-methylphenyl)-3-(trifluoromethyl)-1H-pyrazol-1-yl]benzenesulfonamide, or a pharmaceutically-acceptable salt thereof.*

*24. A method of treating spondyloarthropathy in a subject, said method comprising administering to the subject having or susceptible to spondyloarthropathies, a therapeutically-effective amount of 4-[5-(4-methylphenyl)-3-(trifluoromethyl)-1H-pyrazol-1-yl]benzenesulfonamide, or a pharmaceutically-acceptable salt thereof.*

*25. A method of treating menstrual cramps in a subject, said method comprising administering to the subject having or susceptible to menstrual cramps, a therapeutically-effective amount of 4-[5-(4-methylphenyl)-3-(trifluoromethyl)-1H-pyrazol-1-yl]benzenesulfonamide, or a pharmaceutically-acceptable salt thereof.*

* * * * *